US007138420B2

(12) United States Patent  
Bentzien et al.

(10) Patent No.: US 7,138,420 B2  
(45) Date of Patent: Nov. 21, 2006

(54) SUBSTITUTED BENZIMIDAZOLE COMPOUNDS

(75) Inventors: Joerg Martin Bentzien, White Plains, NY (US); Brian Nicholas Cook, Danbury, CT (US); Charles Cywin, Bethel, CT (US); Roman Wolfgang Fleck, Greenwich, CT (US); Ho Yin Lo, Bethel, CT (US); Peter Allen Nemoto, Southbury, CT (US); Steven S. Pullen, Danbury, CT (US); Gregory Paul Roth, Woodstock, CT (US); Roger John Snow, Danbury, CT (US); Hidenori Takahashi, LaGrangeville, NY (US); Ji Wang, Danbury, CT (US); Kevin J. Moriarty, East Norriton, PA (US); Lei Qiao, Downingtown, PA (US); Michael Winters, Morgantown, PA (US)

(73) Assignee: Boehringer Ingelheim Pharmaceuticals Inc., Ridgefield, CT (US)

( * ) Notice: Subject to any disclaimer, the term of this patent is extended or adjusted under 35 U.S.C. 154(b) by 0 days.

(21) Appl. No.: 10/632,888

(22) Filed: Aug. 1, 2003

(65) Prior Publication Data

US 2005/0203158 A1   Sep. 15, 2005

Related U.S. Application Data

(60) Provisional application No. 60/402,009, filed on Aug. 8, 2002.

(51) Int. Cl.
    *A61K 31/4184* (2006.01)
    *C07D 235/30* (2006.01)

(52) U.S. Cl. ............... 514/388; 548/304.7; 548/307.4; 548/248; 546/273.4; 544/121; 544/132; 544/370; 514/378; 514/338; 514/234.5; 514/254.06

(58) Field of Classification Search ............ 548/304.7, 548/307.4; 514/388
    See application file for complete search history.

(56) References Cited

U.S. PATENT DOCUMENTS

| | | | |
|---|---|---|---|
| 3,336,191 A | 8/1967 | Craig et al. | |
| 3,401,171 A | 9/1968 | Craig et al. | |
| 3,401,173 A * | 9/1968 | Chow et al. ............. | 548/304.7 |
| 4,011,236 A * | 3/1977 | Grier ..................... | 548/307.4 |
| 4,139,626 A | 2/1979 | Beard | |
| 4,191,764 A | 3/1980 | Beard | |
| 4,312,873 A | 1/1982 | Beard | |
| 4,948,891 A | 8/1990 | Schnur et al. | |
| 5,141,950 A | 8/1992 | Nakane et al. | |
| 5,180,724 A | 1/1993 | Bowles et al. | |
| 5,270,148 A | 12/1993 | Morigaki et al. | |
| 5,541,339 A | 7/1996 | Kelly et al. | |
| 5,559,127 A | 9/1996 | Hartman et al. | |
| 5,616,537 A | 4/1997 | Yokota et al. | |
| 5,770,544 A | 6/1998 | Yokota et al. | |
| 2002/0123484 A1 | 9/2002 | Das et al. | |
| 2003/0070902 A1 | 4/2003 | Weinand et al. | |
| 2003/0125550 A1 | 7/2003 | Blume et al. | |
| 2003/0144286 A1 | 7/2003 | Frenkel et al. | |
| 2003/0166929 A1 | 9/2003 | Snow et al. | |

FOREIGN PATENT DOCUMENTS

| | | |
|---|---|---|
| CA | 1094061 | 1/1981 |
| CA | 2115737 | 8/1994 |
| EP | 0 343 894 A1 | 11/1989 |
| GB | 1 122 957 A | 8/1968 |
| WO | WO99/24035 | 5/1999 |
| WO | WO 01/21634 A1 | 3/2001 |
| WO | WO 01/25238 | 4/2001 |
| WO | WO 01/70705 A1 | 9/2001 |
| WO | WO 02/14319 A2 | 2/2002 |
| WO | WO 03/006438 | 1/2003 |
| WO | WO 03/030902 | 4/2003 |

OTHER PUBLICATIONS

Fang, J. et al; 2-Aminobenzimidazoles as Neuropeptide Y Y5 Antagonists: Solution Phase Synthesis and Structure Relationships, ACS National Meeting, Chicago, IL, Aug. 26, 2001 Abstract Medi 26.

(Continued)

*Primary Examiner*—Laura L. Stockton  
(74) *Attorney, Agent, or Firm*—Michael P. Morris; Mary-Ellen Devlin; Anthony P. Bottino

(57) ABSTRACT

Disclosed are substituted benzimidazole compounds of formula (I):

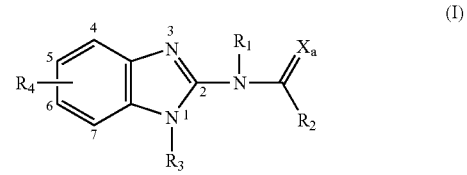

wherein $R_1$, $R_2$, $R_3$, $R_4$ and $X_a$ are defined herein. The compounds of the invention inhibit Itk kinase and are therefore useful for treating diseases and pathological conditions involving inflammation, immunological disorders and allergic disorders. Also disclosed are processes for preparing these compounds and to pharmaceutical compositions comprising these compounds.

11 Claims, No Drawings

OTHER PUBLICATIONS

Linn, J., et al; Benzimidazole Neuropeptide Y Y5 Antagonists: Rapid SAR Development Using a Solid-Phase Approach, ACS National Meeting, Chicago, IL Aug. 26, 2001 Abstract Medi 27.

Heyer, D. et al; Discovery of a Novel Series of Benzimidazole-based Neuropeptide Y Y5 Antagonists from a 7-TM Targeted Chemical Library, ACS National Meeting, Chicago, II Aug. 26, 2001 Abstract Medi 30.

Akwabi-Ameyaw, A. et al; Synthesis and SAR of Substituted 5 Acylamino Benzimidazoles as Potent Neuropeptide Y Y5 Antagonist,- ACS National Meeting, Chicago, IL, Aug. 26, 2001 Abstract Medi Poster 33.

Kong, D. et al; Chemical Components of Viscum Coloratum V. Chinese Journal of Pharmaceuticals, 1989, 20(3), pp. 110-115.

Abstracts- American Chemical Society-Division of Medicinal Chemistry—222nd ACS National Meeting, Chicago, IL—Aug. 26-30, 2001.

* cited by examiner

SUBSTITUTED BENZIMIDAZOLE COMPOUNDS

APPLICATION DATA

This application claims benefit to U.S. provisional application Ser. No. 60/402,009 filed Aug. 8, 2002.

TECHNICAL FIELD OF THE INVENTION

This invention relates to substituted benzimidazole compounds of formula (I):

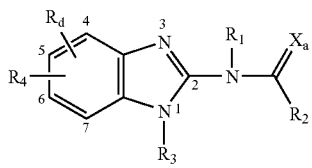

wherein $R_1$, $R_2$, $R_3$, $R_4$ and $X_a$ are defined herein below. The compounds of the invention inhibit Itk kinase and are therefore useful for treating diseases and pathological conditions involving inflammation, immunological disorders and allergic disorders. This invention also relates to processes for preparing these compounds and to pharmaceutical compositions comprising these compounds.

BACKGROUND OF THE INVENTION

Protein kinases play a critical role in mediating signaling events leading to cellular responses such as activation, growth and differentiation, in response to extracellular signals. Protein kinases transmit their signal by phosphorylating specific residues in a target protein. Protein kinases that specifically phosphorylate tyrosine residues are referred to as protein tyrosine kinases. Protein tyrosine kinases can be divided into two general groups: receptor such as epidermal growth factor (EGF) receptor (S. Iwashita and M. Kobayashi, 1992, Cellular Signalling, 4, 123–132) and cytosolic non-receptor (C. Chan et al., 1994, Ann. Rev. Immunol., 12, 555–592).

Interleukin-2-inducible T cell kinase (Itk), also referred to as T cell-specific kinase (Tsk) and expressed mainly in T-lymphocytes (EMT), is a member of the Tec family of protein tyrosine kinases that also includes Txk, Tec, Btk, and Bmx. Tec family members are characterized by the presence of a pleckstrin-homology domain (PH), a proline rich Tec homology domain (TH) and Src homology SH3, SH2 and SH1 kinase domains positioned from the N-terminus to the C-terminus respectively (S. Gibson et al., 1993, Blood, 82,1561–1572; J. D. Siliciano et al., 1992, Proc. Nat. Acad. Sci., 89, 11194–11198; N. Yamada et al., 1993 Biochem. and Biophys Res. Comm., 192, 231–240).

Itk is expressed in T cells, mast cells and natural killer cells. It is activated in T cells upon stimulation of the T cell receptor (TCR), and in mast cells upon activation of the high affinity IgE receptor. Following receptor stimulation in T cells, Lck, a src tyrosine kinase family member, phosphorylates Y511 in the kinase domain activation loop of Itk (S. D. Heyeck et al., 1997, J. Biol. Chem, 272, 25401–25408). Activated Itk, together with Zap-70 is required for phosphorylation and activation of PLC-γ (S. C. Bunnell et al., 2000, J. Biol. Chem., 275, 2219–2230). PLC-γ catalyzes the formation of inositol 1,4,5-triphosphate and diacylglycerol, leading to calcium mobilization and PKC activation, respectively. These events activate numerous downstream pathways and lead ultimately to degranulation (mast cells) and cytokine gene expression (T cells) (Y. Kawakami et al., 1999, J. Leukocyte Biol., 65, 286–290).

The role of Itk in T cell activation has been confirmed in Itk knockout mice. CD4$^+$T cells from Itk knockout mice have a diminished proliferative response in a mixed lymphocyte reaction or upon Con A or anti-CD3 stimulation. (X. C. Liao and D. R. Littman, 1995, Immunity, 3, 757–769). Also, T cells from Itk knockout mice produced little IL-2 upon TCR stimulation resulting in reduced proliferation of these cells. In another study, Itk deficient CD4$^+$ T cells produced reduced levels of cytokines including IL-4, IL-5 and IL-13 upon stimulation of the TCR, even after priming with inducing conditions. (D. J. Fowell, 1999, Immunity, 11, 399–409).

The role of Itk in PLC-γ activation and in calcium mobilization was also confirmed in the T cells of these knockout mice, which had severely impaired IP$_3$ generation and no extracellular calcium influx upon TCR stimulation (K. Liu et al., 1998, J. Exp. Med. 187, 1721–1727). The studies described above support a key role for Itk in activation of T cells and mast cells. Thus an inhibitor of Itk would be of therapeutic benefit in diseases mediated by inappropriate activation of these cells.

It has been well established that T cells play an important role in regulating the immune response (Powrie and Coffman, 1993, Immunology Today, 14, 270–274). Indeed, activation of T cells is often the initiating event in immunological disorders. Following activation of the TCR, there is an influx of calcium that is required for T cell activation. Upon activation, T cells produce cytokines, including IL-2, 4, 5, 9, 10, and 13 leading to T cell proliferation, differentiation, and effector function. Clinical studies with inhibitors of IL-2 have shown that interference with T cell activation and proliferation effectively suppresses immune response in vivo (Waldmann, 1993, Immunology Today, 14, 264–270). Accordingly, agents that inhibit T lymphocyte activation and subsequent cytokine production, are therapeutically useful for selectively suppressing the immune response in a patient in need of such immunosuppression.

Mast cells play a critical roll in asthma and allergic disorders by releasing pro-inflammatory mediators and cytokines. Antigen-mediated aggregation of FcεRI, the high-affinity receptor for IgE results in activation of mast cells (D. B. Corry et al., 1999, Nature, 402, B18–23). This triggers a series of signaling events resulting in the release of mediators, including histamine, proteases, leukotrienes and cytokines (J. R. Gordon et al., 1990, Immunology Today, 11, 458–464.) These mediators cause increased vascular permeability, mucus production, bronchoconstriction, tissue degradation and inflammation thus playing key roles in the etiology and symptoms of asthma and allergic disorders.

Recent published data using Itk knockout mice suggests that in the absence of Itk function, increased numbers of memory T cells are generated (A. T. Miller et al., 2002 The Journal of Immunology, 168, 2163–2172). One strategy to improve vaccination methods is to increase the number of memory T cells generated (S. M. Kaech et al., Nature Reviews Immunology, 2, 251–262).

All documents cited in this application are incorporated by reference in their entirety.

SUMMARY OF THE INVENTION

It is therefore an object of the invention to provide a compound of the formula (I):

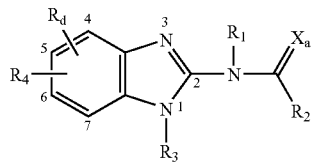

wherein $R_1$, $R_2$, $R_3$, $R_4$ and $X_a$ are defined herein below.

It is another object of the invention to provide a method of inhibiting the Tec kinase family, including Itk kinase, and methods of treating diseases or conditions related to such kinase activity activity, by administering to a patient in need thereof a therapeutically effective amount of a compound of the formula (I).

It is yet another object of the invention to provide pharmaceutical compositions and processes of making compounds of the formula (I) as described herein below.

DETAILED DESCRIPTION OF THE PREFERRED EMBODIMENTS

In it's broadest generic embodiment, the invention provides for a compound of the formula (I):

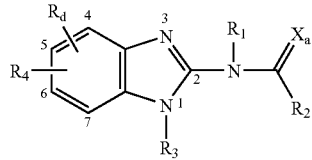

wherein:

$R_1$ is hydrogen or alkyl;

$R_2$ is chosen from aryl and heteroaryl each $R_2$ is optionally substituted with one or more $R_a$;

$R_3$ is $C_{1-10}$ alkyl chain branched or unbranched optionally substituted with one or more $R_b$, or $R_3$ is the group:

—$(CH_2)_n$-L-$R_6$, wherein L is chosen from a bond, —NH—C(O)—, —O—C(O)—, —C(O)— and —S(O)$_m$— wherein m is 0, 1 or 2, and wherein said group is optionally substituted by one or more $R_b$;

wherein $R_6$ is independently chosen from hydrogen, hydroxy, alkyl, alkoxy, alkylthio, aryl$C_{0-5}$ alkyl, aryloxy$C_{0-5}$ alkyl, heteroaryl$C_{0-5}$ alkyl, cycloalkyl$C_{0-5}$ alkyl, heterocyclyl$C_{0-5}$ alkyl and amino said amino is optionally mono-or di-substituted by acyl, alkyl, alkoxycarbonyl, cycloalkyl$C_{0-5}$ alkyl, aryl$C_{0-5}$ alkyl, heteroaryl$C_{0-5}$ alkyl or heterocyclyl$C_{0-5}$ alkyl;

n is 1–10;

$R_4$ is a group chosen from:

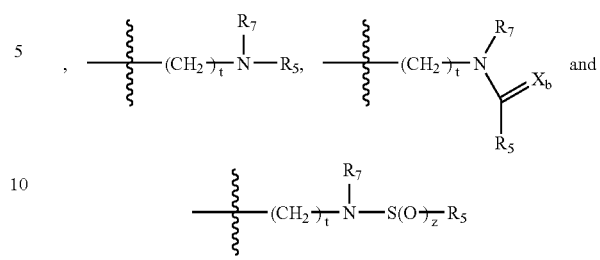

wherein $R_4$ is covalently attached at the indicated 5- or 6-position of the formula (I), t and z are each independently chosen from 0,1 or 2;

$R_5$ is chosen from aryl$C_{0-5}$ alkyl, alkyl, heteroaryl$C_{0-5}$ alkyl, cycloalkyl$C_{0-5}$ alkyl and heterocyclyl$C_{0-5}$ alkyl, each $R_5$ optionally substituted with one or more $R_c$;

$R_7$ is hydrogen, alkenyl or alkyl;

or $R_5$ and $R_7$ together with the nitrogen atom to which they are attached form:

a 4–7-membered monocyclic ring or an 8–14-membered bicyclic ring, wherein each monocyclic or bicyclic ring optionally contains an additional 1 to 3 heteroatoms chosen from N, O and S and each ring is aromatic or nonaromatic, and wherein each monocyclic or bicyclic ring is optionally substituted by one or more $R_c$;

each $R_a$, $R_b$ or $R_c$ are independently chosen from hydrogen, alkyl, alkenyl, alkynyl, cycloalkyl, aryl, arylalkyl, aryloxy, alkoxy, alkylthio, acyl, alkoxycarbonyl, acyloxy, acylamino, sulphonylamino, aminosulfonyl, alkylsulfonyl, carboxy, carboxamide, oxo, hydroxy, halogen, trifluoromethyl, nitro, nitrile and amino optionally mono-or -di-substituted by alkyl, acyl or alkoxycarbonyl, wherein any of the above $R_a$, $R_b$ or $R_c$ are optionally halogenated where possible;

$R_d$, covalently attached at the indicated 4-, 5-, 6- or 7-position of the formula (I), is chosen from hydrogen, alkyl, alkoxy and halogen and $X_a$ and $X_b$ are oxygen or sulfur;

or the pharmaceutically acceptable salts, esters, acids, isomers or tautomers thereof.

In another embodiment, there is provided a compound of the formula (I) as described immediately above and wherein:

$R_1$ is hydrogen;

$R_2$ is chosen from phenyl, naphthyl, and heteroaryl chosen from thienyl, furanyl, isoxazolyl, oxazolyl, thiazolyl, thiadiazolyl, tetrazolyl, pyrazolyl, pyrrolyl, imidazolyl, pyridinyl, pyrimidinyl, pyrazinyl, pyridazinyl, pyranyl, quinoxalinyl, indolyl, benzimidazolyl, benzoxazolyl, benzothiazolyl, benzothienyl, quinolinyl, quinazolinyl and indazolyl each $R_2$ is optionally substituted with one or more $R_a$;

$R_3$ is $C_{1-10}$ alkyl chain branched or unbranched optionally substituted with one or more $R_b$, or $R_3$ is:

—$(CH_2)_n$-L-$R_6$, wherein L is chosen from a bond, —O—C(O)—, —C(O)— and —S(O)$_m$— wherein m is 0, 1 or 2, and wherein said group is optionally substituted by one or more $R_b$;

wherein $R_6$ is independently chosen from hydrogen, hydroxy, $C_{1-5}$ alkyl, $C_{1-5}$ alkoxy, $C_{1-5}$ alkylthio, phenyl, naphthyl, benzyl, phenethyl, heteroaryl$C_{0-5}$ alkyl, $C_{3-7}$ cycloalkylC$_{0-5}$ alkyl, heterocyclylC$_{0-5}$ alkyl and amino said amino is optionally mono-or di-substituted by C$_{1-5}$ acyl, C$_{1-5}$ alkyl, C$_{1-5}$ alkoxycarbonyl, arylC$_{0-5}$ alkyl, heteroarylC$_{0-5}$ alkyl or heterocyclylC$_{0-5}$ alkyl; and wherein each recited heteroaryl in this paragraph is chosen from thienyl, furanyl, isoxazolyl, oxazolyl, thiazolyl, thiadiazolyl, tetrazolyl, pyrazolyl, pyrrolyl, imidazolyl, pyridinyl, pyrimidinyl, pyrazinyl, pyridazinyl and pyranyl and wherein each recited heterocyclyl in this paragraph is chosen from pyrrolidinyl, morpholinyl, thiomorpholinyl, dioxalanyl, piperidinyl and piperazinyl;

R$_4$ is a group chosen from:

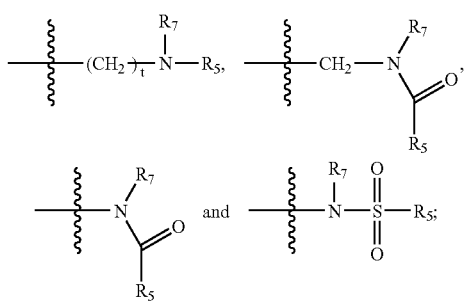

R$_5$ is chosen from phenyl, naphthyl, benzyl, phenethyl, C$_{1-5}$ alkyl, heteroarylC$_{0-5}$ alkyl wherein the heteroaryl is chosen from thienyl, furanyl, isoxazolyl, oxazolyl, thiazolyl, thiadiazolyl, tetrazolyl, pyrazolyl, pyrrolyl, imidazolyl, pyridinyl, pyrimidinyl, pyrazinyl, pyridazinyl and pyranyl, C$_{3-7}$ cycloalkylC$_{0-5}$ alkyl and heterocyclylC$_{0-5}$ alkyl wherein the heterocyclyl is chosen from aziridinyl, pyrrolidinyl, morpholinyl, thiomorpholinyl, tetrahydrofuranyl, dioxalanyl, piperidinyl and piperazinyl, each R$_5$ is optionally substituted with one or more R$_c$;

each R$_a$, R$_b$ or R$_c$ are independently chosen from hydrogen, C$_{1-5}$ alkyl, C$_{2-5}$ alkenyl, C$_{2-5}$ alkynyl, C$_{3-8}$ cycloalkyl, phenyl, benzyl, phenoxy, C$_{1-5}$ alkoxy, C$_{1-5}$ alkylthio, C$_{1-5}$ acyl, C$_{1-5}$ alkoxycarbonyl, C$_{1-5}$ acyloxy, C$_{1-5}$ acylamino, C$_{1-5}$ sulphonylamino, aminosulfonyl, C$_{1-5}$ alkylsulfonyl, carboxy, carboxamide, oxo, hydroxy, halogen, trifluoromethyl, nitro, nitrile and amino optionally mono-or -di-substituted by C$_{1-5}$ alkyl, C$_{1-5}$ acyl or C$_{1-5}$ alkoxycarbonyl, wherein any of the above R$_a$, R$_b$ or R$_c$ are optionally halogenated where possible;

R$_d$ is chosen from hydrogen, C$_{1-3}$ alkyl, C$_{1-3}$ alkoxy and halogen;

R$_7$ is hydrogen, C$_{3-10}$ alkenyl or C$_{1-5}$ alkyl; and

X$_a$ is oxygen.

In yet another embodiment, there is provided a compound of the formula (I) as described immediately above and wherein:

R$_2$ is chosen from phenyl, naphthyl and heteroaryl chosen from thienyl, furanyl, isoxazolyl, oxazolyl, imidazolyl, thiadiazolyl, pyrazolyl, pyridinyl, quinoxalinyl and benzothienyl each R$_2$ is optionally substituted with one or more R$_a$;

R$_6$ is independently chosen from hydroxy, C$_{1-5}$ alkyl, C$_{1-5}$ alkoxy, phenyl, benzyl, phenethyl, heteroarylC$_{0-5}$ alkyl, heterocyclylC$_{0-5}$ alkyl, C$_{3-7}$ cycloalkyl and amino said amino is optionally mono-or di-substituted by C$_{1-5}$ acyl, C$_{1-5}$ alkyl, C$_{1-5}$ alkoxycarbonyl, arylC$_{0-5}$ alkyl or heteroarylC$_{0-5}$ alkyl;

and wherein each recited heteroaryl in this paragraph is chosen from thienyl, furanyl, isoxazolyl, oxazolyl, thiazolyl, thiadiazolyl, tetrazolyl, pyrazolyl, pyrrolyl and imidazolyl, each optionally substituted by R$_b$;

n is 1–6;

R$_5$ is chosen from phenyl, naphthyl, benzyl, phenethyl, C$_{1-5}$ alkyl, heteroarylC$_{0-5}$ alkyl wherein the heteroaryl in this paragraph is chosen from thienyl, furanyl, imidazolyl and pyridinyl, C$_{3-7}$ cycloalkylC$_{0-5}$ alkyl and heterocyclylC$_{0-5}$ alkyl wherein the heterocyclyl is chosen from aziridinyl, pyrrolidinyl, tetrahydrofuranyl, tetrahydropyridinyl, morpholinyl, thiomorpholinyl, piperidinyl and piperazinyl, each R$_5$ is optionally substituted with one or more R$_c$;

R$_7$ is hydrogen, propenyl or C$_{1-3}$ alkyl and

R$_d$ is chosen from hydrogen and C$_{1-3}$ alkyl.

In yet still another embodiment, there is provided a compound of the formula (I) as described immediately above and wherein:

R$_2$ is chosen from phenyl and heteroaryl chosen from thienyl, furanyl, isoxazolyl, thiadiazolyl, pyrazolyl and pyridinyl each R$_2$ is optionally substituted with one or more R$_a$;

R$_3$ is:
—(CH$_2$)$_n$—C(O)—R$_6$ or
—(CH$_2$)$_n$—R$_6$;

wherein R$_6$ is independently chosen from hydroxy, C$_{1-5}$ alkyl, C$_{1-5}$ alkoxy, phenyl, morpholinylC$_{0-5}$ alkyl, piperazinylC$_{0-5}$ alkyl, imidazolylC$_{0-5}$ alkyl, pyrrolidinylC$_{0-5}$ alkyl, pyrrolidinonylC$_{0-5}$ alkyl, thienylC$_{0-5}$ alkyl, C$_{3-7}$ cycloalkyl and amino said amino is optionally mono-or di-substituted by C$_{1-5}$ alkyl or C$_{1-5}$ alkoxycarbonyl;

R$_5$ is chosen from phenyl, furanyl, benzyl, phenethyl, C$_{1-3}$ alkyl and C$_{3-7}$ cycloalkylC$_{0-5}$ alkyl each optionally substituted with one or more R$_c$;

each R$_a$, R$_b$ or R$_c$ are independently chosen from C$_{1-5}$ alkyl, C$_{3-8}$ cycloalkyl, phenyl, C$_{1-5}$ alkoxy, amino optionally mono-or -di-substituted by C$_{1-5}$ alkyl, C$_{1-5}$ alkoxycarbonyl, carboxamide, hydroxy, halogen, trifluoromethyl, nitro and nitrile, wherein any of the above R$_a$, R$_b$ or R$_c$ are optionally halogenated where possible;

R$_7$ is C$_{1-3}$ alkyl; and

R$_d$ is chosen from hydrogen and methyl.

In a further embodiment, there is provided a compound of the formula (I) as described immediately above and wherein:

R$_2$ is chosen from phenyl, thienyl, furanyl, isoxazolyl and pyridinyl each optionally substituted with one or more R$_a$;

R$_5$ is chosen from methyl, CF$_3$, cyclopentyl, phenyl and cyclohexyl each optionally substituted with one or more R$_c$;

R$_d$ is hydrogen and n is 2–5.

In yet another embodiment, there is provided a compound of the formula (I) as described immediately above and wherein:

R$_2$ is chosen from phenyl, thien-2-yl, isoxazol-5-yl and pyridin-3-yl each optionally substituted with one or more R$_a$;

R$_4$ is chosen from:

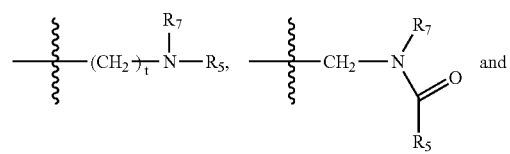

-continued

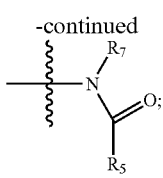

$R_6$ is independently chosen from hydroxy, methyl, ethyl, $C_{1-3}$ alkoxy, phenyl, morpholinyl, piperazinyl, imidazolyl, pyrrolidinyl, pyrrolidinonyl, thienyl$C_{0-5}$ alkyl, $C_{3-7}$ cycloalkyl and amino said amino is optionally mono-or di-substituted by $C_{1-5}$ alkyl or $C_{1-5}$ alkoxycarbonyl; and each $R_a$, $R_b$ or $R_c$ are independently chosen from $C_{1-3}$ alkoxy, amino optionally mono-or -di-substituted by $C_{1-3}$ alkyl, carboxamide, hydroxy, fluoro, chloro, bromo, trifluoromethyl, nitro and nitrile.

In any of the aforementioned embodiments, there are provided compounds of the formula (I) wherein:

$R_4$ is covalently attached at the indicated 5-position of the formula (I) or in another embodiment $R_4$ is covalently attached at the indicated 6-position of the formula (I).

In another embodiment there is provided representative compounds of the invention which can be made in accordance with the general schemes and working examples presented below:

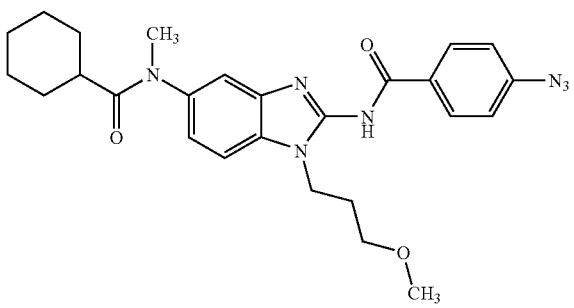

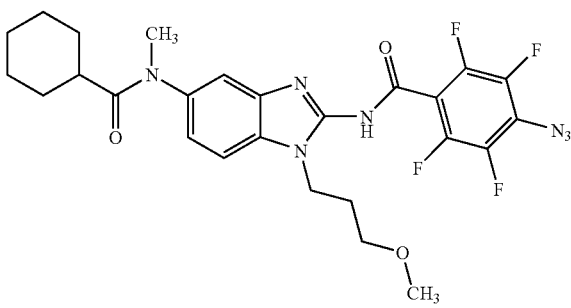

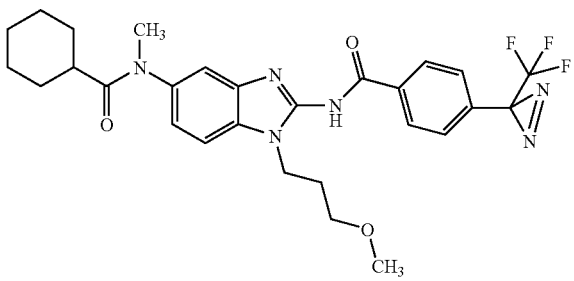

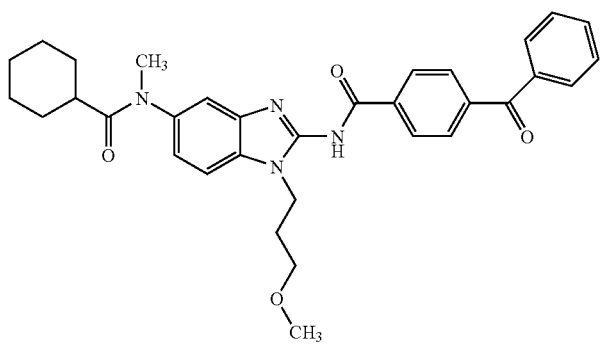

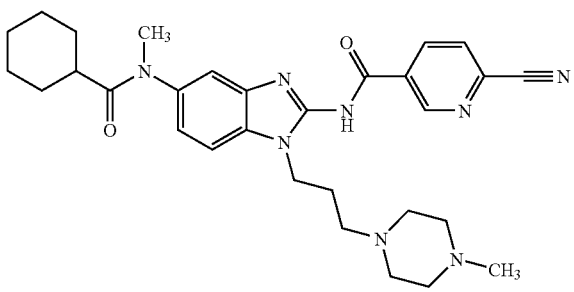

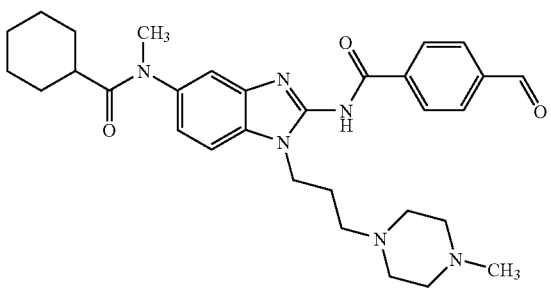

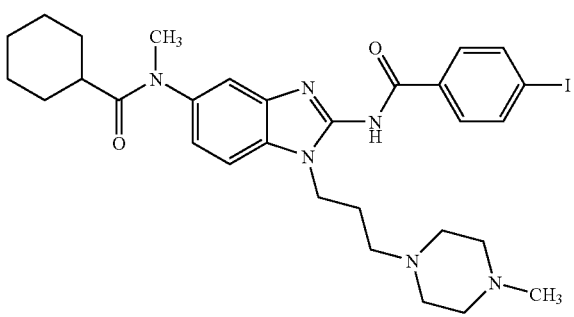

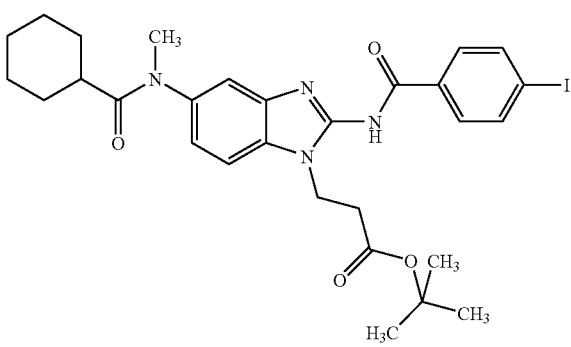

-continued
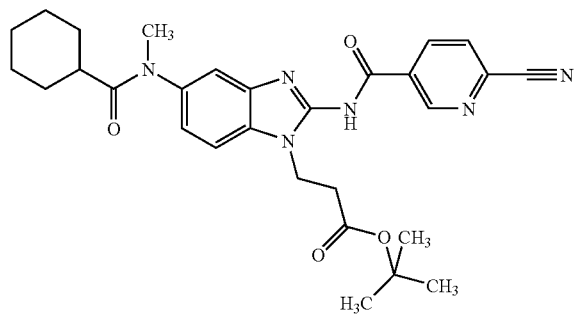
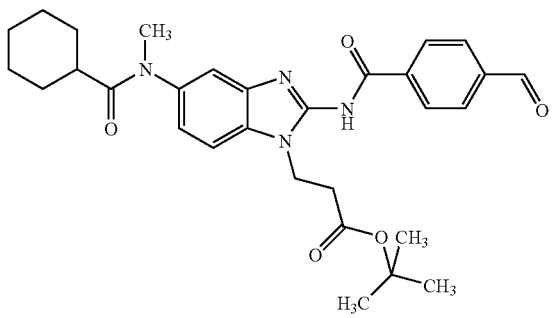
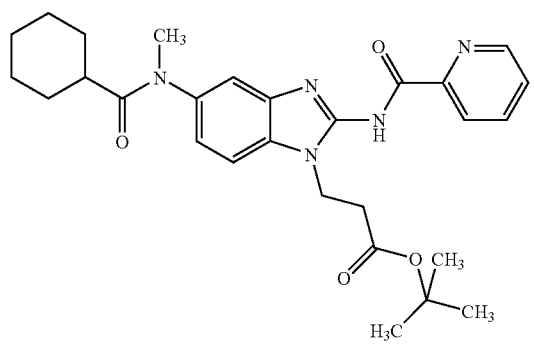
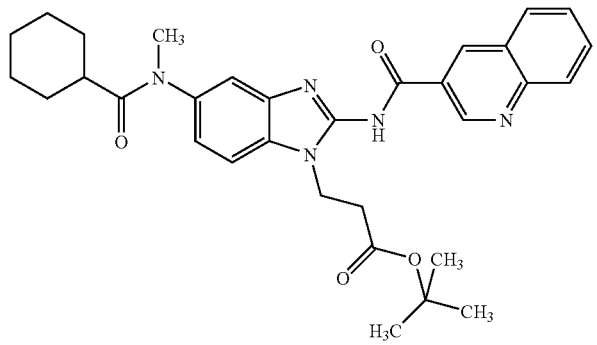
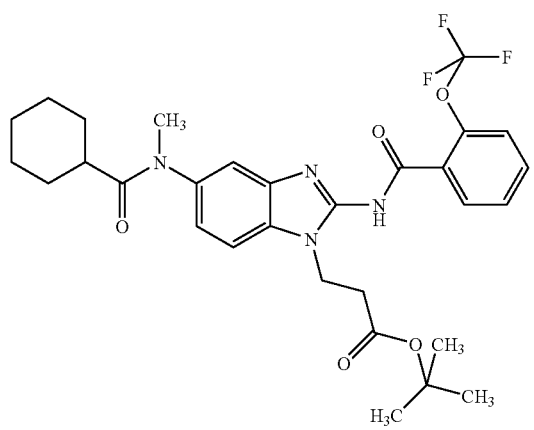
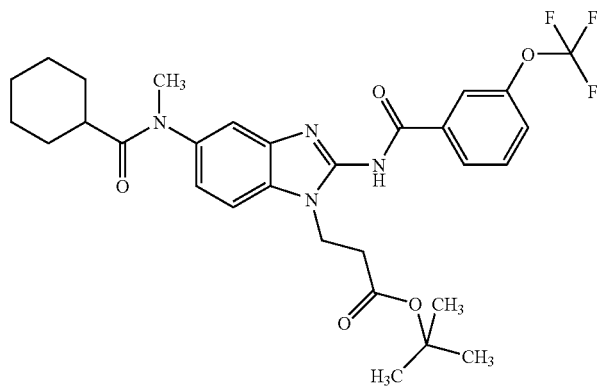
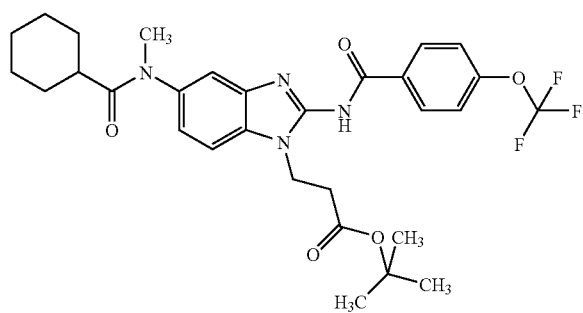
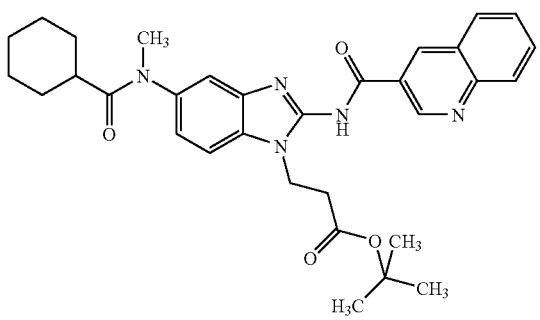

-continued
| 11 | 12 |
|---|---|
| 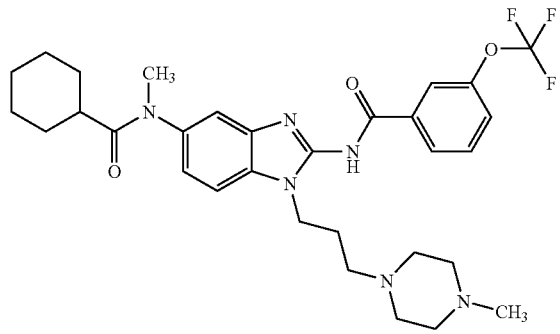 | 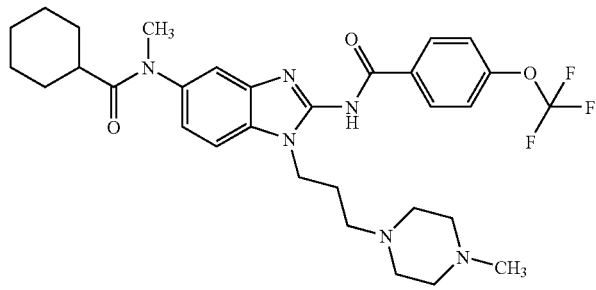 |
| 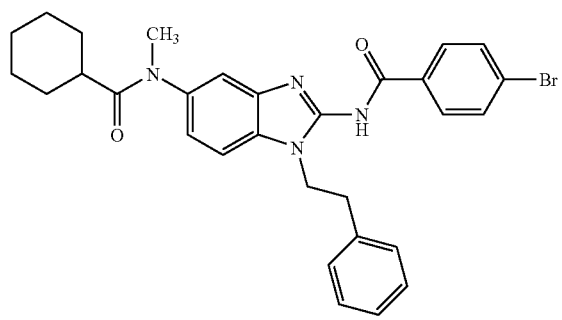 | 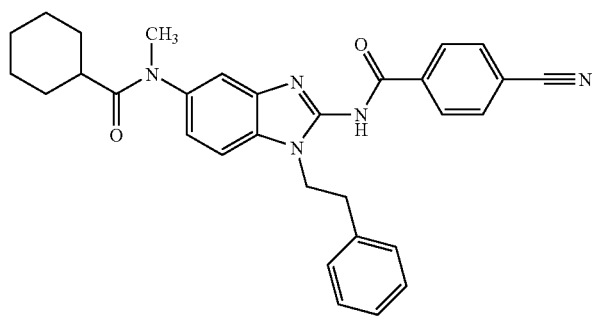 |
| 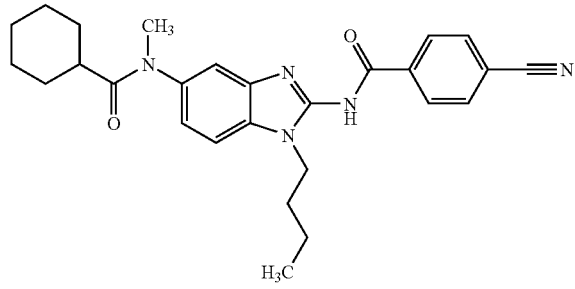 | 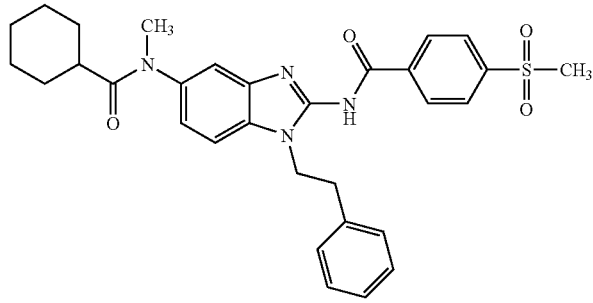 |
| 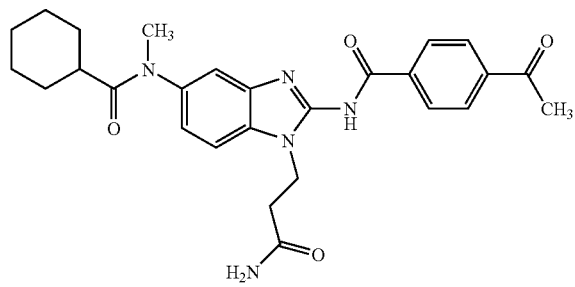 | 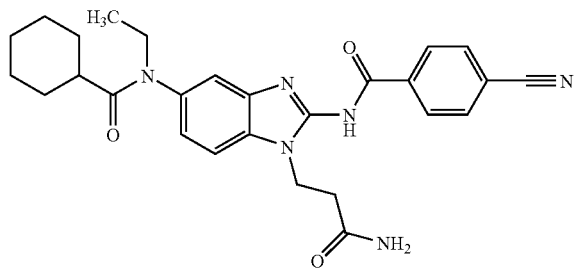 |
| 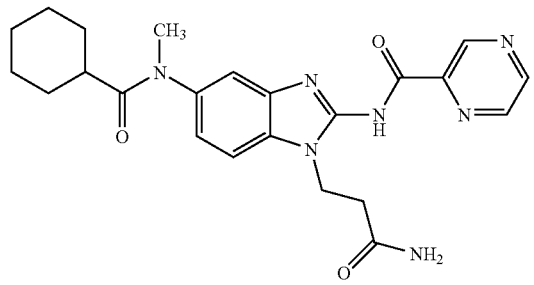 | 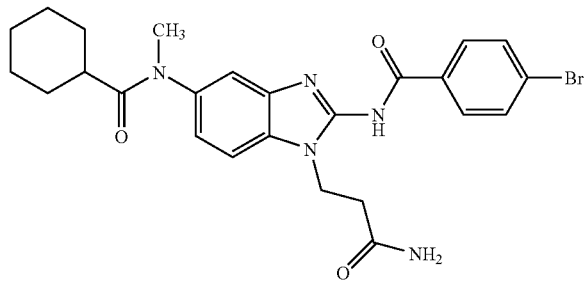 |

-continued
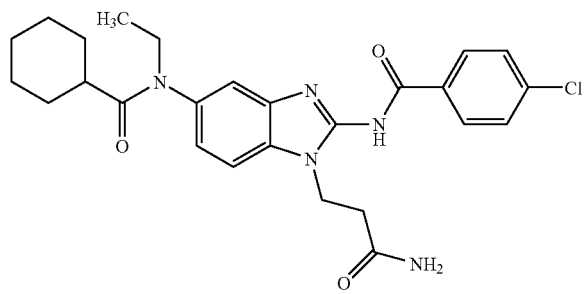
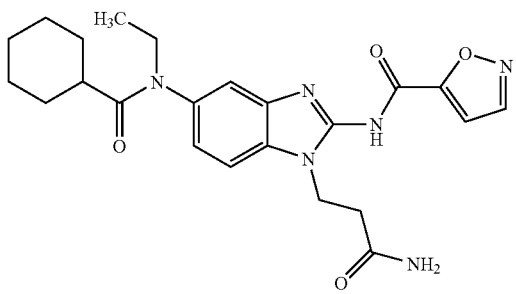
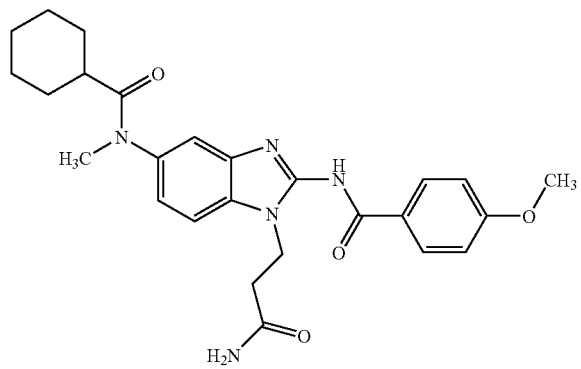
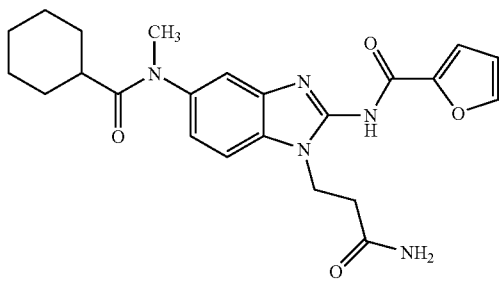
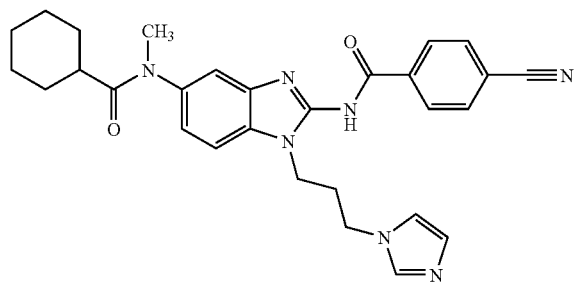
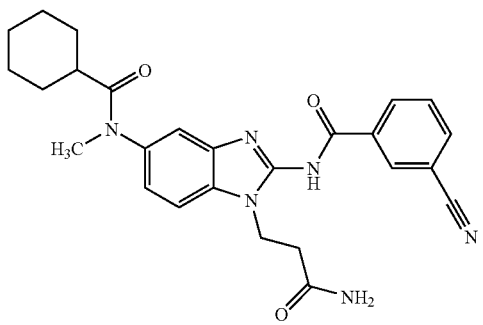
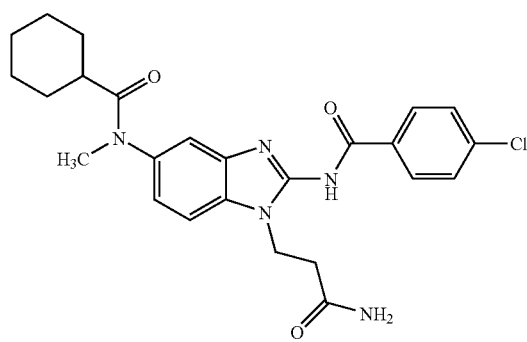
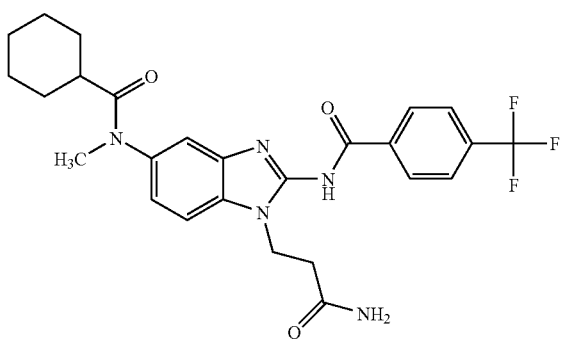

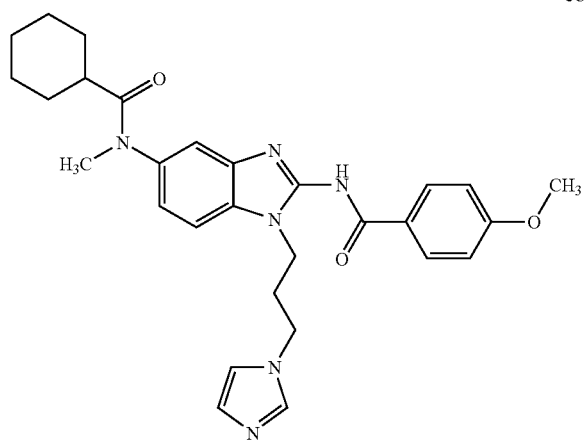
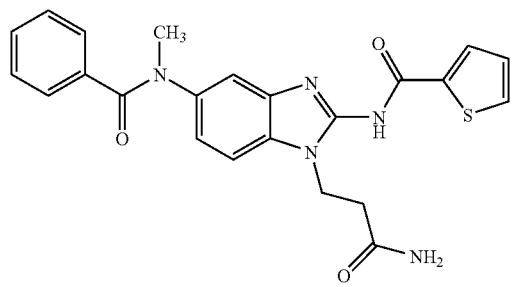
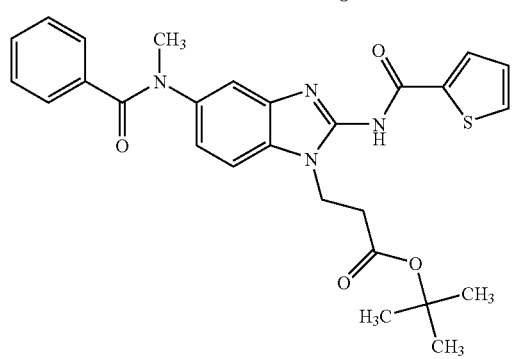
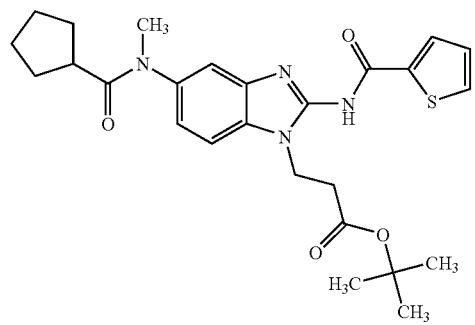
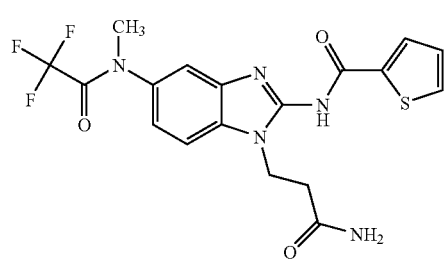
-continued
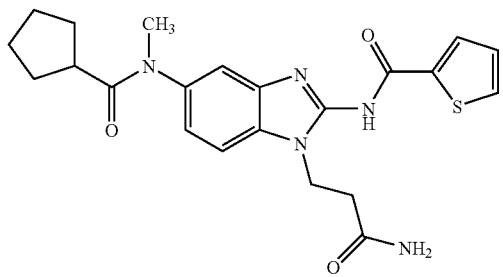
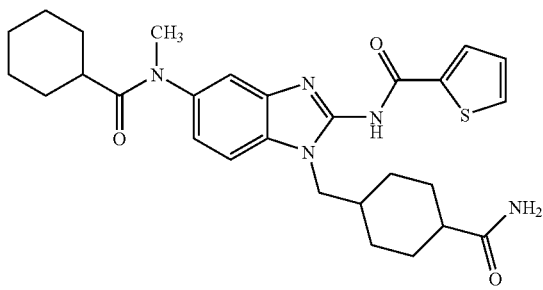
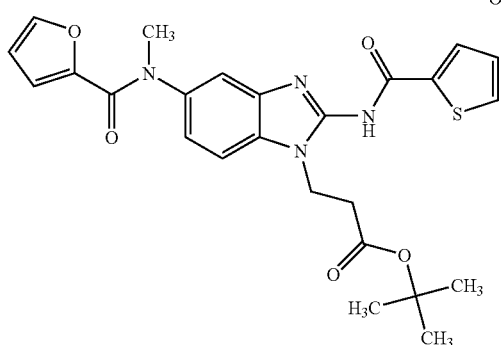
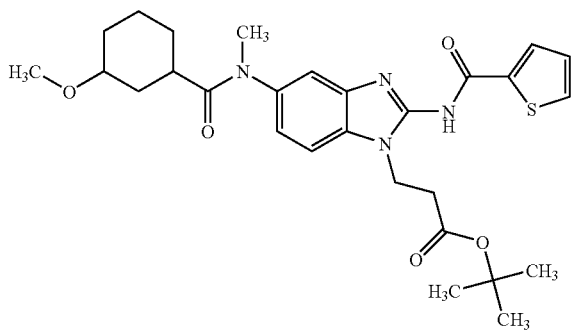
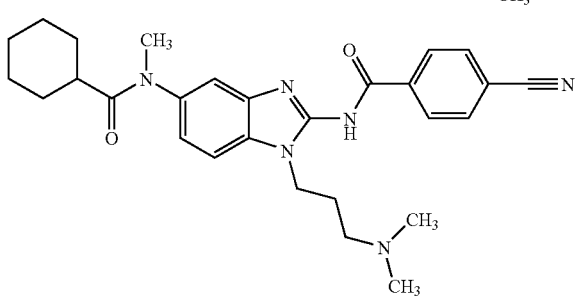

-continued
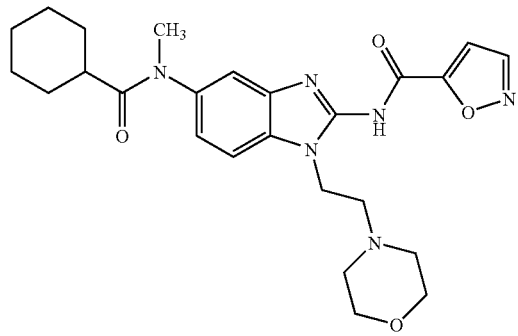
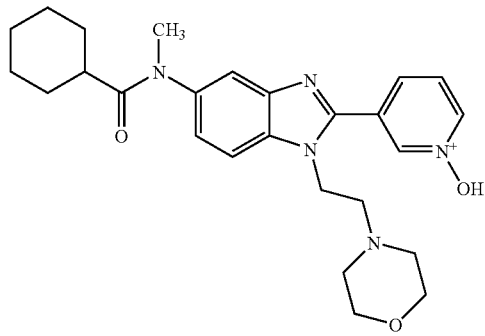
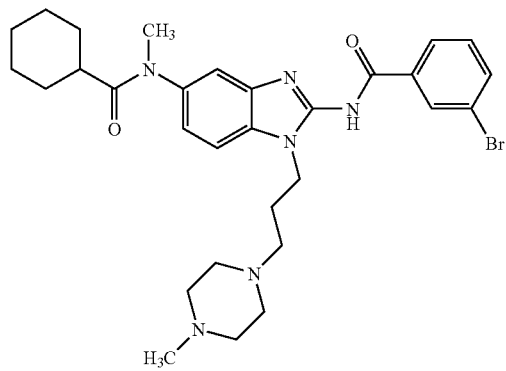
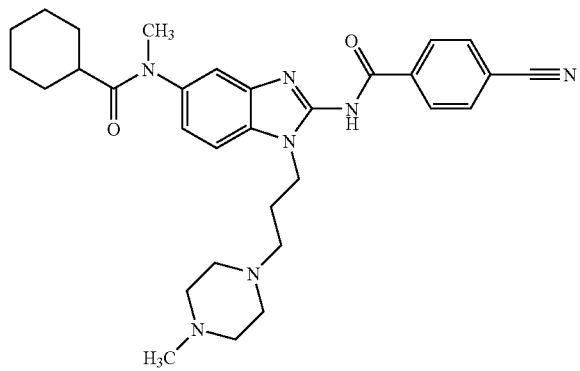
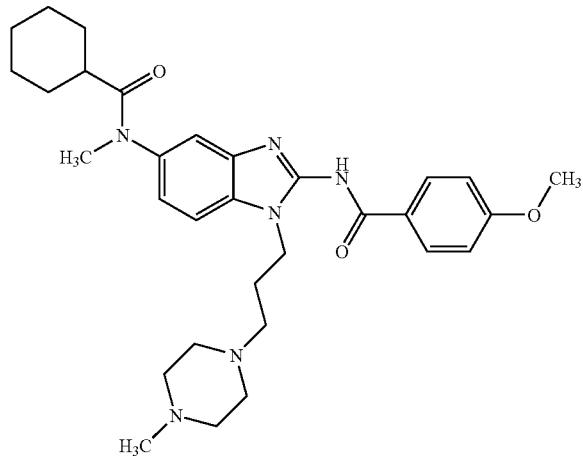
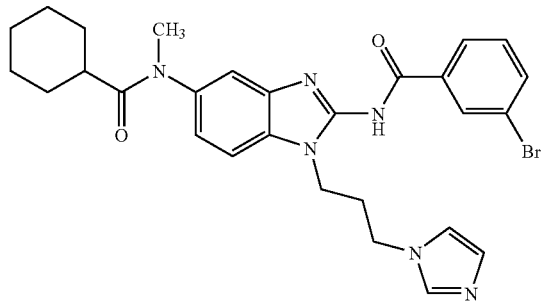
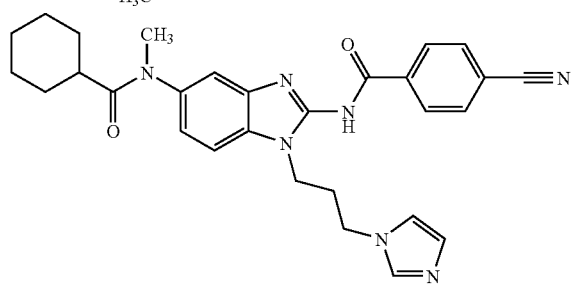
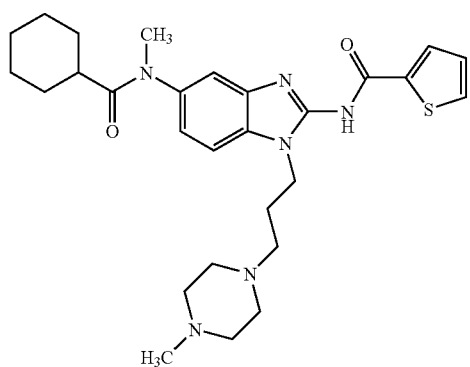

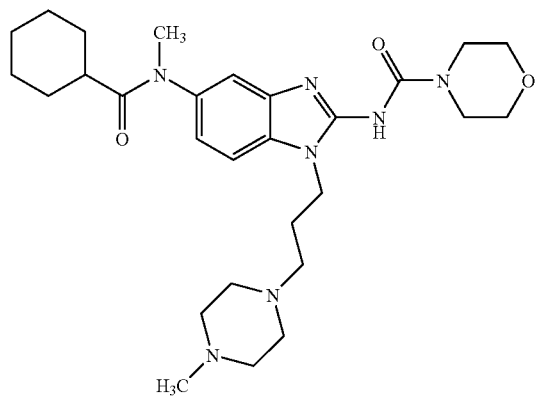
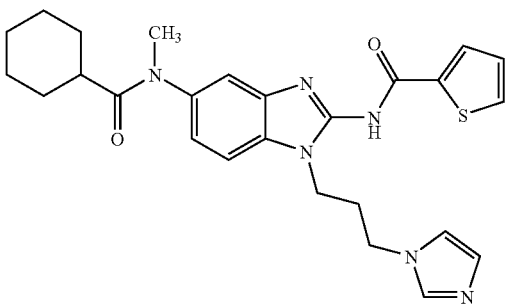
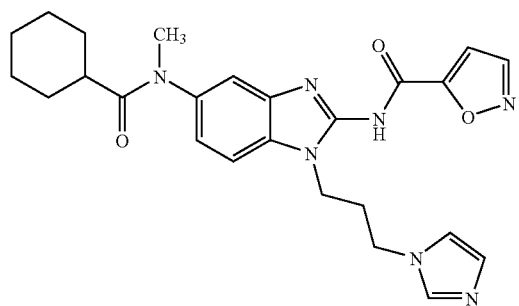
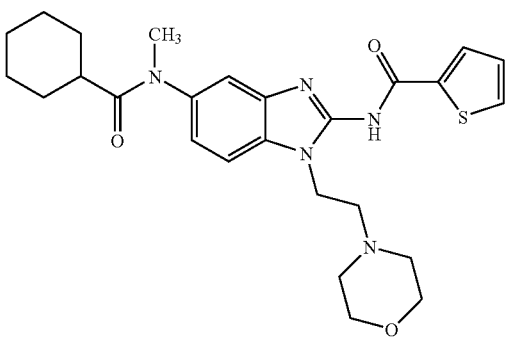
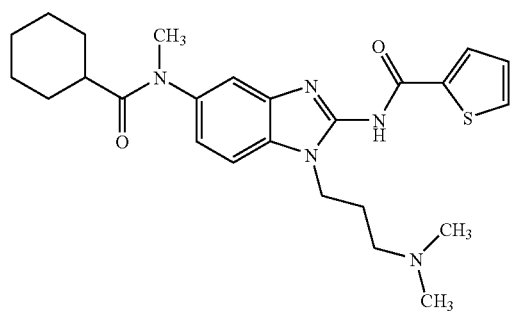
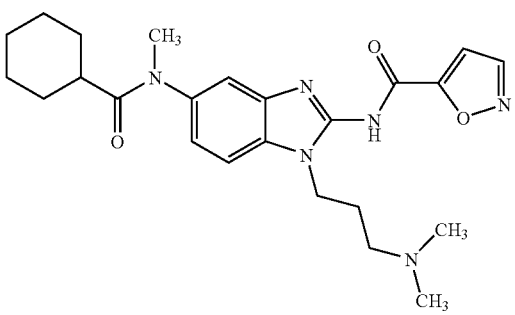
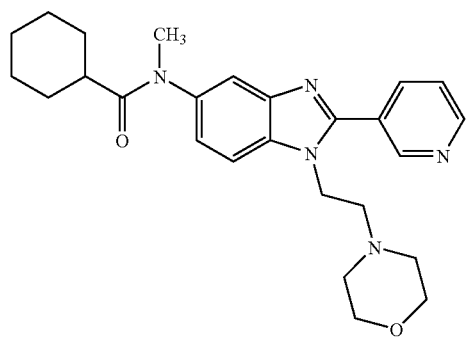
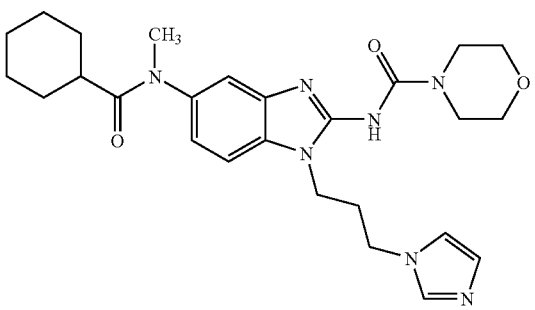
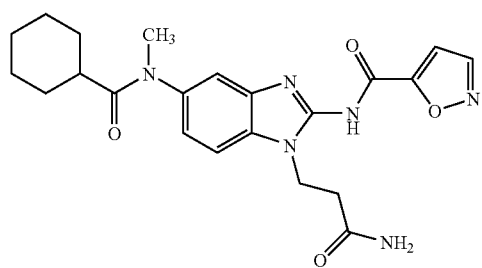
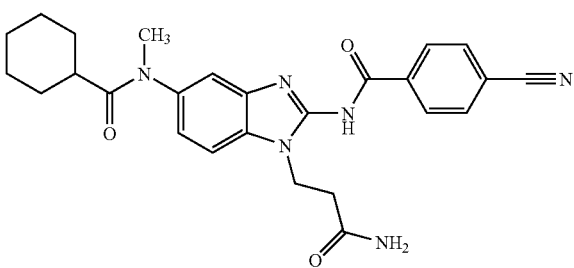

-continued
| 21 | 22 |
|---|---|
| 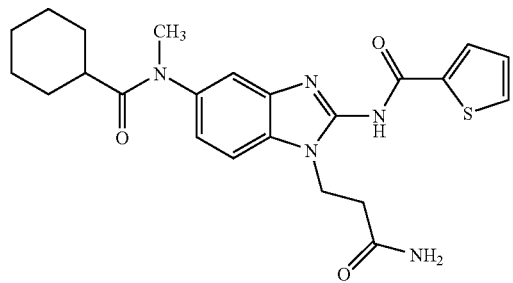 | 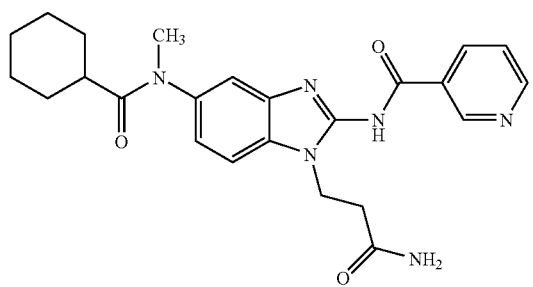 |
| 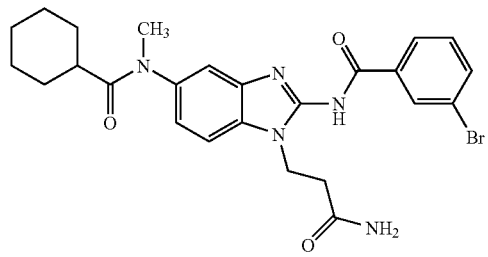 | 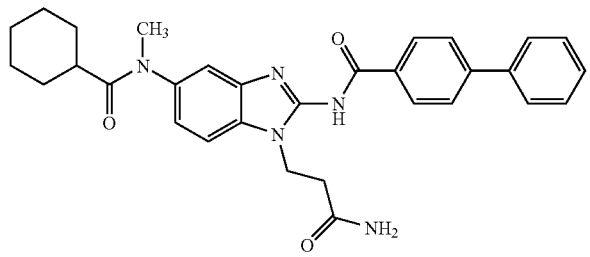 |
| 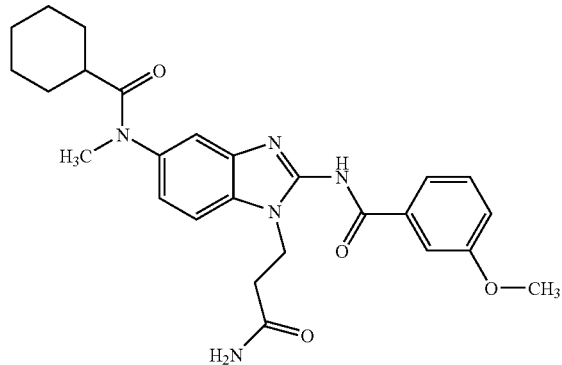 | 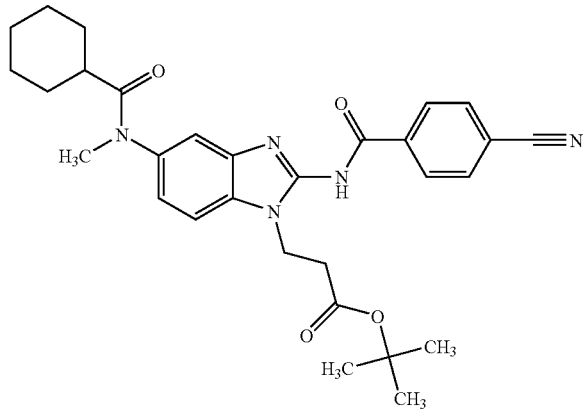 |
| 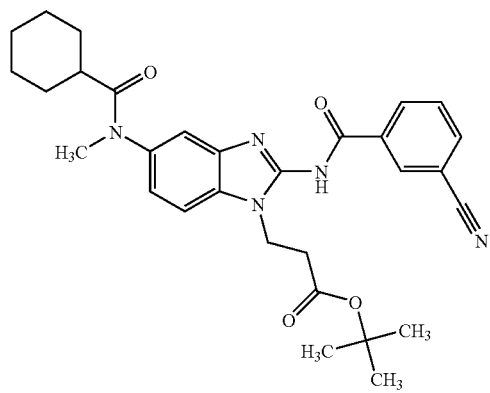 | 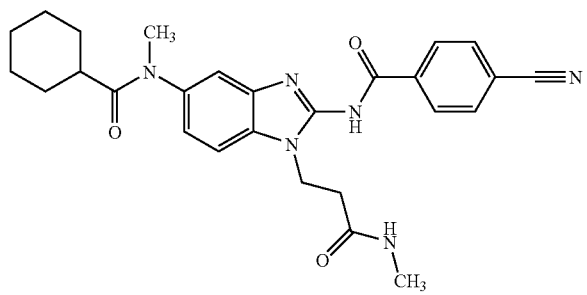 |
| 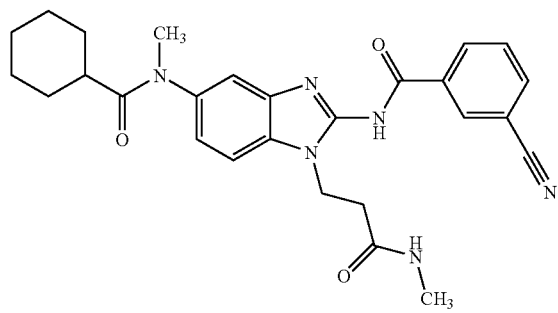 | 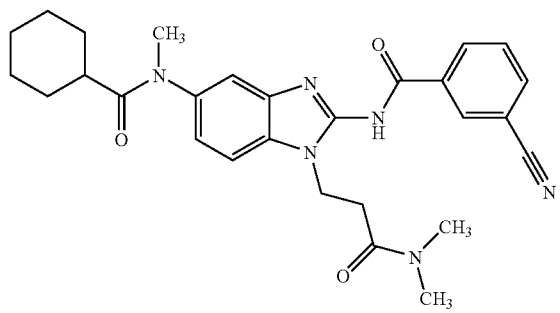 |

-continued
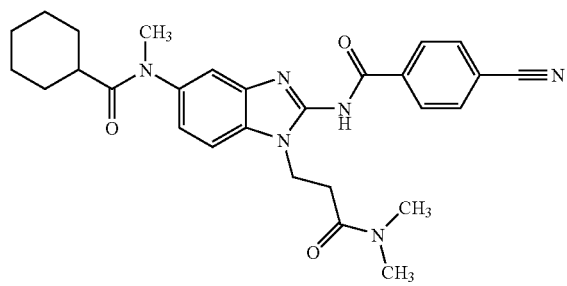
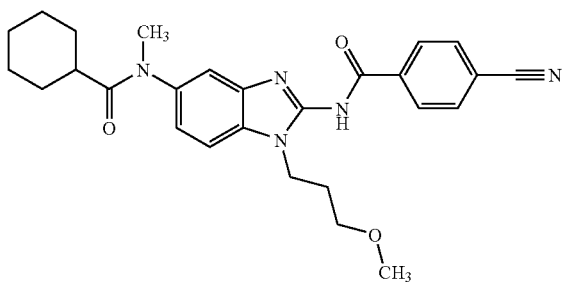
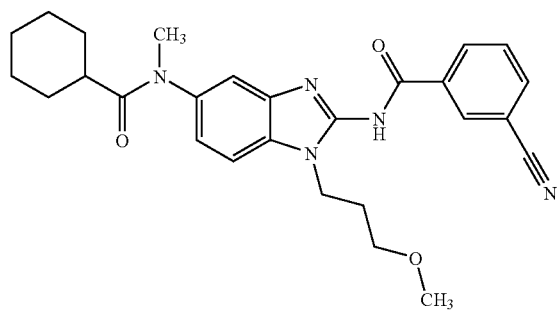
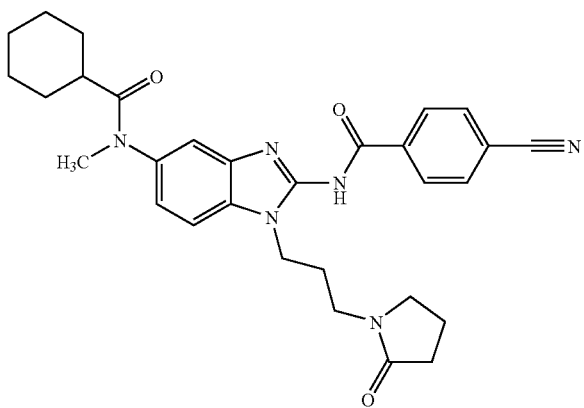
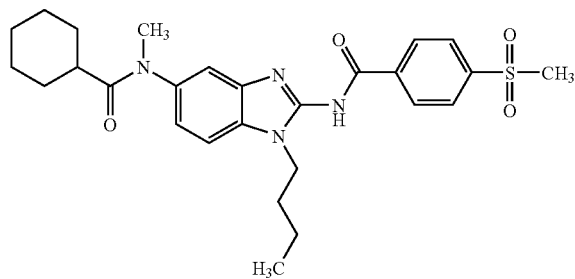
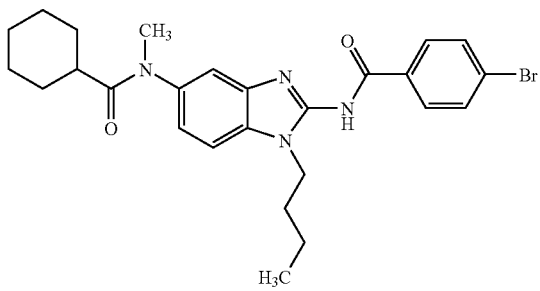
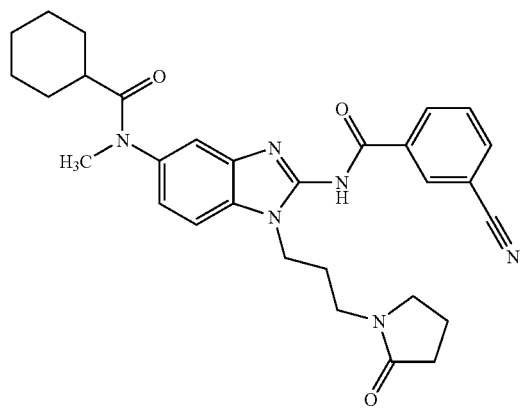
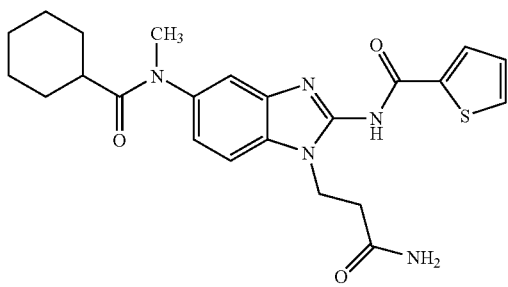

-continued
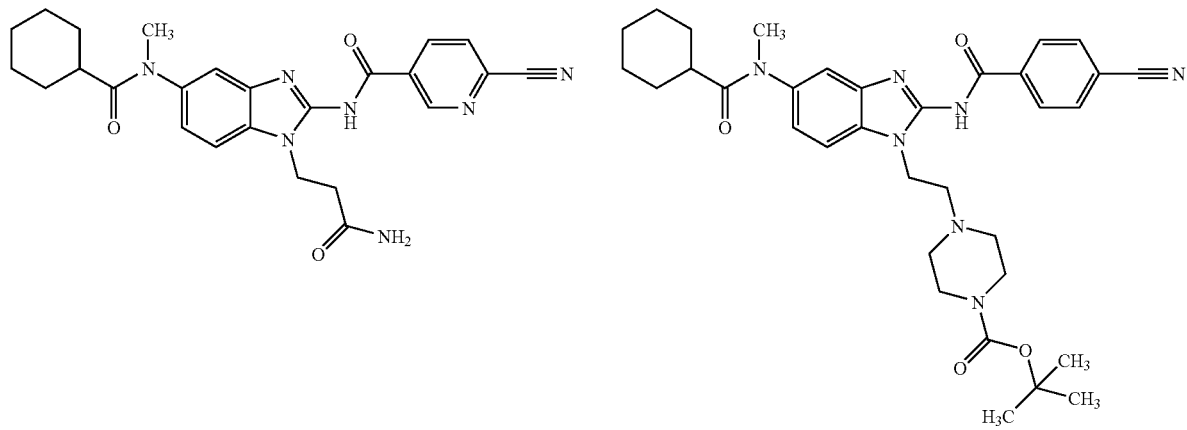
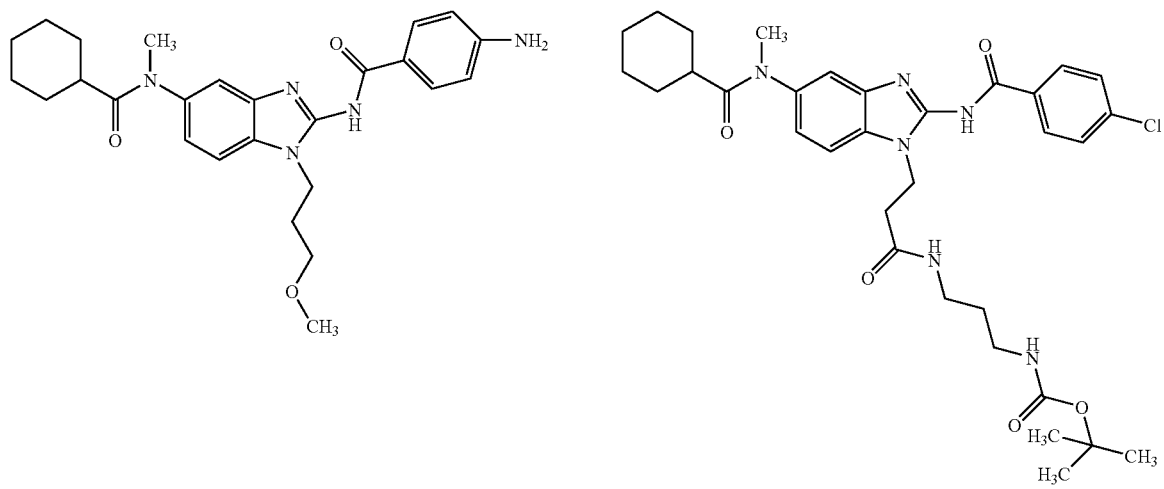
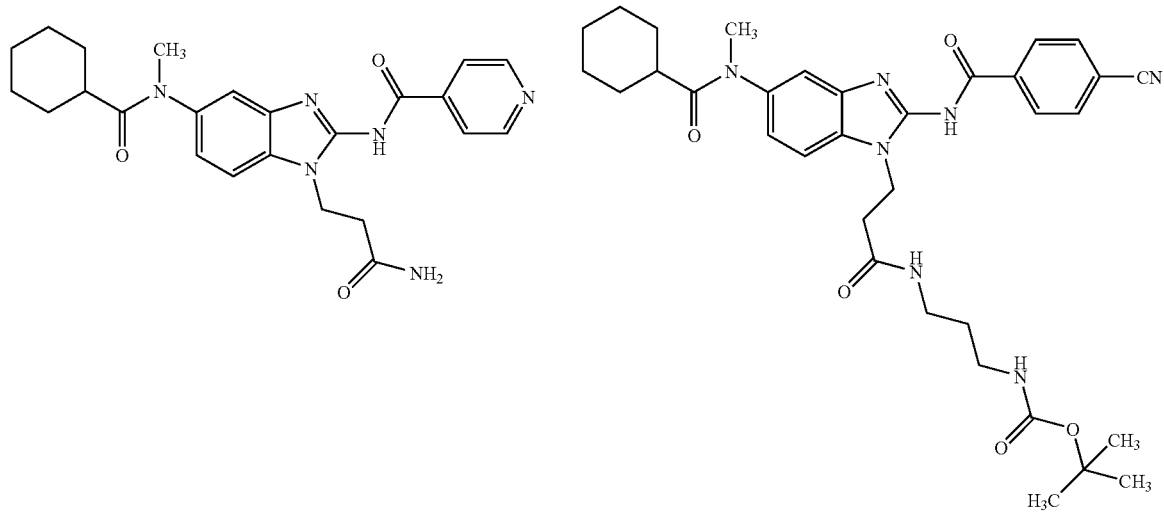

-continued
27
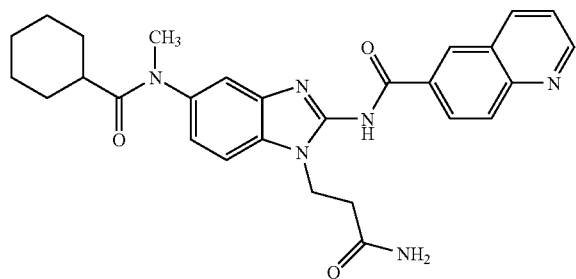
28
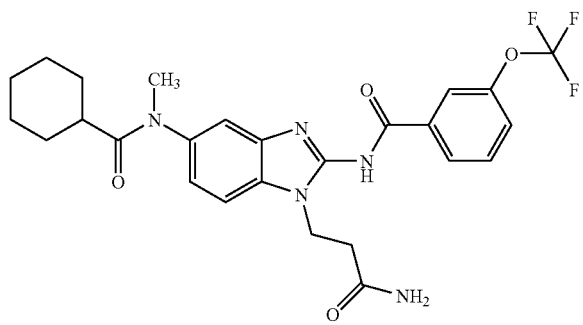
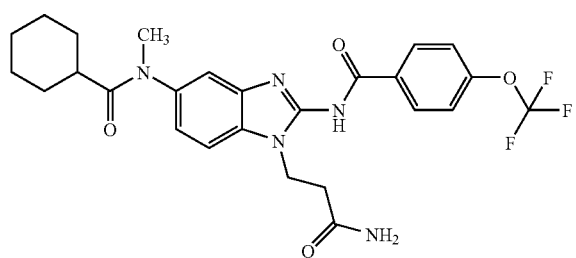
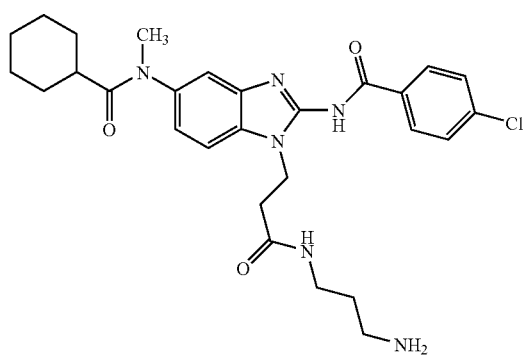
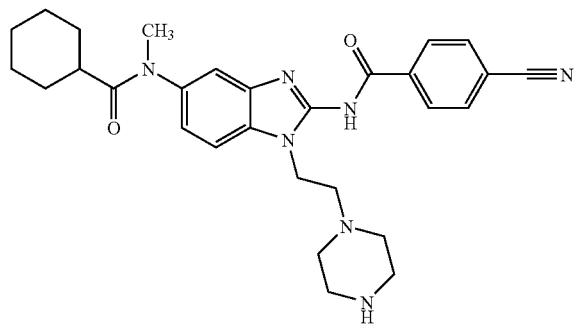
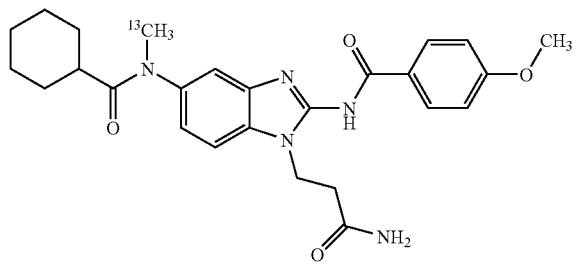
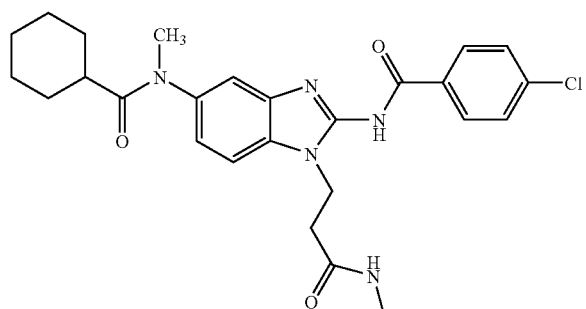
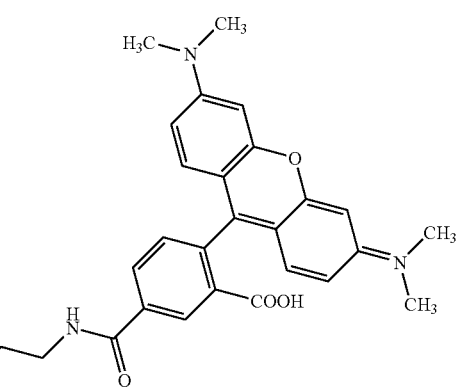

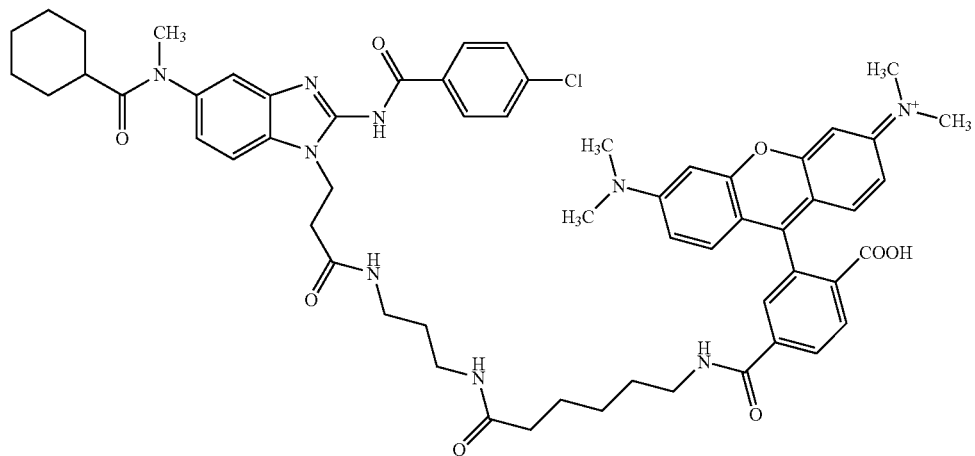
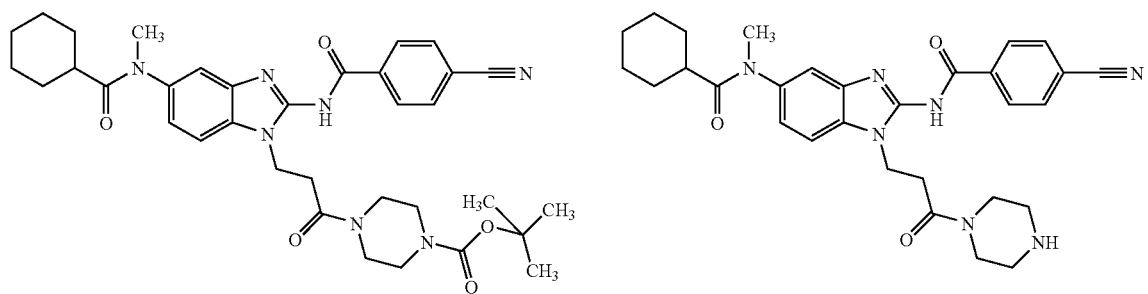
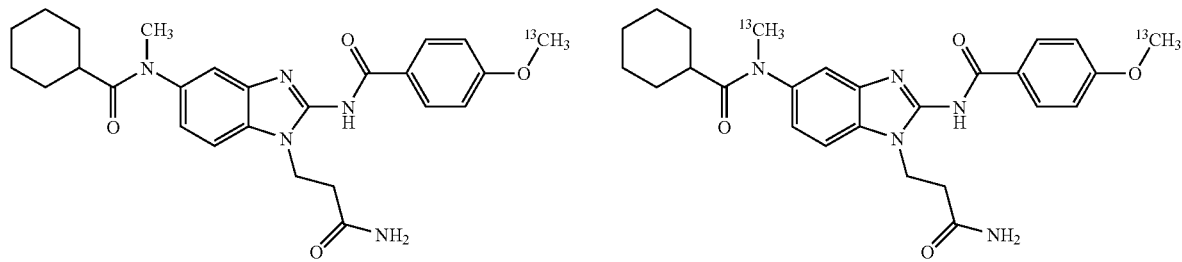
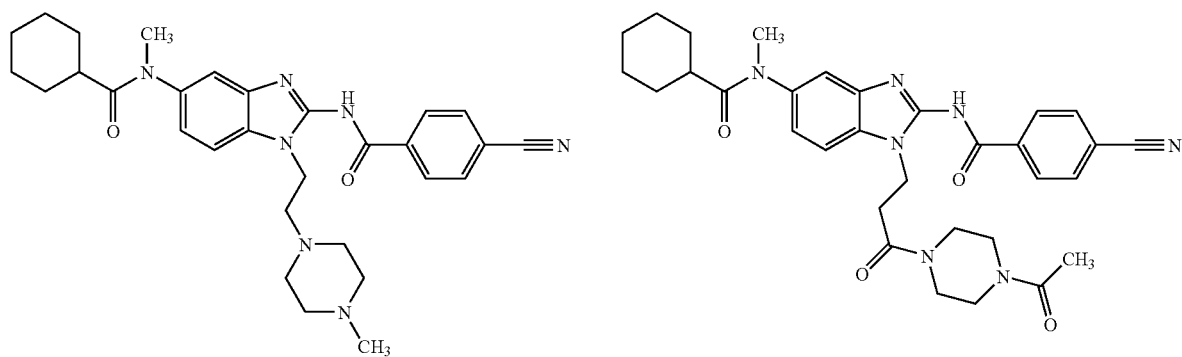

-continued
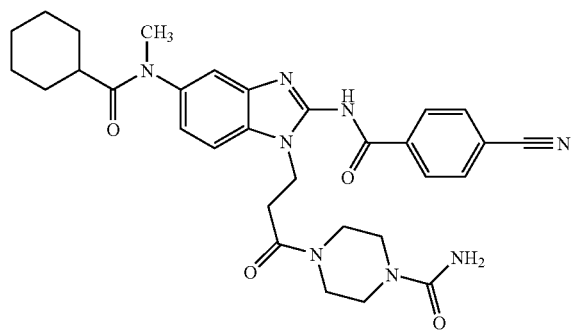
31
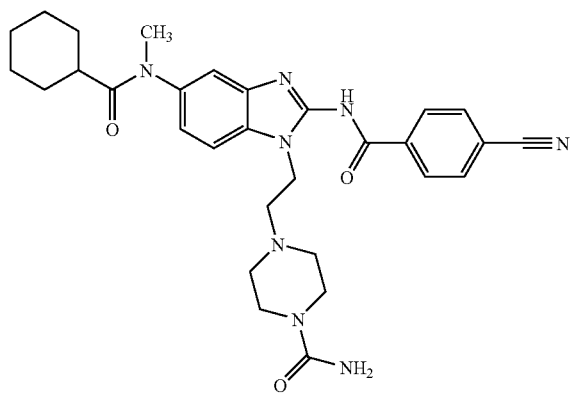
32
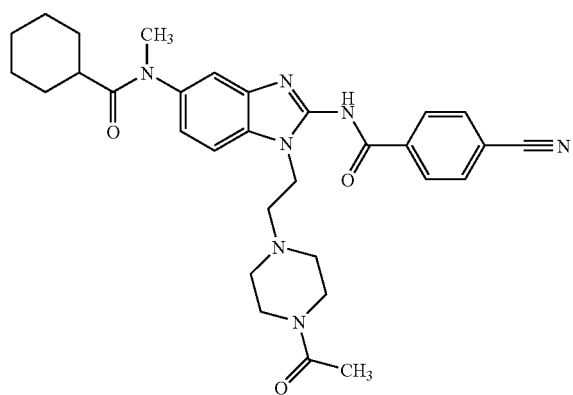
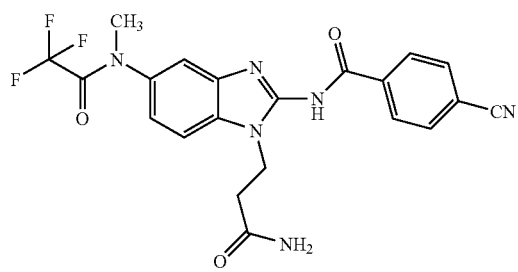
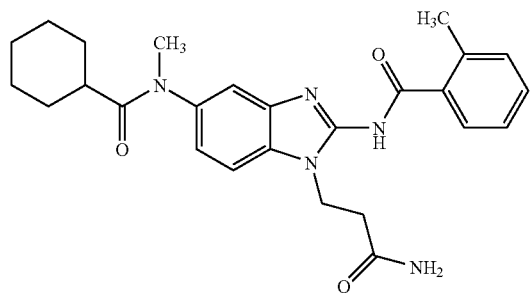
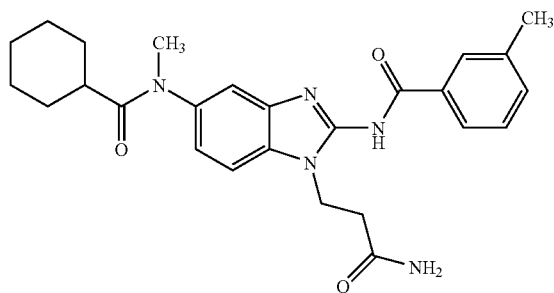
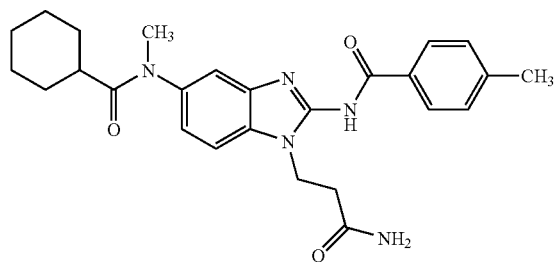
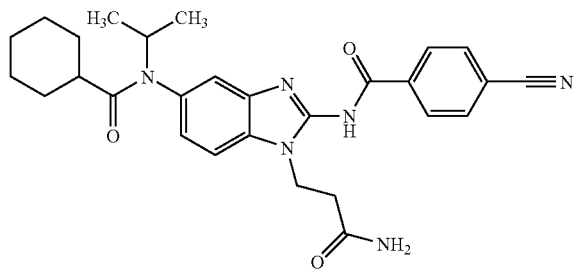

-continued
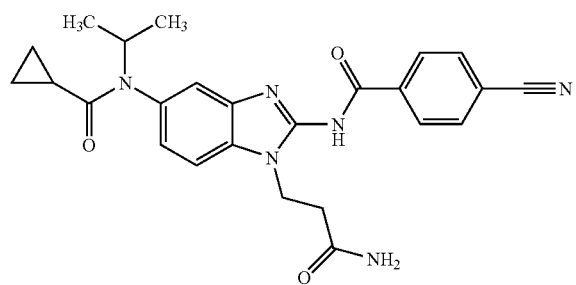
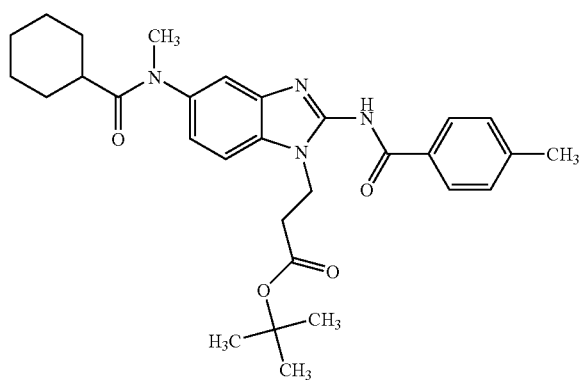
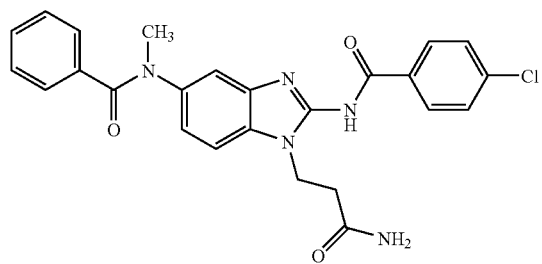
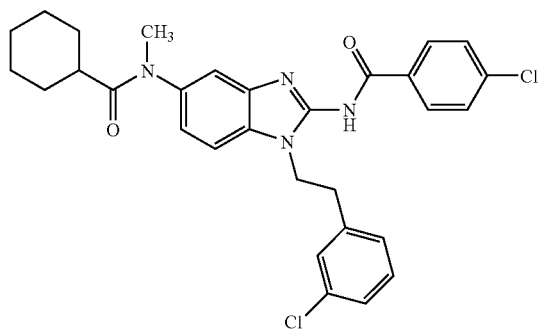
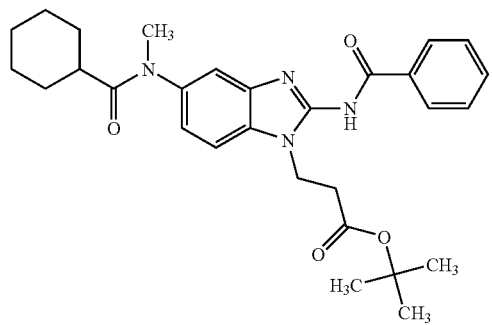
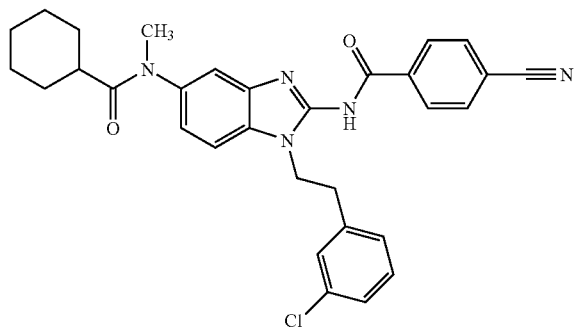
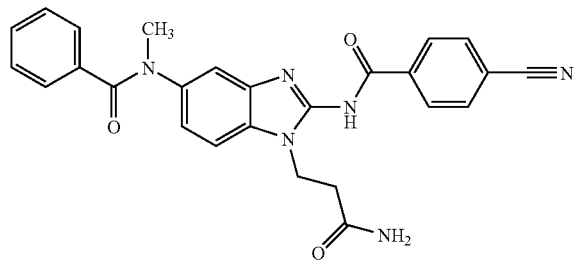
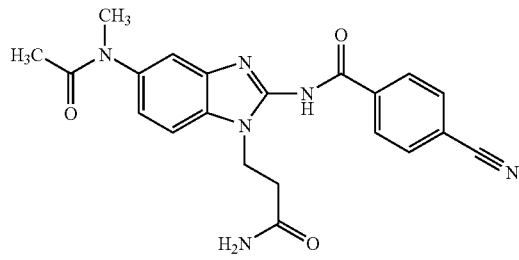
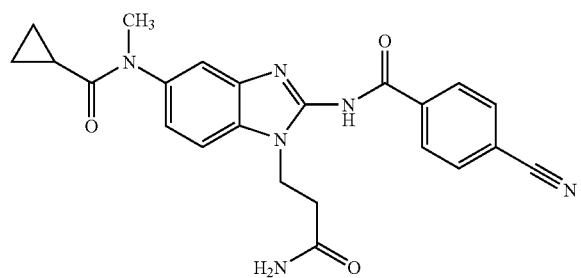
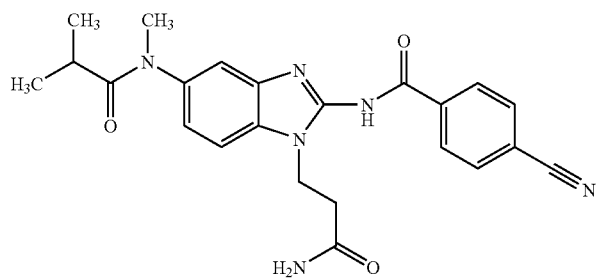

35
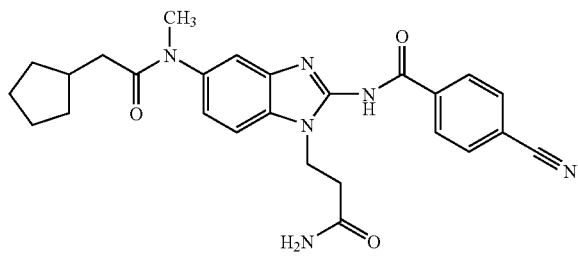
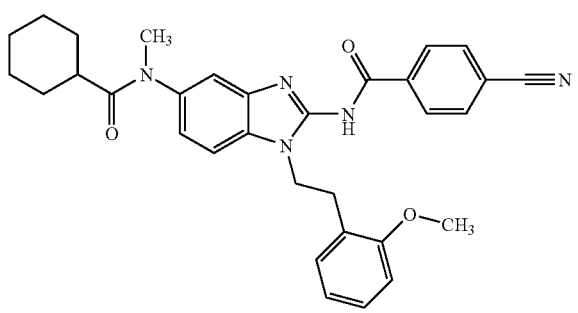
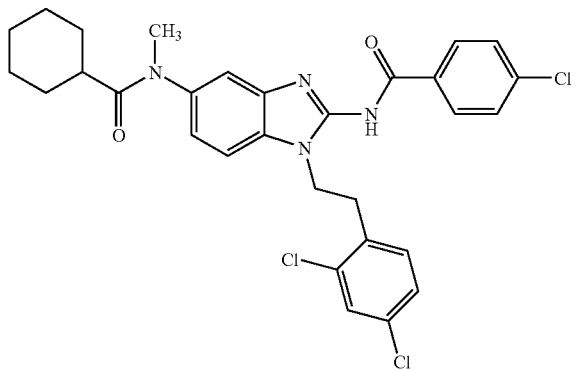
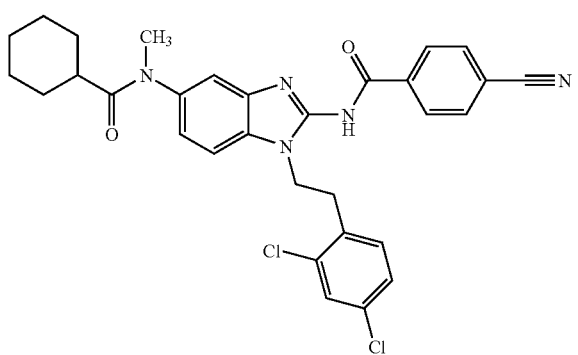
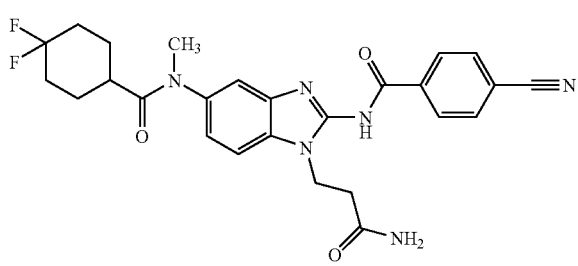
36
-continued
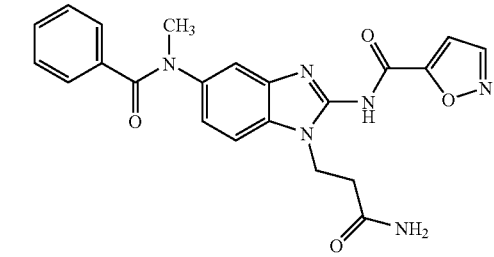
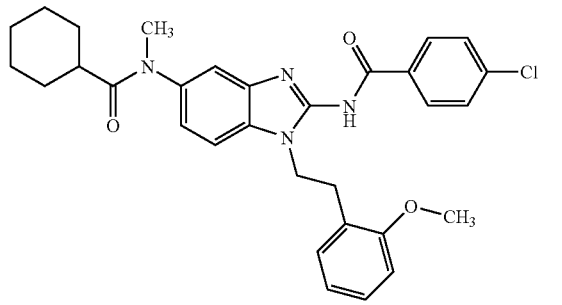
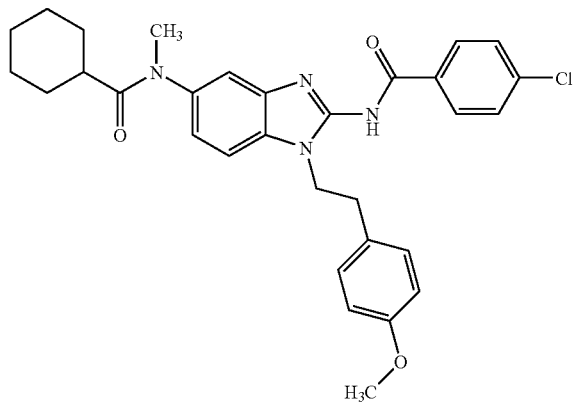
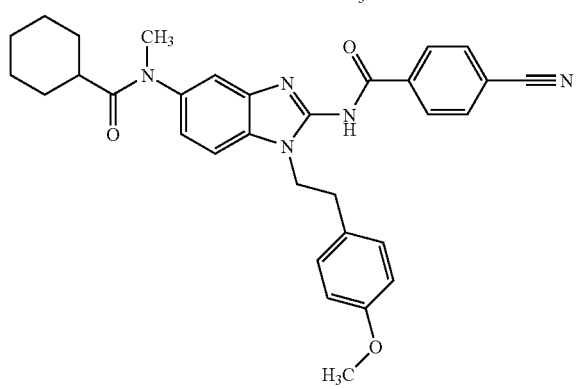
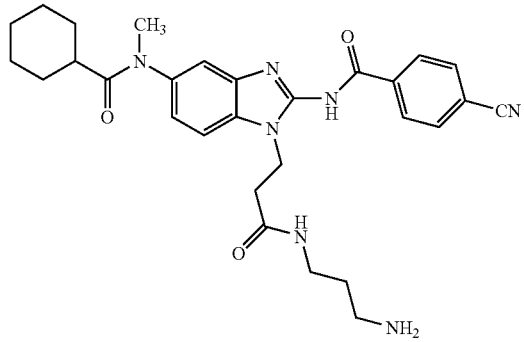

-continued
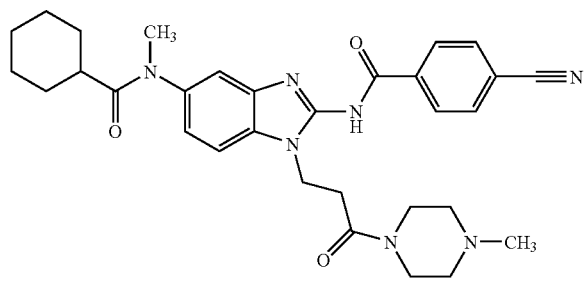
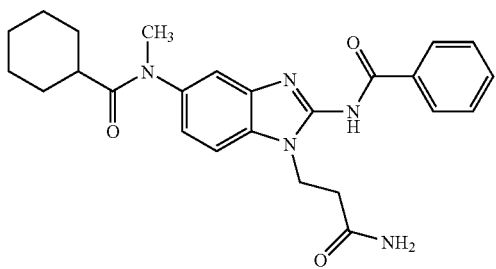
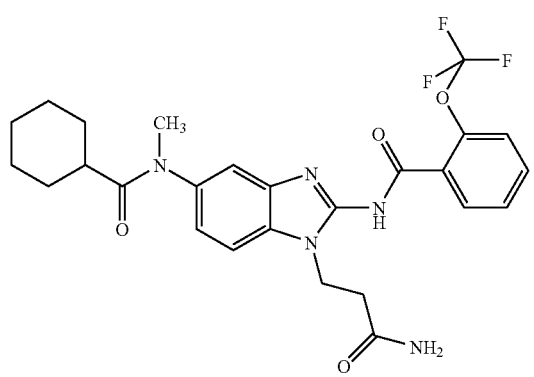
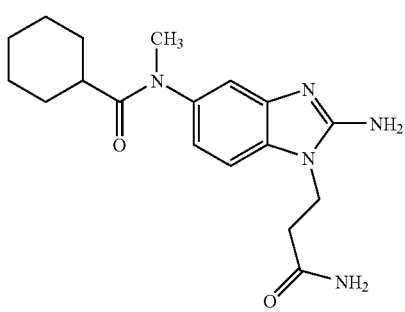
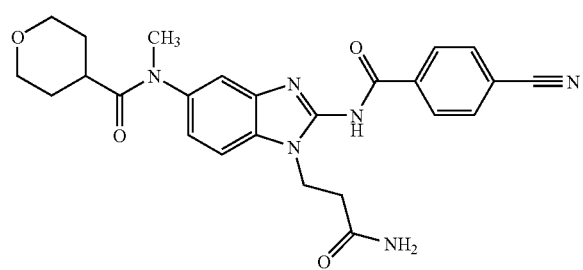
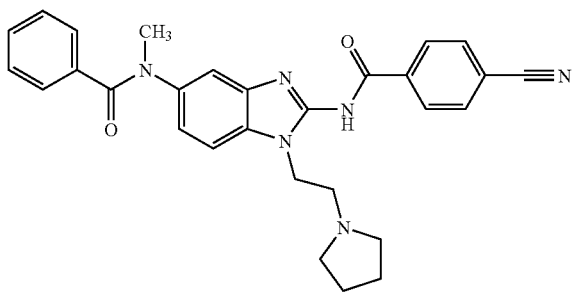
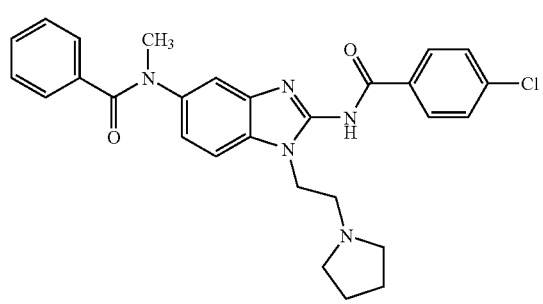
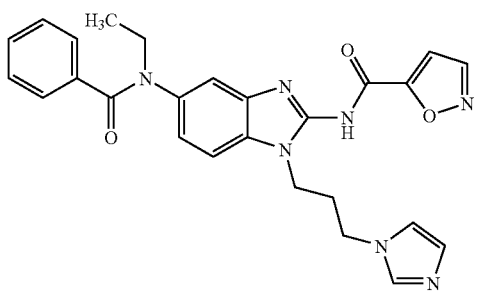
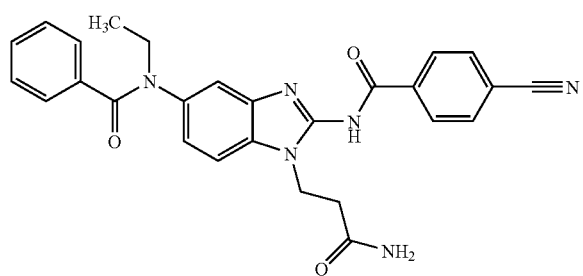
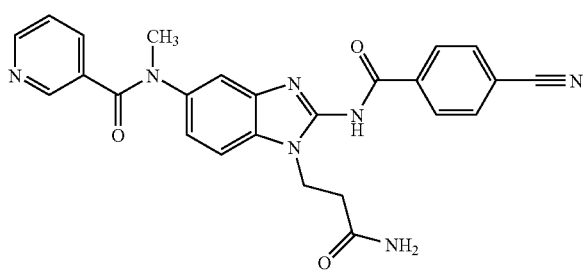

-continued
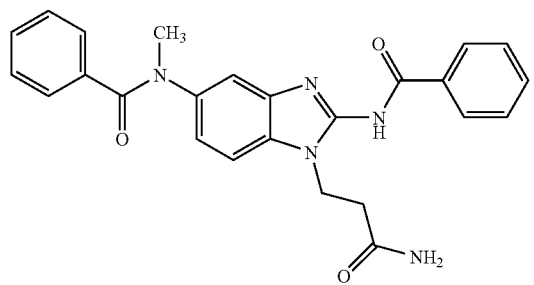
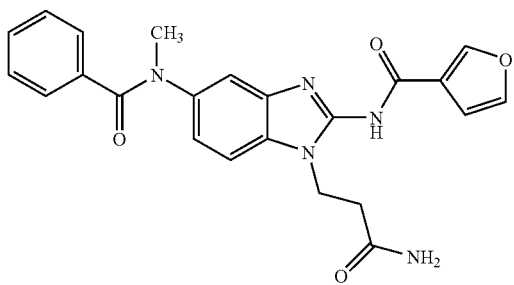
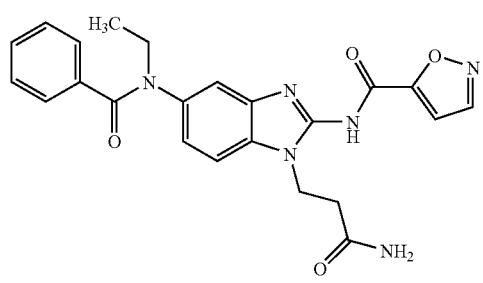
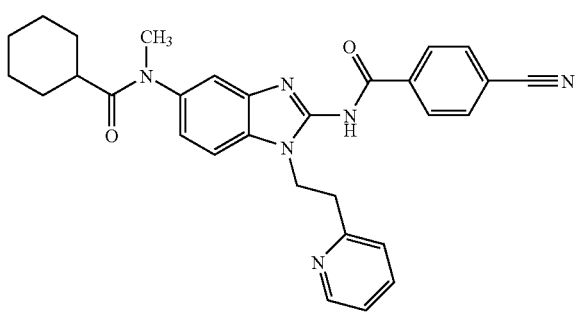
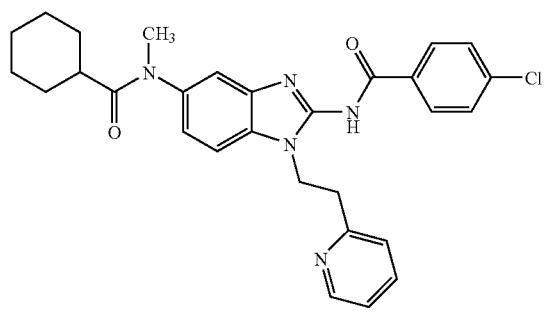
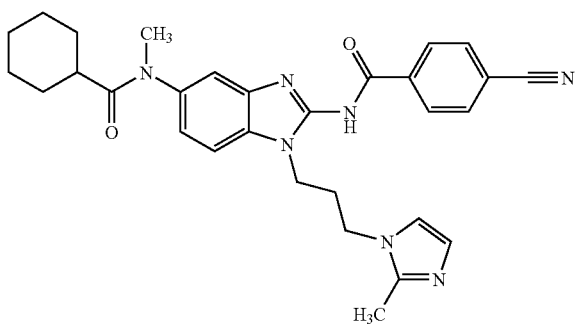
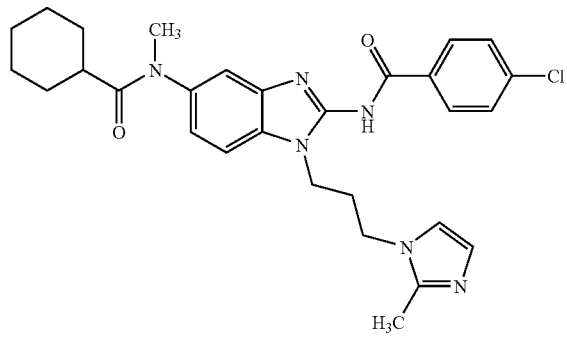
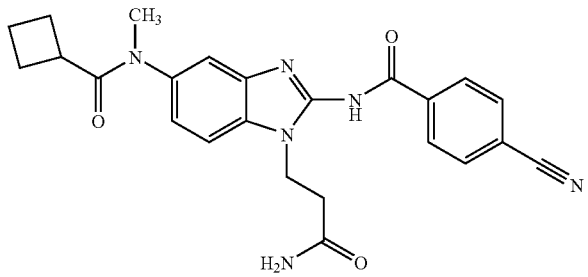
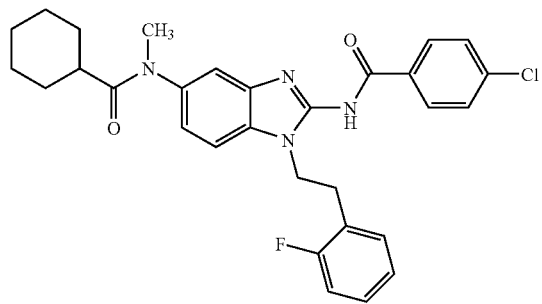
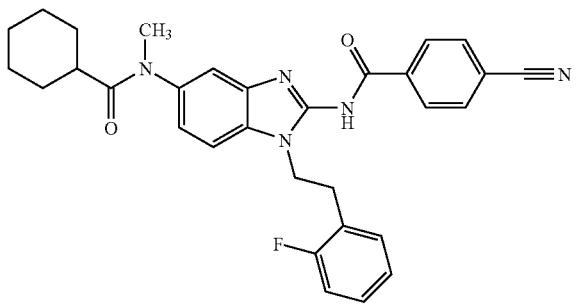

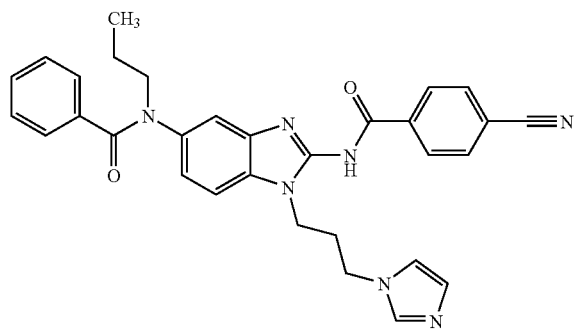
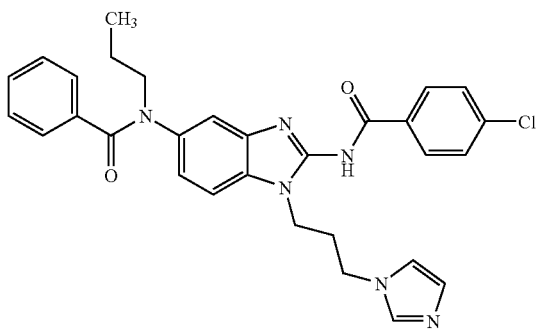
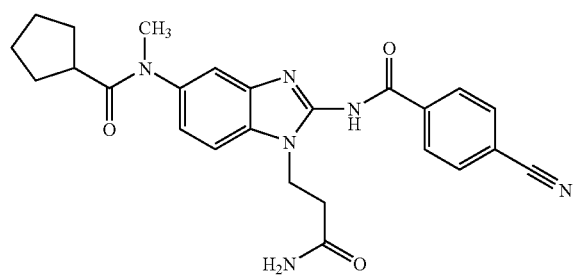
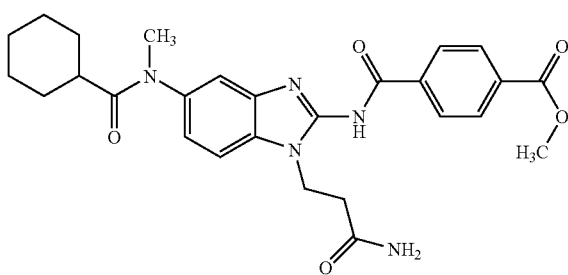
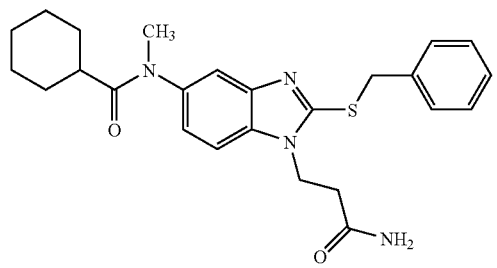
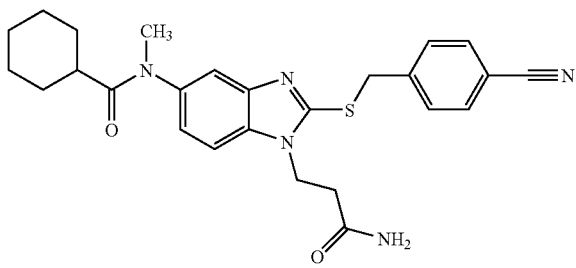
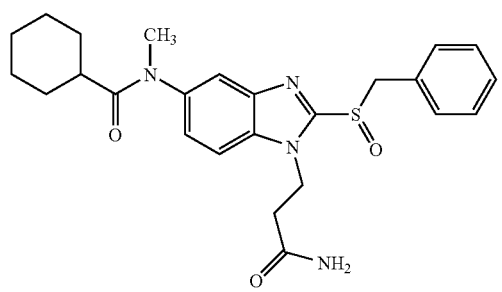
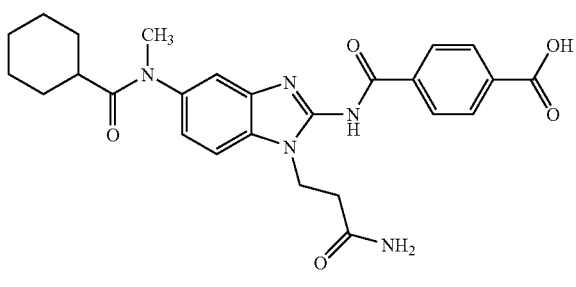
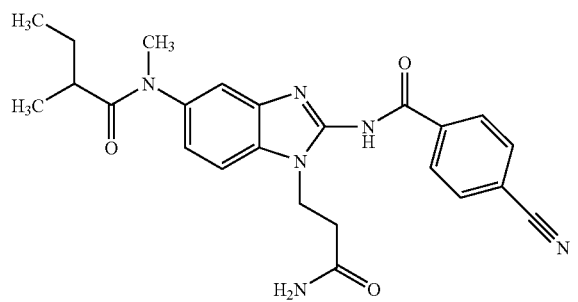
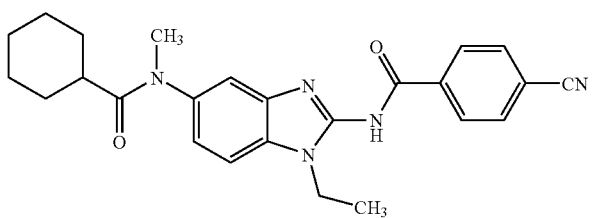

-continued
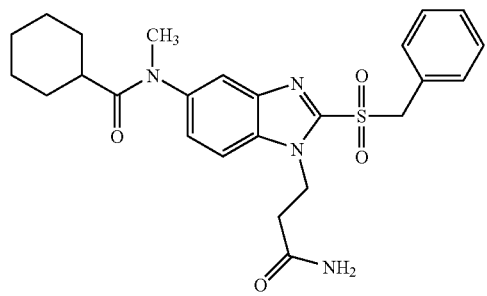
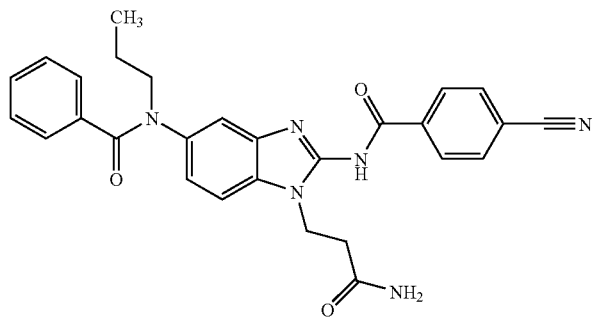
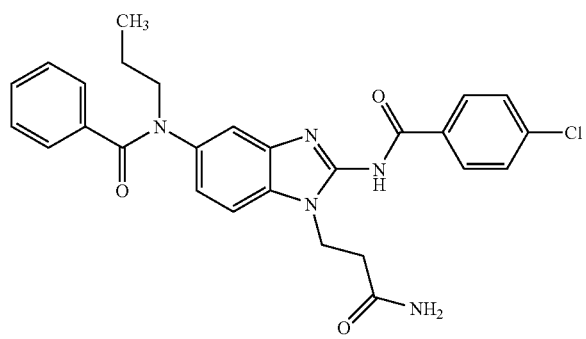
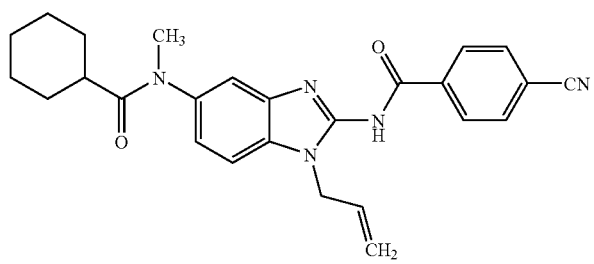
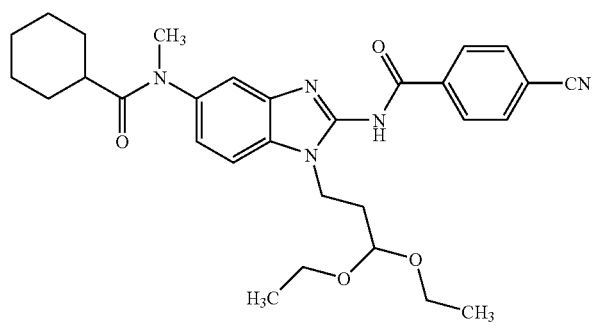
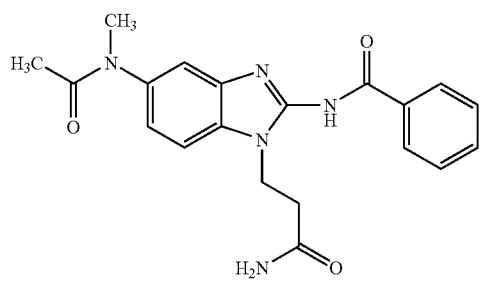
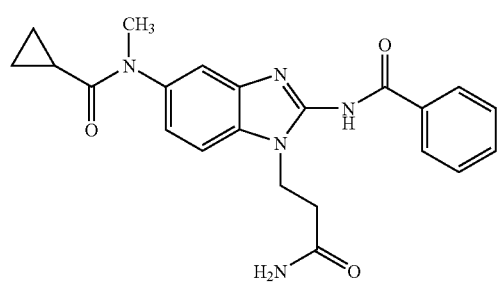
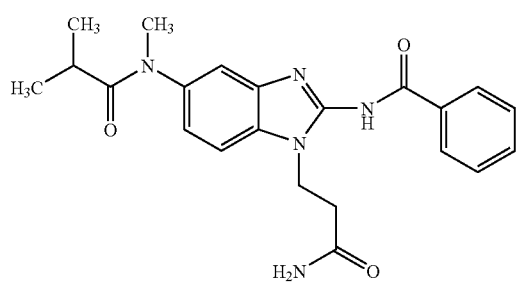
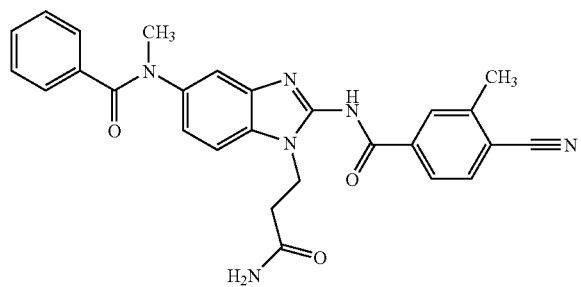
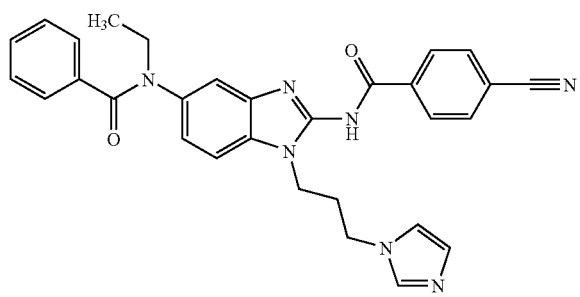

-continued
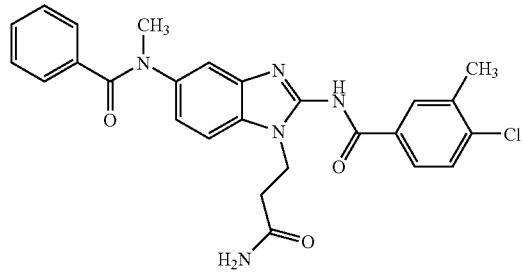
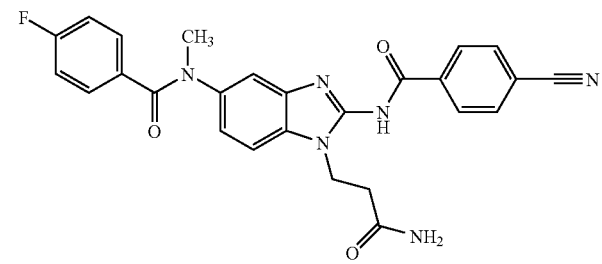
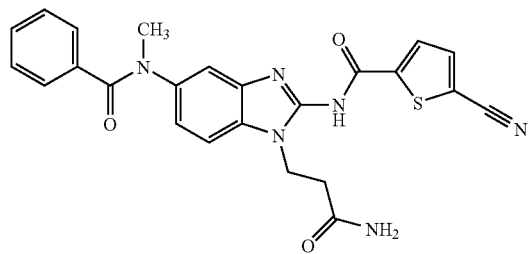
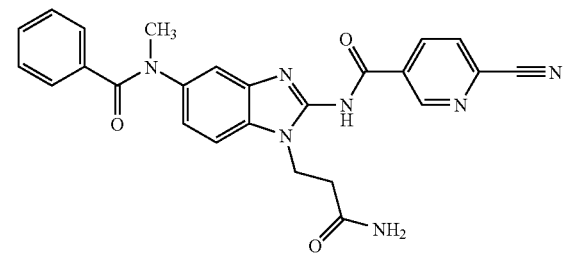
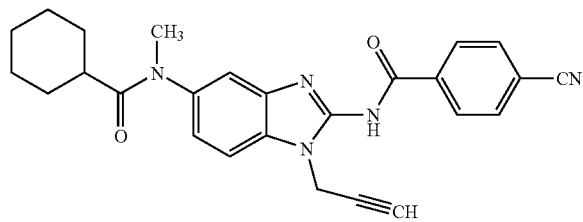
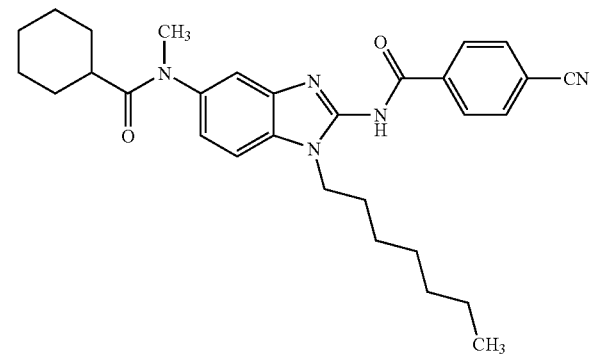
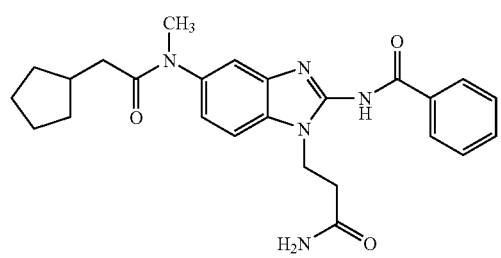
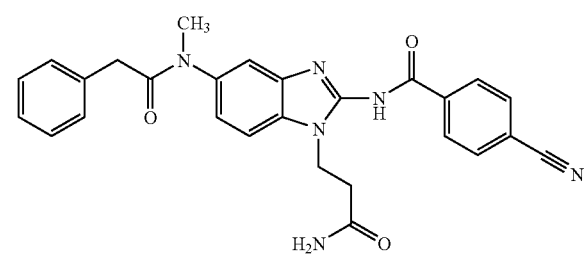
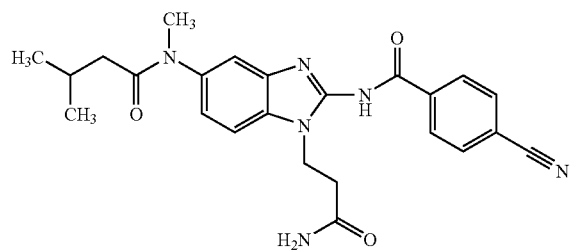
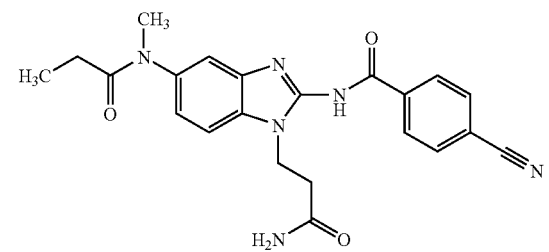
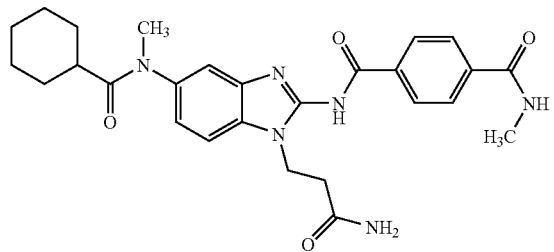
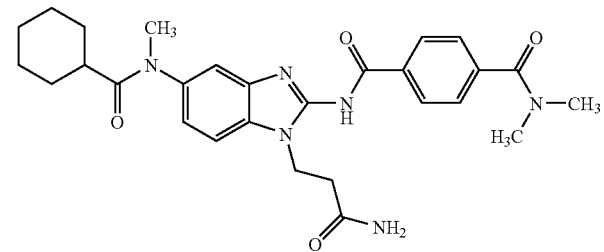

-continued
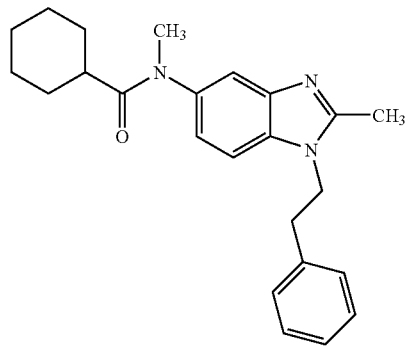
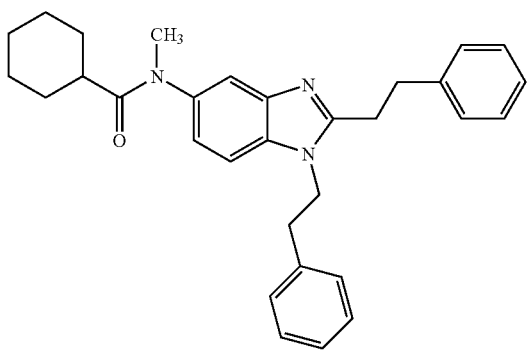
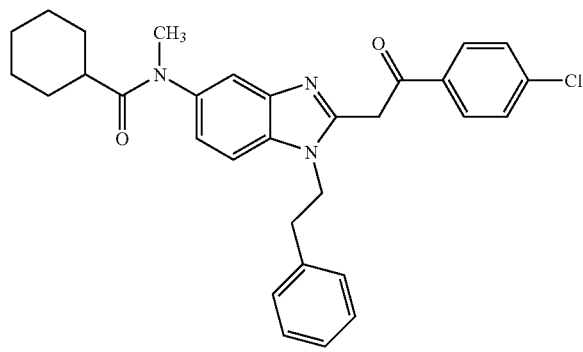
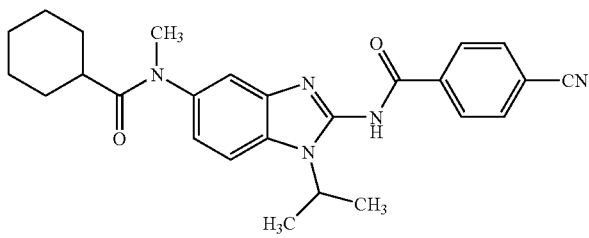
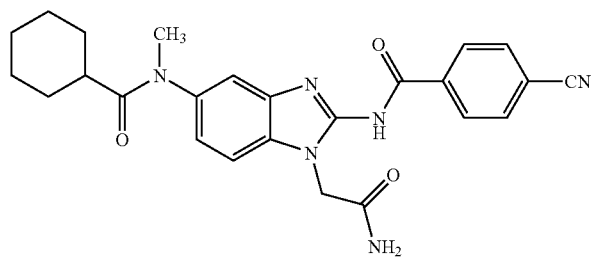
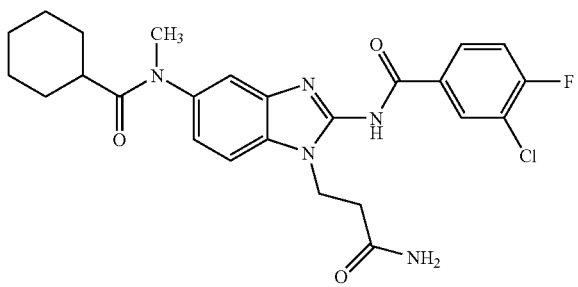
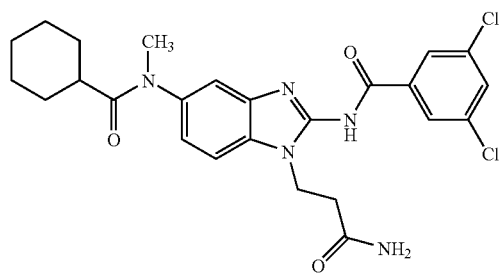
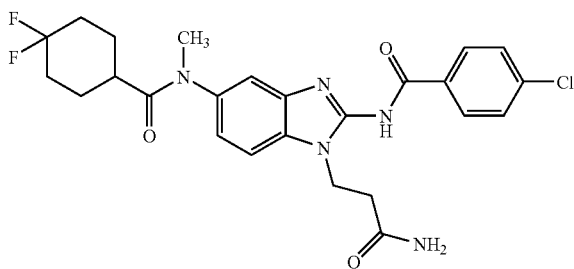
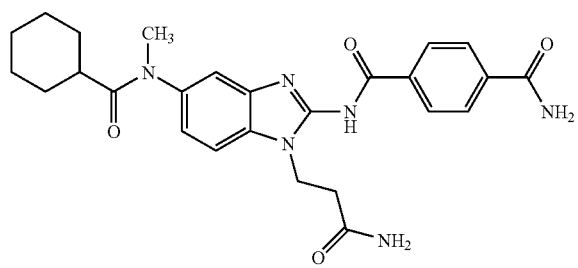
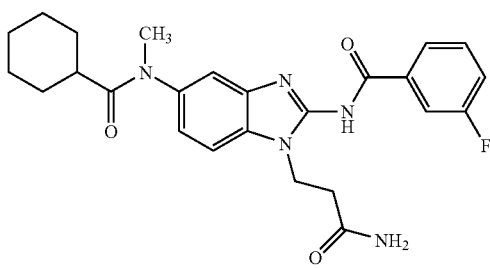

-continued
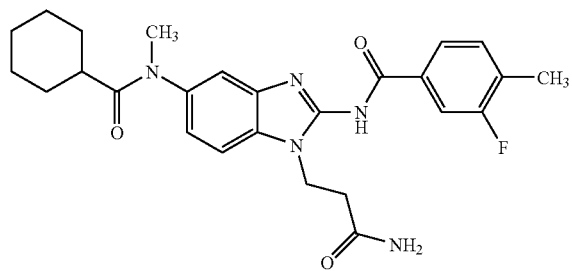
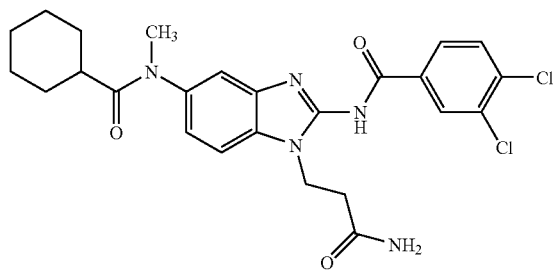
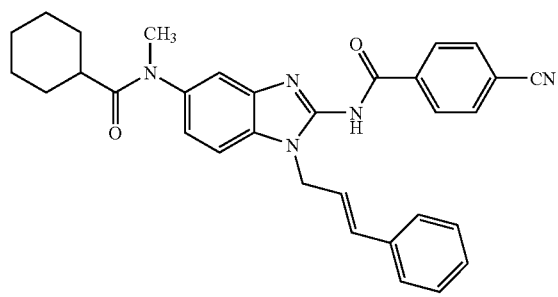
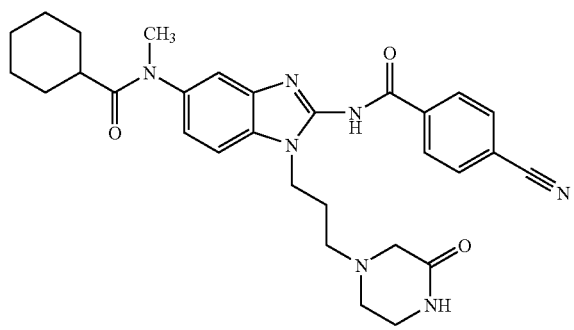
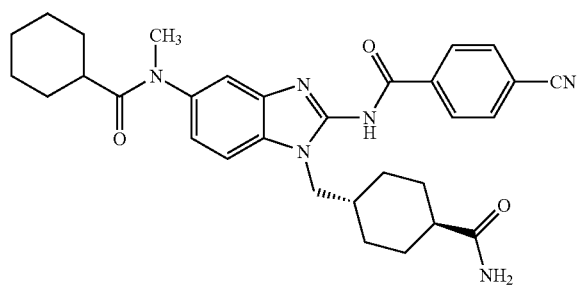
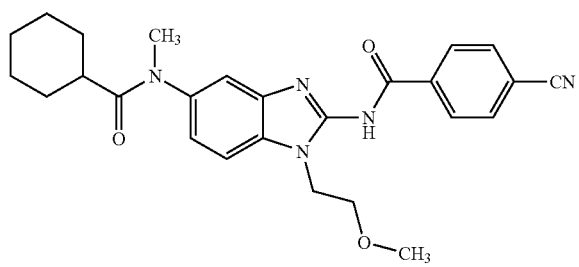
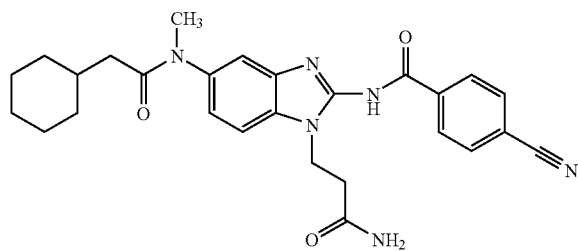
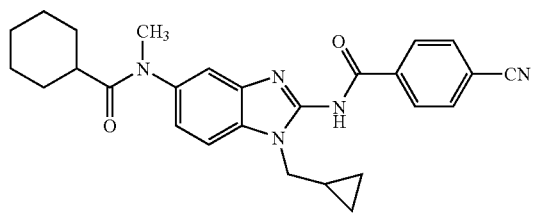
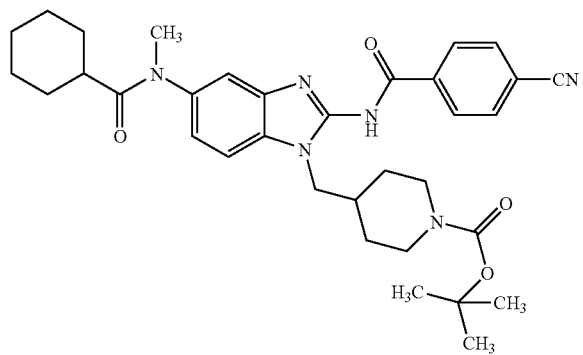
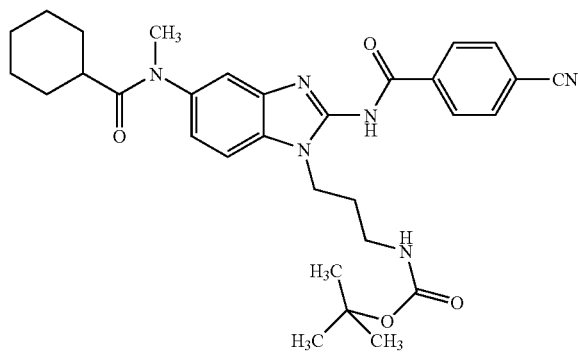

51
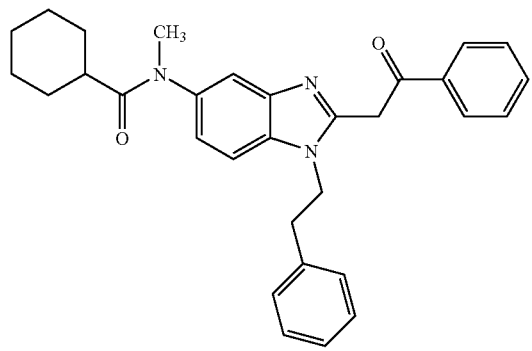
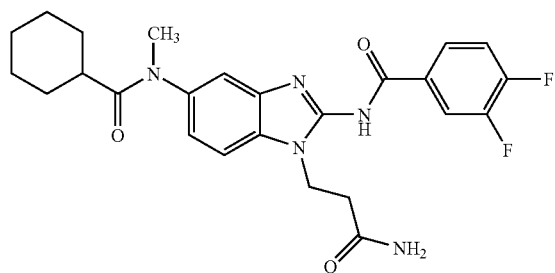
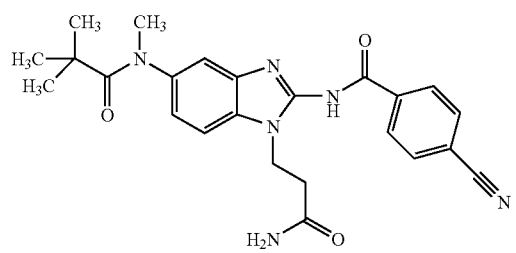
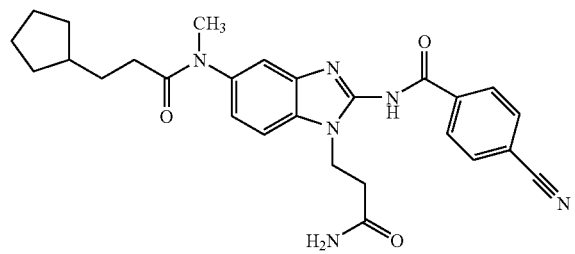
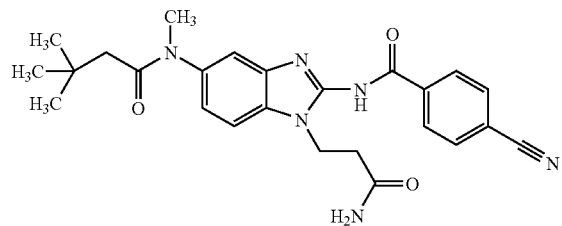
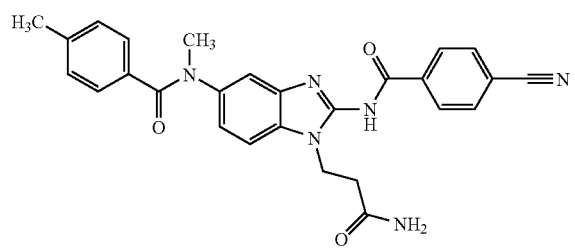
-continued
52
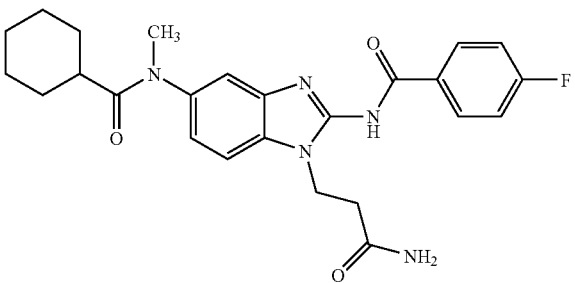
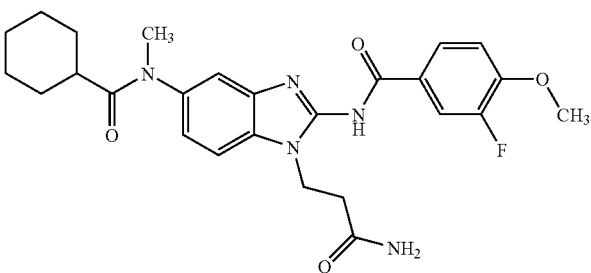
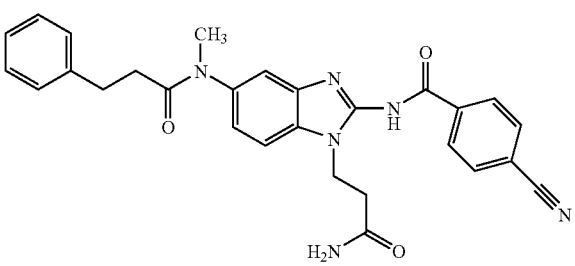
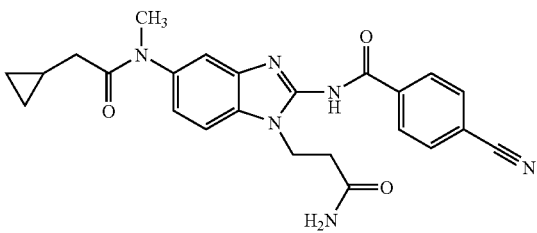
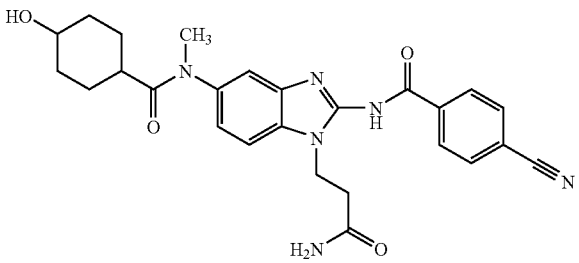
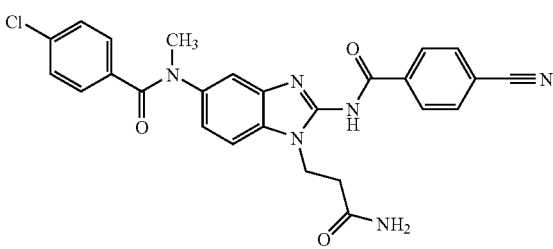

-continued
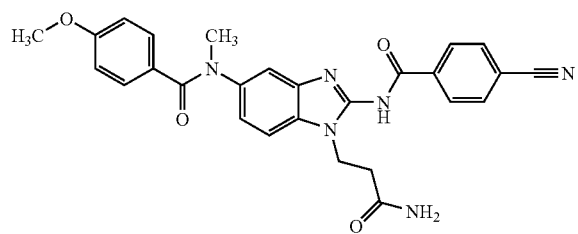
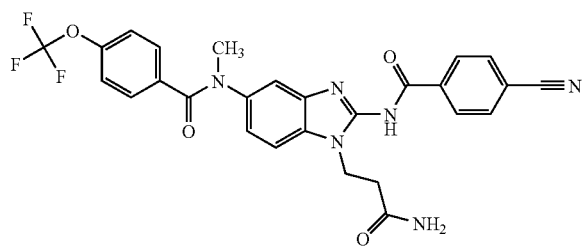
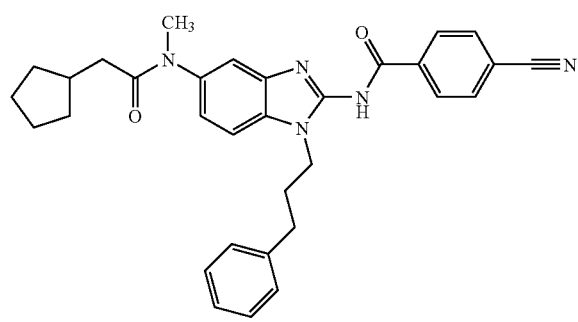
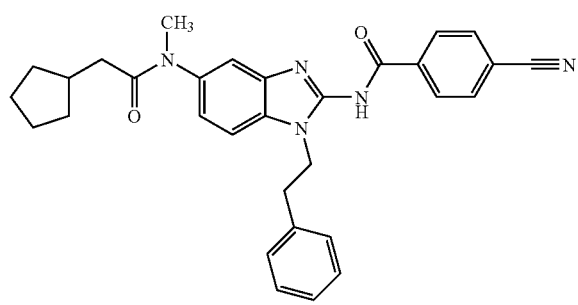
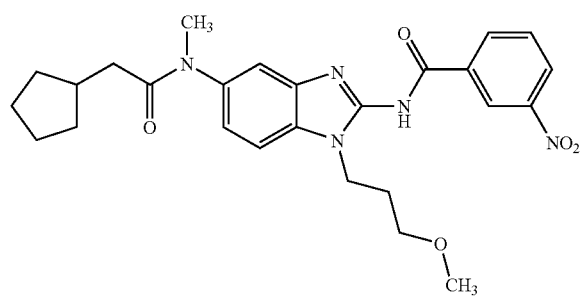
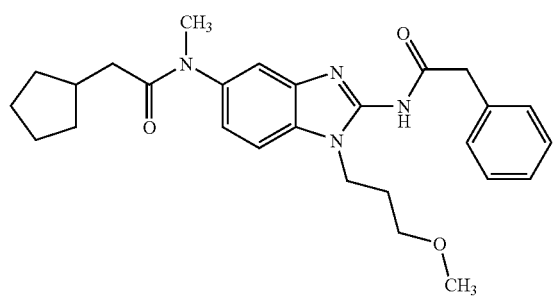
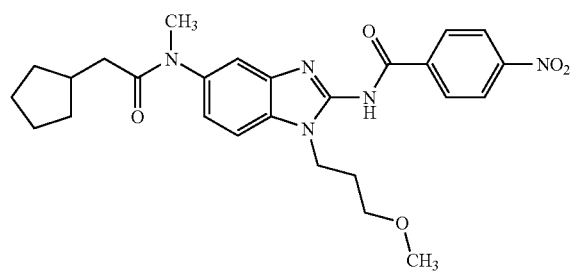
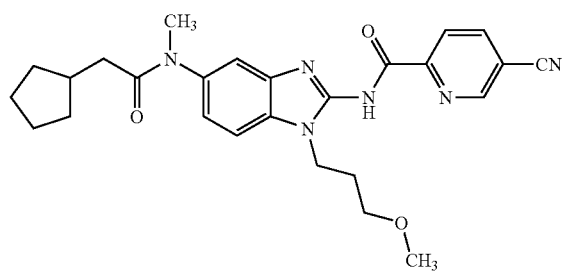
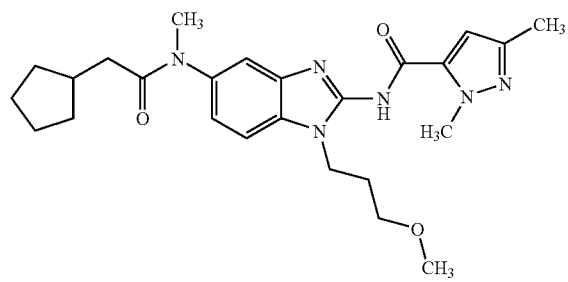
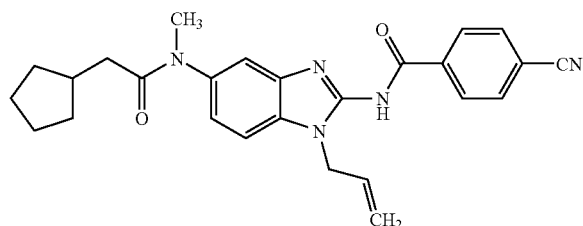

-continued
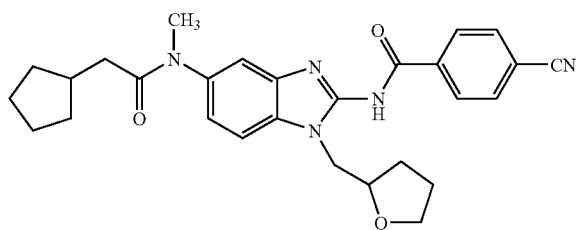
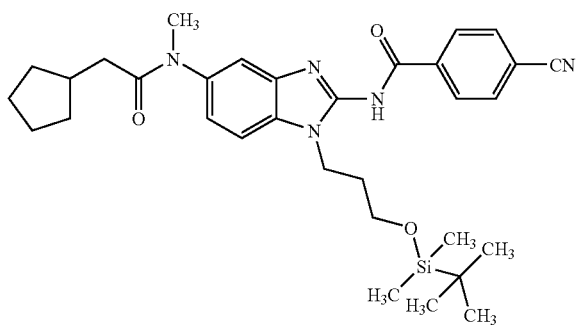
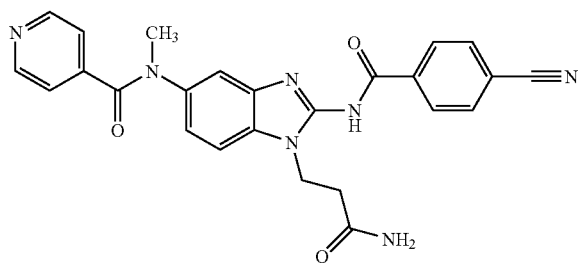
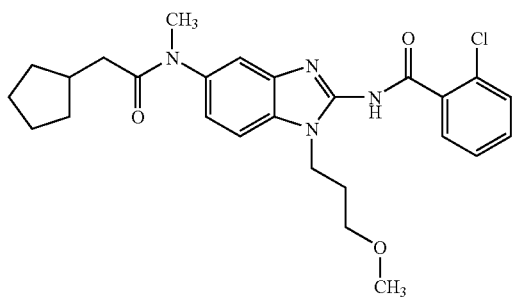
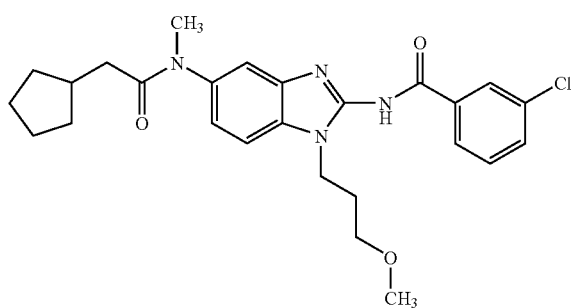
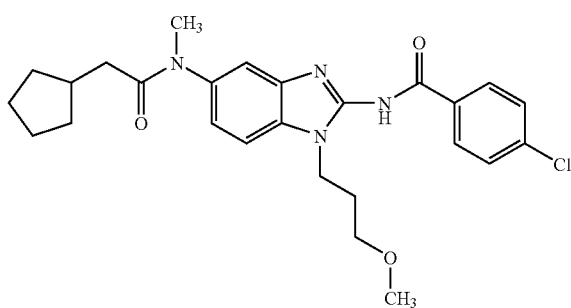
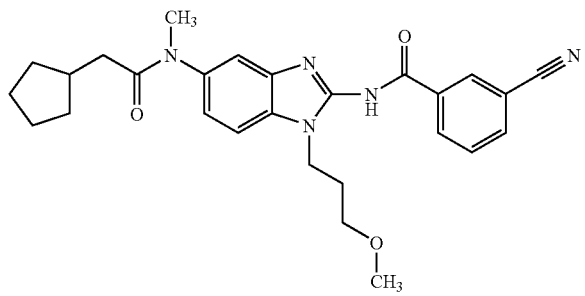
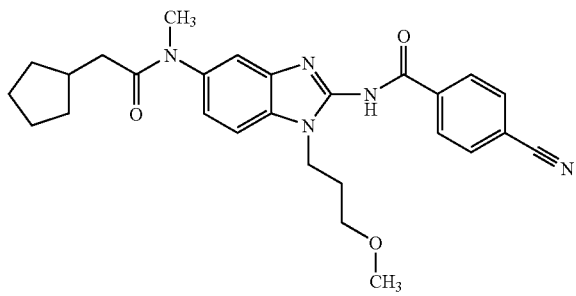
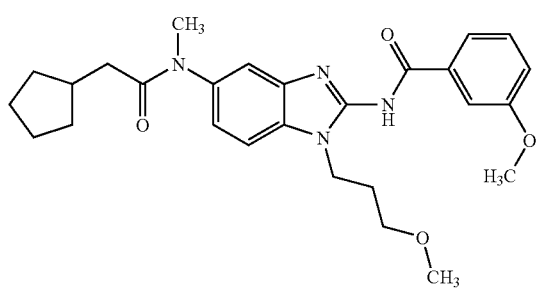
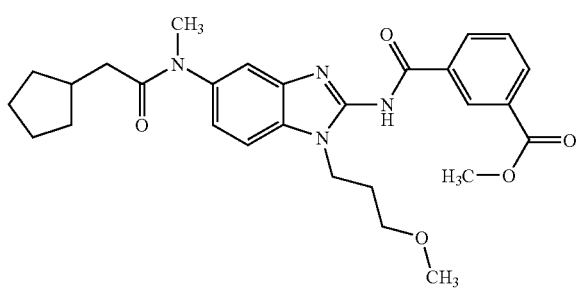

-continued
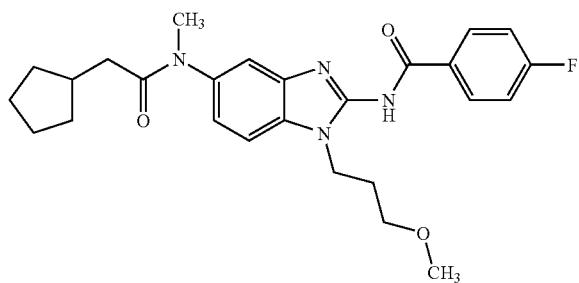
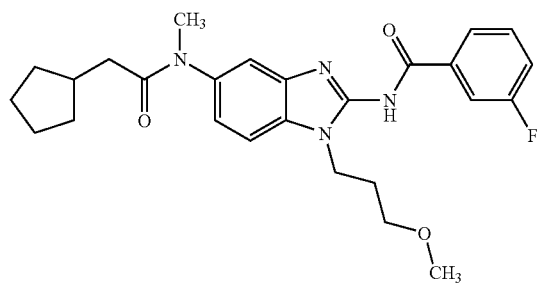
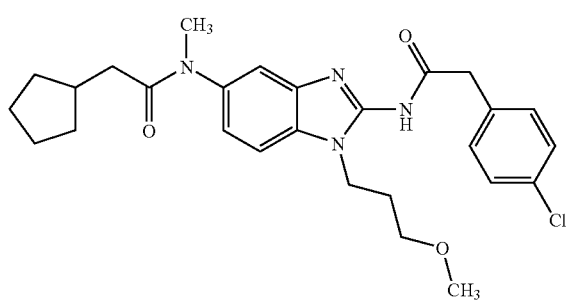
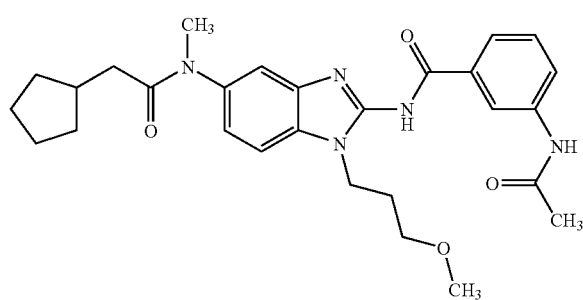
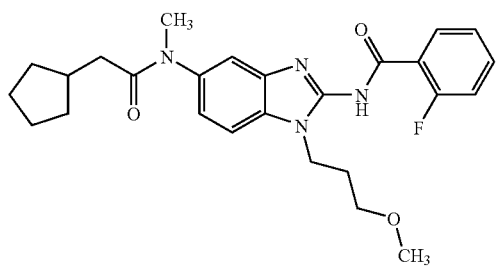
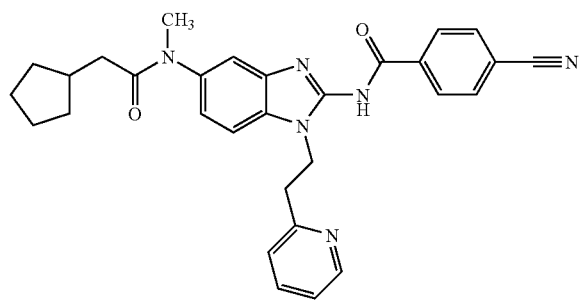
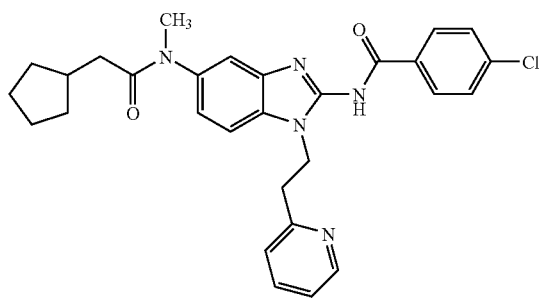
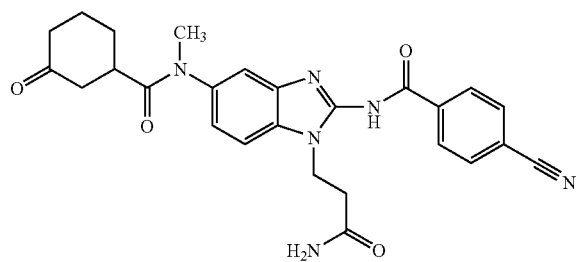
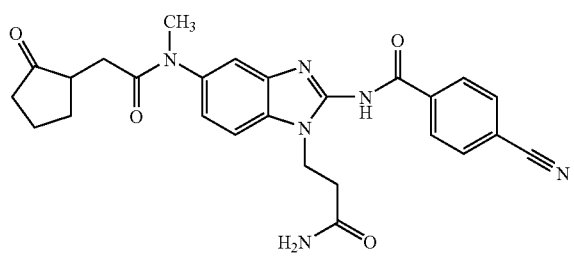
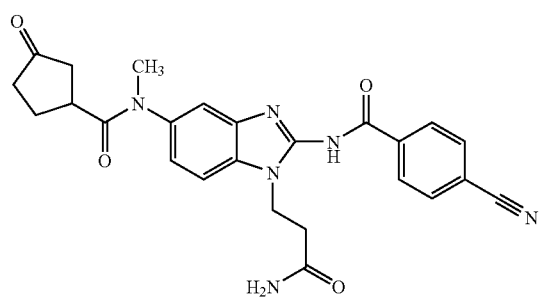

-continued
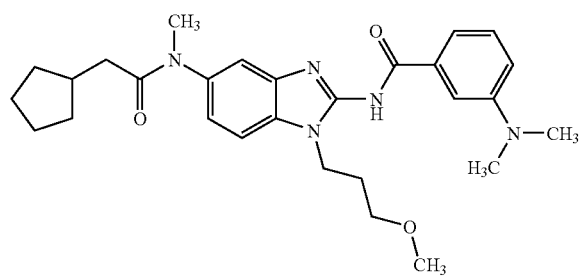
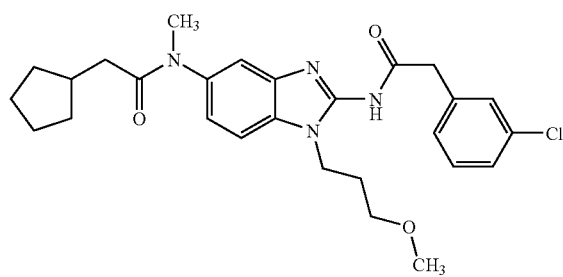
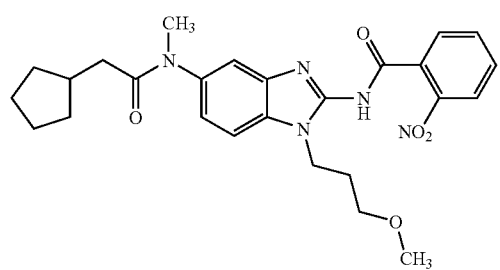
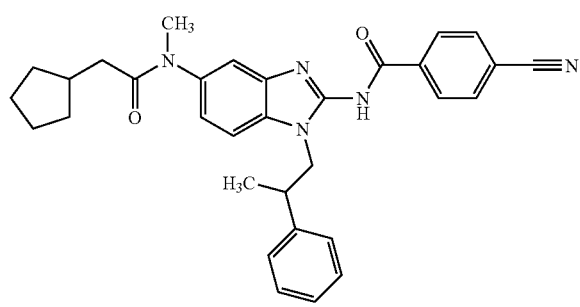
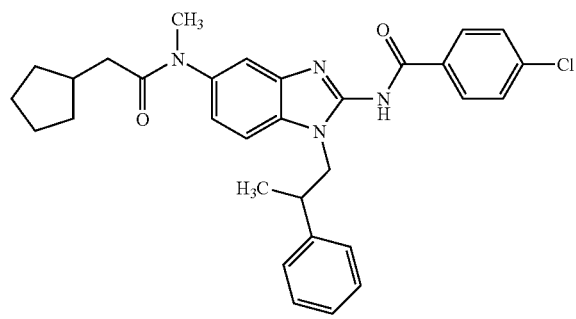
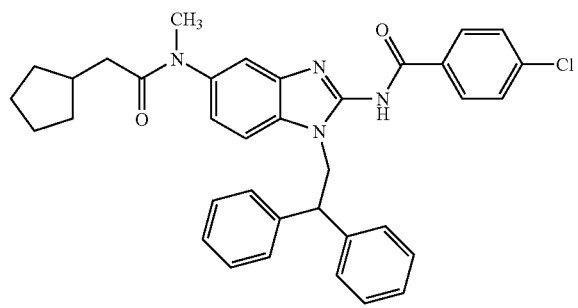
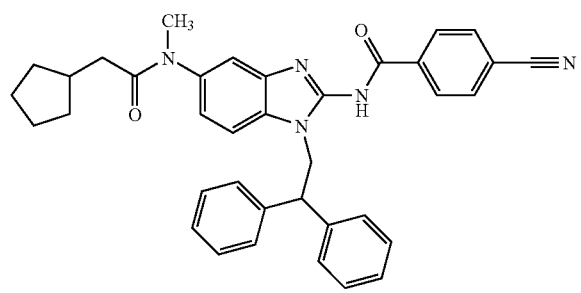
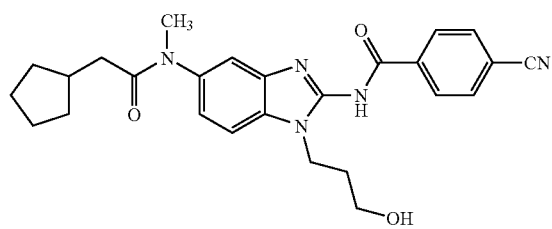
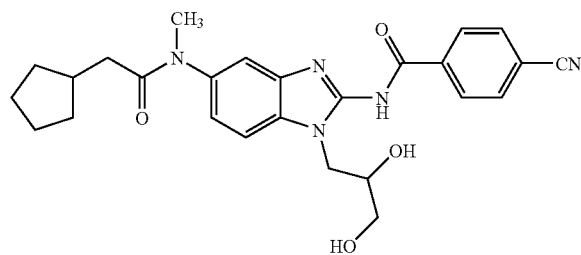
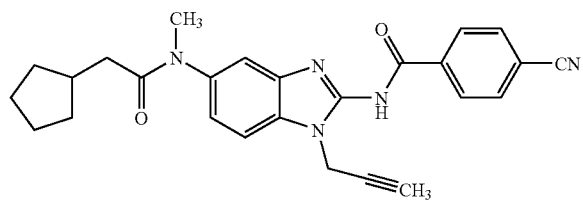

-continued
| 61 | 62 |
|---|---|
| 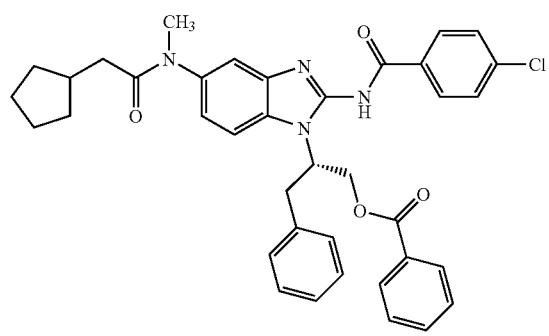 | 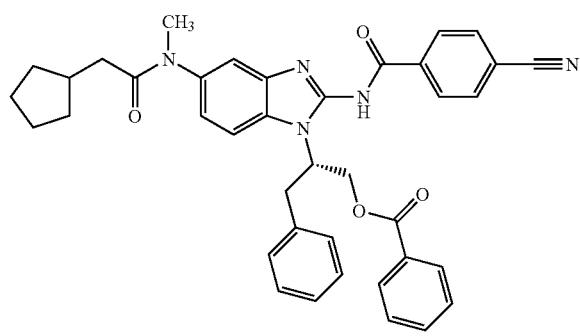 |
| 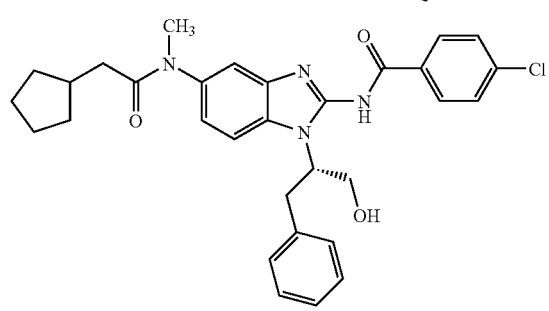 | 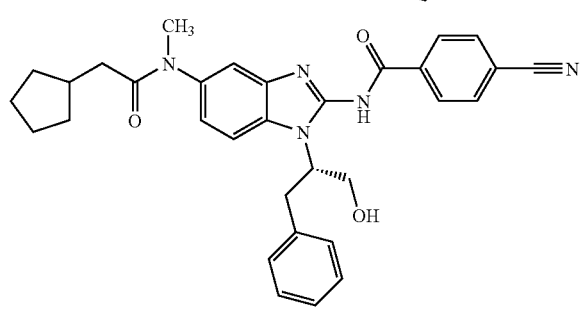 |
| 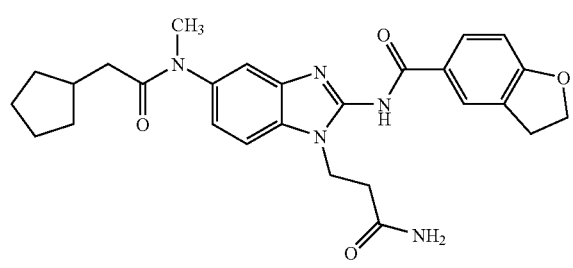 | 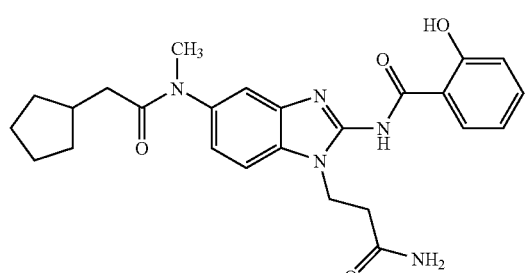 |
| 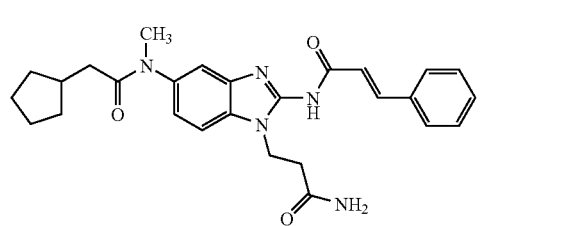 | 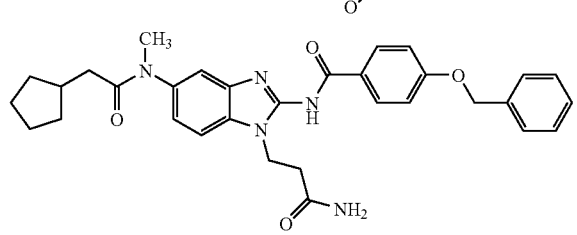 |
| 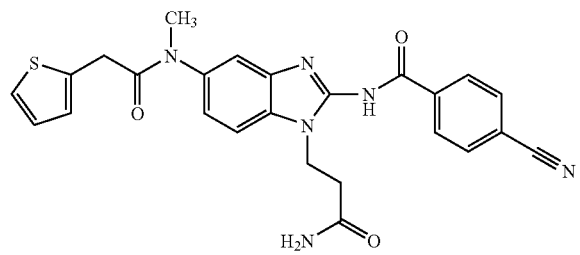 | 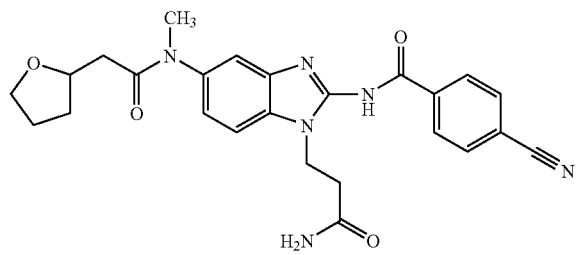 |
| 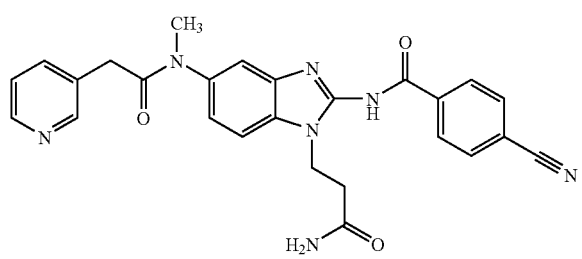 | 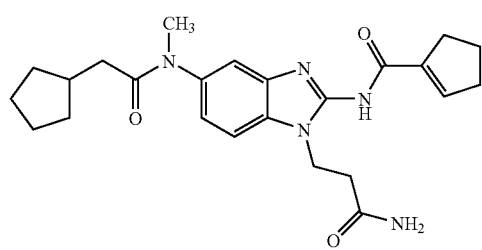 |

-continued
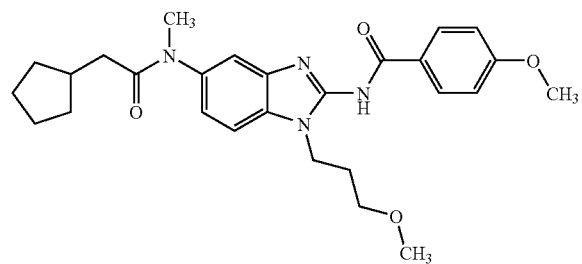
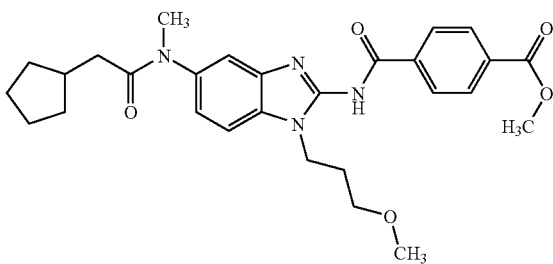
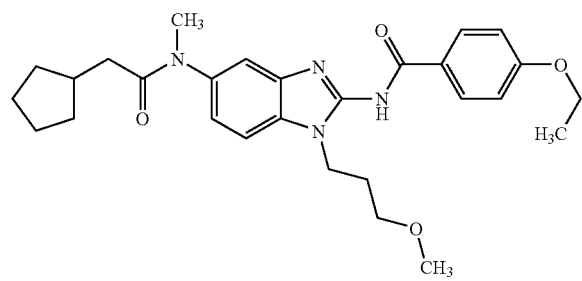
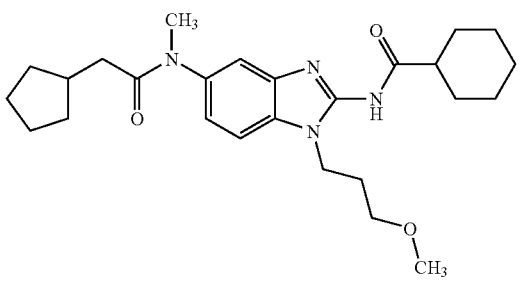
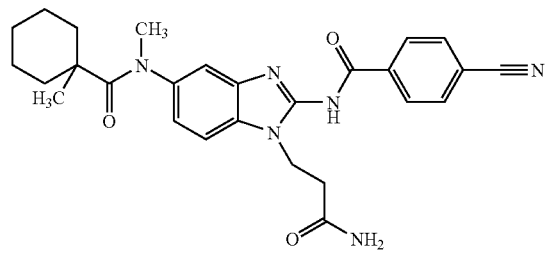
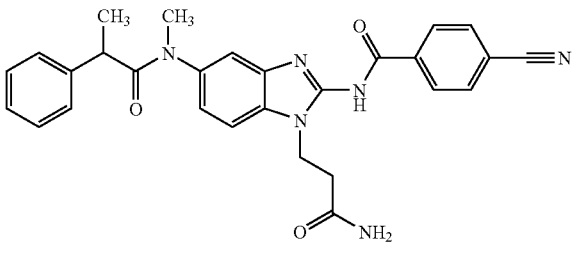
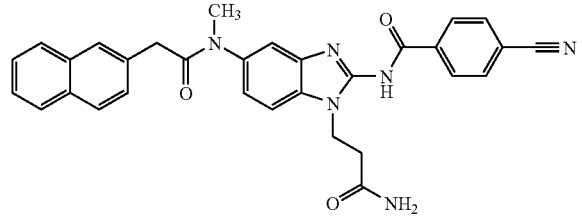
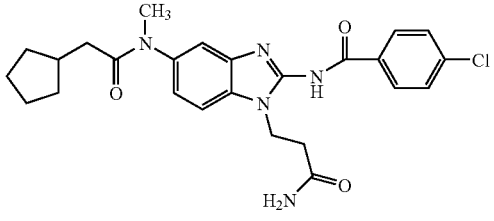
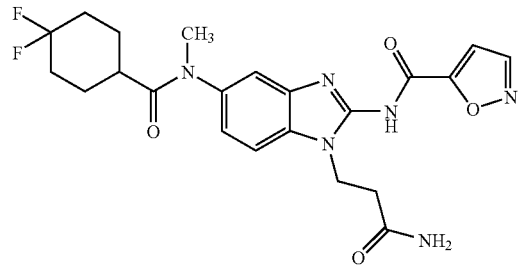
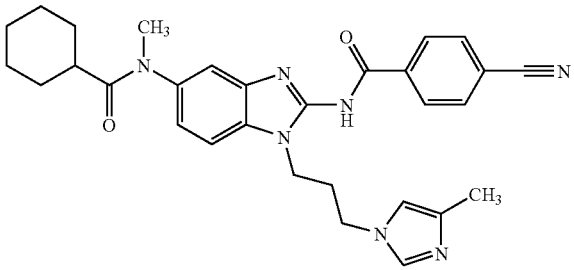
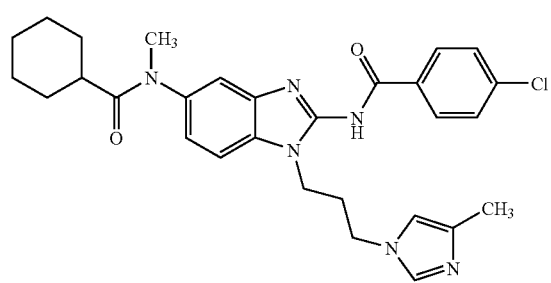
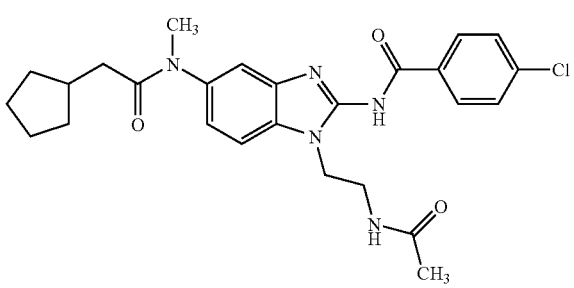

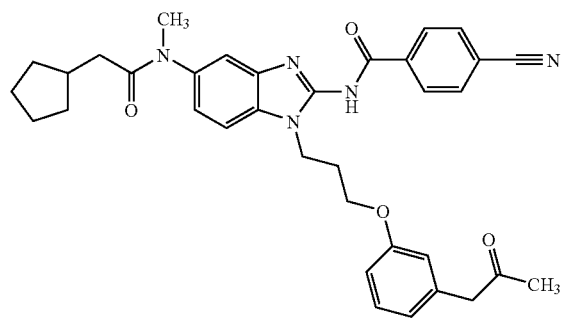
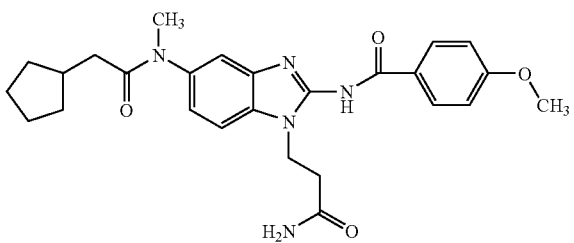
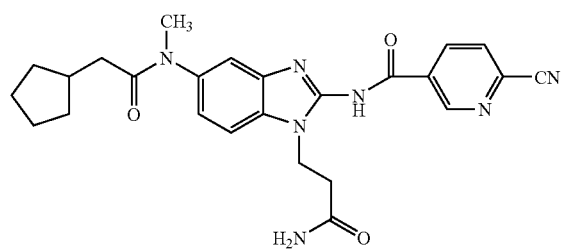
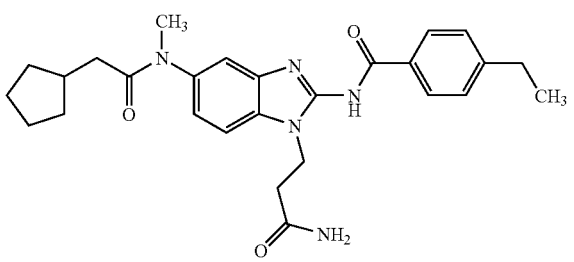
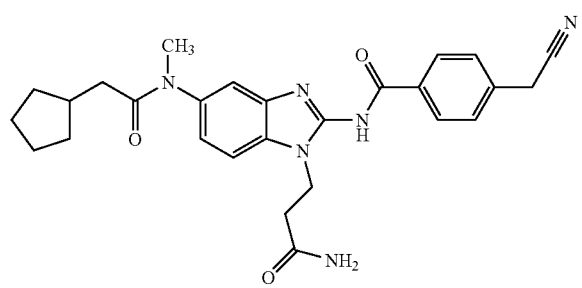
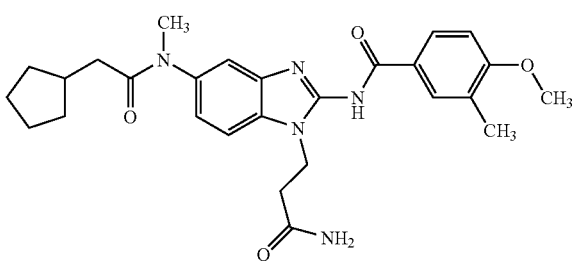
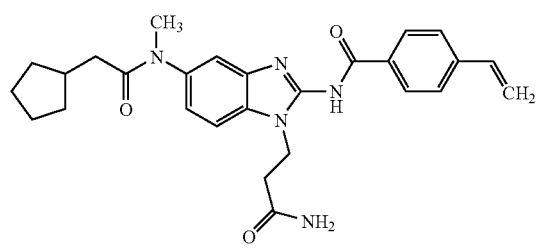
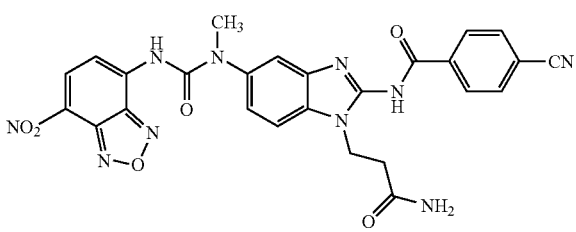
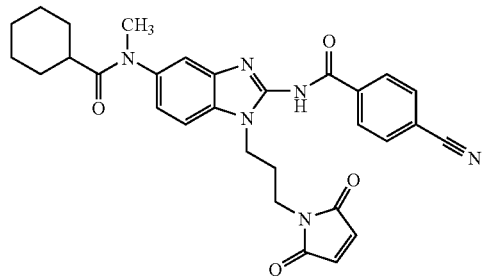
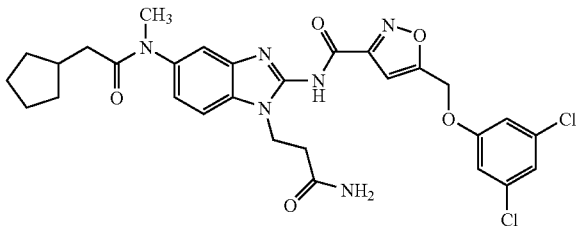
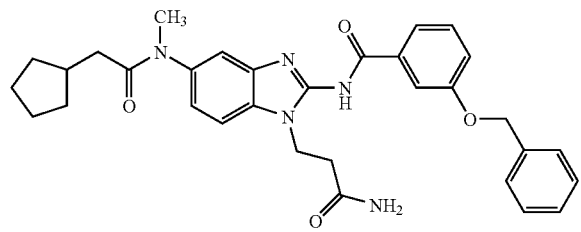
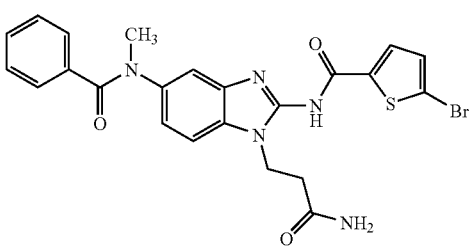

-continued
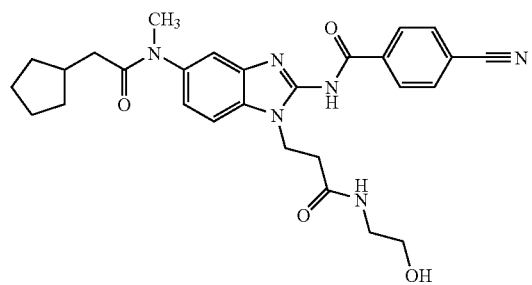
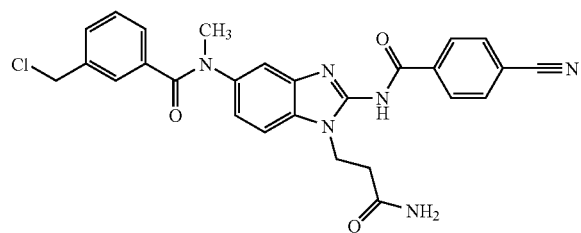
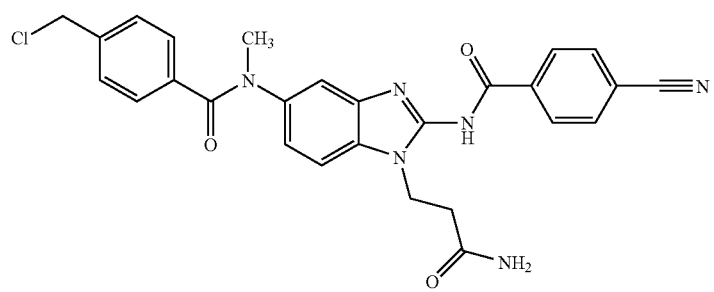
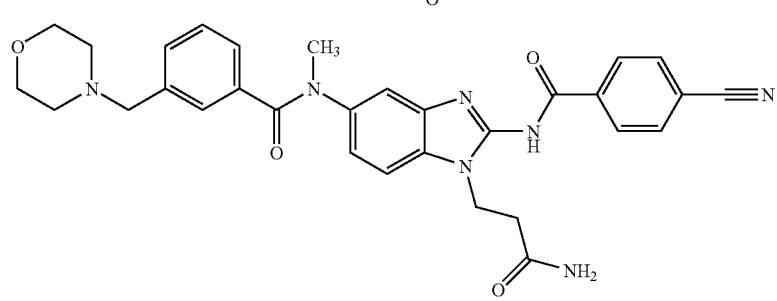
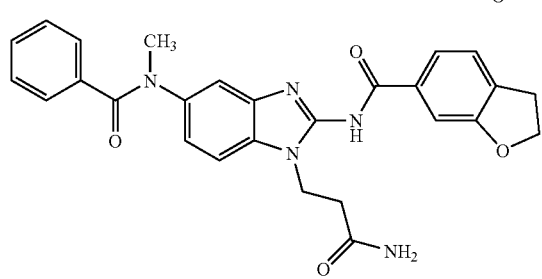
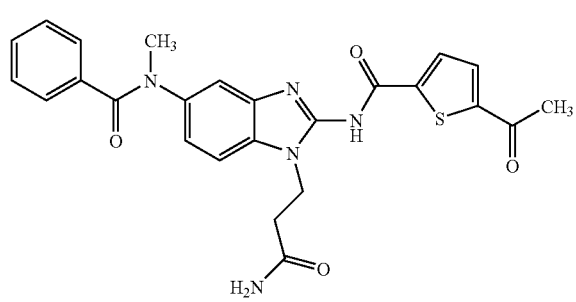
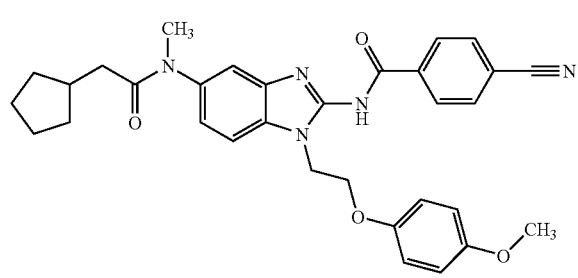
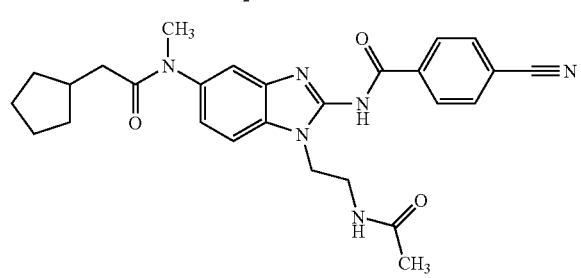
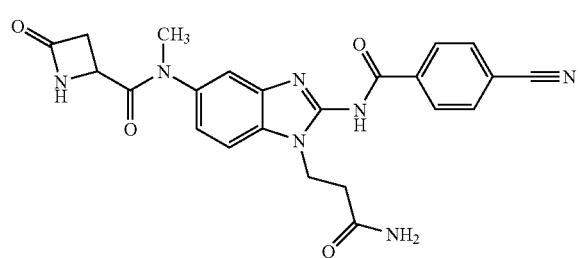
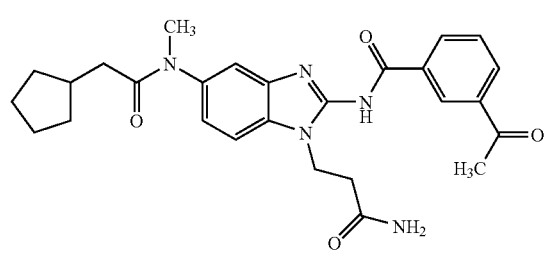

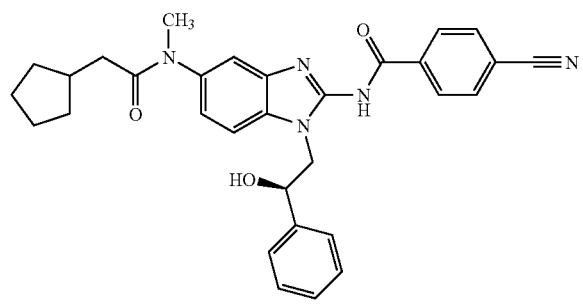
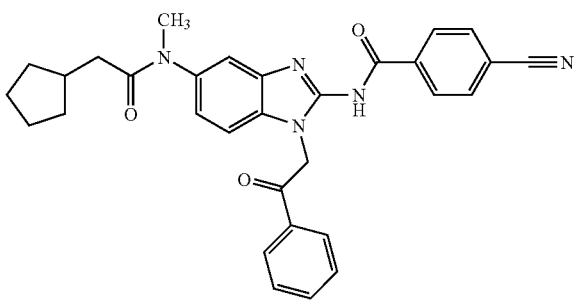
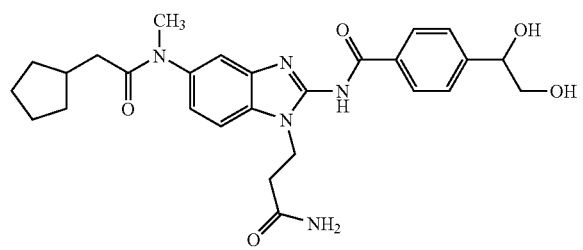
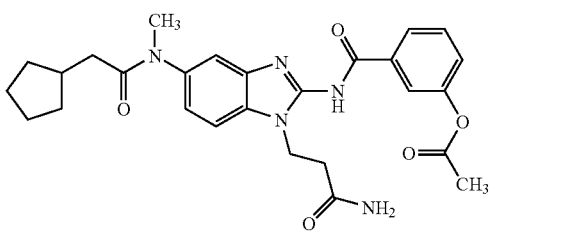
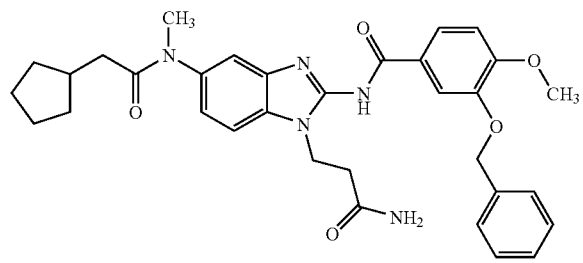
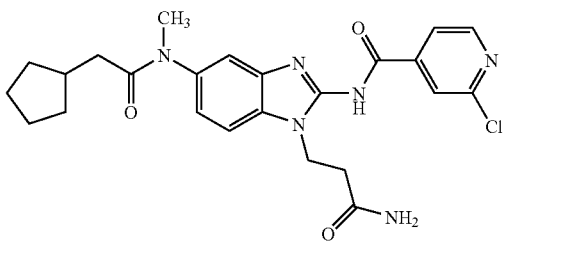
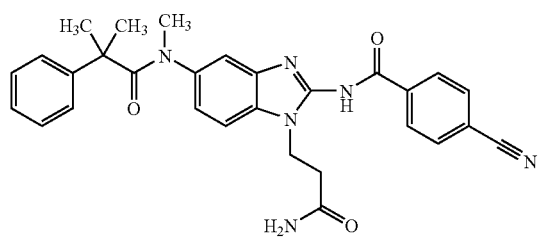
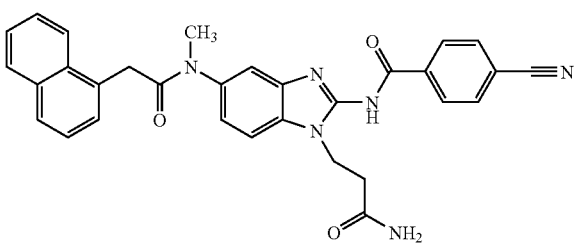
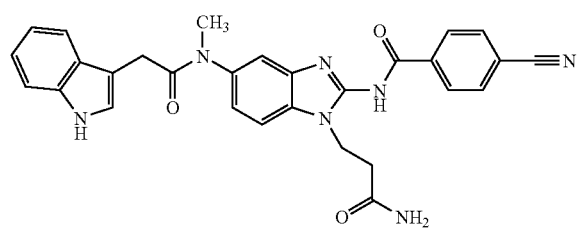
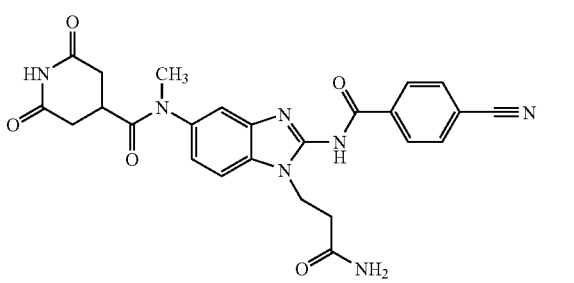
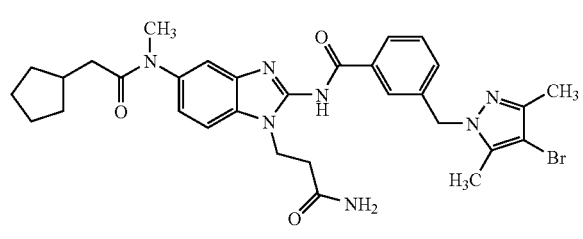
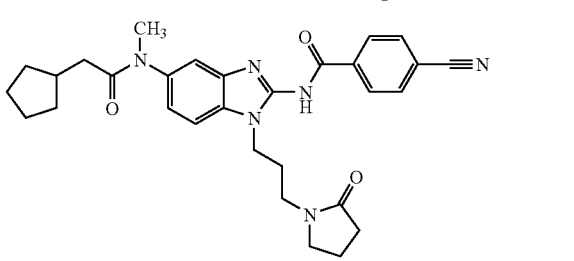

-continued
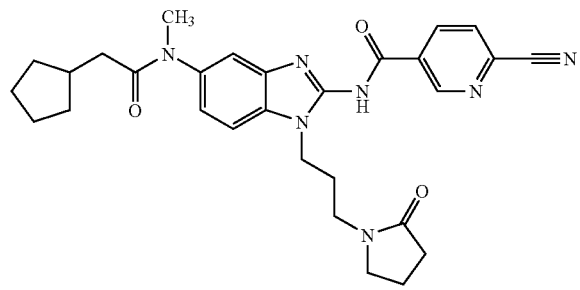
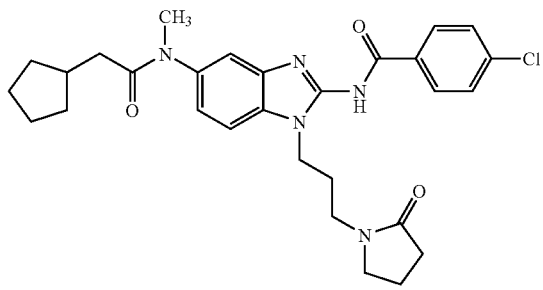
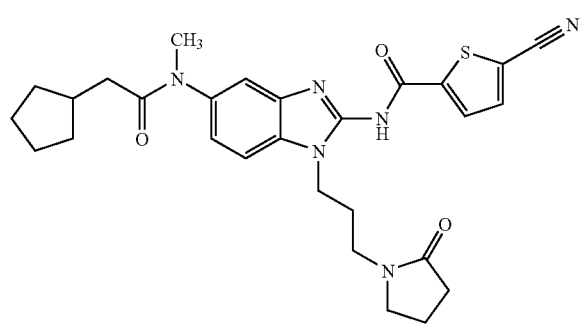
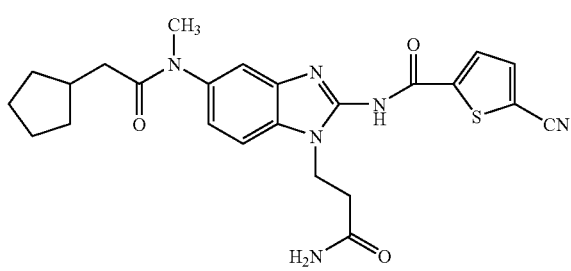
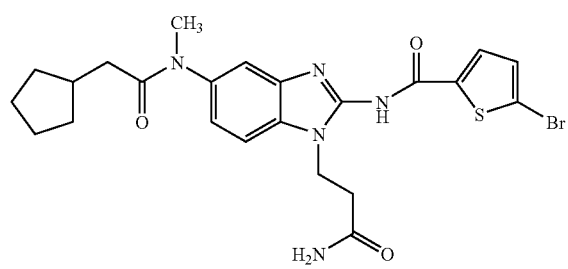
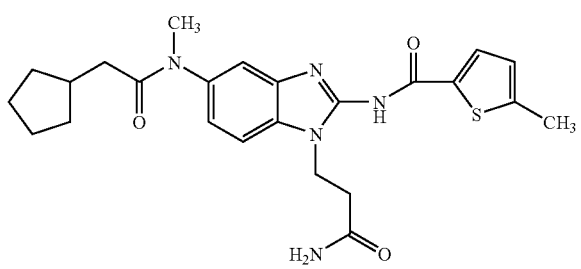
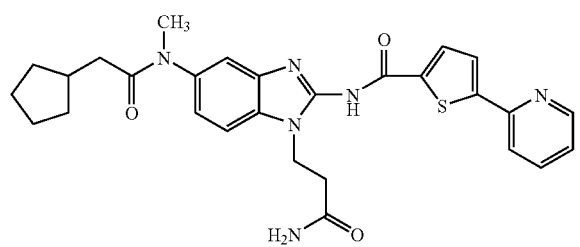
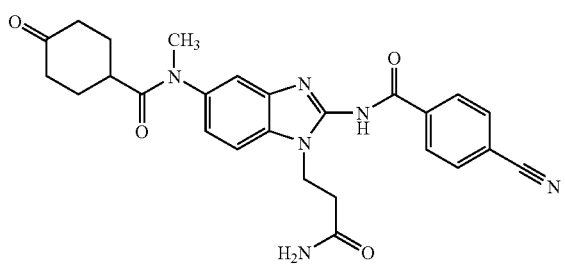
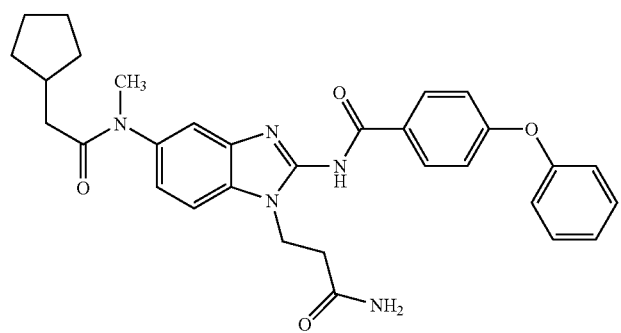

-continued
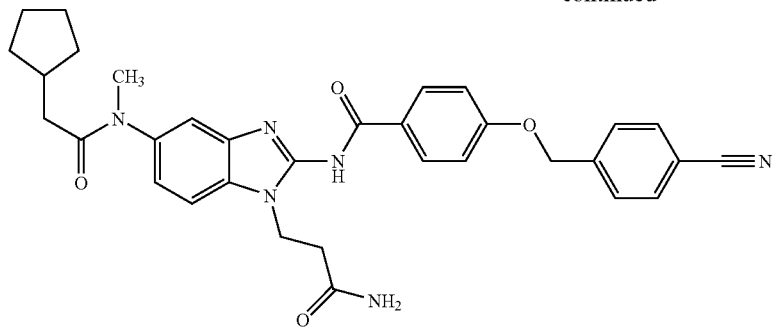
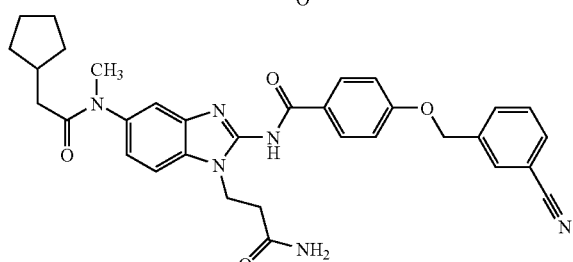
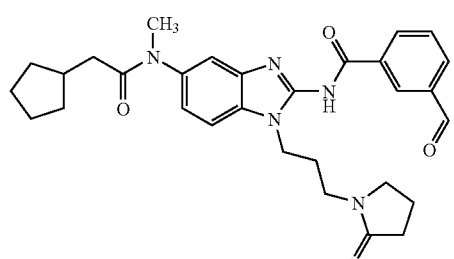
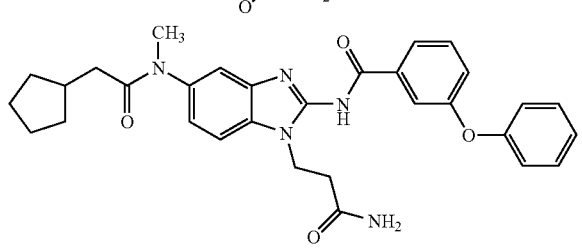
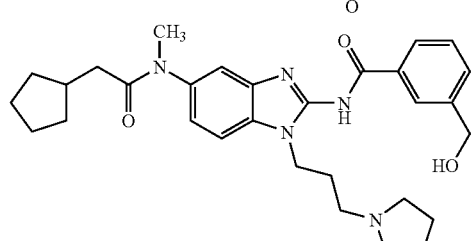
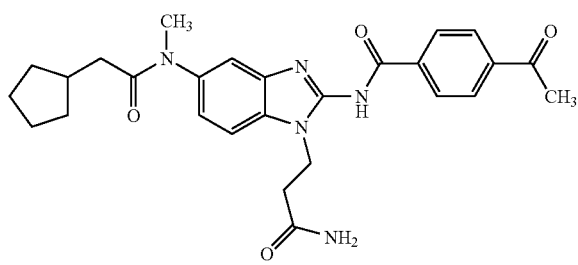
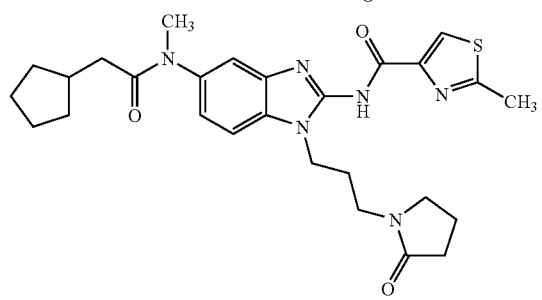
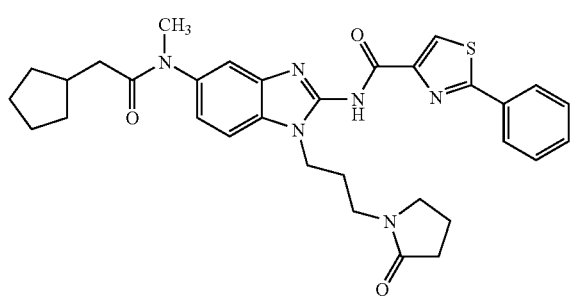
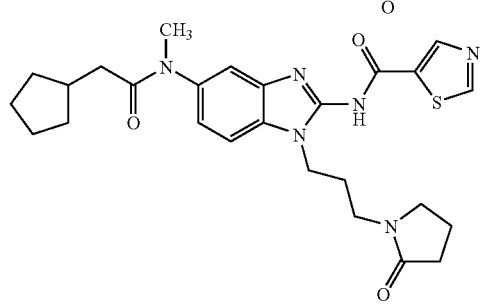
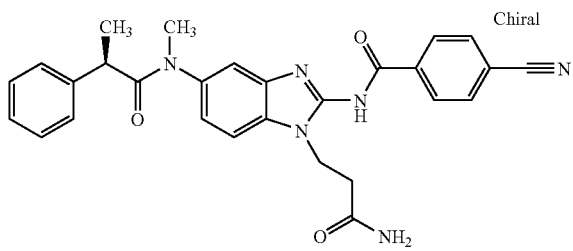
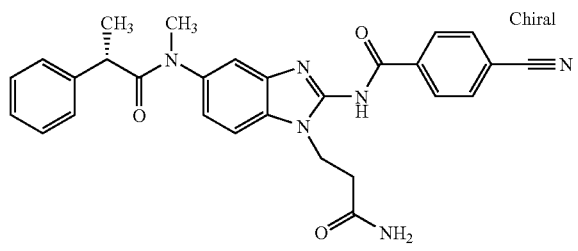

-continued
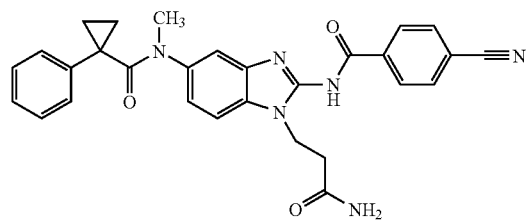
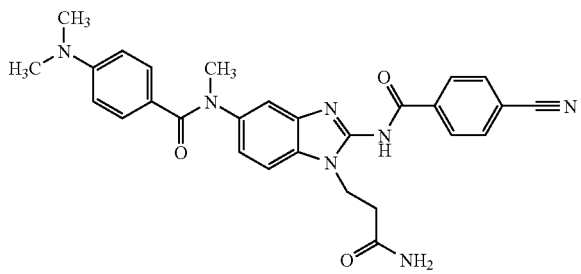
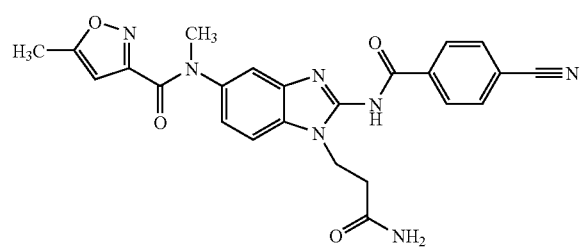
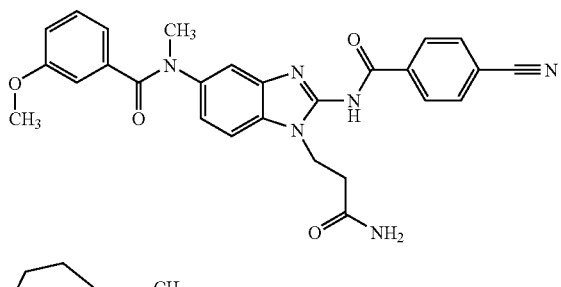
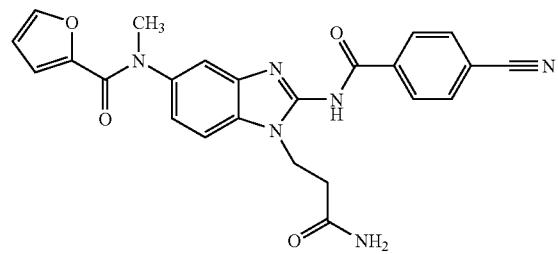
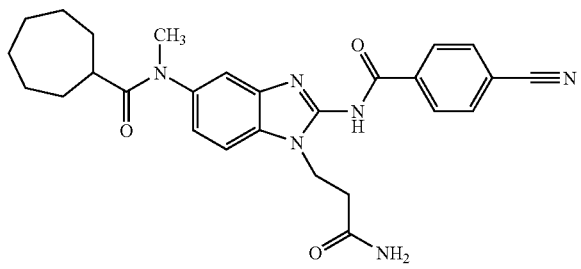
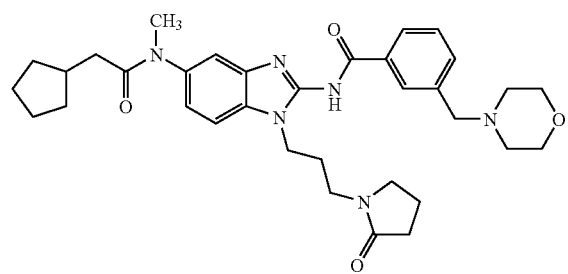
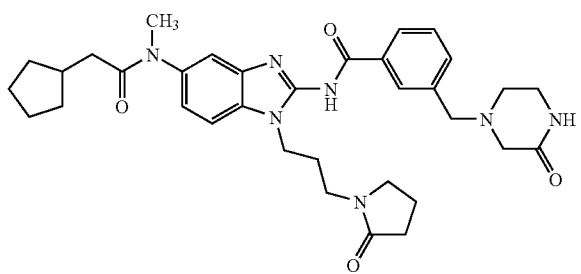
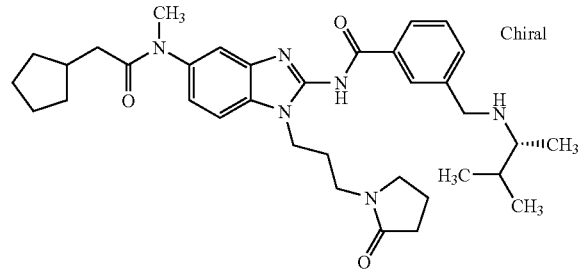
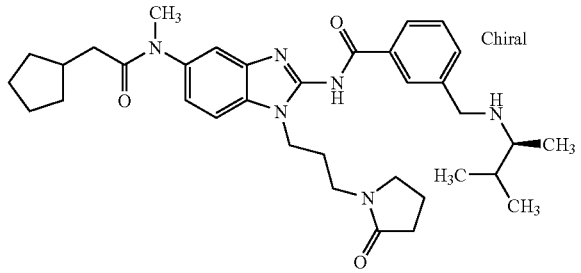
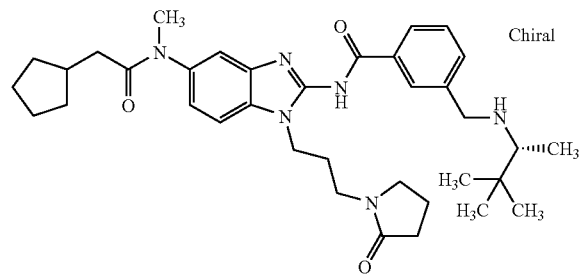
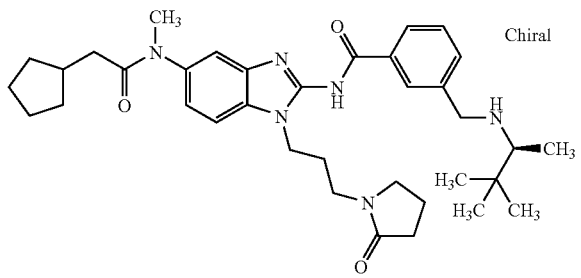

77
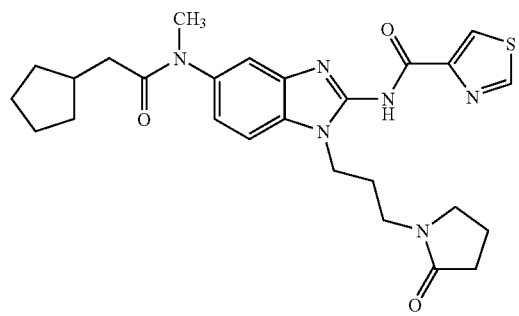
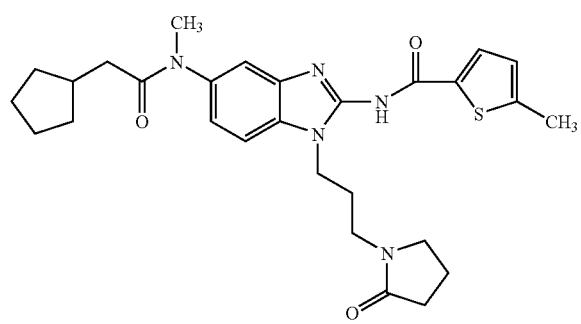
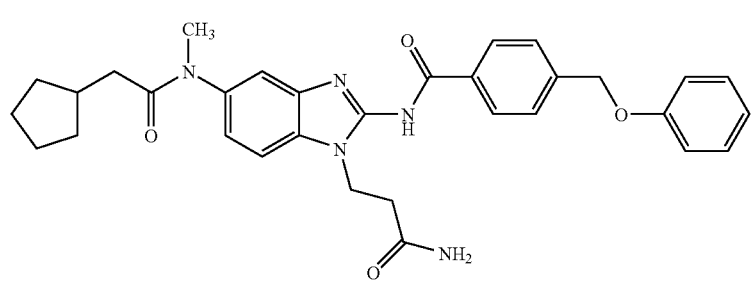
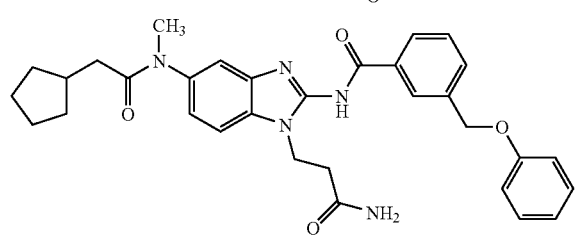
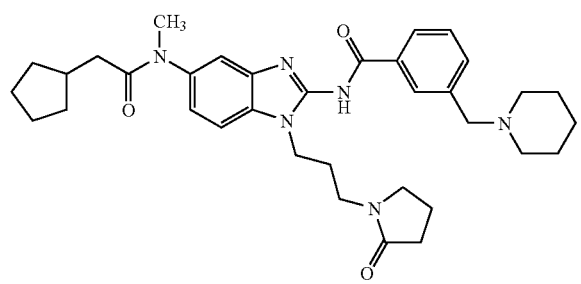
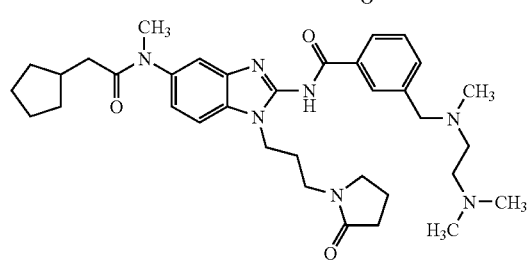
78
-continued
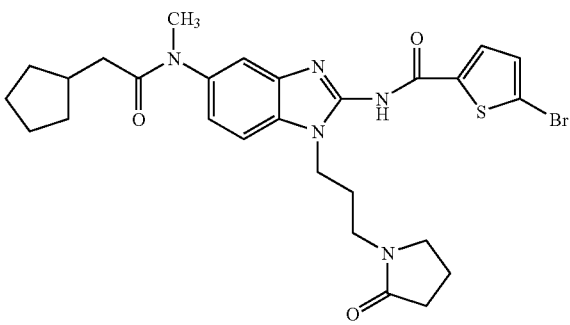
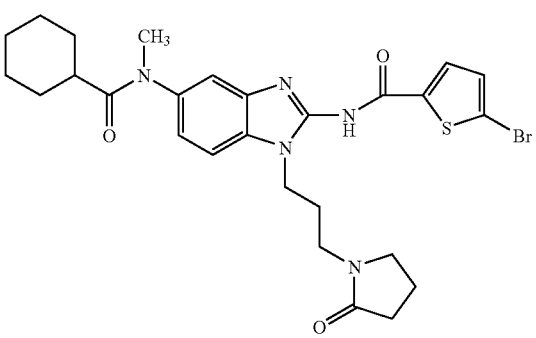
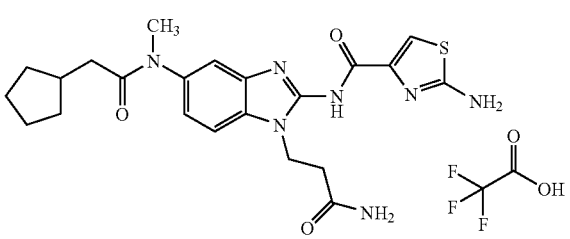
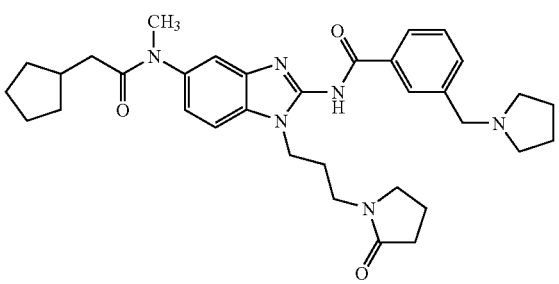
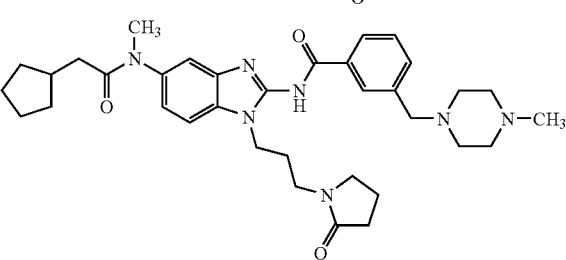

79
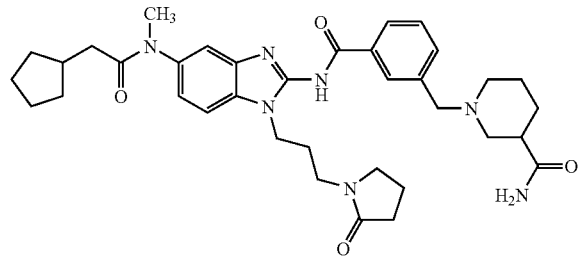
80
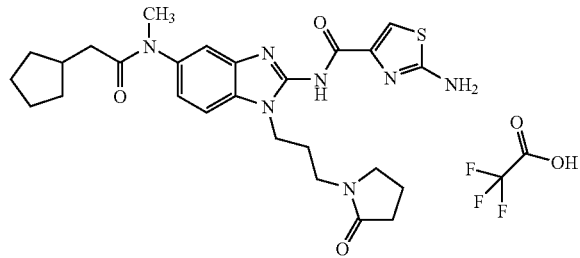
-continued
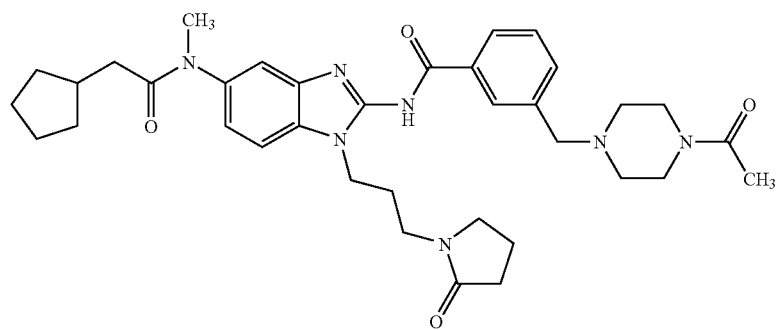
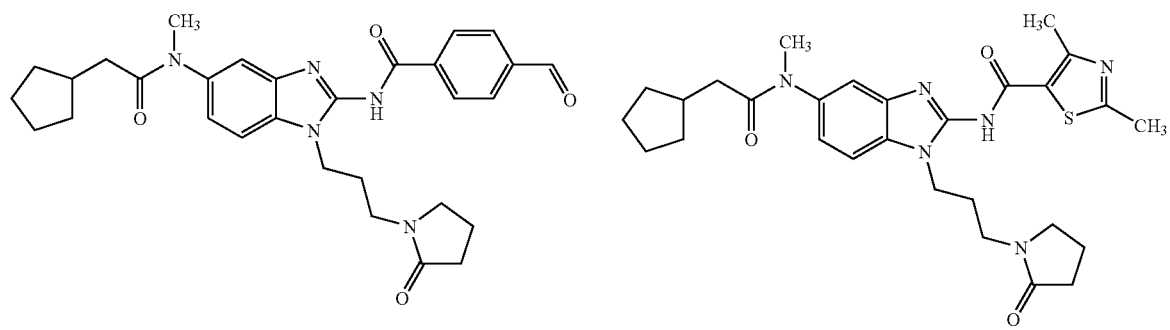
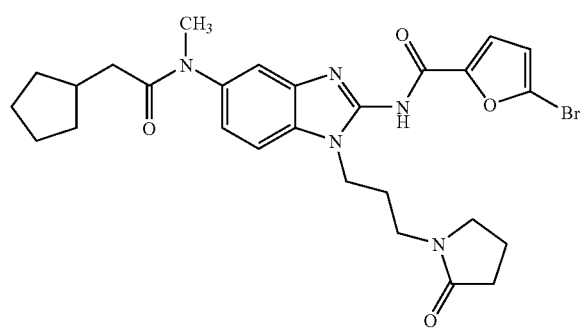
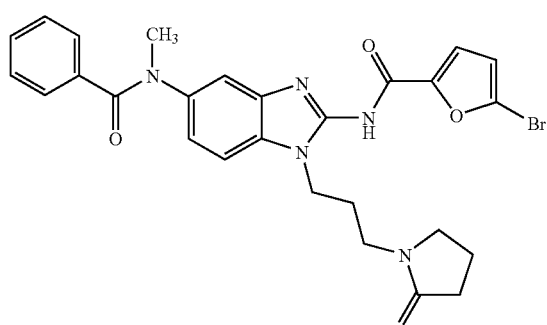
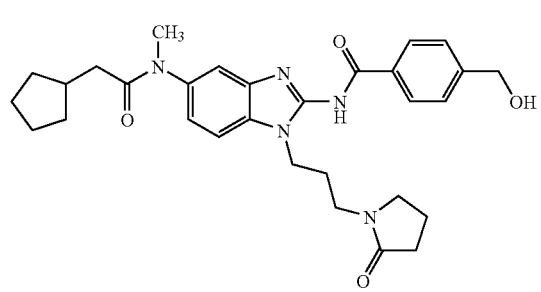
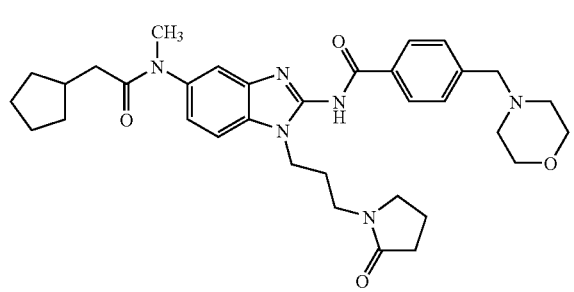

-continued
| 81 | 82 |
|---|---|
| 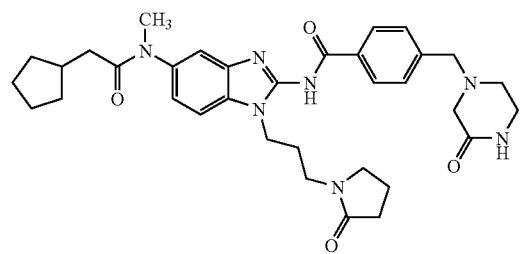 | 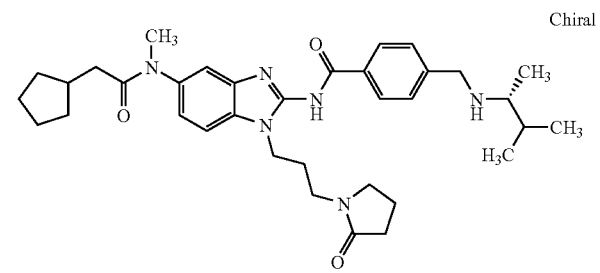 |
| 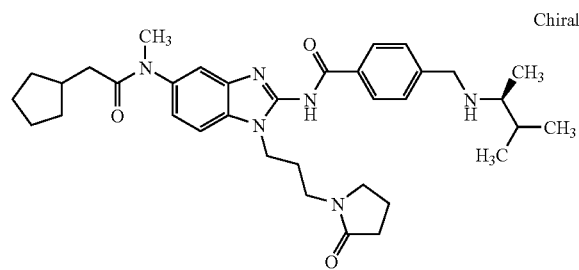 | 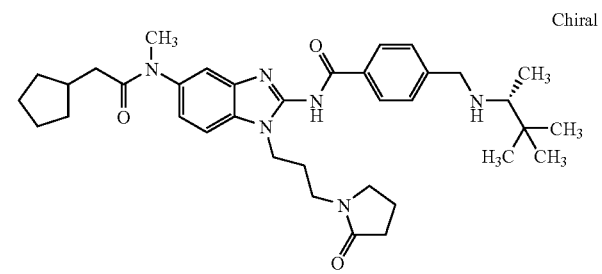 |
| 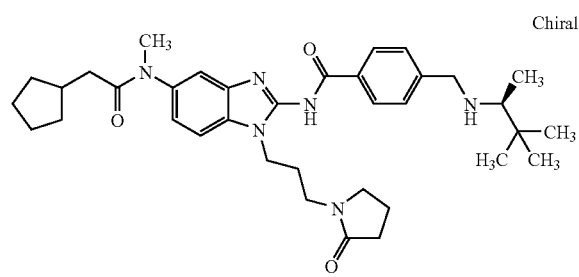 | 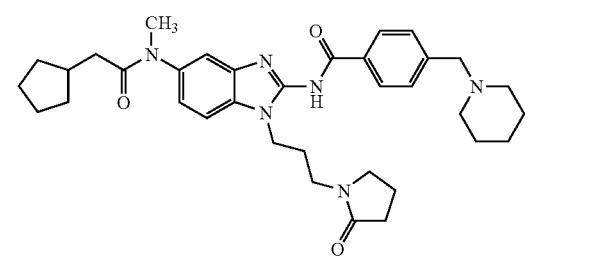 |
| 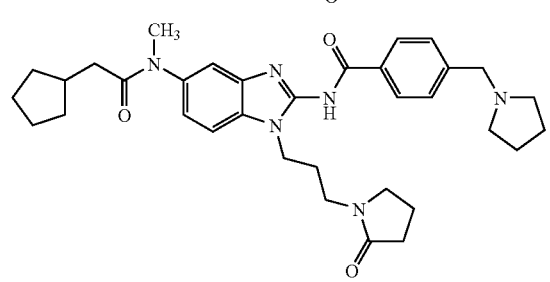 | 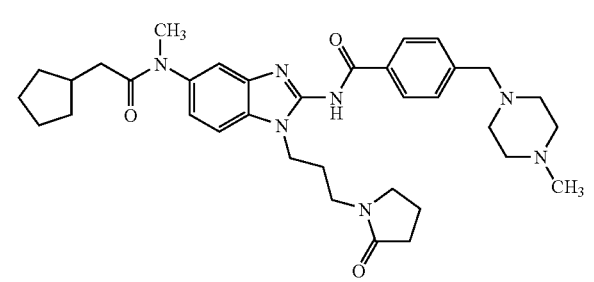 |
| 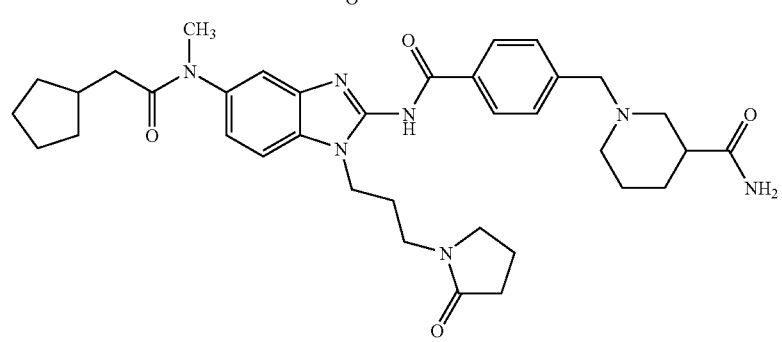 | 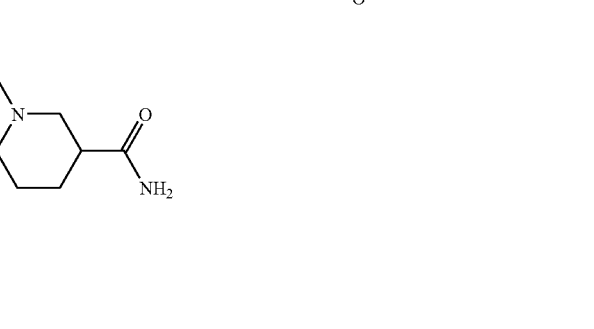 |
| 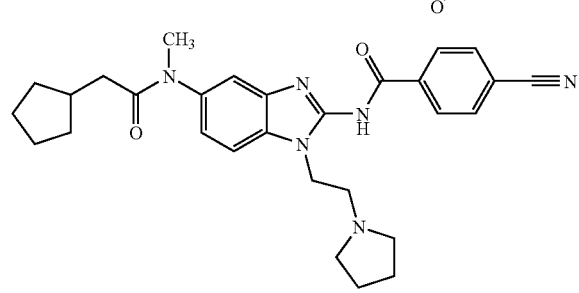 | 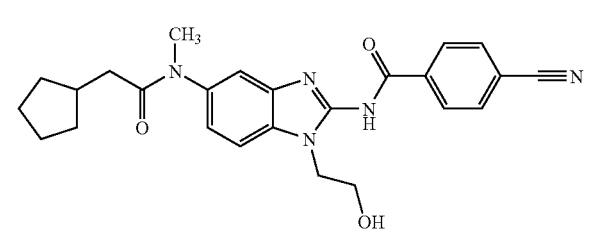 |

83
84
-continued
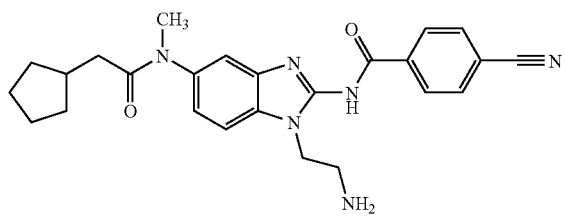
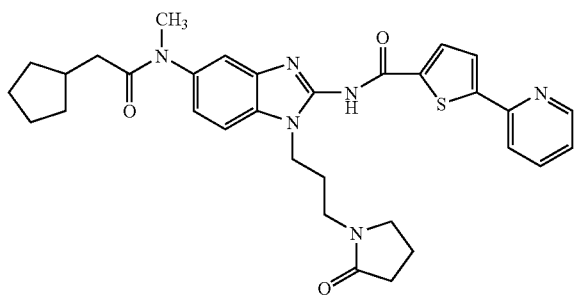
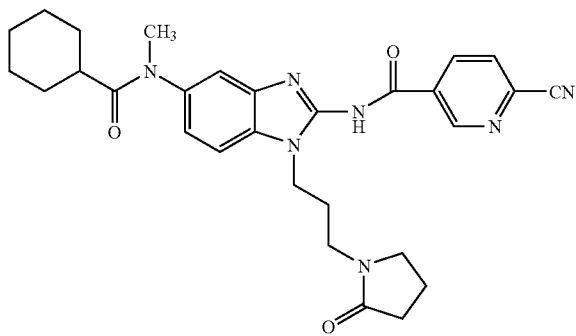
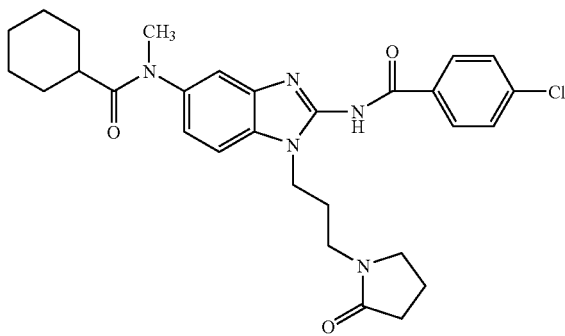
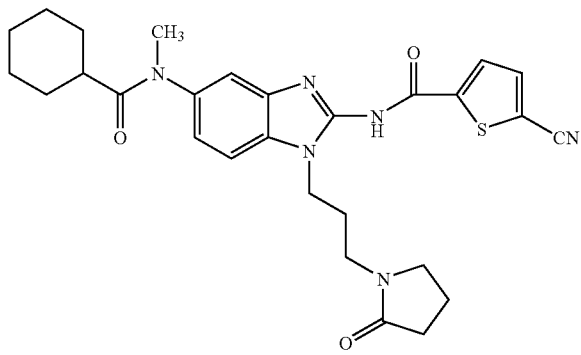
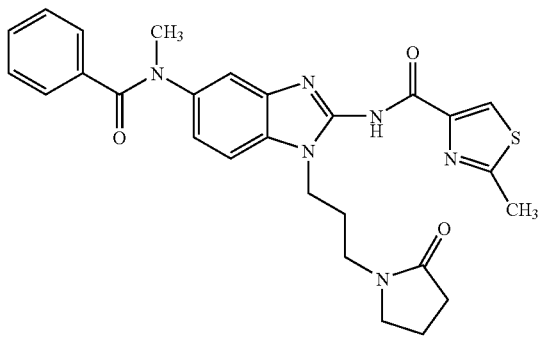
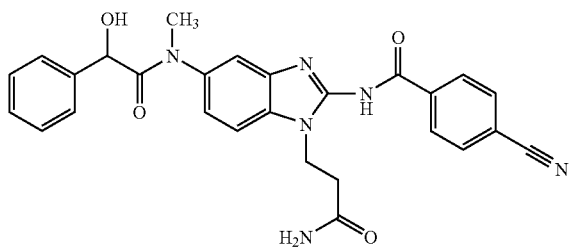
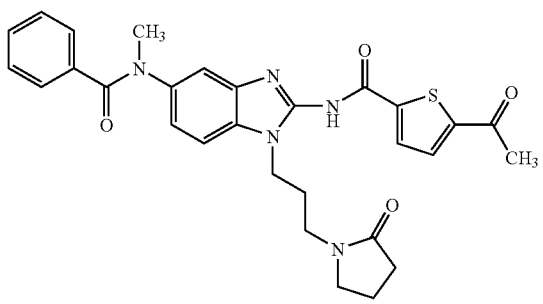
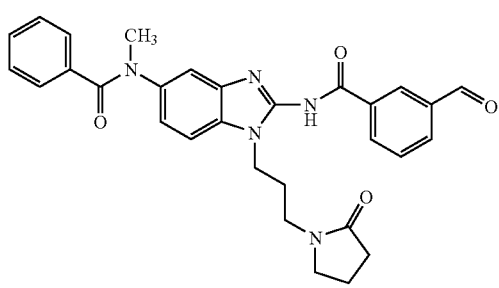
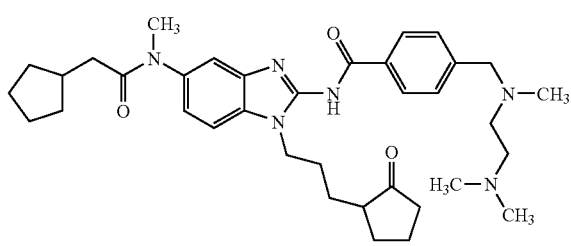

-continued
85
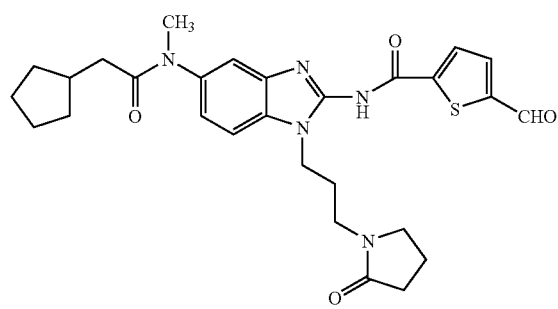
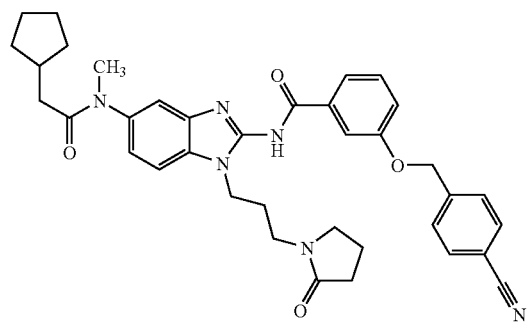
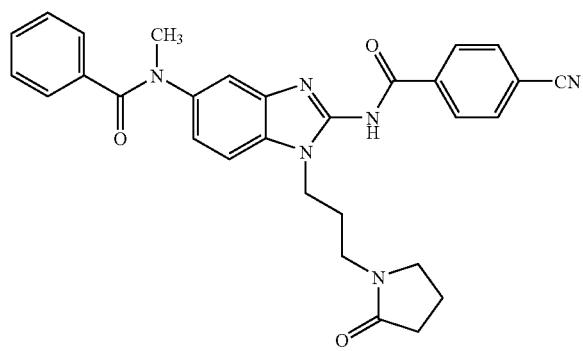
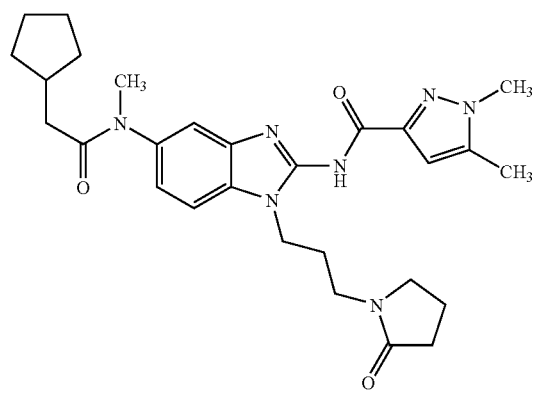
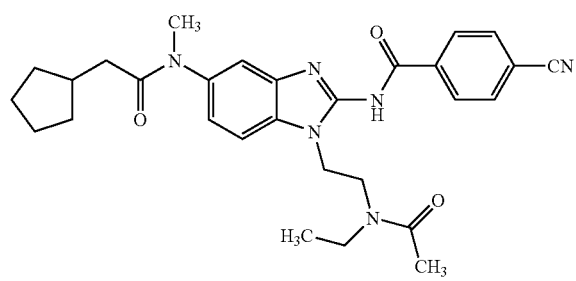
86
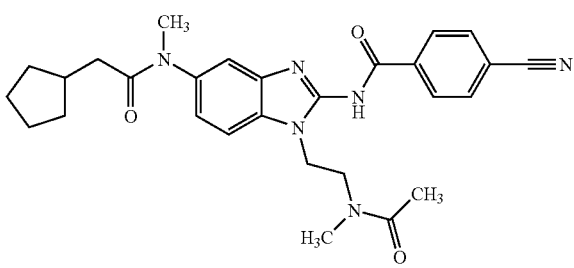
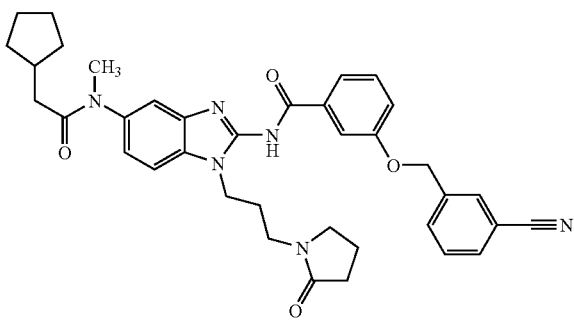
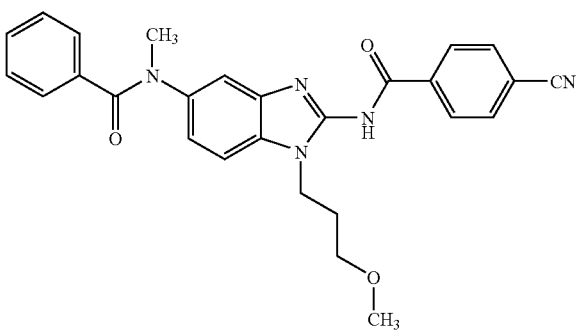
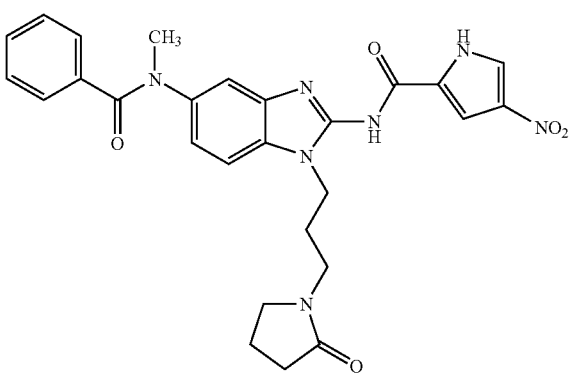
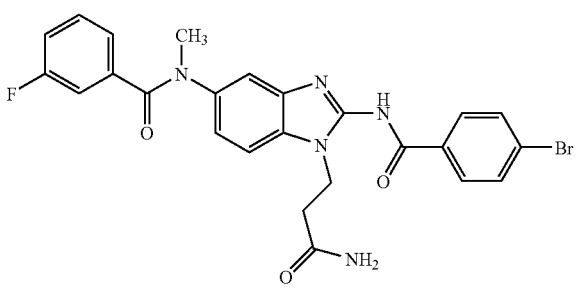

87
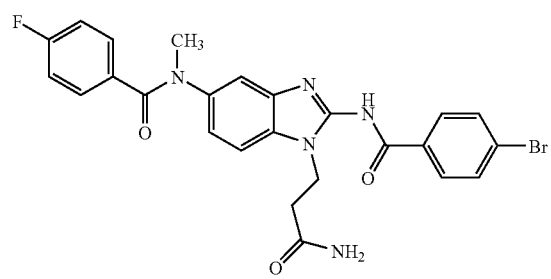
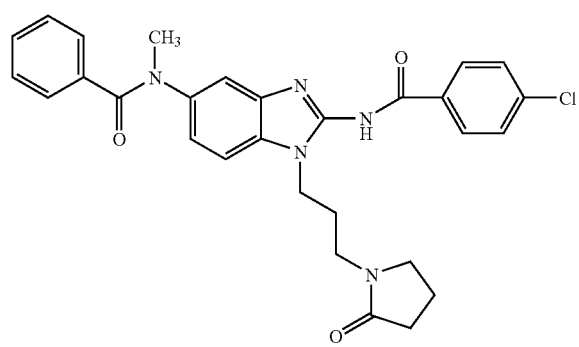
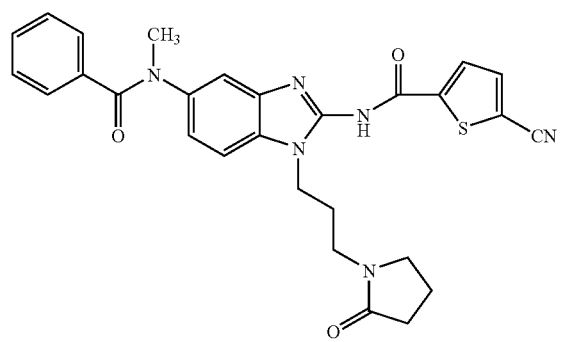
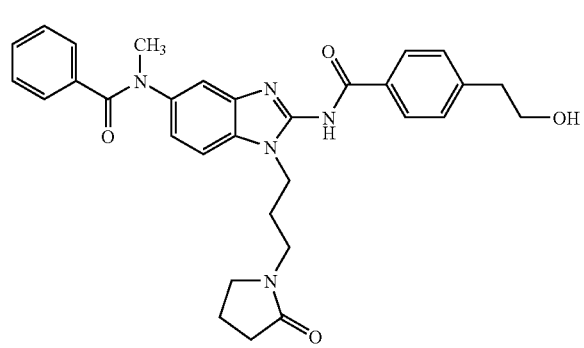
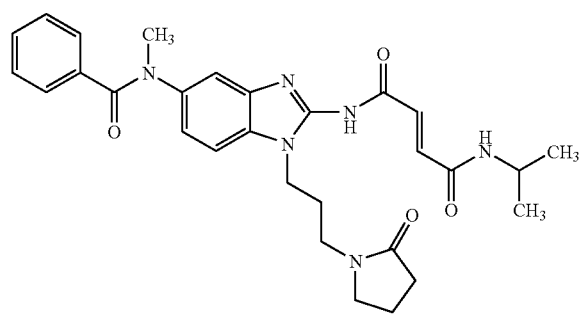
-continued
88
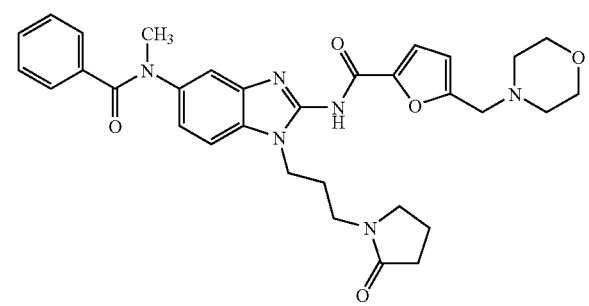
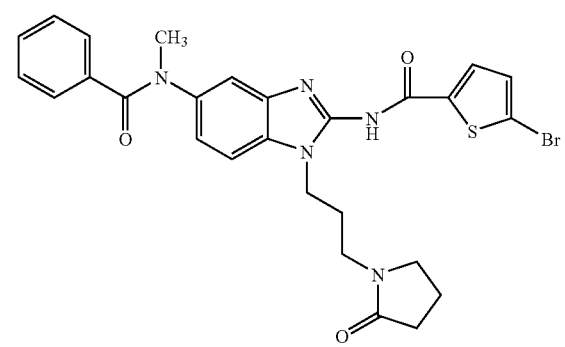
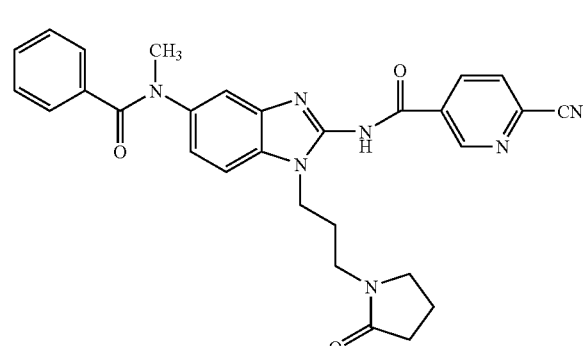
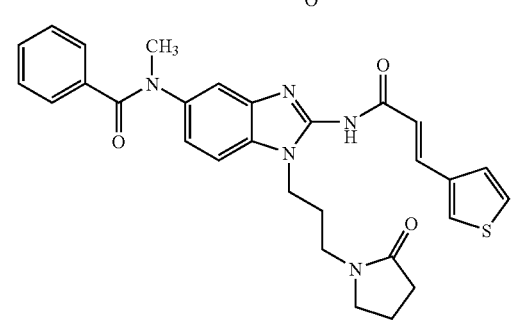
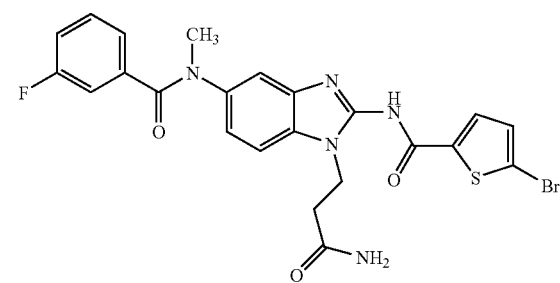

-continued
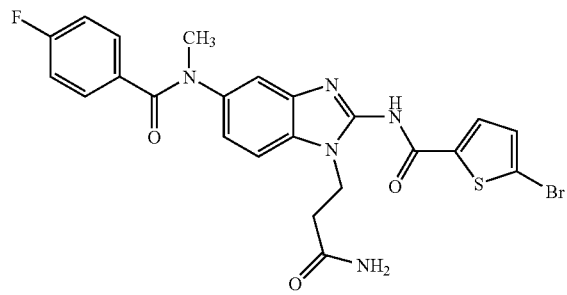
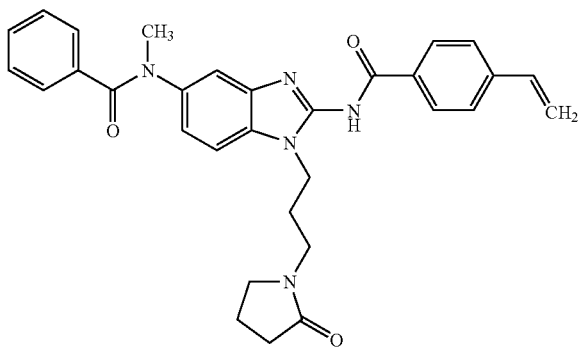
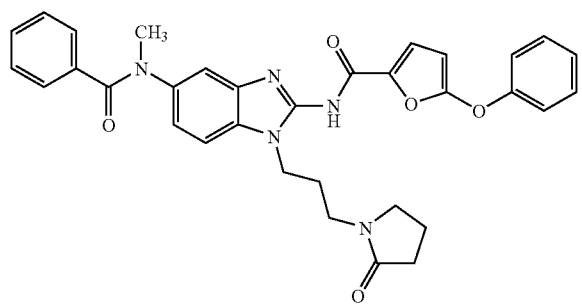
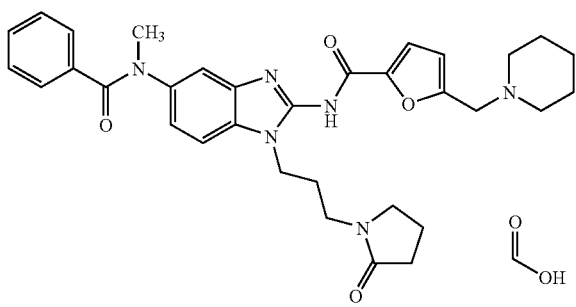
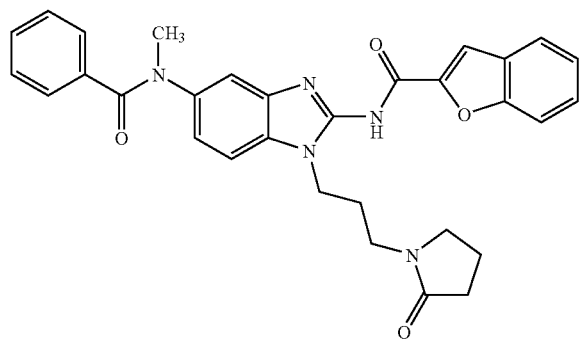
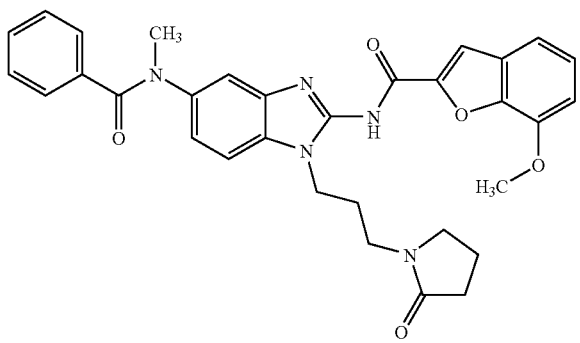
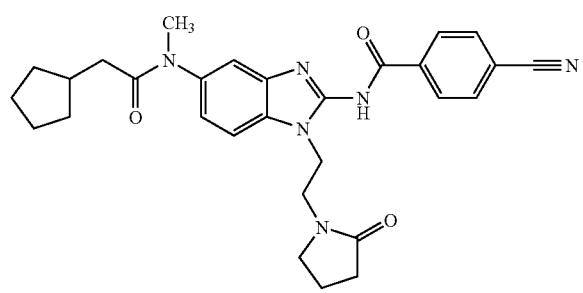
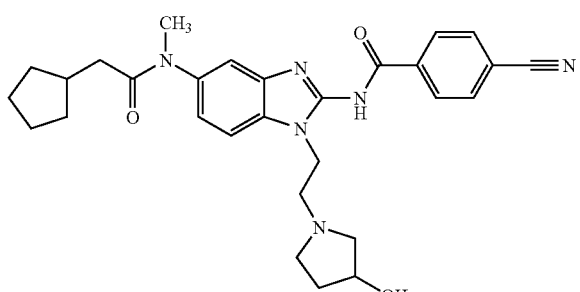
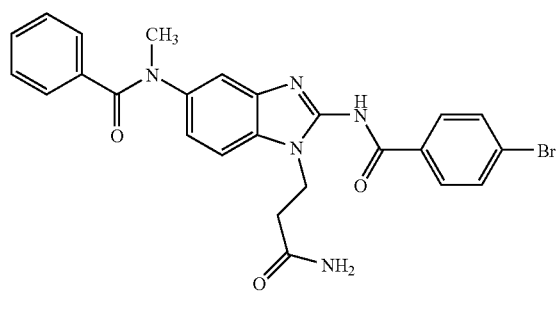
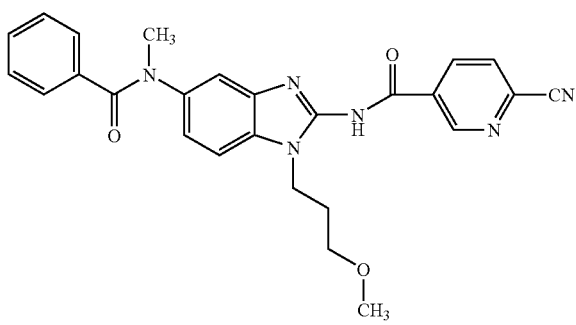

-continued
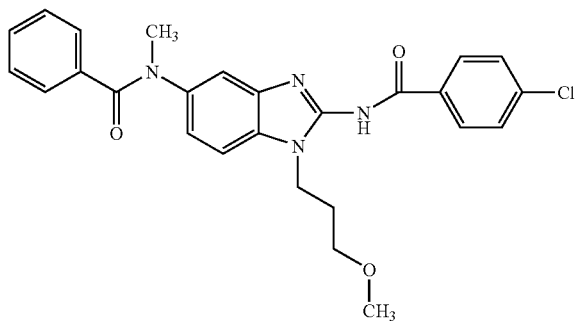
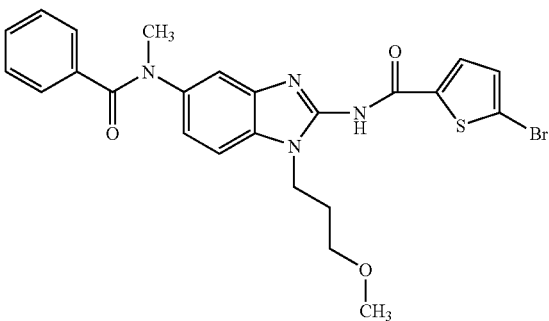
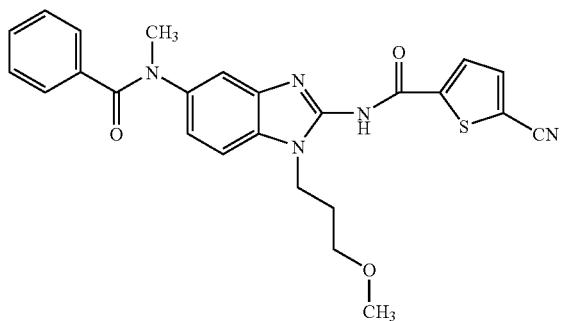
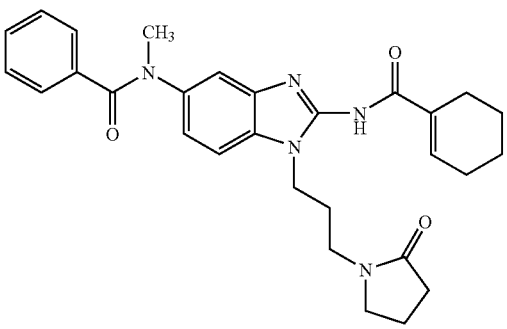
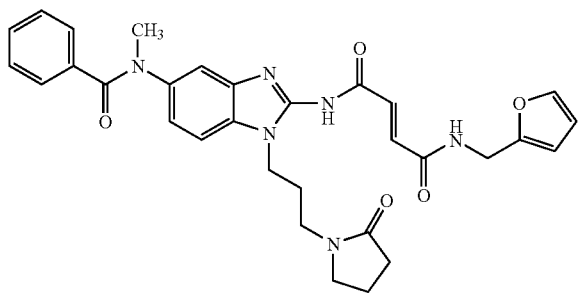
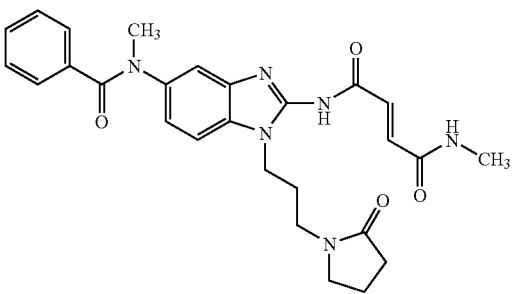
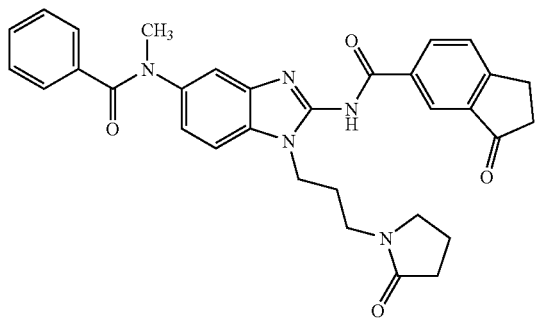
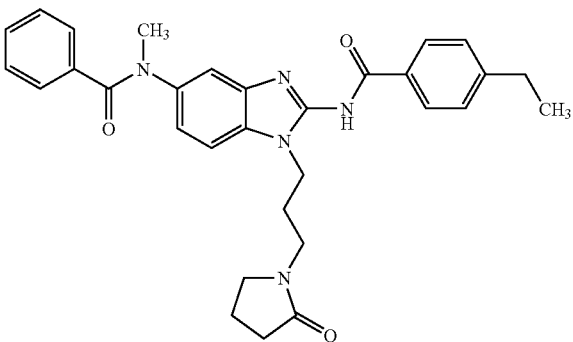
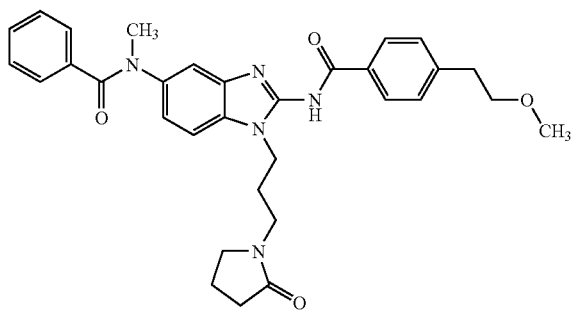
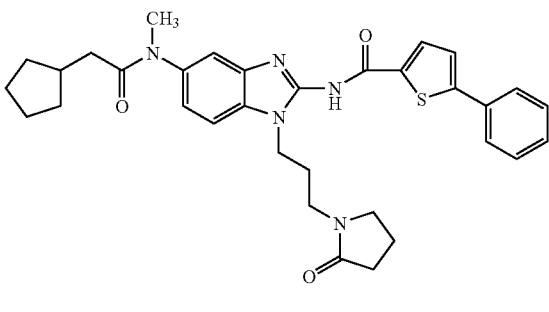

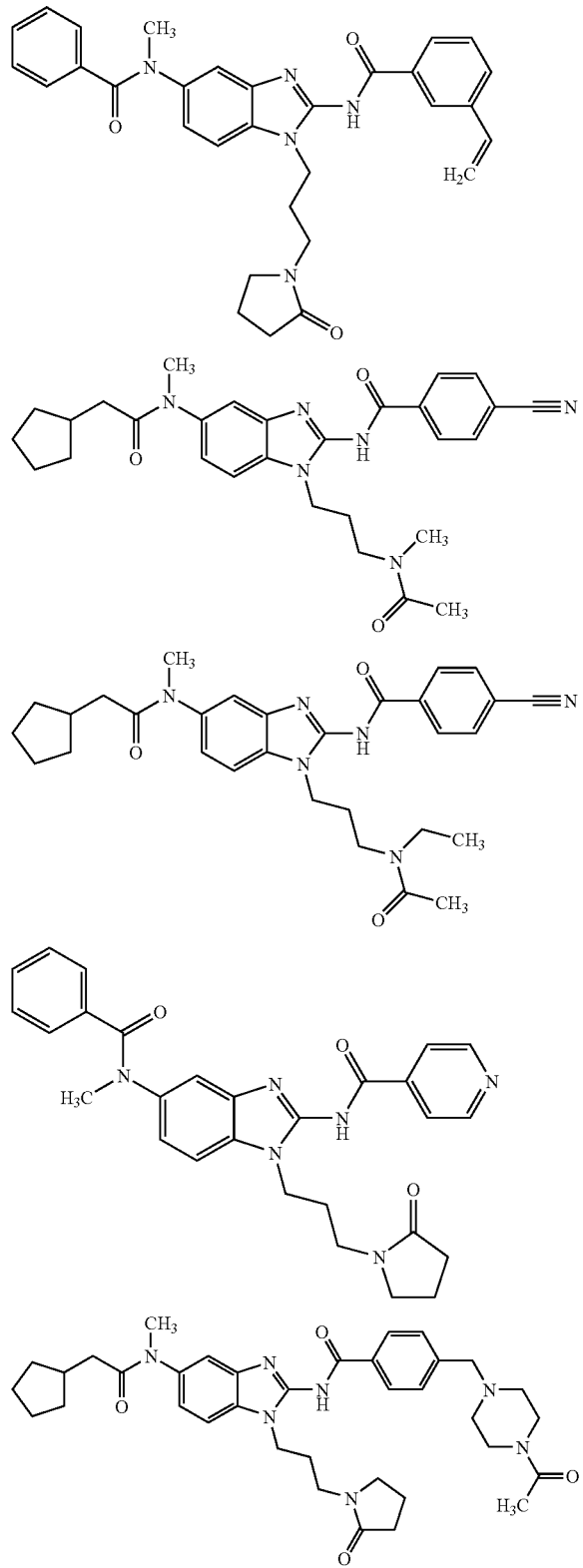
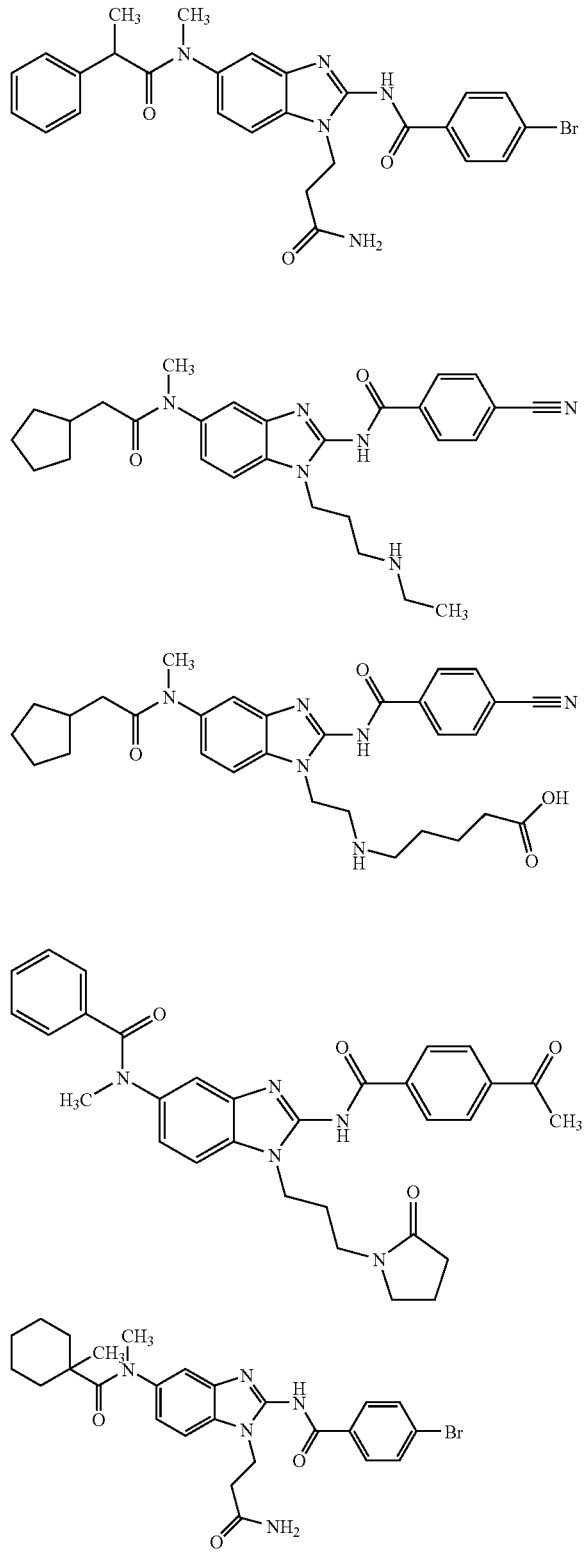

-continued
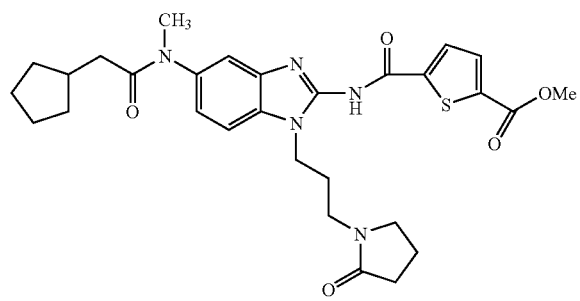
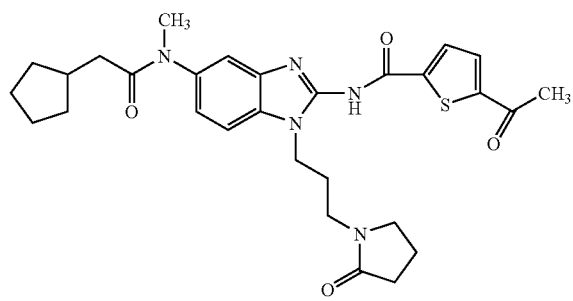
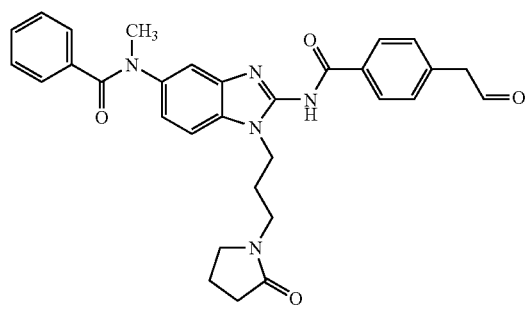
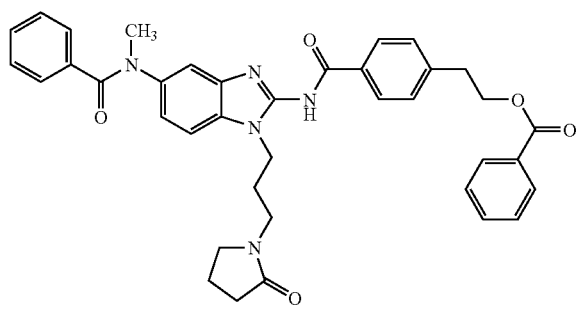
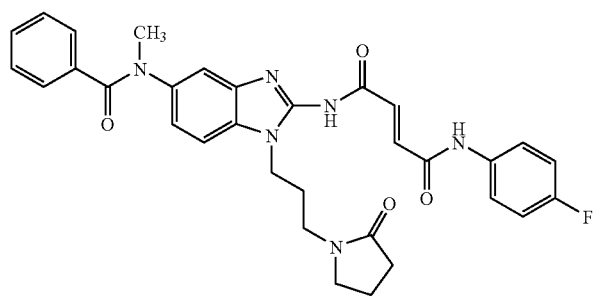
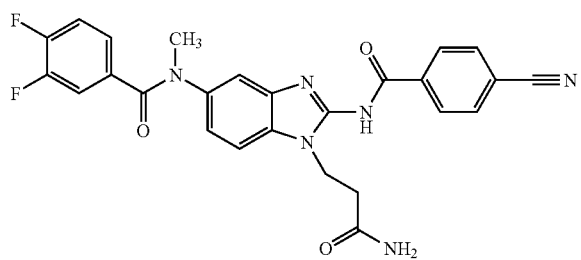
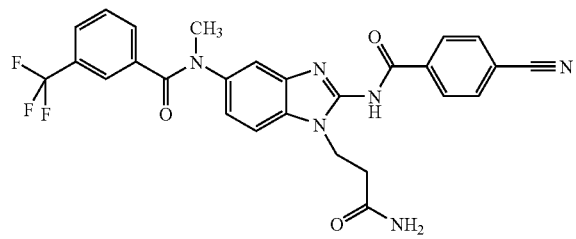
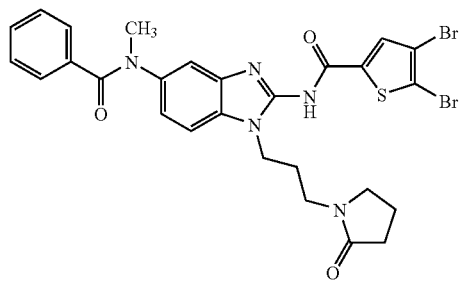
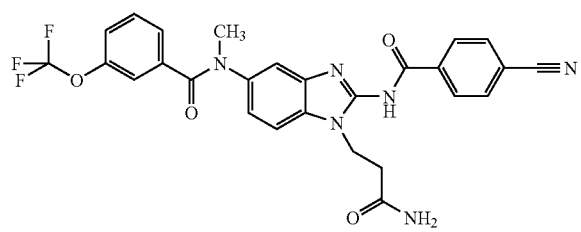
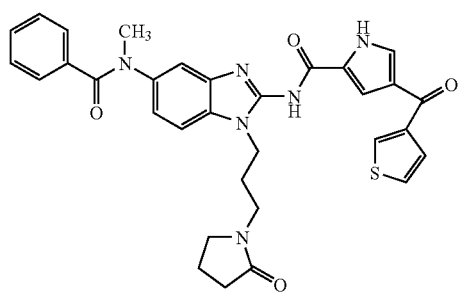

97 98
-continued
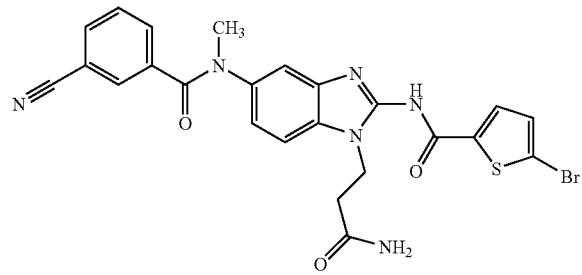
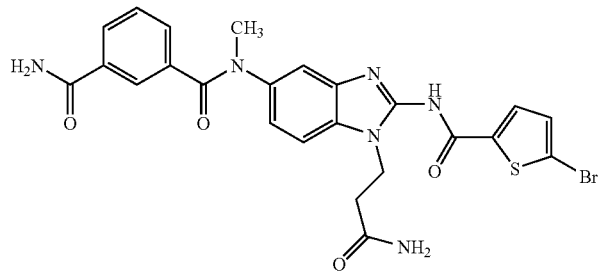
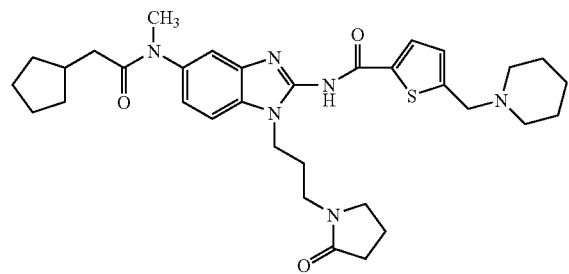
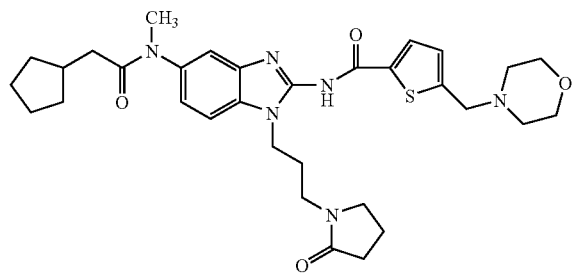
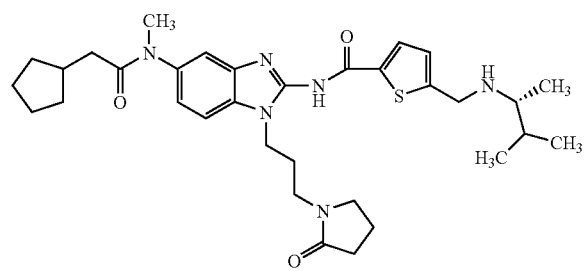
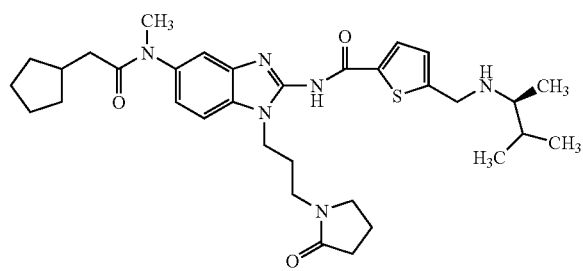
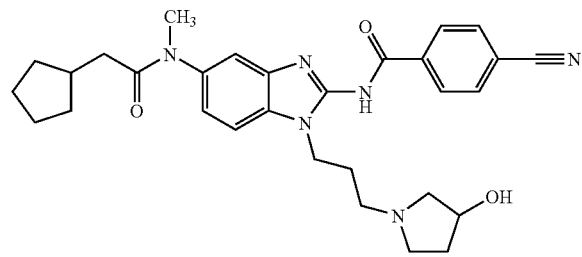
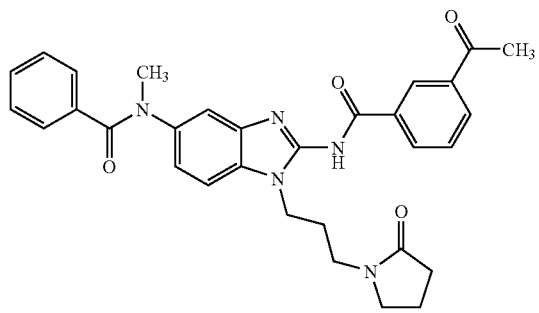
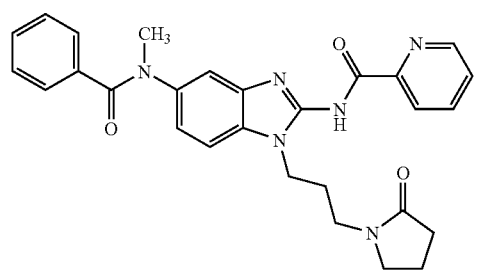
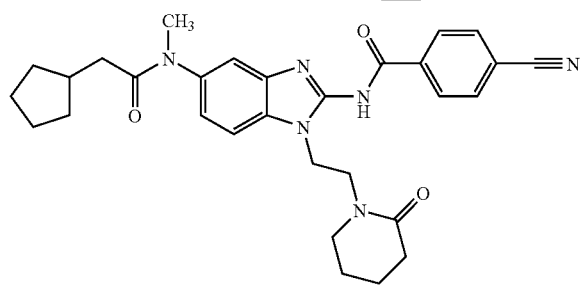
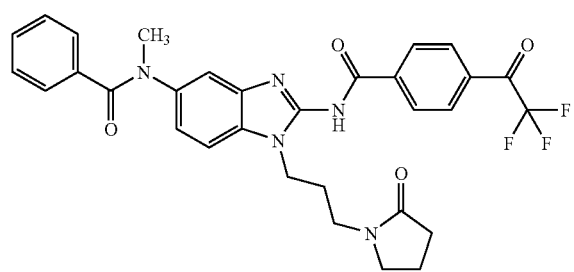
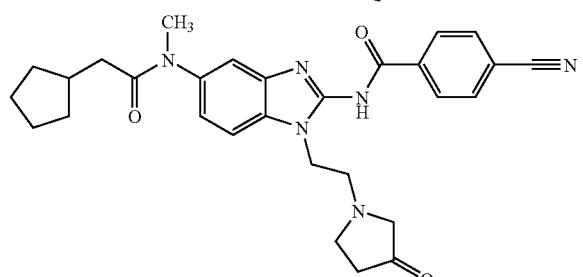

-continued
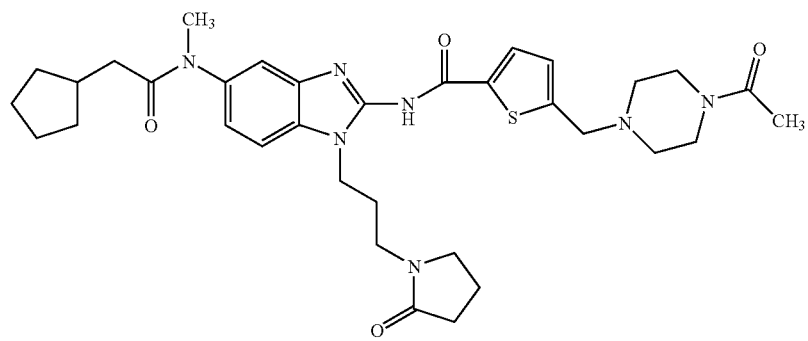
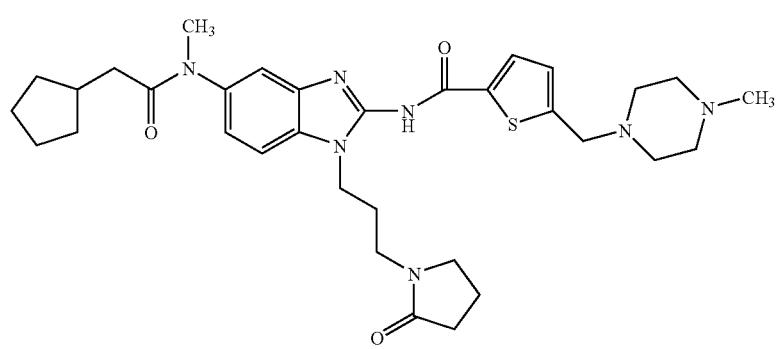
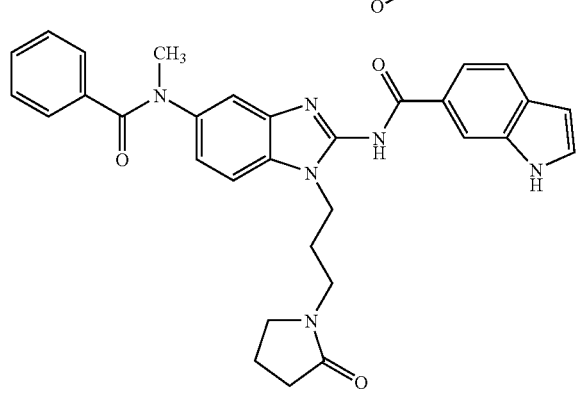
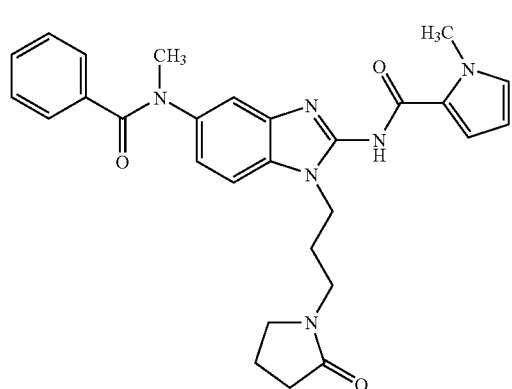
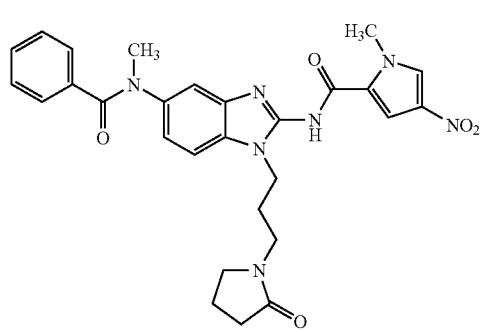
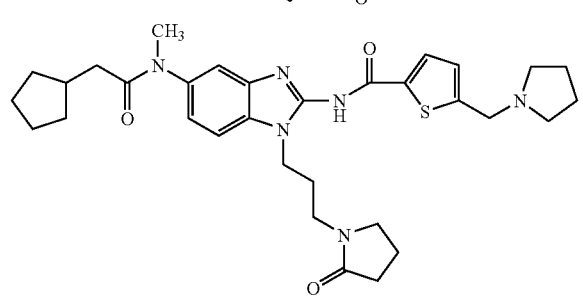
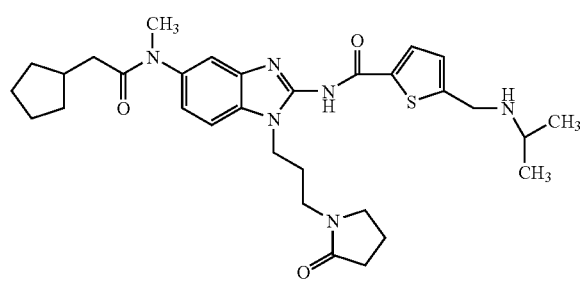
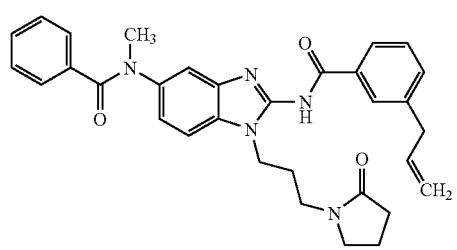

-continued
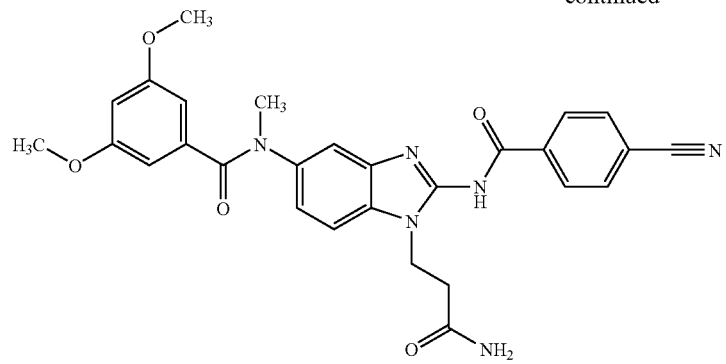
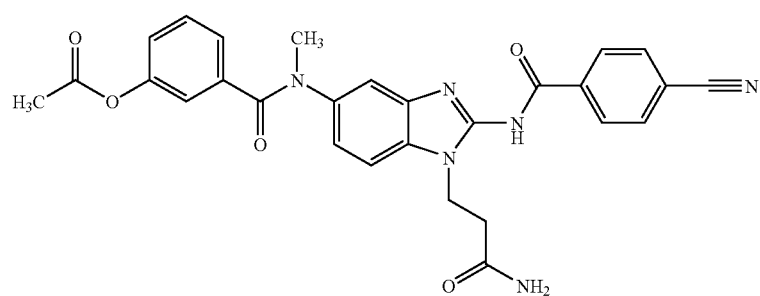
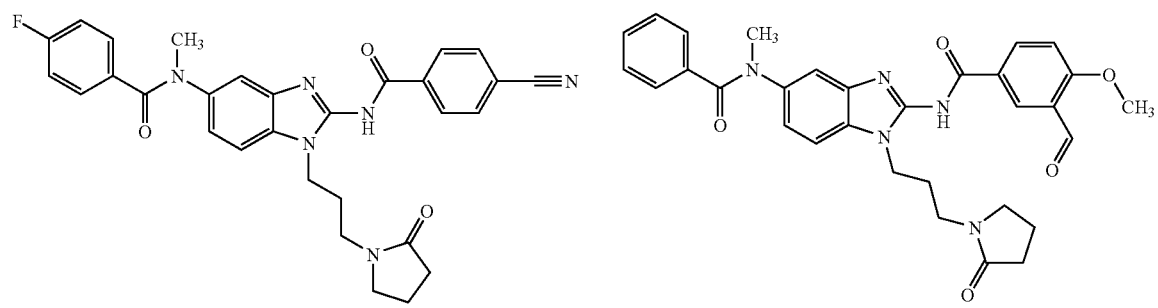
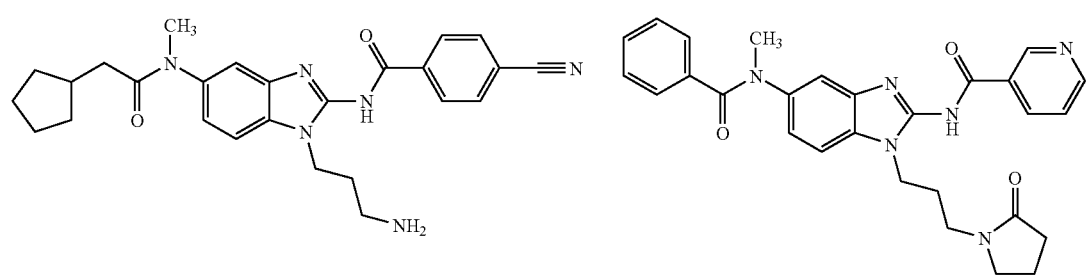
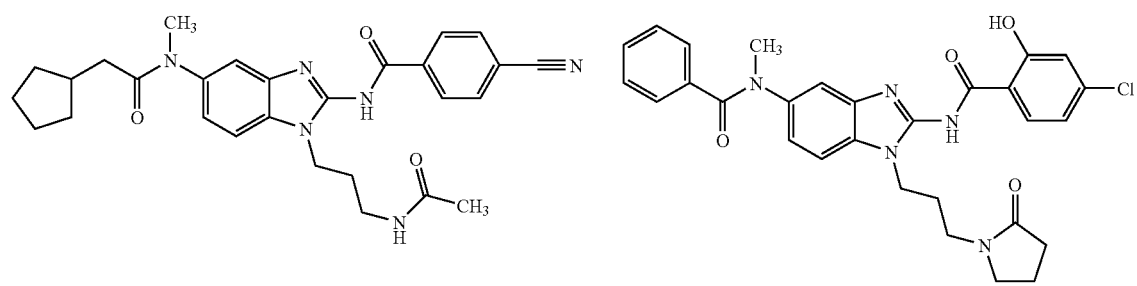

103 104
-continued
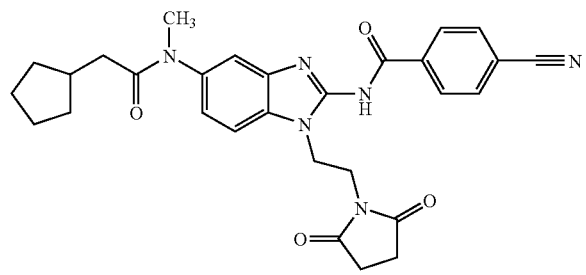
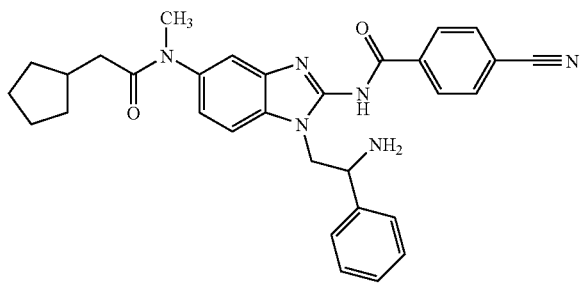
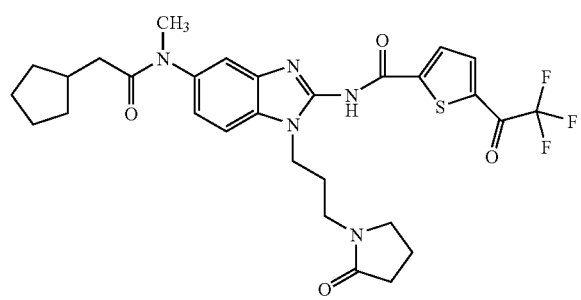
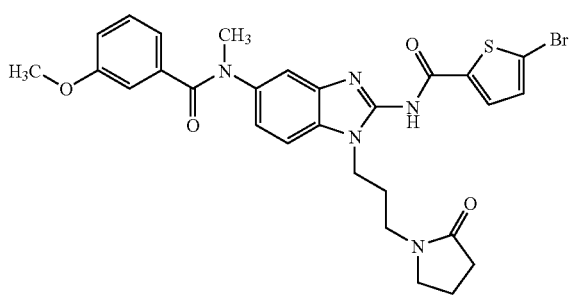
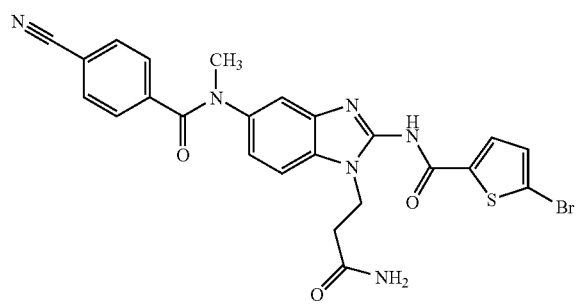
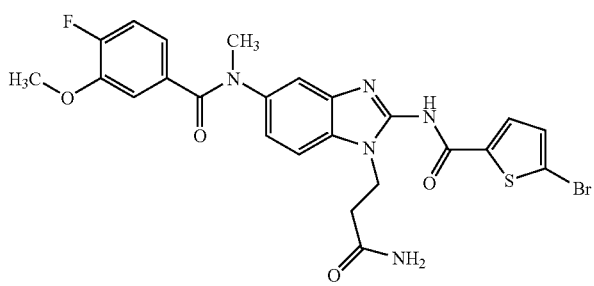
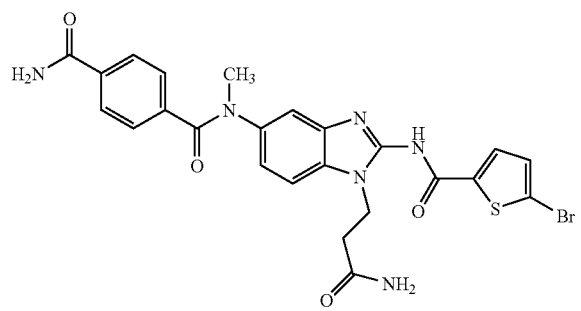
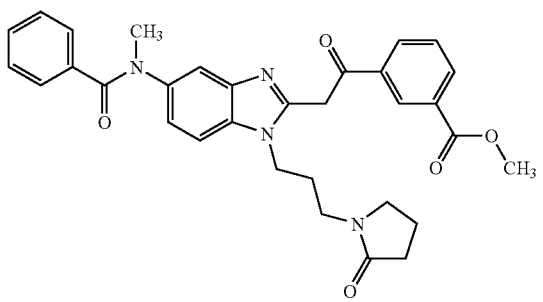
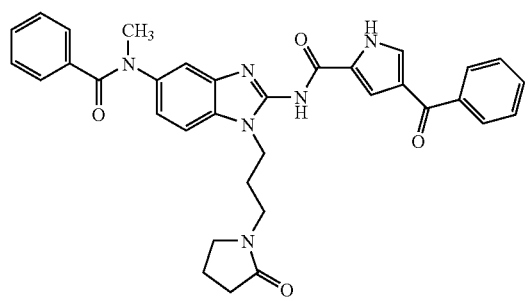
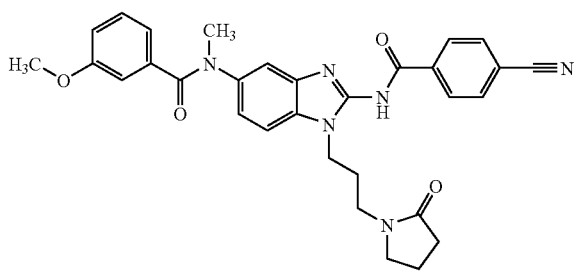

105
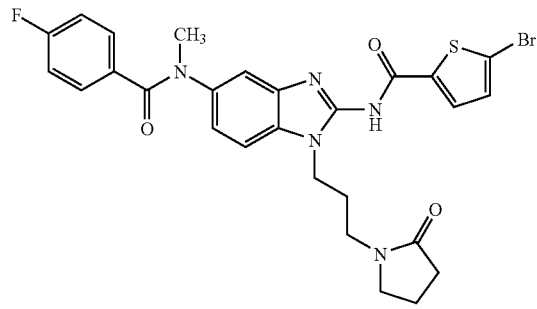
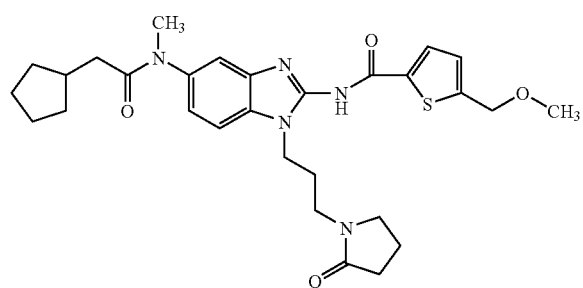
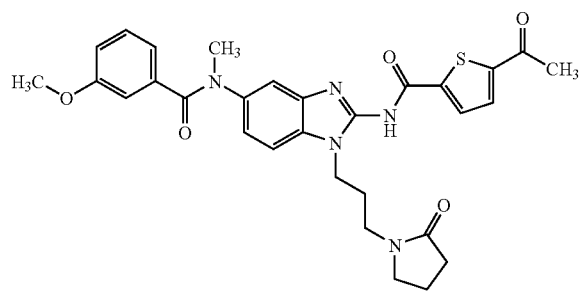
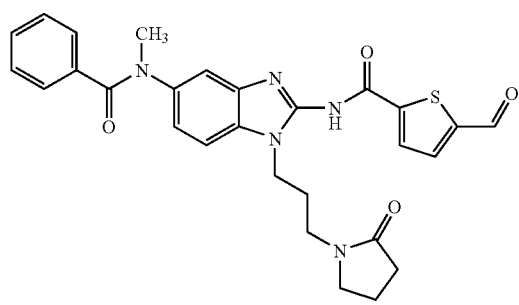
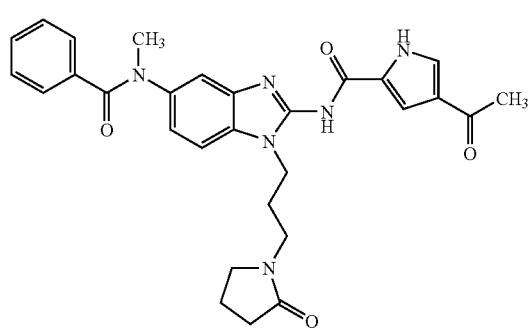
106
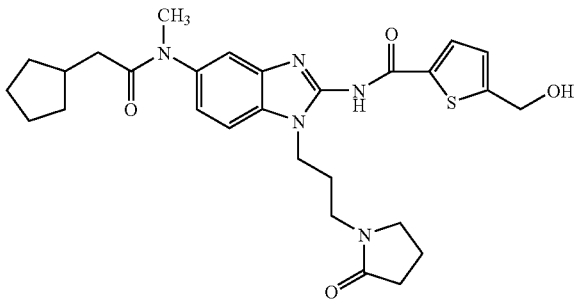
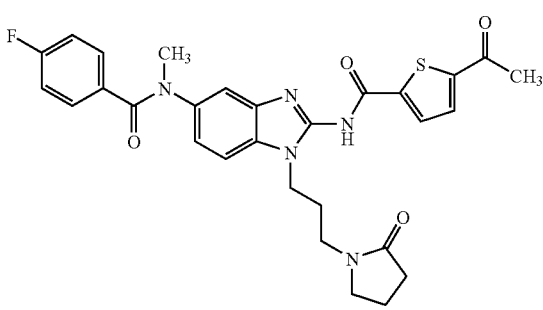
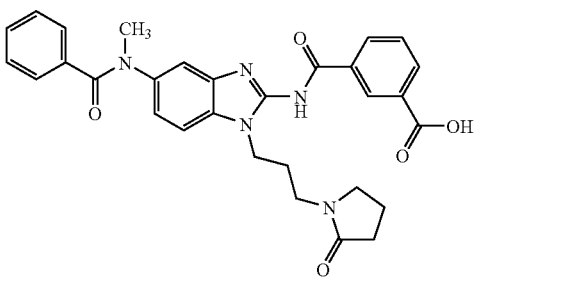
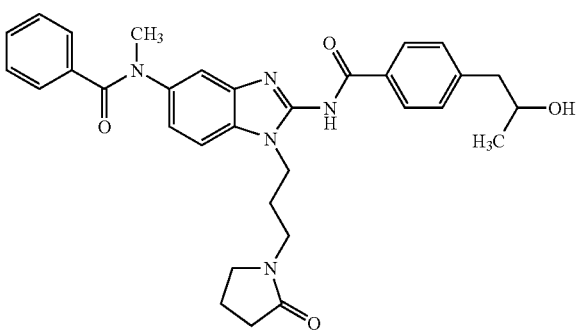
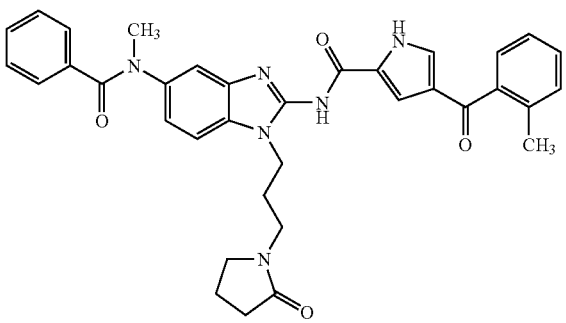

-continued
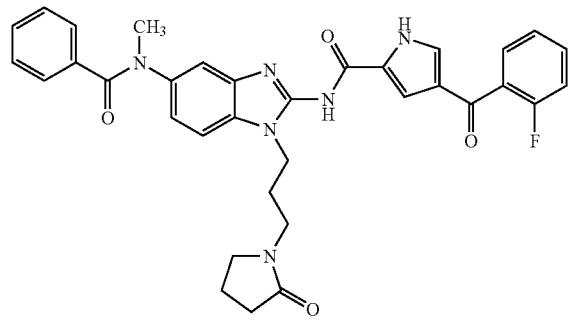
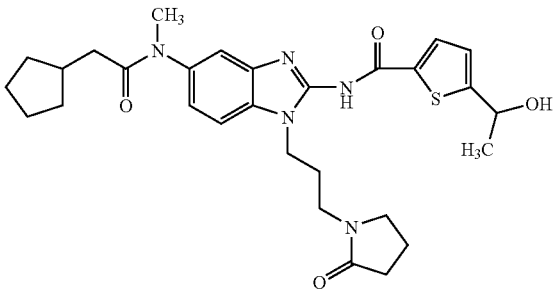
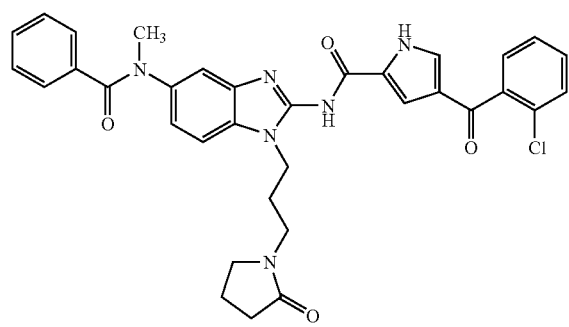
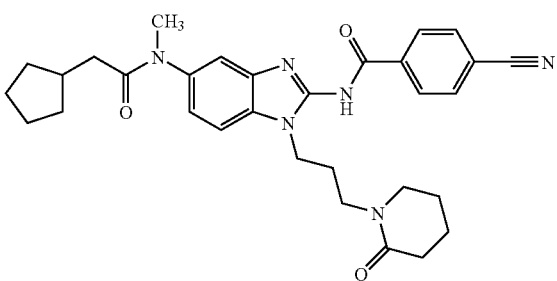
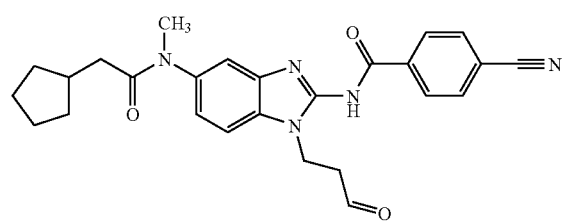
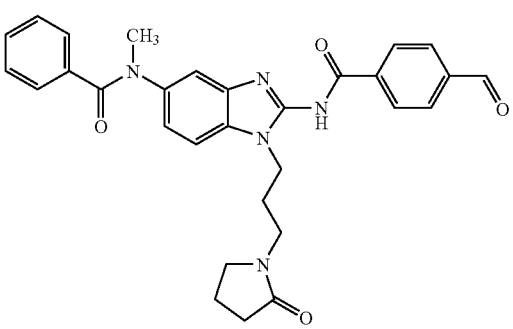
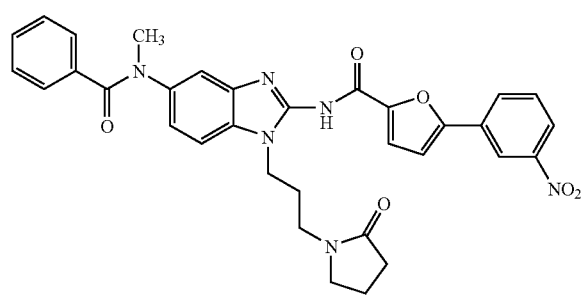
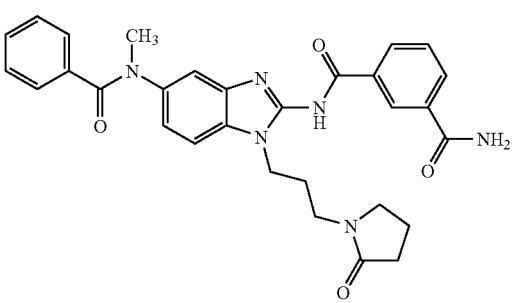
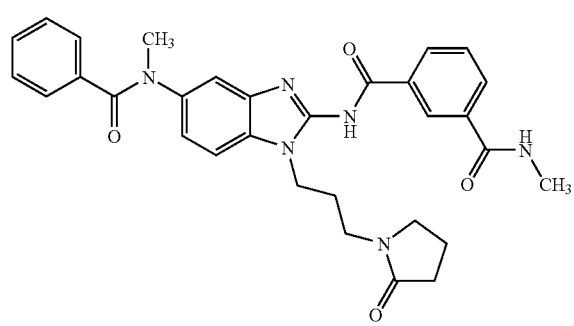
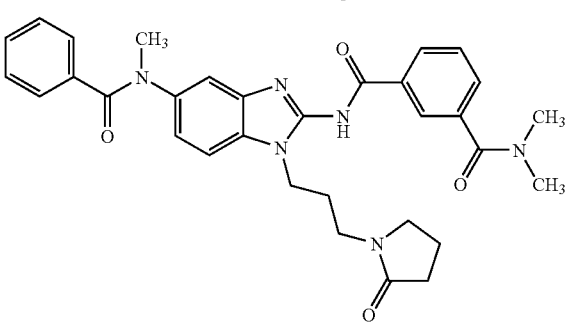

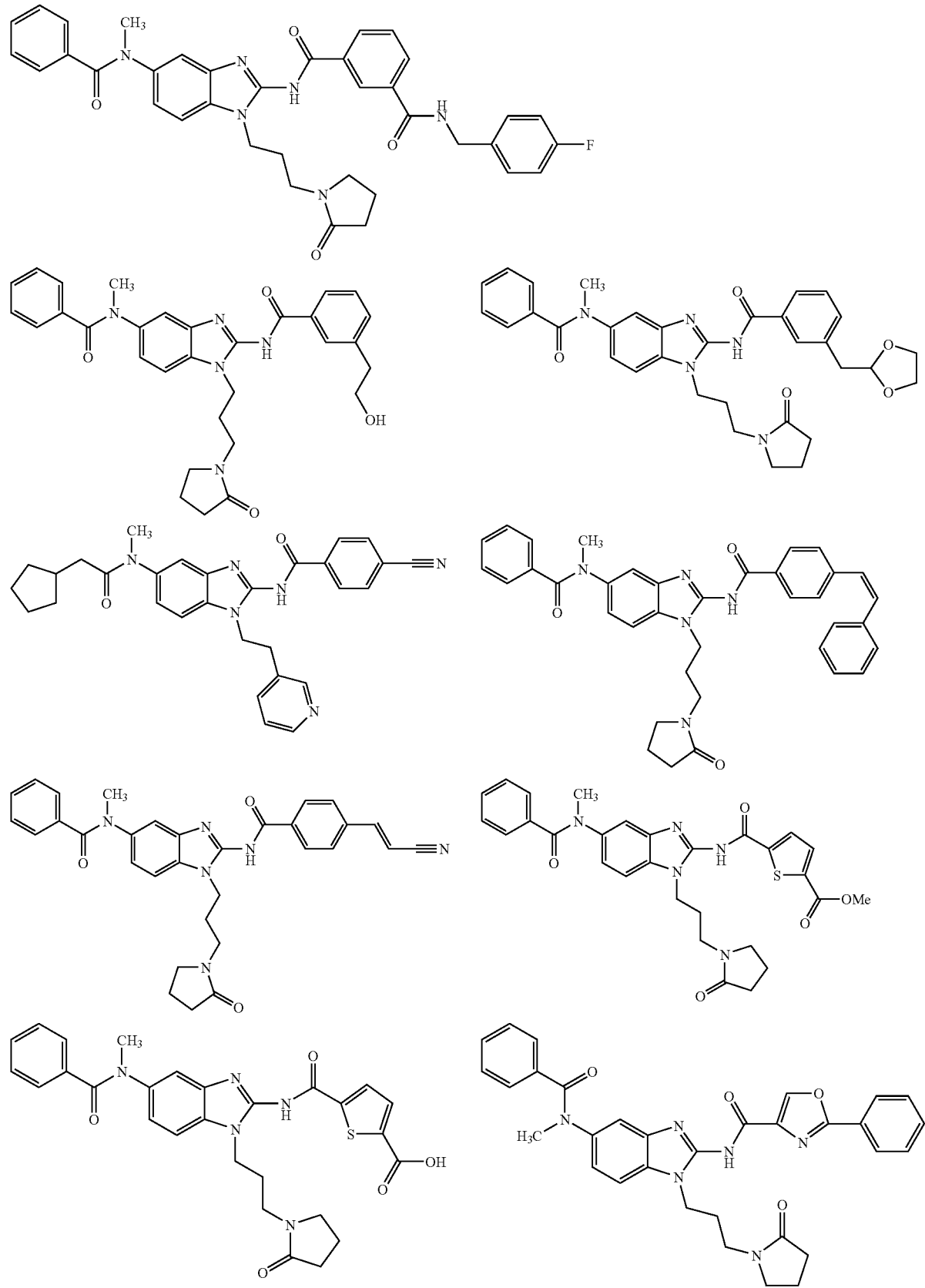

| 111 | 112 |
|---|---|
| 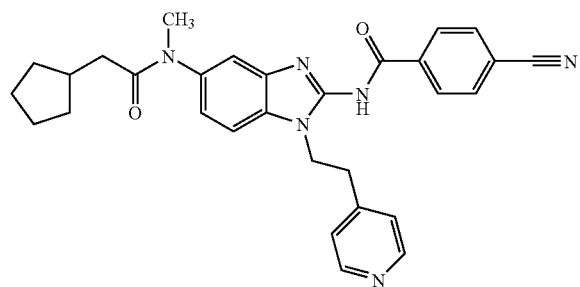 | 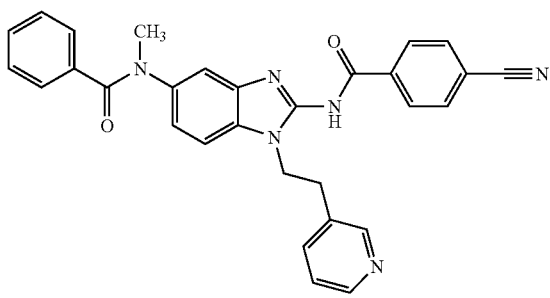 |
| 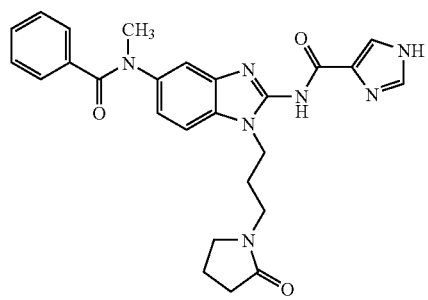 | 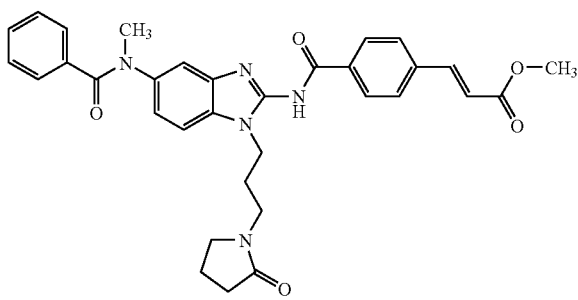 |
| 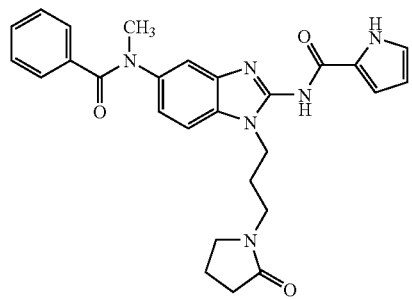 | 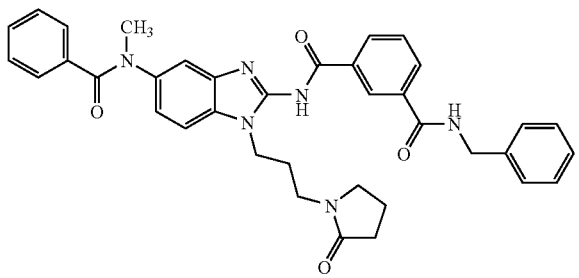 |
| 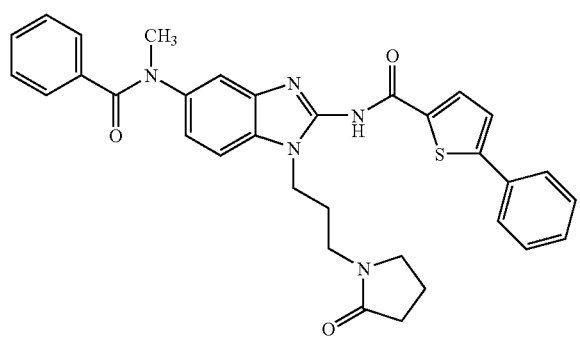 | 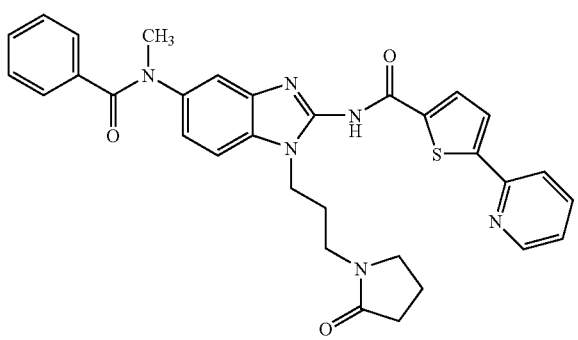 |
| 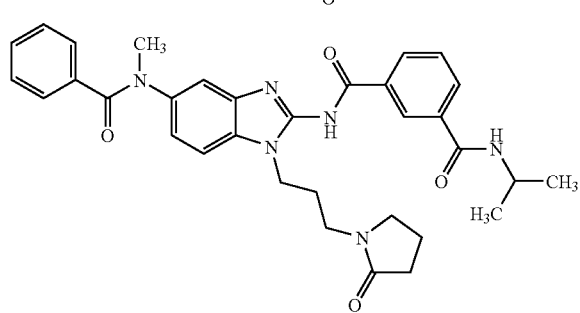 | 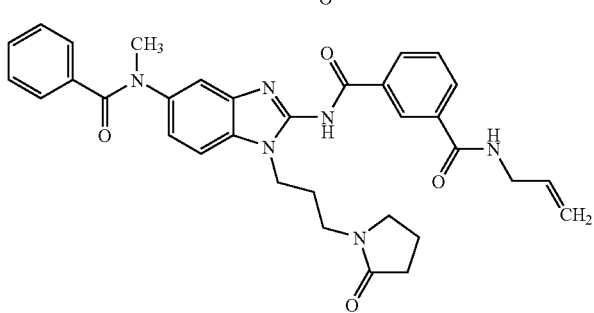 |

-continued
| 113 | 114 |
|---|---|
| 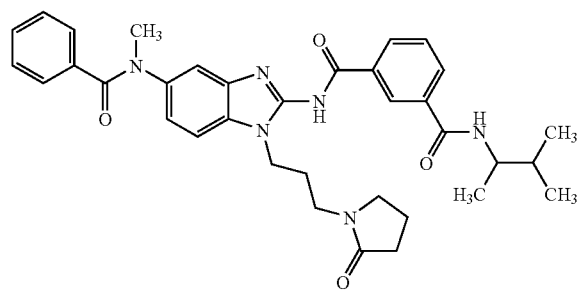 | 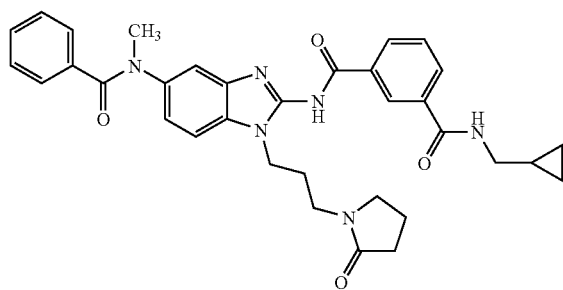 |
| 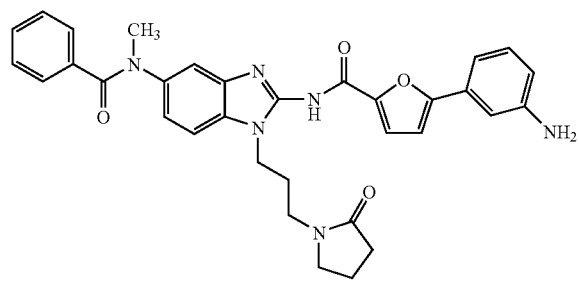 | 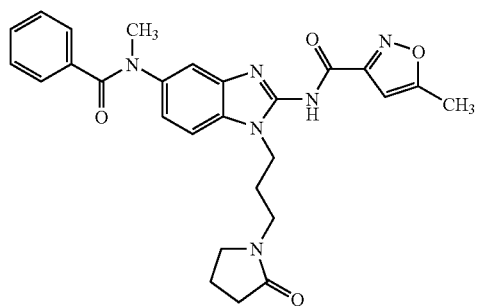 |
| 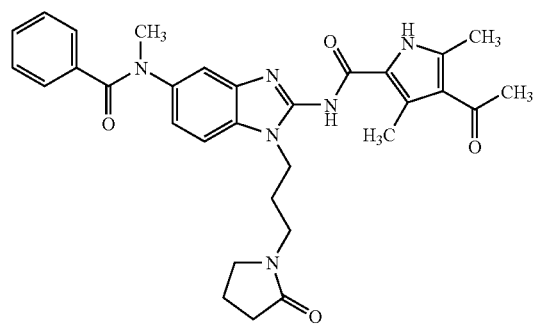 | 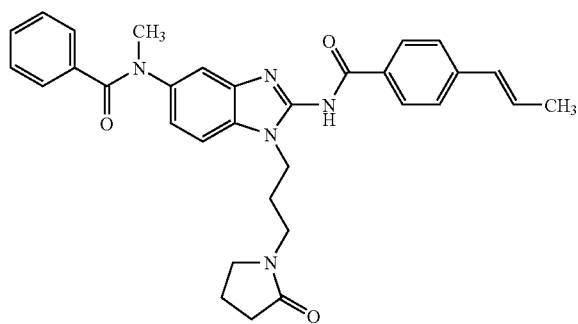 |
| 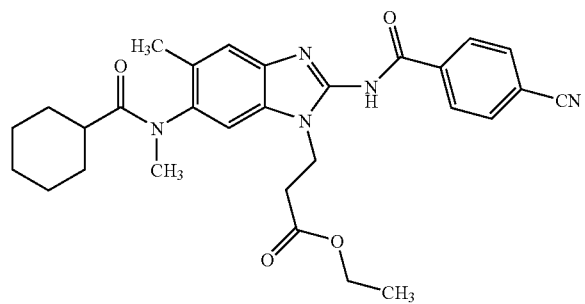 | 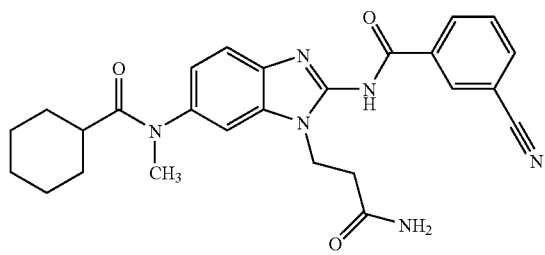 |
| 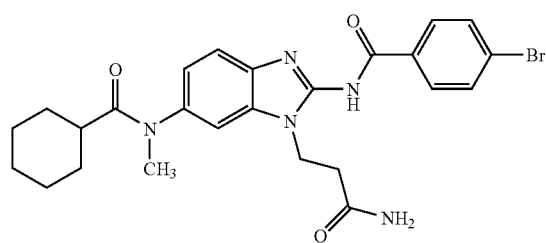 | 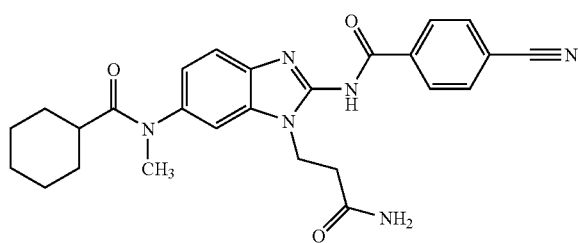 |

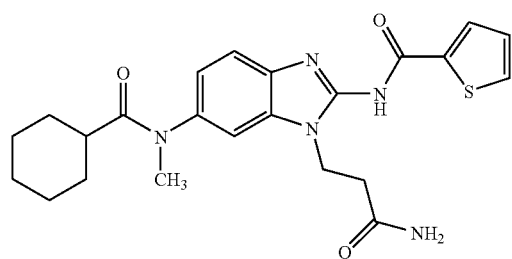
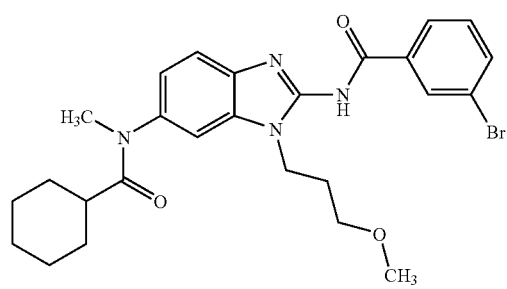
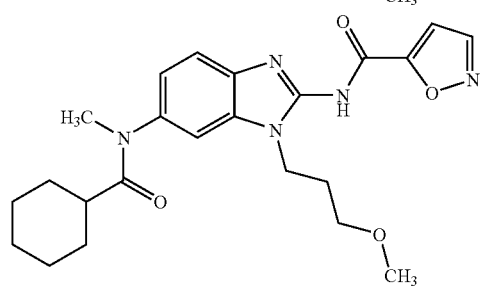
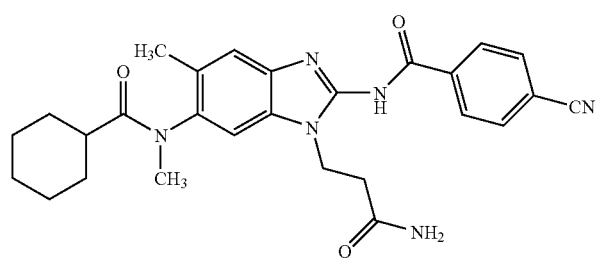
or
the pharmaceutically acceptable derivatives thereof.
In another embodiment there is provided representative compounds of the invention which can be made in accordance with the general schemes and working examples presented below:
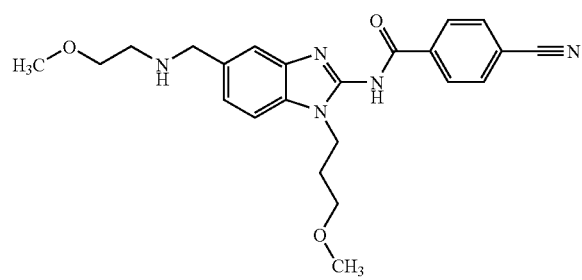
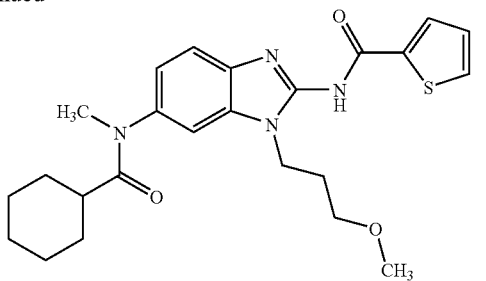
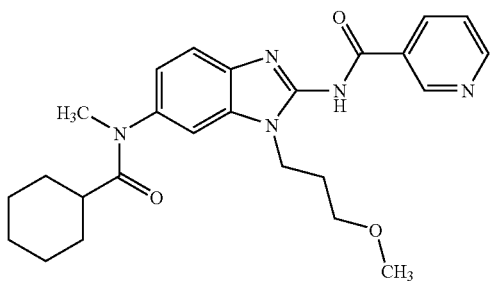
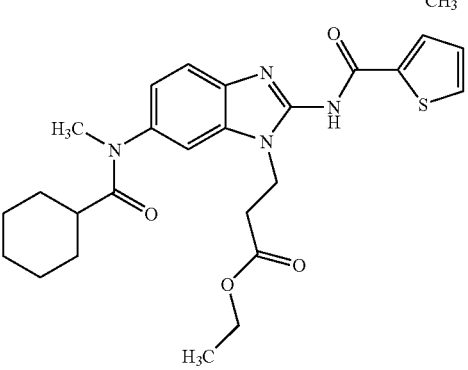
and
-continued
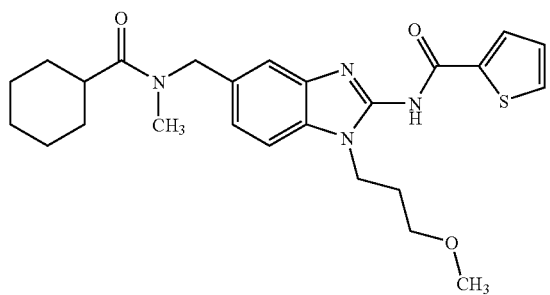

-continued
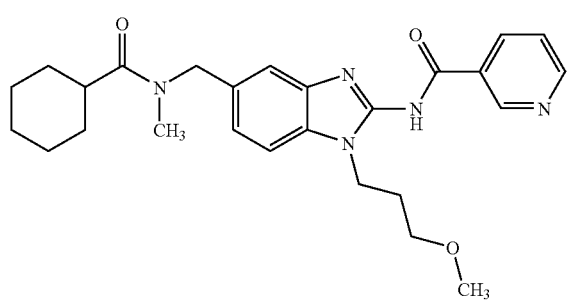
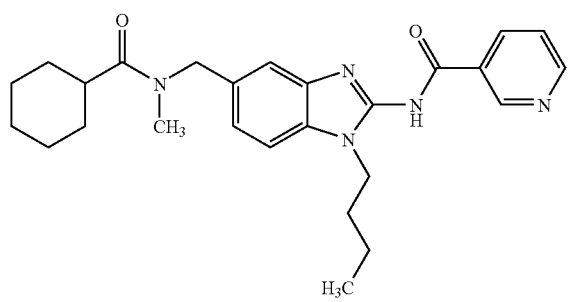
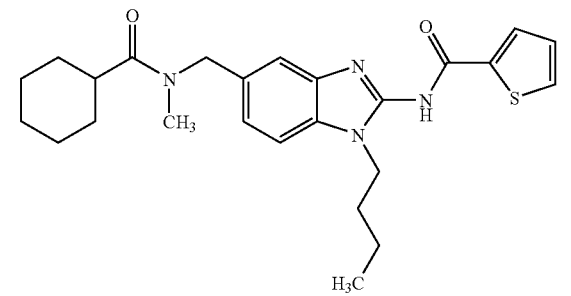
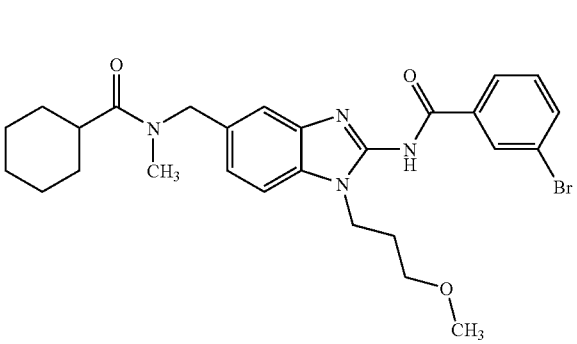
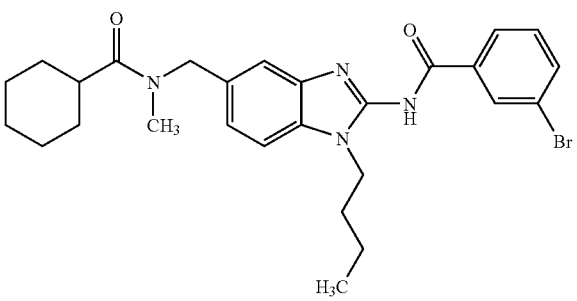
-continued
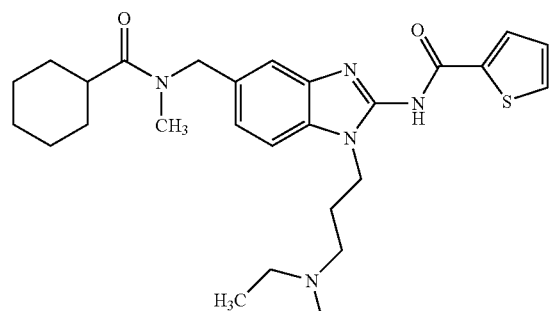
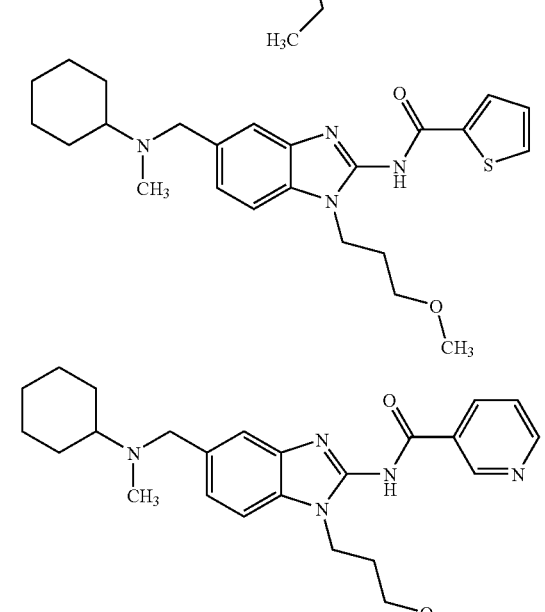
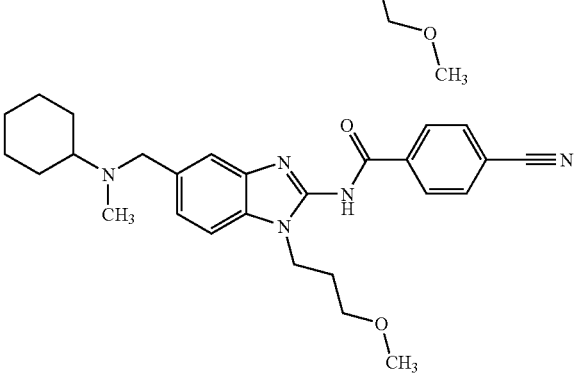

119
-continued
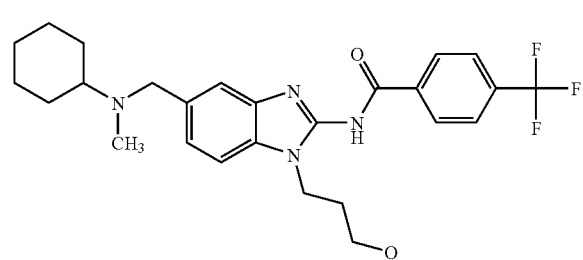
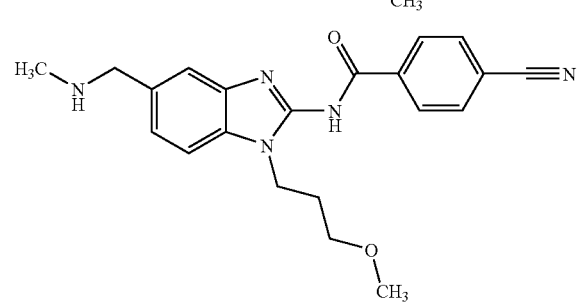
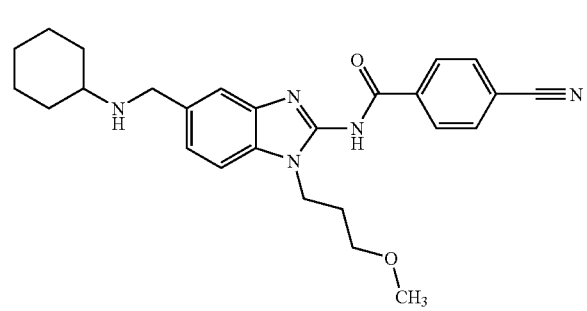
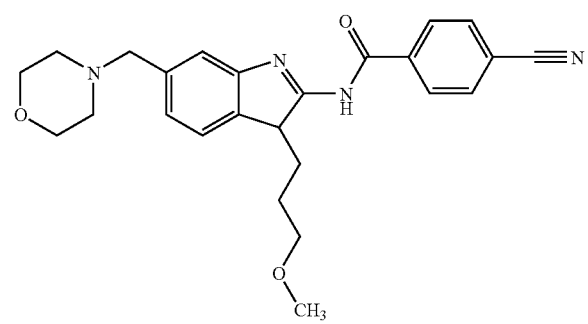
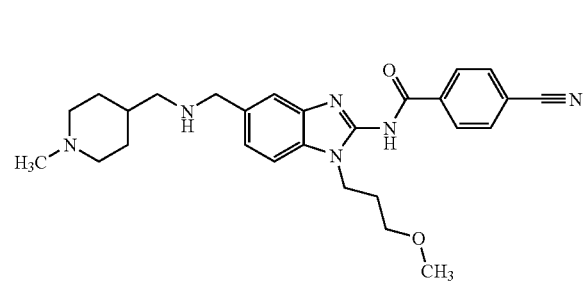
120
-continued
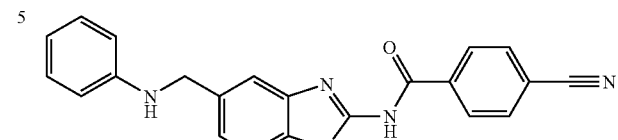
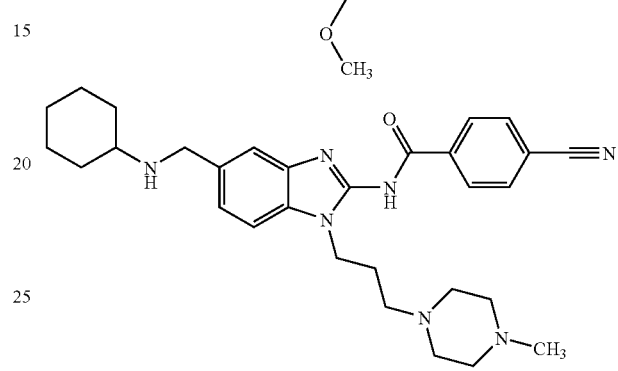
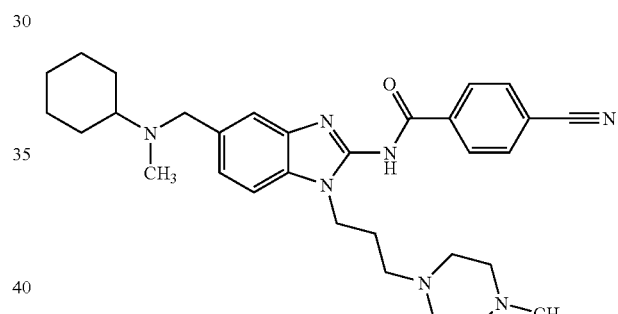
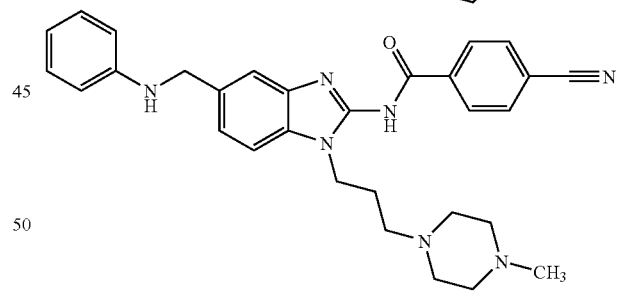
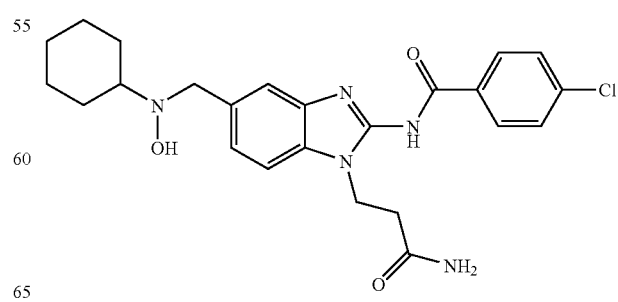

-continued
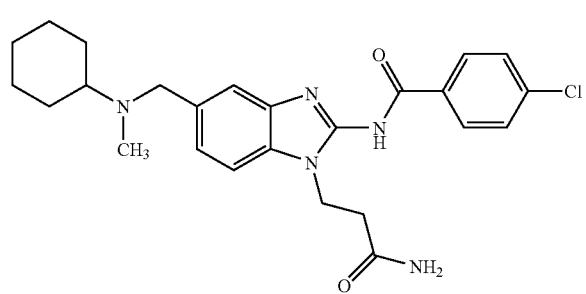
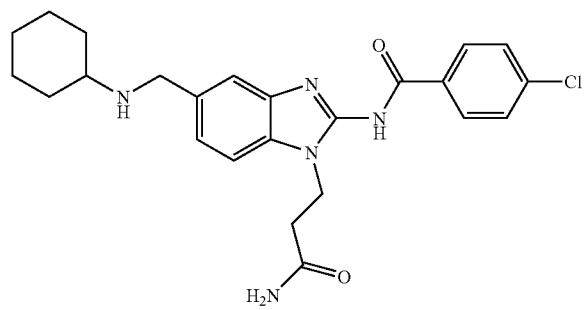
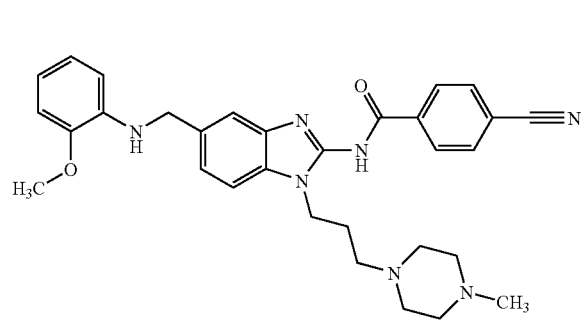
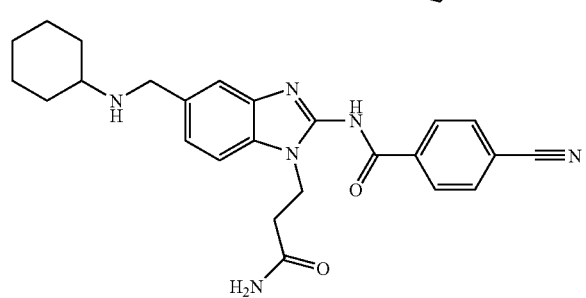
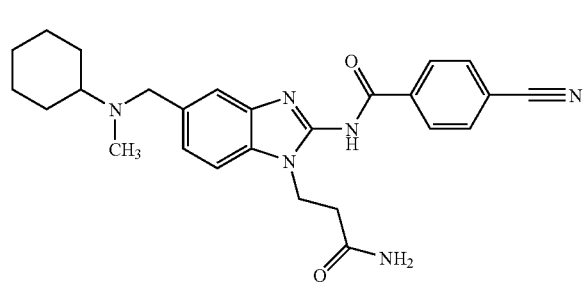
-continued
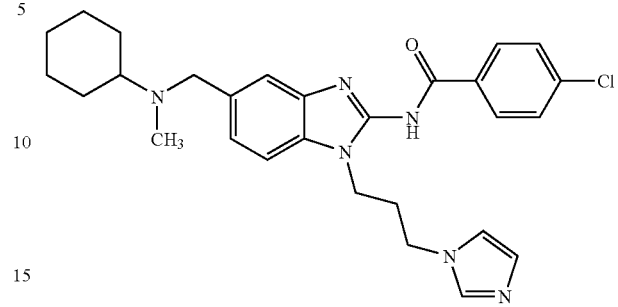
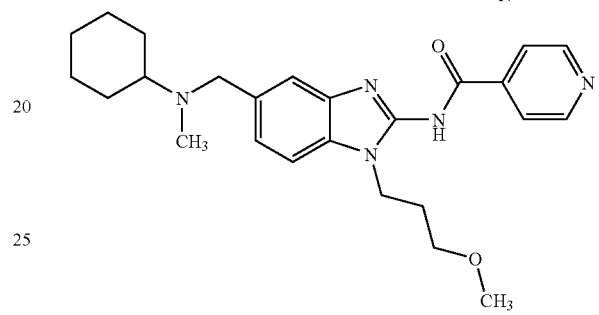
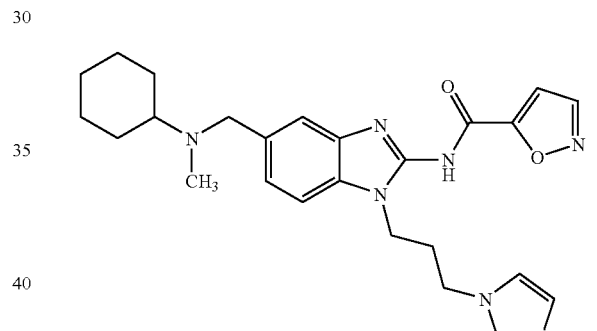
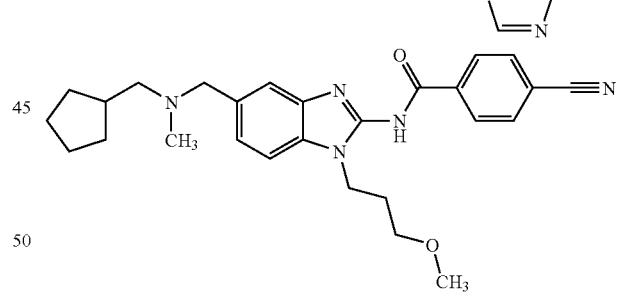
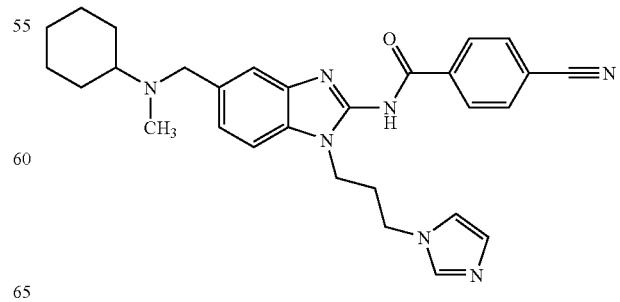

-continued
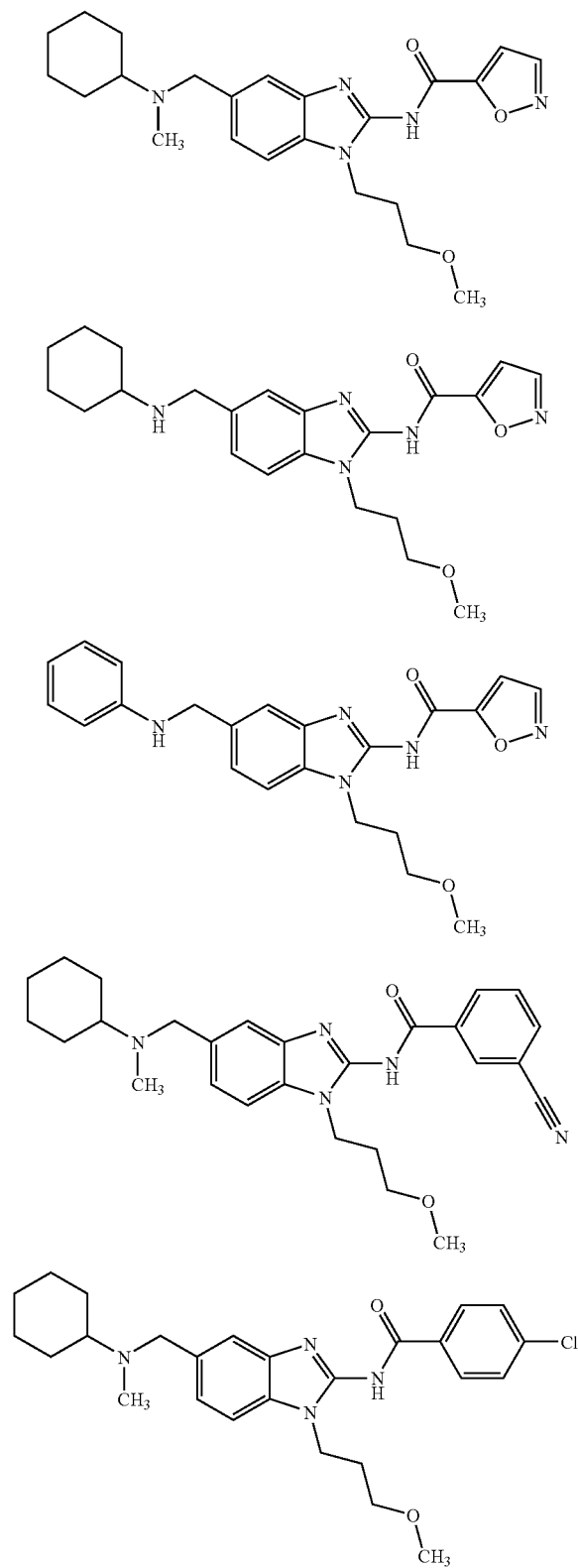
-continued
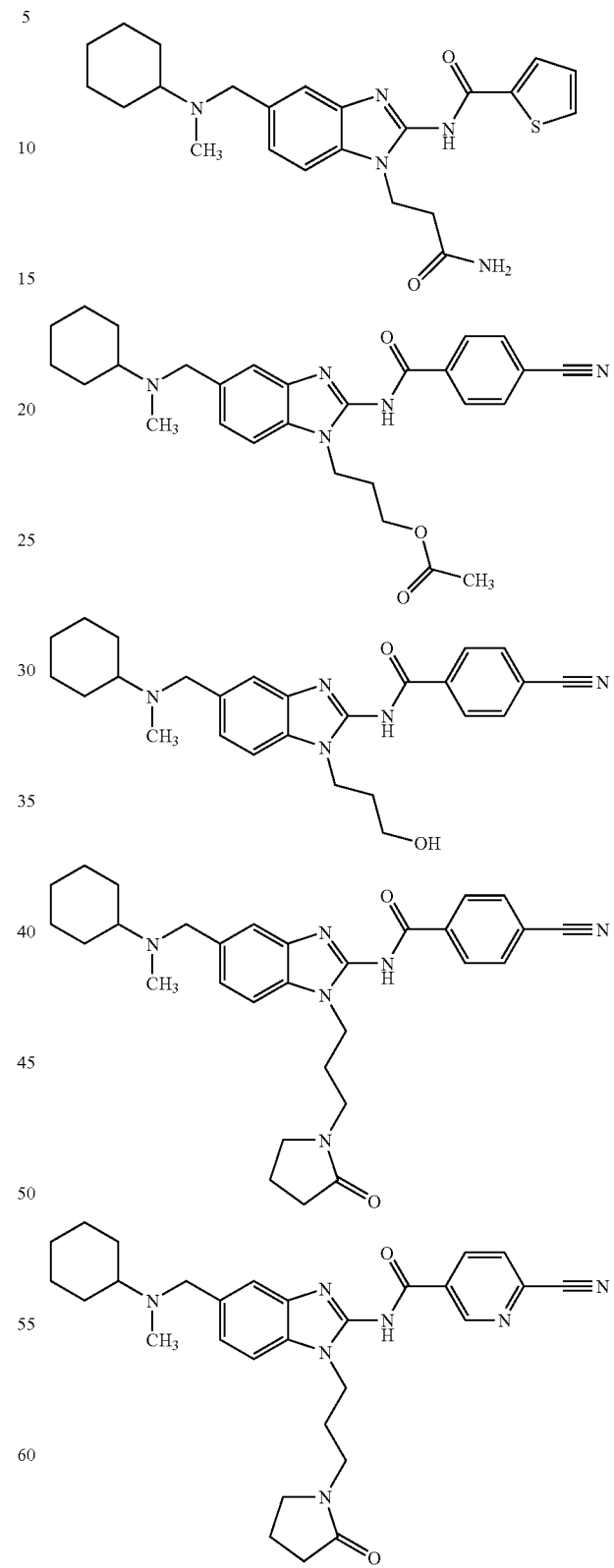

-continued
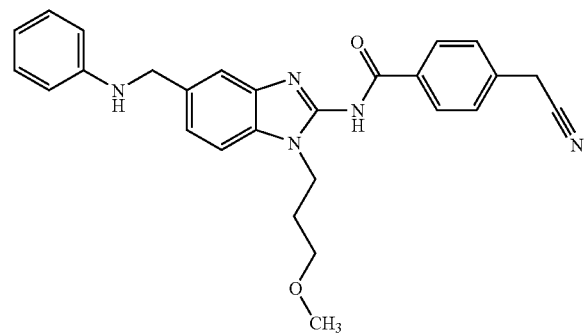
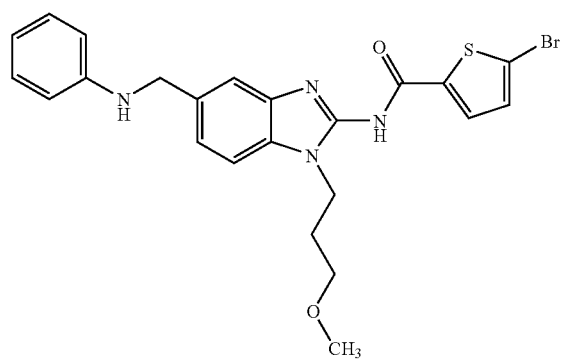
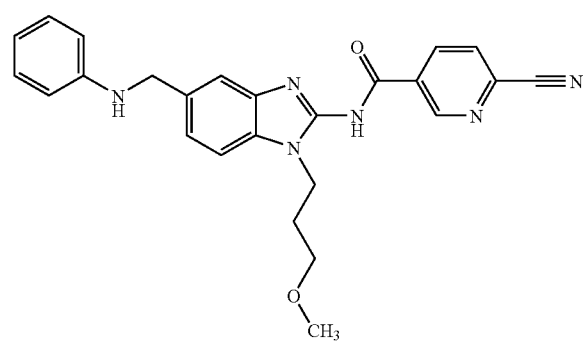
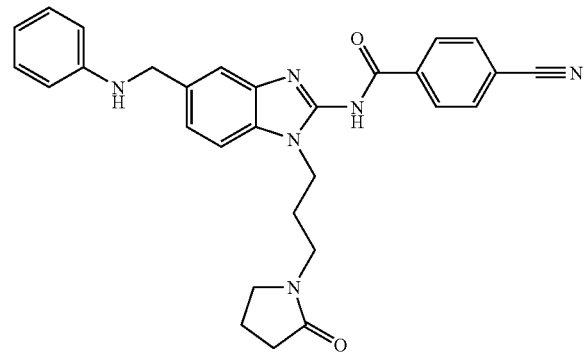
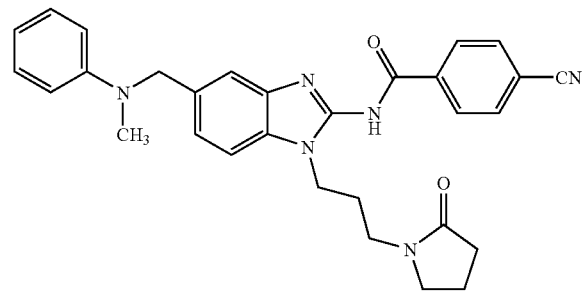
-continued
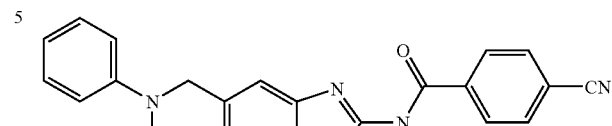
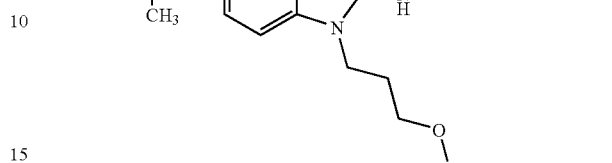
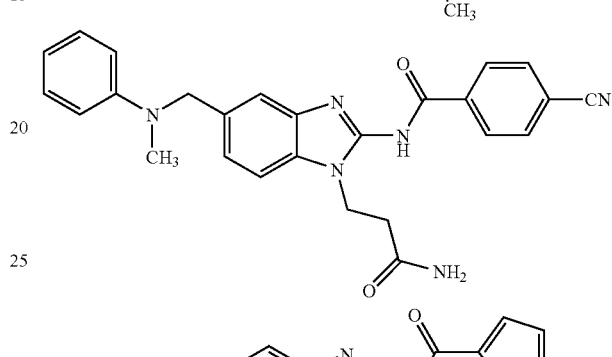
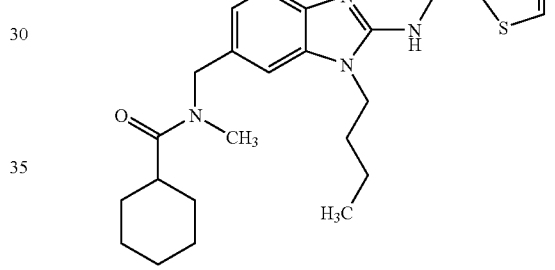
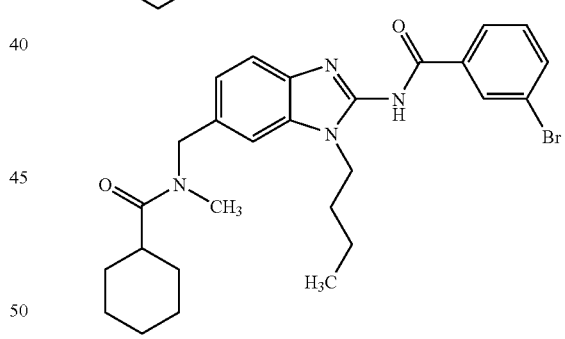
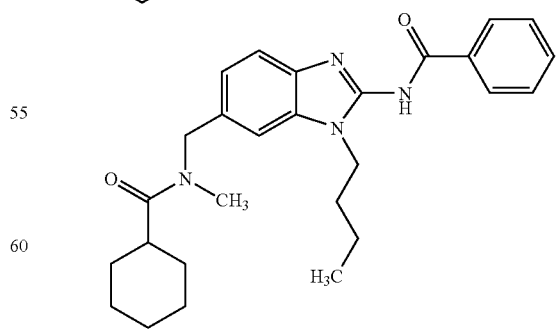

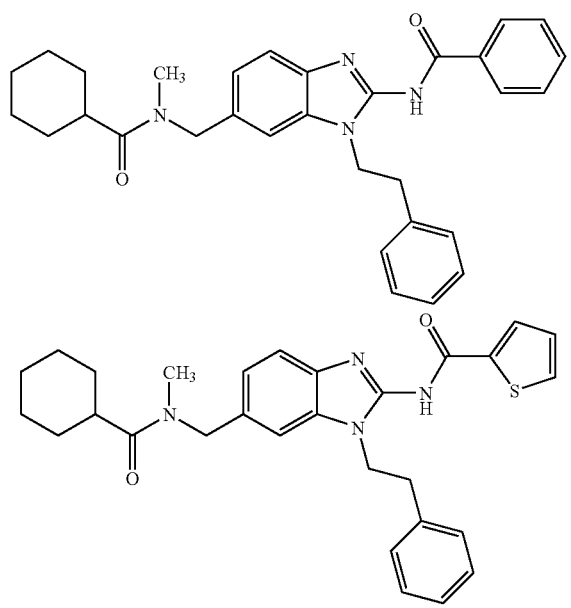
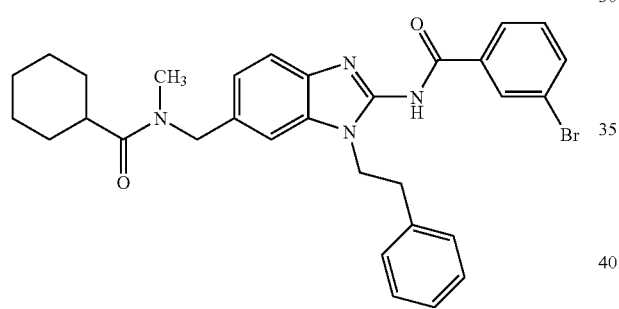
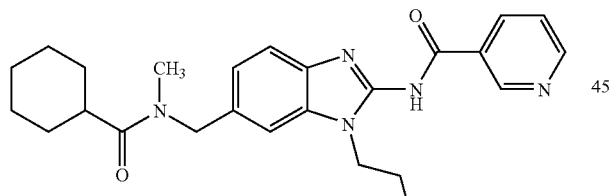
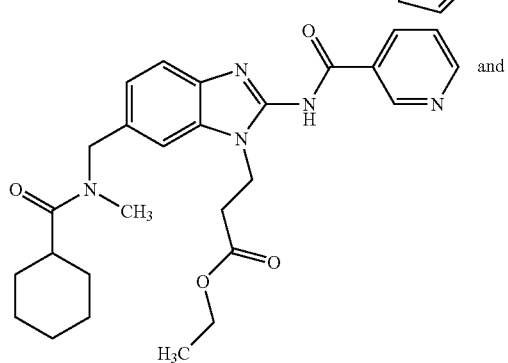
and
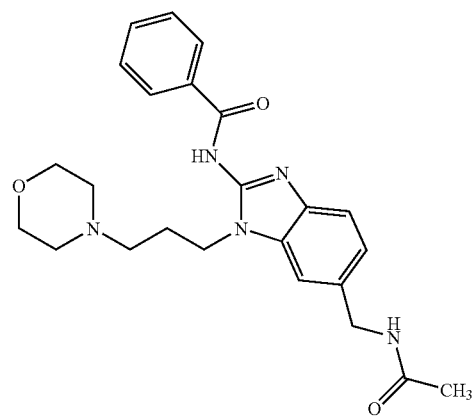
or the pharmaceutically acceptable derivatives thereof.
In another embodiment there is provided representative compounds of the invention which be made in accordance with the general schemes and working examples presented below:
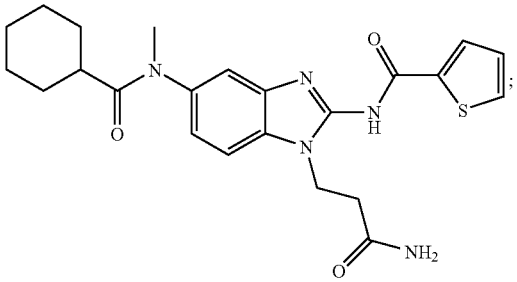
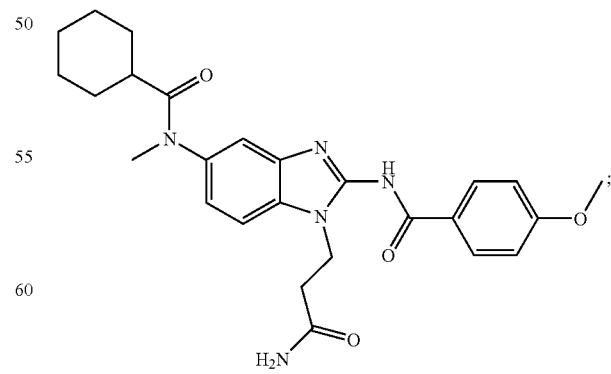

-continued
129
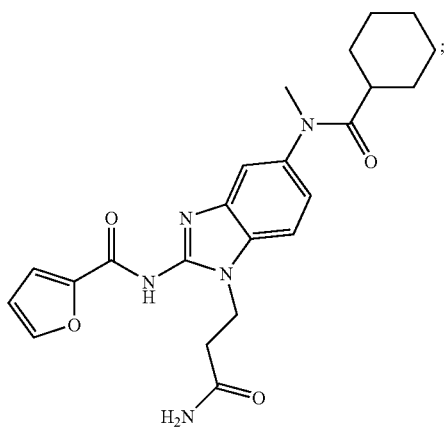
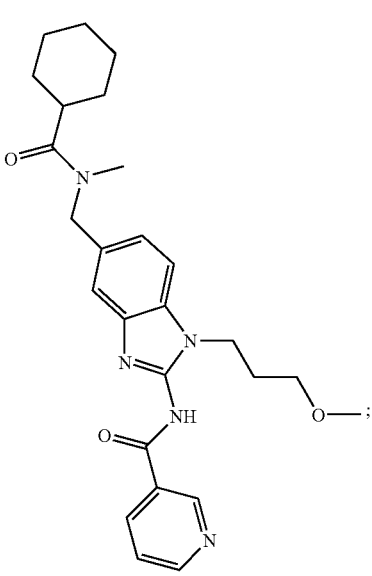
130
-continued
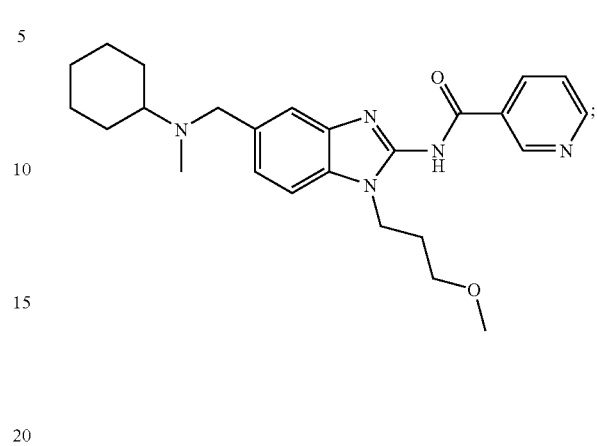
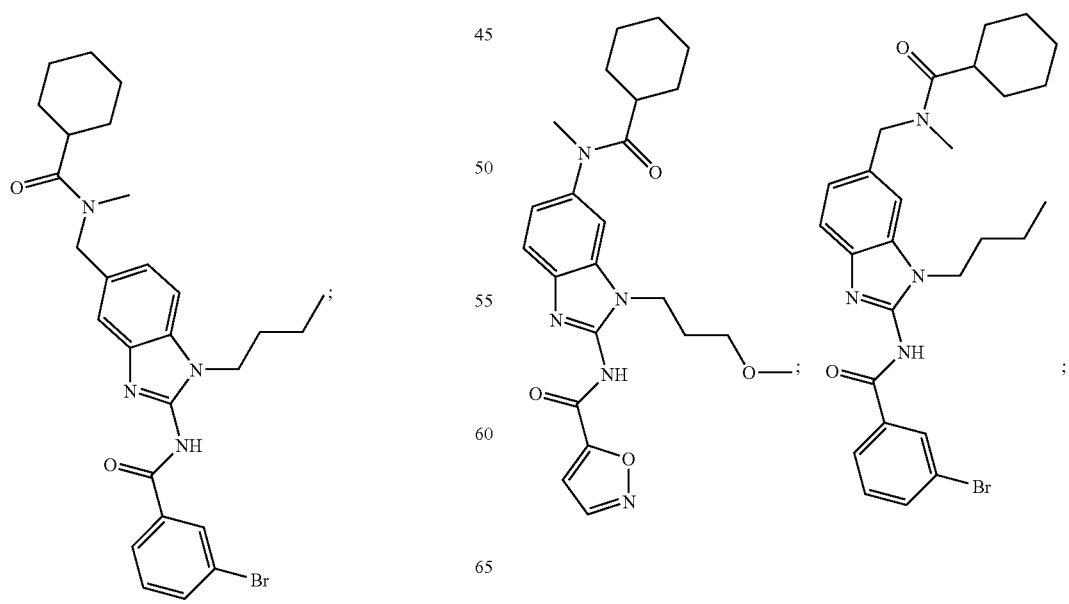

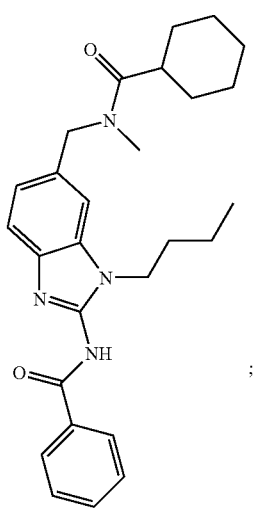
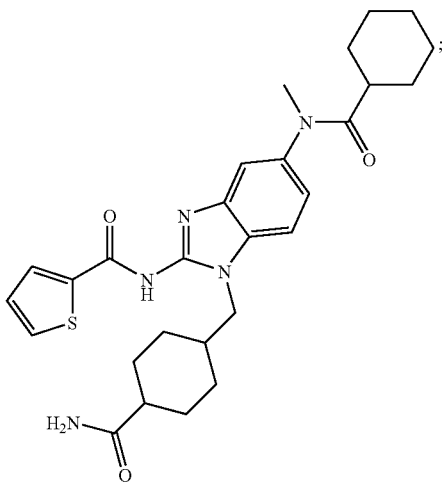
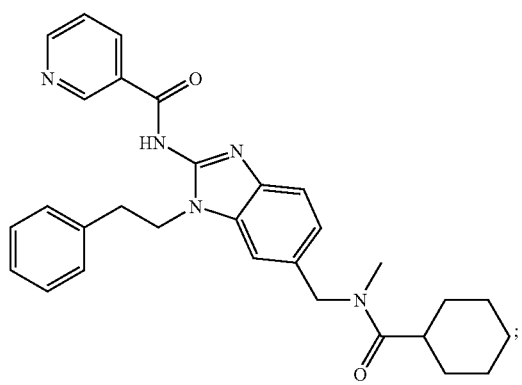
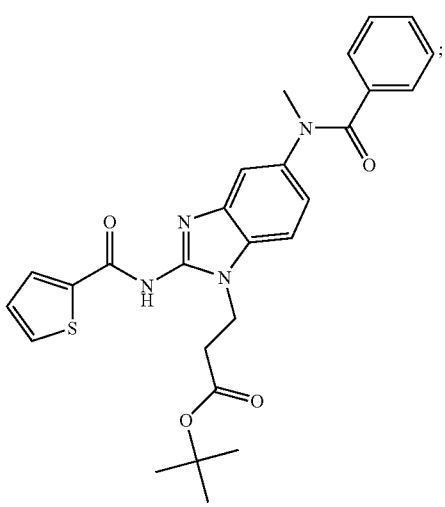
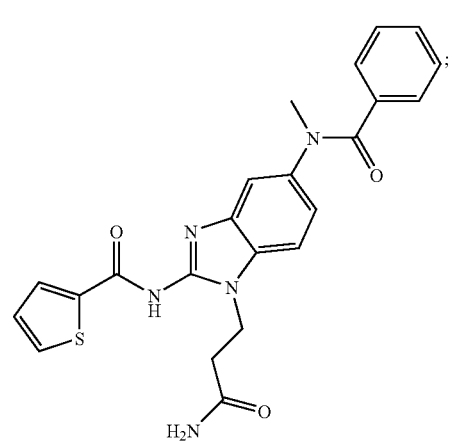
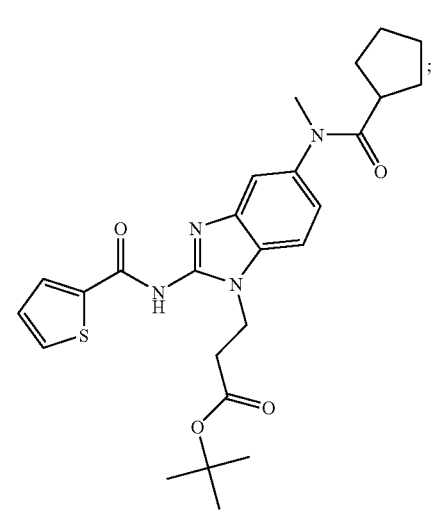

133
-continued
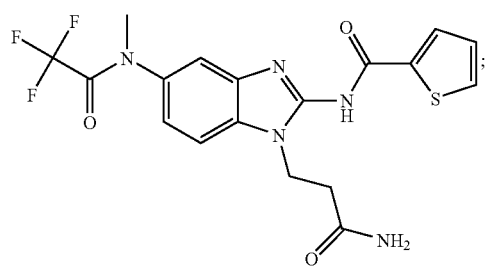
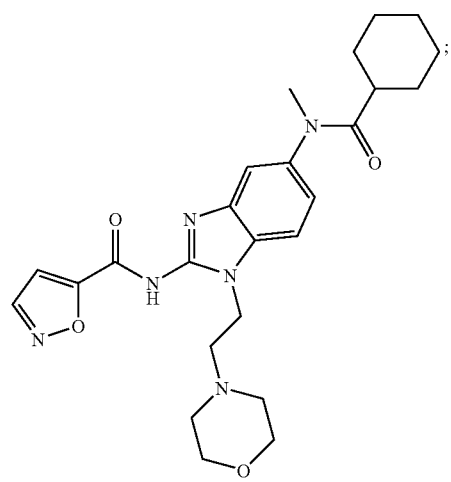
134
-continued
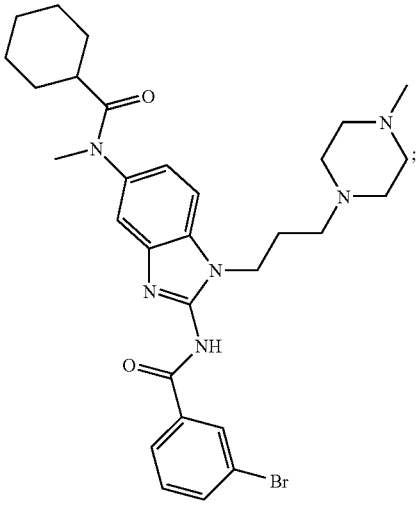

135
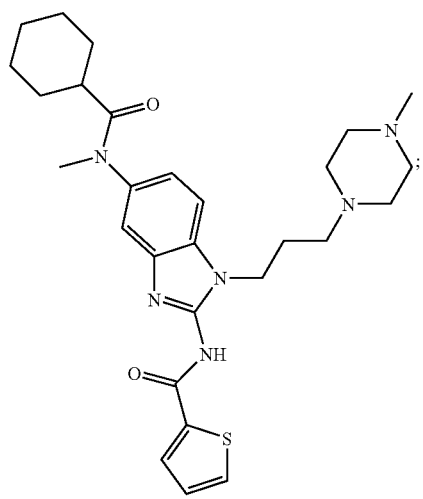
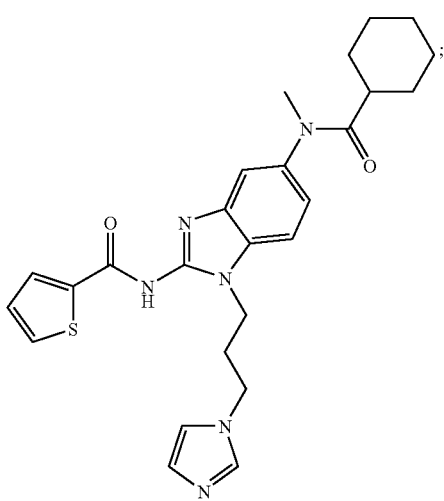
136
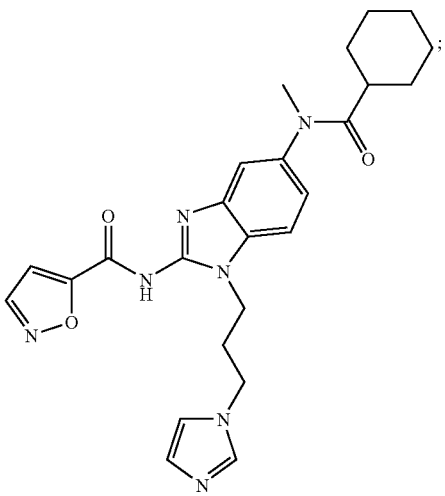
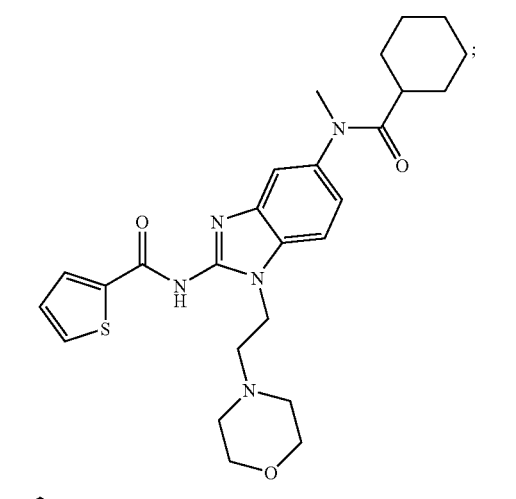
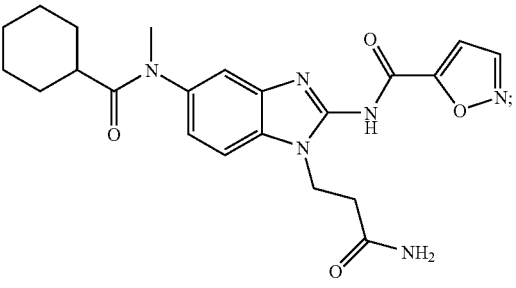
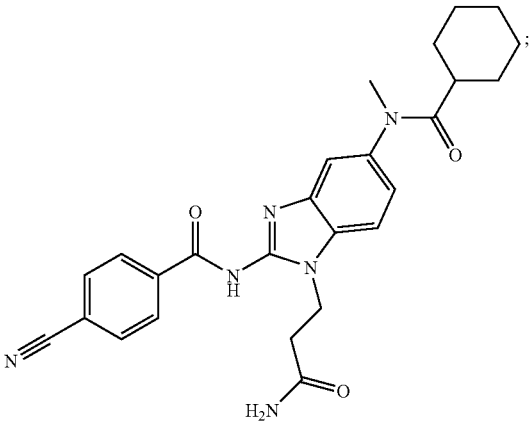

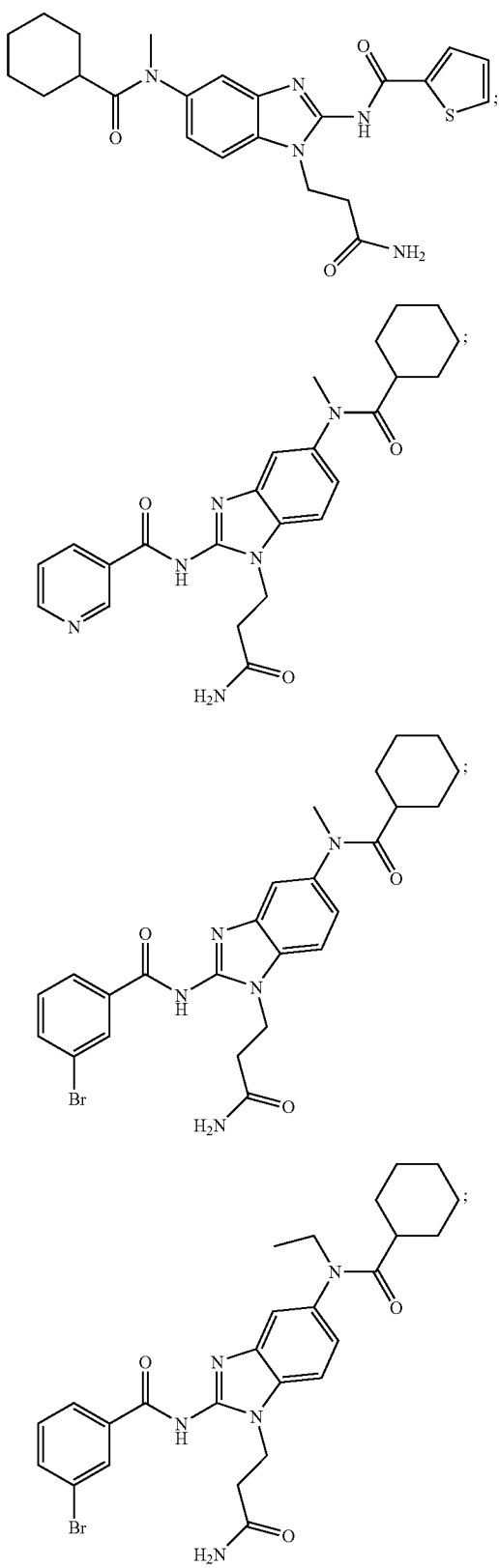

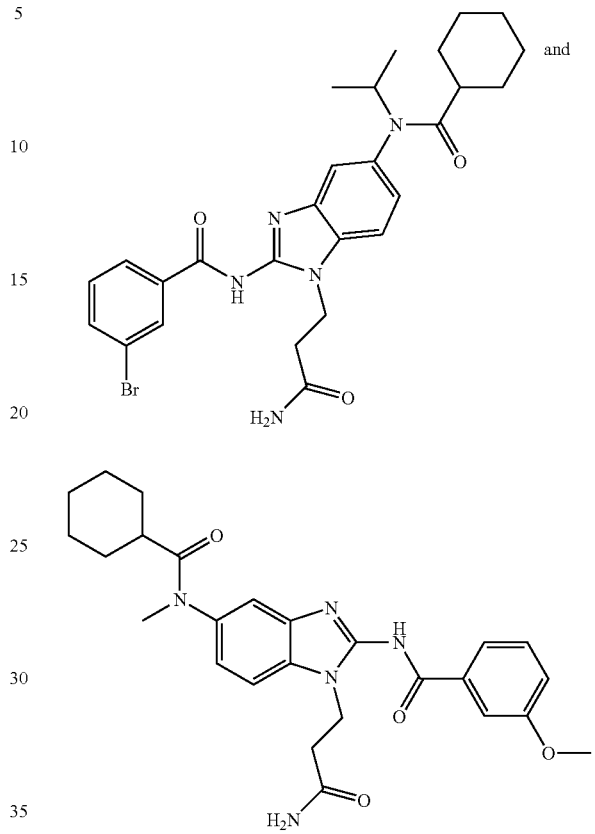

or the pharmaceutically acceptable derivatives thereof.

Any of the aforementioned embodiments disclosed above may have $R_a$, $R_b$ or $R_c$ also being defined as azido. Such compounds are useful as photolabeling probes and include, for example, 4-azido-phenyl moieties.

In all the compounds disclosed herein above in this application, in the event the nomenclature is in conflict with the structure, it shall be understood that the compound is defined by the structure.

The invention includes the use of any compounds described above containing one or more asymmetric carbon atoms which may occur as racemates and racemic mixtures, single enantiomers, diastereomeric mixtures and individual diastereomers. All such isomeric forms of these compounds are expressly included in the present invention. Each stereogenic carbon may be in the R or S configuration, or a combination of configurations.

Some of the compounds of formula (I) can exist in more than one tautomeric form. The invention includes methods using all such tautomers.

All terms as used herein in this specification, unless otherwise stated, shall be understood in their ordinary meaning as known in the art.

Alkyl, alkenyl, alkynyl, alkoxy, alkylthio, acyl, alkoxycarbonyl, acyloxy, acylamino, alkylsulfonyl and all other alkyl containing groups shall be understood unless otherwise specified as being C1–10, branched or unbranched where structurally possible, and optionally partially or fully halogenated. For 'C$_{0-n}$ alkyl', where n is an integer 1,2,3 etc, shall be understood to be a bond when the definition is 'C$_0$', and alkyl when n is greater than or equal to 1. Other more specific definitions are as follows:

BOC or t-BOC is tertiary-butoxycarbonyl.
t-Bu is tertiary-butyl.
DMF is dimethylformamide.
EtOAc is ethyl acetate.
EtOH and MeOH are ethanol and methanol, respectively.
TFA is trifluoroacetic acid.
THF is tetrahydrofuran.
DMSO is dimethylsulfoxide.
TBTU is O-(1H-benzotriazol-1-yl)-N,N,N',N'-tetramethyluronium tetrafluoroborate.
FMOC is 9-fluorenylmethoxycarbonyl.

The term "aroyl" as used in the present specification shall be understood to mean "benzoyl" or "naphthoyl".

The term "carbocycle" shall be understood to mean an aliphatic hydrocarbon radical containing from three to twelve carbon atoms. Carbocycles include hydrocarbon rings containing from three to ten carbon atoms. These carbocycles may be either aromatic and non-aromatic ring systems, and optionally or fully halogenated. The non-aromatic ring systems may be mono- or polyunsaturated. Preferred carbocycles include but are not limited to cyclopropyl, cyclobutyl, cyclopentyl, cyclopentenyl, cyclohexyl, cyclohexenyl, cycloheptanyl, cycloheptenyl, phenyl, indanyl, indenyl, benzocyclobutanyl, dihydronaphthyl, tetrahydronaphthyl, naphthyl, decahydronaphthyl, benzocycloheptanyl and benzocycloheptenyl. Certain terms for cycloalkyl such as cyclobutanyl and cyclobutyl shall be used interchangeably.

The term "heterocycle" refers to a stable nonaromatic 4–8 membered (but preferably, 5 or 6 membered) monocyclic or nonaromatic 8–11 membered bicyclic heterocycle radical which may be either saturated or unsaturated. Each heterocycle consists of carbon atoms and one or more, preferably from 1 to 4 heteroatoms selected from nitrogen, oxygen and sulfur. The heterocycle may be attached by any atom of the cycle, which results in the creation of a stable structure. Unless otherwise stated, heterocycles include but are not limited to, pyrrolidinyl, morpholinyl, thiomorpholinyl, dioxalanyl, piperidinyl, piperazinyl, aziridinyl and tetrahydrofuranyl.

The term "heteroaryl" shall be understood to mean an aromatic 5–8 membered monocyclic or 8–11 membered bicyclic ring containing 1–4 heteroatoms such as N, O and S. Unless otherwise stated, such heteroaryls include but are not limited to thienyl, furanyl, isoxazolyl, oxazolyl, thiazolyl, thiadiazolyl, tetrazolyl, pyrazolyl, pyrrolyl, imidazolyl, pyridinyl, pyrimidinyl, pyrazinyl, pyridazinyl, pyranyl, quinoxalinyl, indolyl, benzimidazolyl, benzoxazolyl, benzothiazolyl, benzothienyl, quinolinyl, quinazolinyl and indazolyl.

The term "heteroatom" as used herein shall be understood to mean atoms other than carbon such as O, N, S and P.

In all alkyl groups or carbon chains within cycloalkyl groups, where one or more carbon atoms are optionally replaced by heteroatoms: O, S or N, it shall be understood that if N is not substituted then it is NH, it shall also be understood that the heteroatoms may replace either terminal carbon atoms or internal carbon atoms within a branched or unbranched carbon chain.

Substitution on a carbon such as a methylene carbon by groups such as oxo result in definitions such as: alkoxycarbonyl, acyl, and amido, or if substituted on a ring can, for example, replace a methylene group —CH$_2$— with a carbonyl>C=O.

The term "aryl" as used herein shall be understood to mean aromatic carbocycle or heteroaryl as defined herein. Each aryl or heteroaryl unless otherwise specified includes its partially or fully hydrogenated derivative. For example, quinolinyl may include decahydroquinolinyl and tetrahydroquinolinyl, naphthyl may include its hydrogenated derivatives such as tetrahydranaphthyl. Each may be partially or fully halogenated. Other partially or fully hydrogenated derivatives of the aryl and heteroaryl compounds described herein will be apparent to one of ordinary skill in the art.

Terms which are analogs of the above cyclic moieties such as aryloxy or heteroaryl amine shall be understood to mean an aryl, heteroaryl, heterocycle as defined above attached to it's respective functional group.

As used herein, "nitrogen" and "sulfur" include any oxidized form of nitrogen and sulfur and the quaternized form of any basic nitrogen. For example, for an alkylthio radical such as —S—C$_{1-6}$ alkyl, unless otherwise specified, this shall be understood to include —S(O)—C$_{1-6}$ alkyl and —S(O)$_2$—C$_{1-6}$ alkyl.

The term "halogen" as used in the present specification shall be understood to mean bromine, chlorine, fluorine or iodine. The definitions "partially or fully halogenated" "substituted by one or more halogen atoms" includes for example, mono, di or tri halo derivatives on one or more carbon atoms. A non-limiting example would be a halogenated alkyl such as —CH$_2$CHF$_2$, —CF$_3$ etc.

The compounds of the invention are only those which are contemplated to be 'chemically stable' as will be appreciated by those skilled in the art. For example, a compound which would have a 'dangling valency', or a 'carbanion' are not compounds contemplated by the inventive methods disclosed herein.

The term "patient" refers to a warm-blooded mammal and preferably, a human.

The invention includes pharmaceutically acceptable derivatives of compounds of formula (I). A "pharmaceutically acceptable derivative" refers to any pharmaceutically acceptable salt or ester, or any other compound which, upon administration to a patient, is capable of providing (directly or indirectly) a compound useful for the invention, or a pharmacologically active metabolite or pharmacologically active residue thereof. A pharmacologically active metabolite shall be understood to mean any compound of the invention capable of being metabolized enzymatically or chemically. This includes, for example, hydroxylated or oxidized derivative compounds of the formula (I).

Pharmaceutically acceptable salts include those derived from pharmaceutically acceptable inorganic and organic acids and bases. Examples of suitable acids include hydrochloric, hydrobromic, sulfuric, nitric, perchloric, fumaric, maleic, phosphoric, glycolic, lactic, salicylic, succinic, toluene-p-sulfuric, tartaric, acetic, citric, methanesulfonic, formic, benzoic, malonic, naphthalene-2-sulfuric and benzenesulfonic acids. Other acids, such as oxalic acid, while not themselves pharmaceutically acceptable, may be employed in the preparation of salts useful as intermediates in obtaining the compounds and their pharmaceutically acceptable acid addition salts. Salts derived from appropriate bases include alkali metal (e.g., sodium), alkaline earth metal (e.g., magnesium), ammonium and N—(C$_1$–C$_4$ alkyl)$_4^+$ salts.

In addition, within the scope of the invention is use of prodrugs of compounds of the formula (I). Prodrugs include those compounds that, upon simple chemical transformation, are modified to produce compounds of the invention. Simple chemical transformations include hydrolysis, oxidation and reduction. Specifically, when a prodrug is administered to a patient, the prodrug may be transformed into a compound disclosed herein above, thereby imparting the desired pharmacological effect.

METHODS OF THERAPEUTIC USE

The compounds of the invention are effective inhibitors of Tec kinase family activity, especially of Itk. Therefore, in one embodiment of the invention, there is provided methods of treating immunological disorders using compounds of the invention. In another embodiment, there is provided methods of treating inflammatory disorders using compounds of the invention. In yet another embodiment, there is provided methods of treating allergic disorders using compounds of the invention. In yet still another embodiment, there is provided methods of enhancing memory cell generation for vaccines using compounds of the invention. In a further embodiment, there is provided methods of treating cell proliferative disorders using compounds of the invention.

Without wishing to be bound by theory, the compounds of this invention modulate T cell and mast cell activation via effective inhibition of Itk. The inhibition of T cell activation is therapeutically useful for selectively suppressing immune function. Thus, the inhibition of Itk is an attractive means for preventing and treating a variety of immune disorders, including inflammatory diseases, autoimmune diseases, organ and bone marrow transplant rejection and other disorders associated with T cell mediated immune response. In particular, the compounds of the invention may be used to prevent or treat acute or chronic inflammation, allergies, contact dermatitis, psoriasis, rheumatoid arthritis, multiple sclerosis, type 1 diabetes, inflammatory bowel disease, Guillain-Barre syndrome, Crohn's disease, ulcerative colitis, cancer, graft versus host disease (and other forms of organ or bone marrow transplant rejection) and lupus erythematosus.

The compounds of the invention are also effective inhibitors of Tec family kinases other than Itk including Txk, Tec, Btk, and Bmx and would thus be useful in treating diseases associated with the activity of one or more of these Tec family kinases.

Inhibitors of mast cell activation and degranulation block the release of allergic and pro-inflammatory mediators and cytokines. Thus inhibitors of Itk have potential utility in treating inflammatory and allergic disorders, including asthma, chronic obstructive pulmonary disease (COPD), adult respiratory distress syndrome (ARDS), bronchitis, conjunctivitis, dermatitis and allergic rhinitis. Other disorders associated with T cell or mast cell mediated immune response will be evident to those of ordinary skill in the art and can also be treated with the compounds and compositions of this invention.

Inhibitors of Itk and other Tec family kinases have potential utility in combination with other therapies for the treatment of immune, inflammatory, proliferative, and allergic disorders. Examples, though not all encompassing, include co-administration with steroids, leukotriene antagonists, anti-histamines, cyclosporin, or rapamycin.

One strategy to improve vaccination methods is to increase the number of memory T cells generated. As described in the Background, in the absence of Itk in mice, increased numbers of memory cells are generated. Thus, within the scope of the invention is the use of the present compounds in the formulation of improved vaccines that generate increased numbers of memory T cells.

For therapeutic use, the compounds of the invention may be administered in any conventional dosage form in any conventional manner. Routes of administration include, but are not limited to, intravenously, intramuscularly, subcutaneously, intrasynovially, by infusion, sublingually, transdermally, orally, topically or by inhalation. The preferred modes of administration are oral and intravenous.

The compounds of this invention may be administered alone or in combination with adjuvants that enhance stability of the inhibitors, facilitate administration of pharmaceutic compositions containing them in certain embodiments, provide increased dissolution or dispersion, increase inhibitory activity, provide adjunct therapy, and the like, including other active ingredients. Advantageously, such combination therapies utilize lower dosages of the conventional therapeutics, thus avoiding possible toxicity and adverse side effects incurred when those agents are used as monotherapies. Compounds of the invention may be physically combined with the conventional therapeutics or other adjuvants into a single pharmaceutical composition. Advantageously, the compounds may then be administered together in a single dosage form. In some embodiments, the pharmaceutical compositions comprising such combinations of compounds contain at least about 5%, but more preferably at least about 20%, of a compound of formula (I) (w/w) or a combination thereof. The optimum percentage (w/w) of a compound of the invention may vary and is within the purview of those skilled in the art. Alternatively, the compounds may be administered separately (either serially or in parallel). Separate dosing allows for greater flexibility in the dosing regime.

As mentioned above, dosage forms of the compounds of this invention include pharmaceutically acceptable carriers and adjuvants known to those of ordinary skill in the art. These carriers and adjuvants include, for example, ion exchangers, alumina, aluminum stearate, lecithin, serum proteins, buffer substances, water, salts or electrolytes and cellulose-based substances. Preferred dosage forms include, tablet, capsule, caplet, liquid, solution, suspension, emulsion, lozenges, syrup, reconstitutable powder, granule, suppository and transdermal patch. Methods for preparing such dosage forms are known (see, for example, H. C. Ansel and N. G. Popovish, *Pharmaceutical Dosage Forms and Drug Delivery Systems,* 5th ed., Lea and Febiger (1990)). Dosage levels and requirements are well-recognized in the art and may be selected by those of ordinary skill in the art from available methods and techniques suitable for a particular patient. In some embodiments, dosage levels range from about 1–1000 mg/dose for a 70 kg patient. Although one dose per day may be sufficient, up to 5 doses per day may be given. For oral doses, up to 2000 mg/day may be required. As the skilled artisan will appreciate, lower or higher doses may be required depending on particular factors. For instance, specific dosage and treatment regimens will depend on factors such as the patient's general health profile, the severity and course of the patient's disorder or disposition thereto, and the judgment of the treating physician.

BIOLOGICAL ACTIVITY

Tec Family Kinase Assay

Itk, Txk, Tec, Btk, and Bmx are purified as a GST-fusion protein. The kinase activity is measured using DELFIA (Dissociation Enhanced Lanthanide Fluoroimmunoassay) which utilizes europium chelate-labeled anti-phosphotyrosine antibodies to detect phosphate transfer to a random polymer, poly Glu$_4$: Tyr$_1$ (PGTYR). The screen is run on the Zymark Allegro robot system to dispense reagents, buffers and samples for assay, and also to wash and read plates. The kinase assay is performed in kinase assay buffer (50 mM HEPES, pH 7.0, 25 mM $MgCl_2$, 5 mM $MnCl_2$, 50 mM KCl, 100 μM $Na_3VO_4$, 0.2% BSA, 0.01% CHAPS, 200 μM TCEP). Test samples initially dissolved in DMSO at 1 mg/mL, are pre-diluted for dose response (10 doses with starting final concentration of 3 μg/mL, 1 to 3 serial dilutions) with the assay buffer in 96-well polypropylene microtiter plates. A 50 μL volume/well of a mixture of substrates containing ATP (final ATP concentration in each kinase assay is equal to its apparent ATP $K_m$) and 3.6 ng/μL PGTYR-biotin (CIS Bio International) in kinase buffer is added to neutravidin coated 96-well white plate (PIERCE), followed by 25 μL/well test sample solution and 25 μL/well of diluted enzyme (1–7 nM final conc.). Background wells are incubated with buffer, rather than 25 μL enzyme. The assay plates are incubated for 30 min at room temperature. Following incubation, the assay plates are washed three times with 250 μL DELFIA wash buffer. A 100 μL aliquot of 1 nM europium-labeled anti-phosphotyrosine ($Eu^{3+}$-PT66, Wallac CR04-100) diluted in DELFIA assay buffer is added to each well and incubated for 30 min at room temperature. Upon completion of the incubation, the plate is washed four times with 250 μL of wash buffer and 100 μL of DELFIA Enhancement Solution (Wallac) is added to each well. After 15 min of longer, time-resolved fluorescence is measured (excitation at 360 nm, emission at 620 nm) after a delay time of 250 μs.

Preferred compounds of the invention have an activity of 1 microMolar or less.

In order that this invention be more fully understood, the following examples are set forth. These examples are for the purpose of illustrating preferred embodiments of this invention, and are not to be construed as limiting the scope of the invention in any way.

The examples which follow are illustrative and, as recognized by one skilled in the art, particular reagents or conditions could be modified as needed for individual compounds without undue experimentation. Starting materials used in the schemes below are either commercially available or easily prepared from commercially available materials by those skilled in the art.

GENERAL SYNTHETIC METHODS

The invention also provides processes for making compounds of formula I. In all schemes, unless specified otherwise, R substituents in the formulas below shall have the meaning of R substituents in the formula I of the invention described herein above. Intermediates used in the preparation of compounds of the invention are either commercially available or readily prepared by methods known to those skilled in the art.

Compounds of formula I in which $R_4$ is in the 5-position and is $-N(R_7)C(O)R_5$, $X_a$ is O and $R_1$ is H may be prepared by the method outlined in Scheme I.

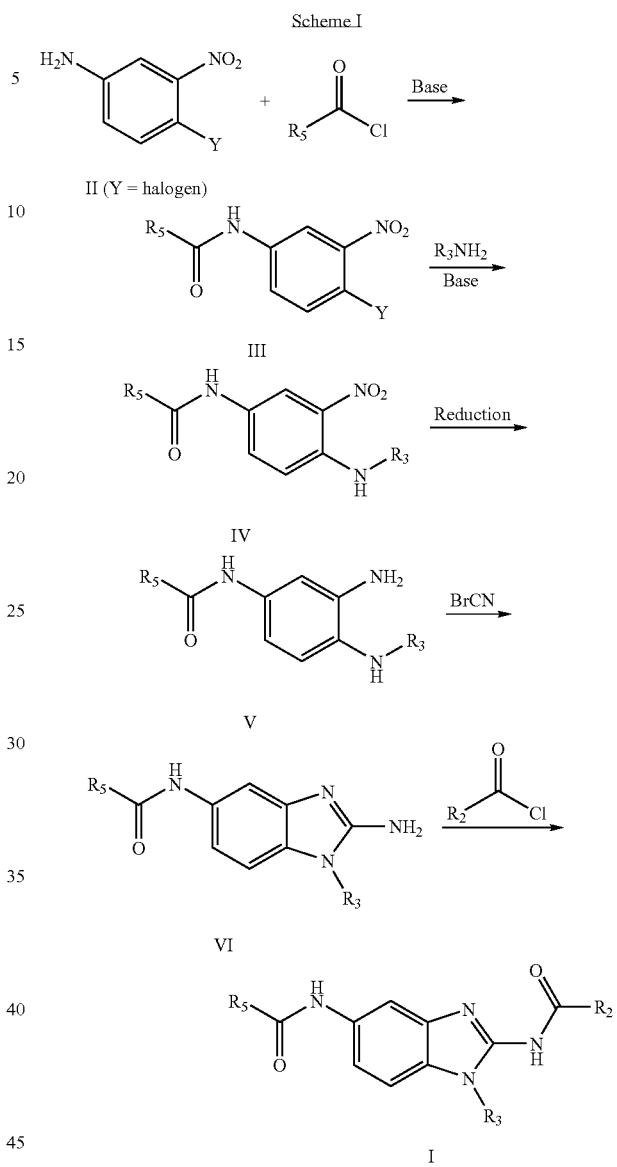

As illustrated in Scheme I, a 4-halo-3-nitroaniline II, preferably 4-fluoro-3-nitroaniline, is reacted with $R_3C(O)Cl$ in the presence of a suitable base such as pyridine to form amide III. This intermediate is then reacted with $R_3NH_2$ in the presence of a base such as triethylamine to form IV. Reduction of the nitro group by methods known in the art, for example by treatment with hydrogen or a hydrogen source such as ammonium carbonate in the presence of a catalyst such as palladium on carbon provides V. Reaction of V with cyanogen bromide in a suitable solvent such as ethanol provides benzimidazole VI. Reaction of VI with $R_2C(O)Cl$ in the presence of a base such as pyridine provides the desired compound of formula (I).

If one desires a compound of formula (I) in which $R_7$ is alkyl, one may react intermediate III with an alkyl halide in the presence of a suitable base such as sodium bistrimethylsilylamide to produce VII as illustrated in Scheme II. One may then proceed with the displacement of the ring halogen with $R_2NH_2$ and subsequent steps as described in Scheme I to produce the desired compound of formula (I).

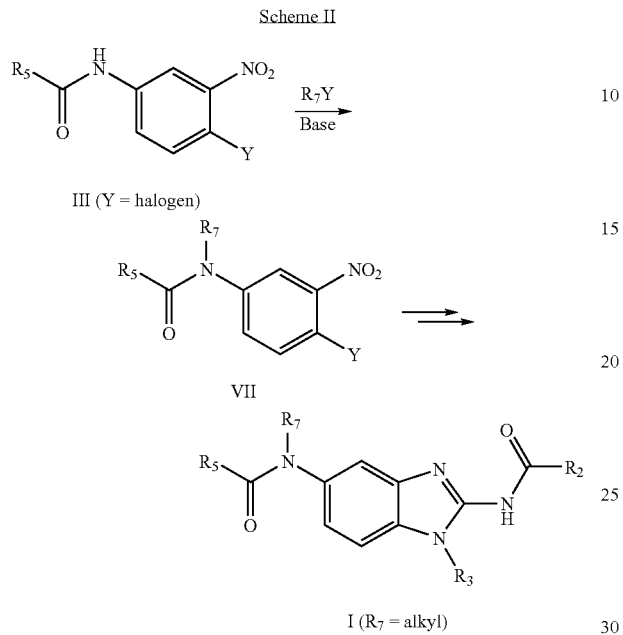

Compounds of formula (I) in which $R_4$ is in the 6-position and is $-N(R_7)C(O)R_5$, $X_a$ is O and $R_1$ is H may be prepared as described in Scheme III. A 4-nitro-3-halotoluene (VIII), preferably 4-nitro-3-fluorotoluene is treated with a suitable oxidizing agent such as sodium dichromate to provide benzoic acid derivative IX. This is converted to an aniline derivative by methods known in the art, for example by refluxing with diphenylphosphorylazide in a mixture of tert-butyl alcohol and dioxane to provide the tert-butoxycarbonyl-protected aniline X. Deprotection of the aniline, in this case by treatment with acid such as trifluoroacetic acid provides XI. This may then be reacted further as described in Schemes I and II to provide the desired compounds of formula (I) having $R_4$ in the 6-position.

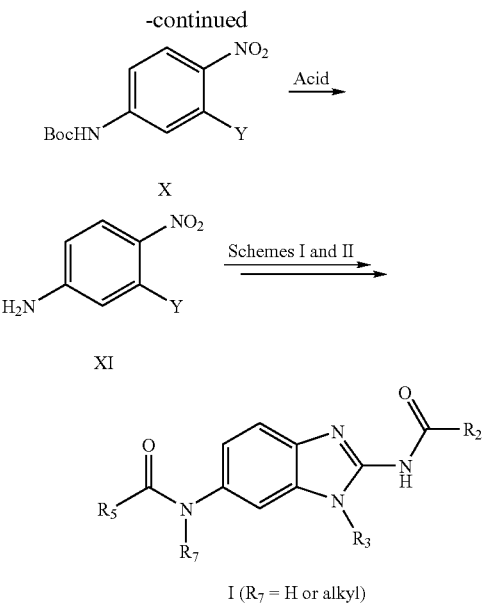

Compounds of formula (I) in which $R_4$ is $-CH_2N(R_7)C(O)R_5$ and is in the 5-position, $X_a$ is O and $R_1$ is H may be prepared as described in Scheme IV. As illustrated below, a 4-halo-3-nitrobenzoic acid (XII), preferably a 4-fluoro-3-nitrobenzoic acid is coupled with $R_7NH_2$ using a suitable coupling reagent such as 1-(3-dimethylaminopropyl)-3-ethylcarbodiimide (EDC) to form XIII. Reaction of XIII with $R_3NH_2$ in the presence of a suitable base such as triethylamine provides XIV. Reduction of the amide functionality with a suitable reducing agent such as borane-tetrahydrofuran complex gives the benzylamine XV. Reaction of XV with $R_5C(O)Cl$, in the presence of a base such as diisopropylethylamine provides XVI. This may then be reduced as described for intermediate IV in Scheme I, and further reacted as described in Scheme I to provide the desired compounds of formula (I) with $R_4$ being $-CH_2N(R_7)C(O)R_5$ and in the 5-position.

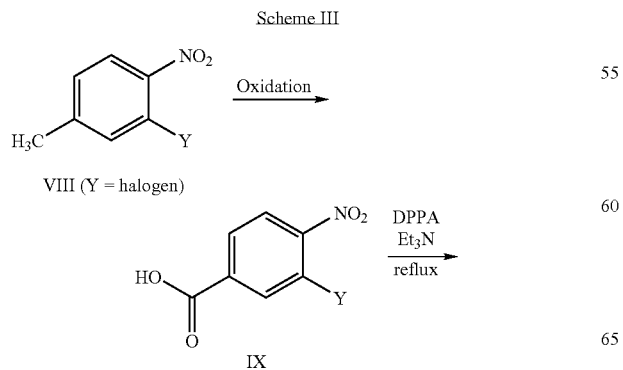

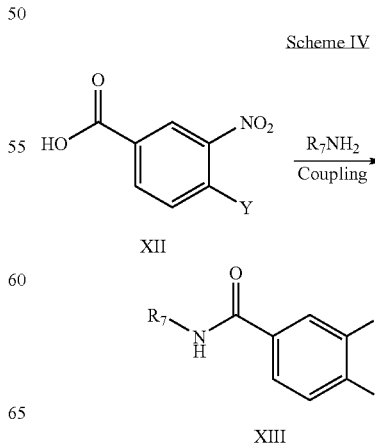

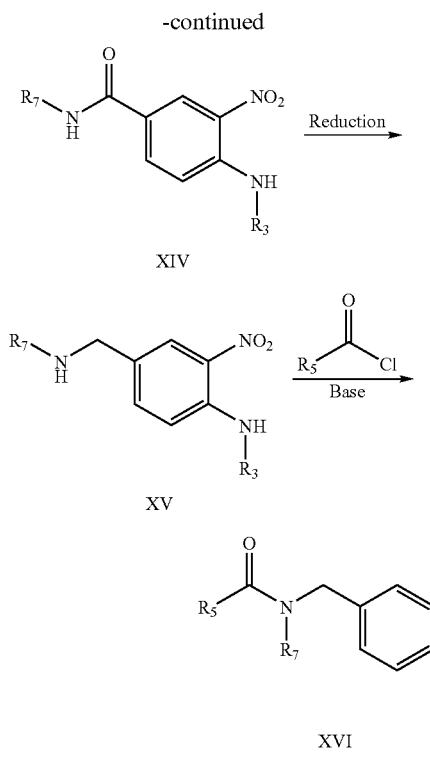
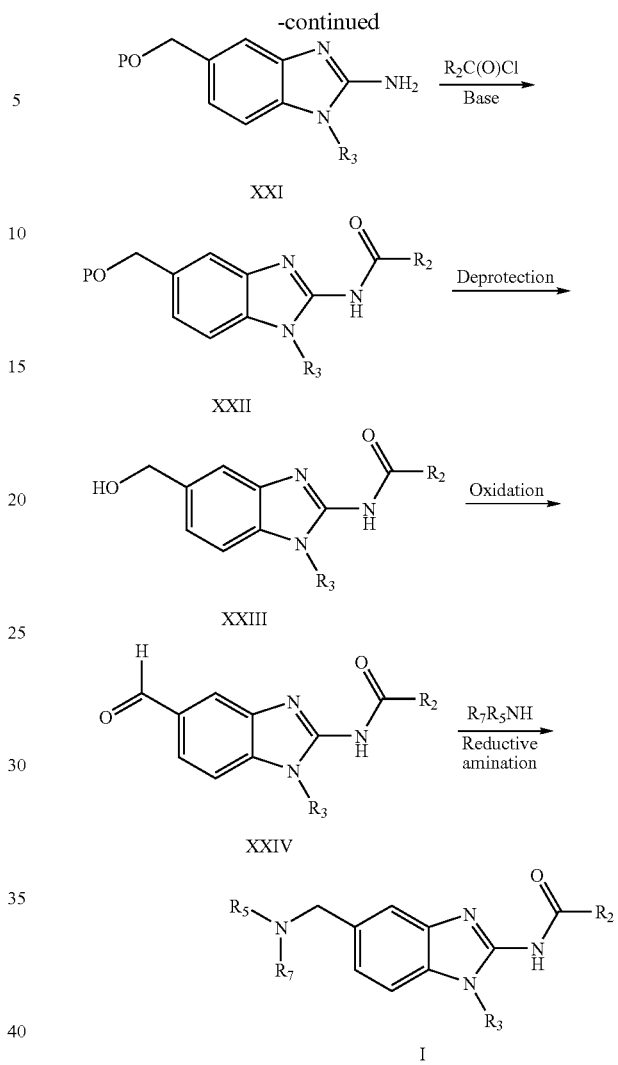

Compounds of formula (I) in which R₄ is —CH₂N(R₇)C(O)R₅ and is in the 6-position, $X_a$ is O and R₁ is H may be prepared starting with intermediate IX in Scheme II. Treatment of IX in the manner described in Scheme IV for intermediate XII will provide the desired compounds.

Compounds of formula (I) in which R₄ is in the 5-position and is —CH₂N(R₅)(R₇) may be prepared by the method outlined in Scheme V.

Scheme V

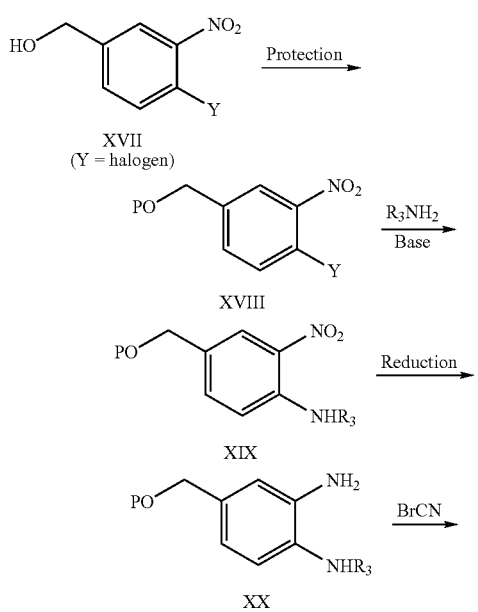

As illustrated in Scheme V, a 4-halo-3-nitro benzyl alcohol (XVII), preferably a 4-fluoro-3-nitro benzyl alcohol is protected with a suitable protecting group such as a triisopropylsilyl group, to provide XVIII, where P is a protecting group. Reaction of XVIII with R₃NH₂ in the presence of a suitable base such as triethylamine provides XIX. Reduction of the nitro group, for example by treatment with a hydrogen source such as ammonium formate in the presence of a catalyst such as palladium on carbon provides XX. Reaction of XX with cyanogen bromide in a suitable solvent such as ethanol provides benzimidazole intermediate XXI. Reaction of XXI with R₂C(O)Cl in the presence of a base such as diisopropylethylamine produces amide XXII. Deprotection of the benzyl alcohol, for example by treatment with dilute acid if P is a triisopropylsilyl group, gives XXIII. The benzyl alcohol is then treated with a suitable oxidizing reagent such as MnO₂ to provide the aldehyde XXIV. Reaction of XXIV with R₇R₅NH under reductive amination conditions provides the desired compound of formula (I) in which R₄ is —CH₂N(R₅)(R₇) and is in the 5-position.

Scheme VI illustrates an additional method for preparation of compounds according to the invention.

Scheme VI

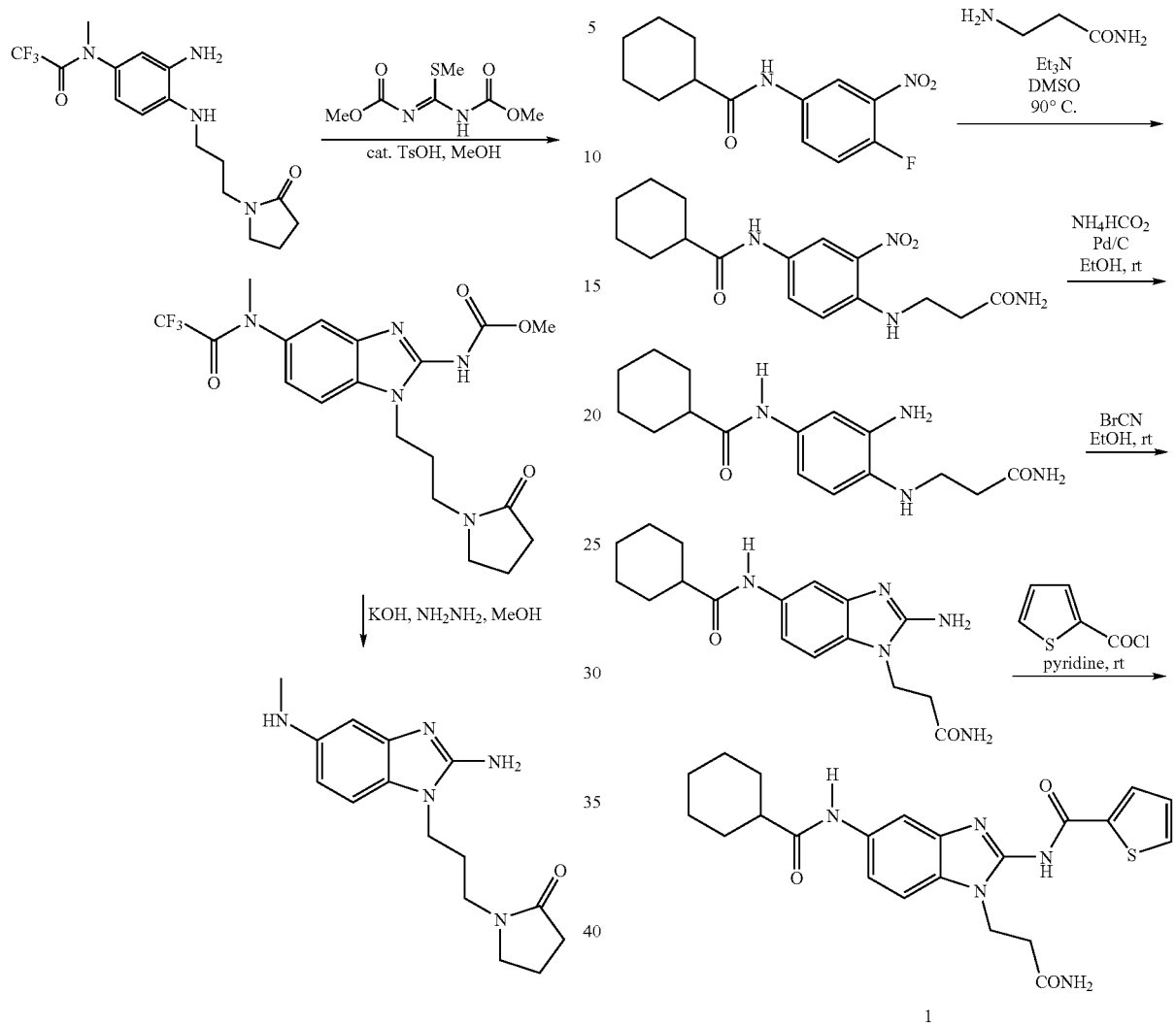

SYNTHETIC EXAMPLES

Example 1

Synthesis of thiophene-2-carboxylic acid [1-(3-carbamoyl-ethyl)-5-(cyclohexanecarbonyl-amino)-1H-benzimidazol-2-yl]-amide

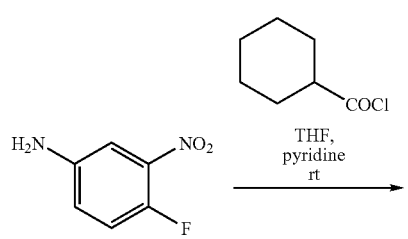

To a solution of 4-fluoro-3-nitro aniline (1.41 g, 9.0 mmol) in THF (50 mL) was added cyclohexanecarbonyl chloride (1.46 g, 9.6 mmol) and pyridine (0.97 mL, 12 mmol), and the mixture stirred for 22 h at room temperature. Ethyl acetate (100 mL) was added, and the solution was washed in turn with 1M HCl (50 mL) and saturated sodium bicarbonate (50 mL). The organic layer was dried over magnesium sulfate and evaporated. The residue was purified by flash chromatography, eluting with hexane/ethyl acetate (7:3) to give cyclohexanecarboxylic acid (4-fluoro-3-nitrophenyl)amide (1.35 g, 56%).

A stirred solution of the above amide (550 mg, 2.07 mmol), β-alanine amide hydrochloride (515 mg, 4.13 mmol), and triethylamine (0.58 mL, 4.1 mmol) in DMSO (10 mL) was heated to 80° C. for 16 h. The reaction mixture was poured into water. The precipitate was washed with water and dried to give cyclohexanecarboxylic acid [4-(3-carbamoyl-ethylamino)-3-nitrophenyl]amide (609 mg, 88%).

A reaction flask equipped with a nitrogen line and a stir bar was charged with 10% palladium on activated carbon (0.06 g) and ethanol (5 mL). A solution of the above amide (0.6 g, 1.8 mmol) in ethanol (20 mL) was added, followed by ammonium formate (1.24 g, 19.7 mmol), and the mixture was stirred at room temperature for 32 h. The reaction mixture was filtered through diatomaceous earth, washing with ethanol, and the filtrate concentrated to a volume of 25 mL. The resulting solution of cyclohexanecarboxylic acid [3-amino-4-(2-carbamoyl-ethylamino)-phenyl]amide was used immediately in the next step.

To the solution obtained above was added cyanogen bromide (0.3 g, 2.7 mmol), and the resulting solution was stirred at room temperature for 24 h. The solvent was evaporated and the residue partitioned between ethyl acetate (10 mL) and saturated sodium carbonate (5 mL). The organic layer was washed with water (5 mL) and dried over magnesium sulfate. The solvent was evaporated and the resulting purple oil was purified by flash chromatography with 5–50% methanol/dichloromethane to give cyclohexanecarboxylic acid [2-amino-1-(2-carbamoyl-ethyl)-1H-benzimidazol-5-yl]-amide (0.23 g, 38%).

To a stirred solution of cyclohexanecarboxylic acid [2-amino-1-(2-carbamoyl-ethyl)-1H-benzimidazol-5-yl]-amide (0.23 g, 0.69 mmol) in pyridine (10 mL) was added 2-thiophenecarbonyl chloride (0.11 mL, 1.04 mmol). The reaction was complete in 6 h. The pyridine was evaporated and the resulting orange solid was purified by flash chromatography with 1% methanol/dichloromethane to give the title compound (0.02 g, 6%), m.p. 239–241° C., ESMS m/z 440 (MH$^+$).

Example 2a

Synthesis of thiophene-2-carboxylic acid [1-(3-carbamoyl-ethyl)-5-(cyclohexanecarbonyl-methyl-amino)-1H-benzimidazol-2-yl]amide

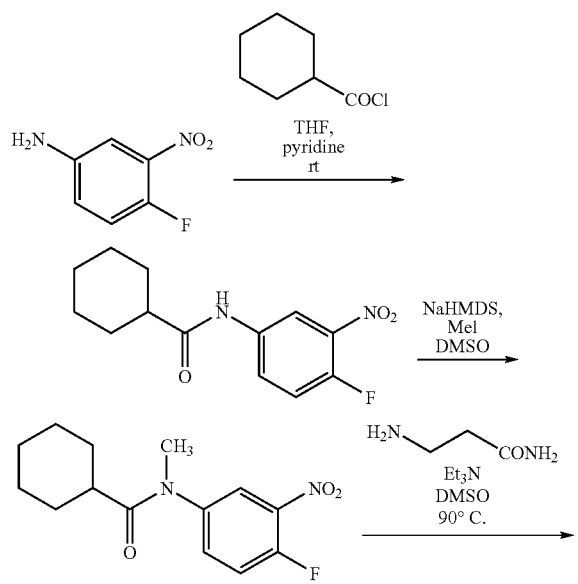

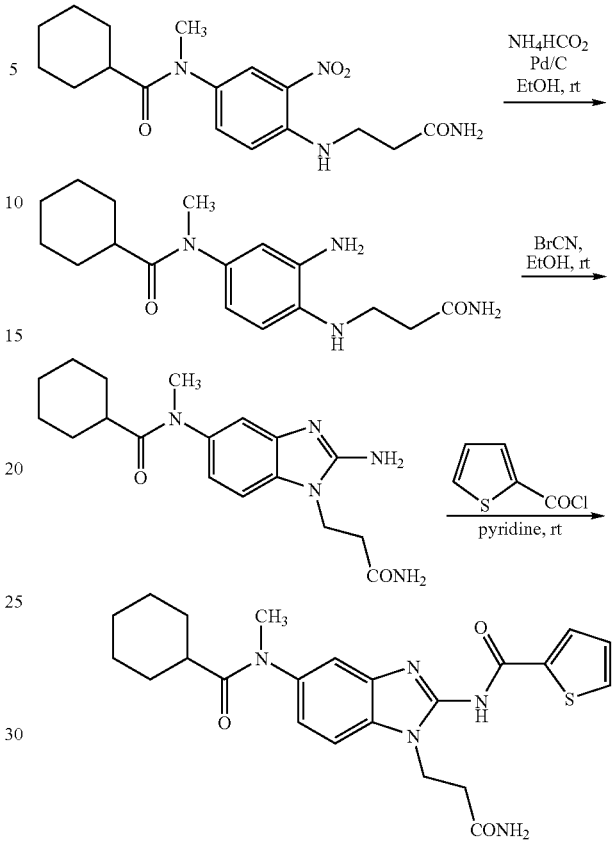

To a solution of cyclohexanecarboxylic acid (4-fluoro-3-nitro-phenyl)amide (see Example 1) (0.75 g, 2.82 mmol) in DMSO (15 mL) was added a 1M solution of sodium bistrimethylsilylamide (3.36 mL, 3.36 mmol), with stirring at room temperature. After 15 min, iodomethane (0.53 mL, 8.5 mmol) was added. After 1 h, the mixture was diluted with ethyl acetate, washed twice with water, dried over magnesium sulfate, and evaporated. The residue was purified by flash chromatography, eluting with hexane/ethyl acetate (7:3) to give cyclohexanecarboxylic acid (4-fluoro-3-nitro-phenyl)-methyl-amide (402 mg, 51%) as the first eluted component.

A stirred solution of the above amide (380 mg, 1.36 mmol), β-alanine amide hydrochloride (125 mg, 2.71 mmol), and triethylamine (0.38 mL, 2.7 mmol) in DMSO (6 mL) was heated to 90° C. for 5 h. The reaction mixture was poured into water. Ethyl acetate (100 mL) was added and the solution was washed in turn with 1M HCl and saturated sodium bicarbonate. The aqueous layers were extracted with ethyl acetate. The combined organic layers were dried over magnesium sulfate and evaporated to give cyclohexanecarboxylic acid [4-(3-carbamoyl-ethylamino)-3-nitrophenyl] methyl amide (434 mg, 92%), which was used in the next step without purification.

A reaction flask equipped with a nitrogen line and a stir bar was charged with 10% palladium on activated carbon (0.05 g) and ethanol (5 mL). A solution of the above amide (0.5 g, 1.3 mmol) in ethanol (15 mL) was added, followed by ammonium formate (1.0 g, 15 mmol). The mixture was stirred at room temperature for 32 h. The reaction mixture was filtered through diatomaceous earth, washing with ethanol, and the filtrate was concentrated to a volume of 25 mL. The resulting solution of cyclohexanecarboxylic acid [3-amino-4-(2-carbamoyl-ethylamino)-phenyl]-methyl-amide was used immediately in the next step.

To the solution obtained above was added cyanogen bromide (0.21 g, 1.95 mmol), and the solution was stirred a room temperature for 24 h. The solvent was evaporated and the residue was partitioned between ethyl acetate (10 mL) and saturated sodium carbonate (5 mL). The organic layer was washed with water (5 mL) and dried over magnesium sulfate. The solvent was evaporated and the resulting purple oil was purified by flash chromatography with 5–50% methanol/dichloromethane to give cyclohexanecarboxylic acid [2-amino-1-(2-carbamoyl-ethyl)-1H-benzimidazol-5-yl]-methyl-amide (0.12 g, 27%)

To a stirred solution of cyclohexanecarboxylic acid [2-amino-1-(2-carbamoyl-ethyl)-1H-benzimidazol-5-yl]-methyl-amide (0.12 g, 0.36 mmol) in pyridine (10 mL) was added 2-thiophenecarbonyl chloride (0.06 mL, 0.54 mmol). The reaction was complete in 6 h. The pyridine was evaporated and the resulting orange solid was purified by flash chromatography with 1% methanol/dichloromethane to give the title compound (0.05 g, 33%), m.p. 144–146° C., ESMS m/z 454 (MH+).

Example 2b

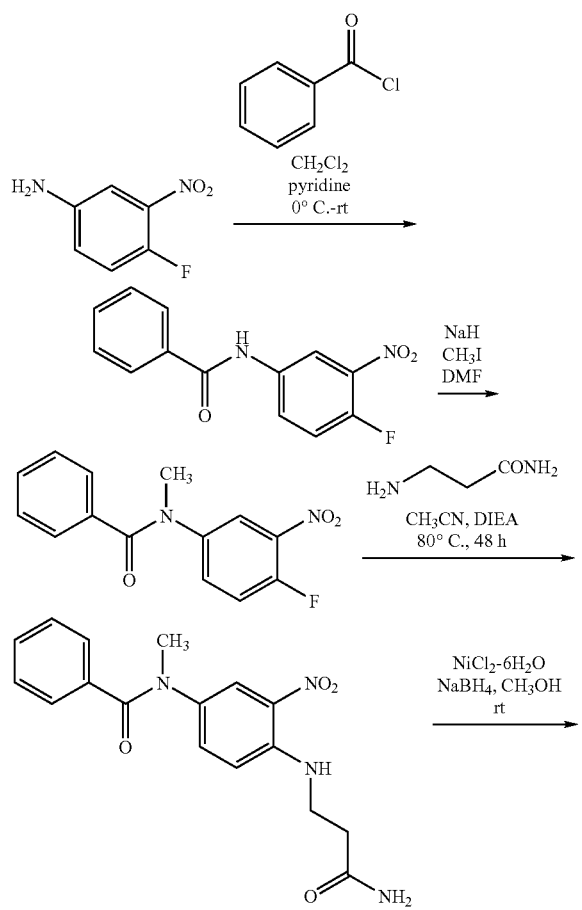

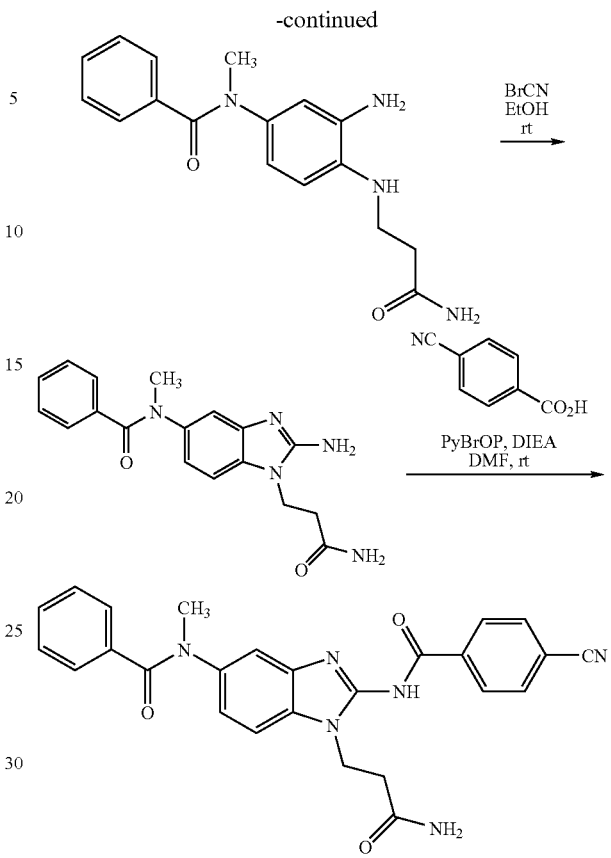

To a solution of 4-fluoro-3-nitro aniline (1.00 g, 6.41 mmol) in anhydrous CH$_2$Cl$_2$ (25 ml) was added pyridine (1.52 g, 19.23 mmol) and the solution was cooled to 0° C. under argon. Benzoyl chloride (0.90 g, 6.41 mmol) was added slowly and the solution was then allowed to slowly warm to room temperature and stir for 24 h. The solution was poured into 1NHCl and the organic layer was separated. The aqueous layer was extracted 3× with ethyl acetate (50 ml). The combined organic layers were washed with saturated sodium bicarbonate, water, brine and dried over anhydrous magnesium sulfate. The solution was filtered and the solvent removed under reduced pressure. The residue was purified by flash chromatography, eluting with hexane/ethyl acetate (4:1) to give N-(4-fluoro-3-nitro-phenyl)-benzamide. (1.60 g, 96%)

To a solution of N-(4-fluoro-3-nitro-phenyl)-benzamide (1.60 g, 6.15 mmol) in anhydrous DMF was added iodomethane (3.49 g, 24.60 mmol, 1.53 ml) under argon. 60% Sodium hydride (0.37 g, 9.23 mmol) was then added portionwise to the cooled solution (0° C.) and the reaction mixture was then stirred at room temperature for 24 h. The solution was poured slowly into water and the aqueous layer was extracted 3× with ethyl acetate. The combined organic layer was dried over anhydrous magnesium sulfate and the solvent was removed under reduced pressure. The residue was purified by flash chromatography, eluting with hexane/ethyl acetate (4:1) to give N-(4-fluoro-3-nitro-phenyl)-N-methyl-benzamide. (1.47 g, 87%)

N-(4-fluoro-3-nitro-phenyl)-N-methyl-benzamide (1.47 g, 5.37 mmol) was taken up in dry acetonitrile under argon, DIEA (2.08 g, 16.11 mmol, 2.80 ml) and β-alanine amide hydrochloride (1.00 g, 8.06 mmol) were added. The reaction mixture was heated to 80° C. for 48 h. The reaction was poured into 1N HCl and the aqueous layer was extracted 3× with ethyl acetate. The combined organic layers were washed with water, brine and dried over magnesium sulfate. The solution was filtered and the solvent removed under reduced pressure. The residue was triturated twice with cold hexane and dried to give N-[4-(2-carbamoyl-ethylamino)-3-nitro-phenyl]-N-methyl-benzamide. (1.75 g, 95%)

$NiCl_2$-$6H_2O$ (0.61 g, 2.55 mmol) was dissolved in methanol (25 ml) and 100 mg of celite was added. $NaBH_4$ (0.29 g, 7.67 mmol) was added slowly (bubbling occurs) and the solution was stirred for 30 min at room temperature. N-[4-(2-carbamoyl-ethylamino)-3-nitro-phenyl]-N-methyl-benzamide (1.75 g, 5.11 mmol) dissolved in methanol (20 ml) was added to the reaction mixture over 5 min. Additional $NaBH_4$ (0.68 g, 17.88 mmol) was added portionwise to the reaction and the reaction was stirred for 15 min. TLC (100/10/0.5; $CH_2Cl_2$, $CH_3OH$, $NH_4OH$) showed no starting material present. The reaction was filtered through a celite pad and the pad was washed with methanol. The methanol was removed under reduced pressure and the residue was taken up in ethyl acetate. The ethyl acetate solution was washed 2× with water and dried over anhydrous magnesium sulfate. The solution was filtered and the solvent removed under reduced pressure. The product, N-[3[amino-4-(2-carbamoyl)-phenyl]-N-methyl benzamide, was sufficiently pure to carry on to the next step without purification. (1.50 g, 94%)

To a solution of N-[3[amino-4-(2-carbamoyl)-phenyl]-N-methyl benzamide (1.50 g, 4.80 mmol) in ethanol (100 ml) at room temperature was added cyanogen bromide (0.81 g, 7.67 mmol). After stirring overnight, the ethanol was removed under reduced pressure and the resulting brown solid was taken up in $CH_2Cl_2$ and the solution was washed with 1 N NaOH, the aqueous layer was extracted 3× with $CH_2Cl_2$, the combined organic layers were dried over anhydrous magnesium sulfate and concentrated. The product, N-[2-amino-1-(2-carbamoyl-ethyl)-1H-benzoimidazol-5-yl]-N-methyl-benzamide, was isolated as an off-white solid, clean by NMR and LC-MS. (1.44 g, 89%)

To a solution of N-[2-amino-1-(2-carbamoyl-ethyl)-1H-benzoimidazol-5-yl]-N-methyl-benzamide (0.50 g, 1.48 mmol) in DMF at room temperature was added 4-cyanobenzoic acid (0.24 g, 1.63 mmol), PyBrOP (1.03 g, 2.22 mmol) and DIEA (0.57 g, 4.44 mmol, 0.8 ml). The solution was stirred for 24 hours at room temperature and the TLC showed no starting material present. The reaction mixture was poured into 1 N HCl and the aqueous layer was extracted 3× with ethyl acetate. The combined organic layers were washed with saturate $NaHCO_3$, water, brine and dried over magnesium sulfate. The solution was filtered and the solvent removed under reduced pressure. Flash chromatography (3% $CH_3OH/CH_2Cl_2$) afforded the title compound. (0.35 g, 51%) ESMS m/z 467 ($MH^+$).

Example 3

Synthesis of cyclohexyl-N-(3-fluoro-4-nitrophenyl)-N-methyl-carboxamide

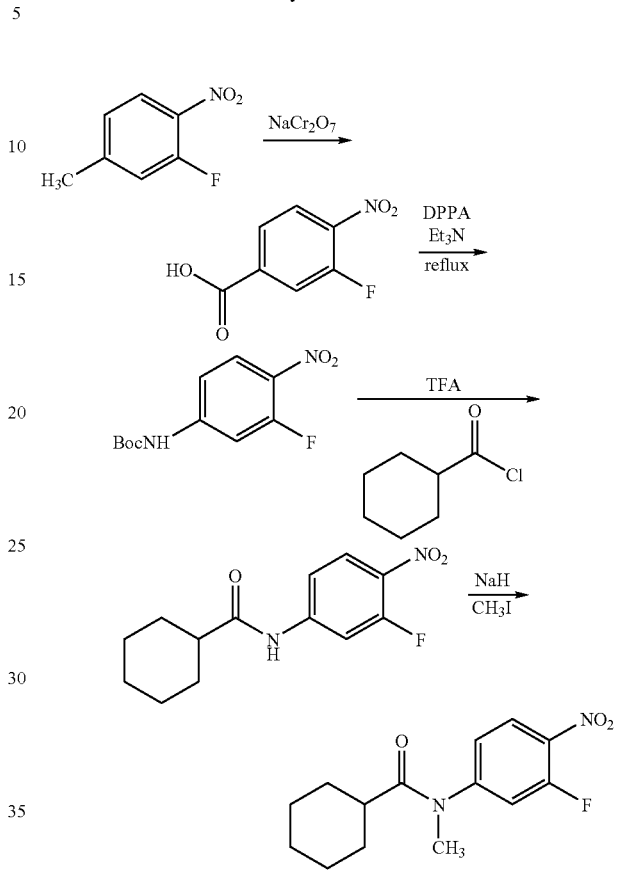

Concentrated $H_2SO_4$ (190 mL) was added dropwise to a cooled solution of 3-fluoro-4-nitrotoluene (161.2 mmol, 25 g) and sodium dichromate dihydrate (225.6 mmol, 67.2 g) in water (200 mL). The addition was carried out while maintaining the temperature of the reaction mixture below 10° C. Once the addition was complete, the solution was refluxed at 100° C. for approximately 2 h. The reaction mixture was cooled to room temperature, diluted with $H_2O$ (200 mL) and the product extracted with ethyl acetate. The organic extracts were combined and extracted with a solution of 2N sodium hydroxide. The basic phase was acidified with concentrated HCl to afford (65.9 mmol, 12.2 g) as an off-white solid precipitate (yield: 40.8%). The precipitate was further purified by recrystallization from an ethanol/water mixture to afford 3-fluoro-4-nitrobenzoic acid as white crystals.

Diphenylphosphorylazide (5.5 mmol, 1.5 g) was added to a solution of 3-fluoro-4-nitrobenzoic acid (5.4 mmol, 1 g) and triethylamine (5.6 mmol, 0.8 mL) in a 1:1 mixture of tert-butyl alcohol/dioxane (60 mL). The reaction mixture was refluxed for 2 days at 95° C. and the solvent was evaporated to give an oily residue. The residue was taken up in ethyl acetate (100 mL) and washed with 10% citric acid, 1N NaOH, brine and $H_2O$. Evaporation of solvent afforded an orange residue that was subsequently purified by flash chromatography eluting with ethyl acetate/hexane to afford (tert-butoxy)-N-(3-fluoro-4-nitrophenyl)carboxamide (1.75 mmol, 0.45 g, yield 32%). 3-Fluoro-4-nitroaniline (0.36 g, 2.3 mmol) was isolated as a byproduct. Treatment of (tert-butoxy)-N-(3-fluoro-4-nitrophenyl)carboxamide with trifluoroacetic acid in methylene chloride afforded additional 3-fluoro-4-nitroaniline.

3-Fluoro-4-Nitroaniline (1 mmol, 0.15 g) was dissolved in a 3:1 mixture of CH$_2$Cl$_2$/THF (4 mL) and pyridine (0.2 mL) was added to the mixture, which was cooled in an ice-water bath under nitrogen. Cyclohexanecarbonylchloride (1.1 mmol, 0.162 g) was dissolved in CH$_2$Cl$_2$ (1 mL) and added dropwise to the above solution at 4° C. and stirred at room temperature for 3 h. The reaction mixture was diluted with CH$_2$Cl$_2$ (50 mL) and washed with 1N HCl, 10% NaHCO$_3$, brine and water, dried over Na$_2$SO$_4$ and the solvent evaporated to afford cyclohexyl-N-(3-fluoro-4-nitrophenyl)carboxamide (0.215 g) of product (Yield: 81%).

60% Sodium hydride powder (1.1 mmol, 0.045 g) was added in portions to a cooled solution of cyclohexyl-N-(3-fluoro-4-nitrophenyl)carboxamide (1 mmol, 0.266 g) and methyl iodide (1.2 mmol, 0.16 g) in DMF (5 mL). The reaction mixture was stirred overnight at room temperature. The solvent was removed under reduced pressure and the residue was dissolved in CH$_2$Cl$_2$ (50 mL) and washed with 10% NaHCO$_3$, brine, H$_2$O, dried over Na$_2$SO$_4$ and the solvent evaporated to afford 0.23 g of the title compound as a yellow oily residue (Yield: 82%).

Further reaction of this product as described for cyclohexanecarboxylic acid (4-fluoro-3-nitrophenyl)-methylamide in Example 2 to provides compounds of formula (I) having R$_4$ in the 6-position and t=0.

Example 4

Synthesis of N-[(3-butylamino-4-nitrophenyl)methyl]-N-methyl-cyclohexanecarboxamide This example illustrates how one may obtain compounds of formula (I) having R$_4$ in the 6-position and t=1.

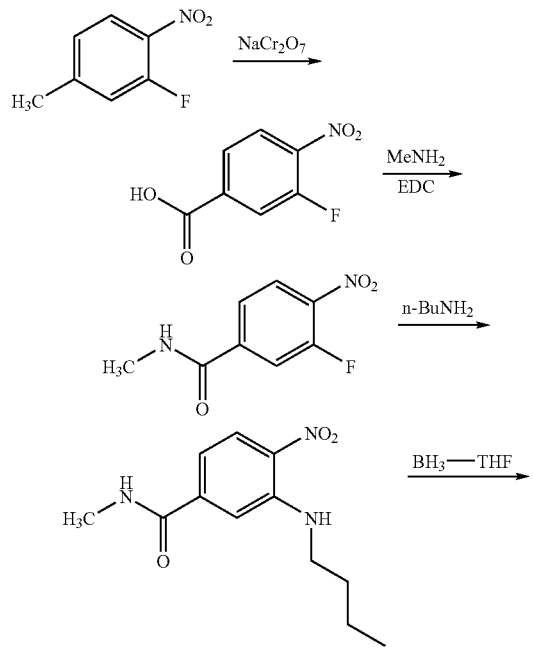

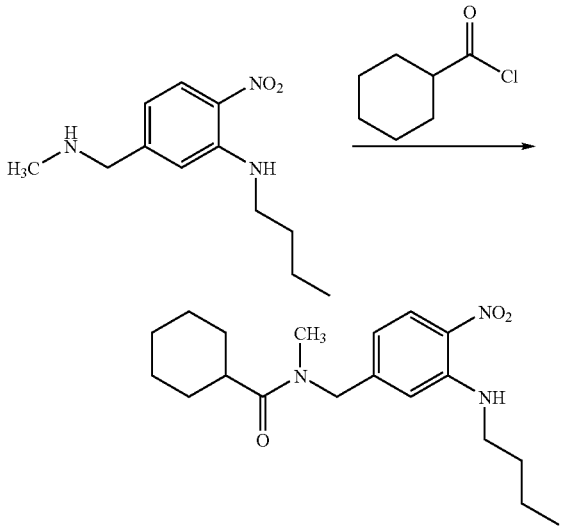

To a solution of 3-fluoro-4-nitrotoluene (22.45 g, 144.7 mmol) and sodium dichromate dihydrate (60.38 g, 202.6 mmol) in water at 0° C. was added concentrated sulfuric acid (140 mL) dropwise over 3 h. When the addition was complete, the solution was allowed to warm to room temperature over 1 h, and then brought to 90° C. for 1 h. The mixture was allowed to cool to room temperature, diluted with 300 mL water and extracted with ethyl acetate (3×250 mL). The combined organic extracts were concentrated down to 300 mL and extracted with 1 N NaOH (3×250 mL). The aqueous extracts were acidified with 6 N HCl and extracted with ethyl acetate (3×300 mL). The combined organic extracts were dried over MgSO$_4$ and concentrated to give a gummy solid. Trituration with hexane gave the 3-fluoro-4-nitrobenzoic acid as a solid that was collected by filtration (6.51 g, 24%).

To a solution of 3-fluoro-4-nitrobenzoic acid (4.0 g, 21.6 mmol) and EDC (1-[3-(dimethylamino)propyl]-3-ethylcarbodiimide hydrochloride) (4.36 g, 28.1 mmol) in methylene chloride (100 mL) was added methylamine (11.3 mL of a 2 M solution in MeOH, 22.7 mmol) and the solution was stirred at room temperature overnight. The solution was washed with 1 N HCl, dried over MgSO$_4$ and concentrated to a solid. The solid was triturated with butyl chloride and collected by filtration to give the N-methyl-3-fluoro-4-nitrobenzamide (3.81 g, 96%).

To a solution of N-methyl-3-fluoro-4-nitrobenzamide (300 mg, 1.64 mmol) and diisopropylethylamine (0.43 mL, 2.46 mmol) in DMF (7 mL) was added butylamine (0.203 mL, 2.05 mmol) and the solution was stirred at room temperature overnight. The solution was concentrated, the residue dissolved in ethyl acetate and washed with 1 N HCl. The organic phase was dried over MgSO$_4$ and concentrated to give N-methyl-3-butylamino-4-nitrobenzamide as a yellow oil that was used without further purification (380 mg, 92%).

To a solution of N-methyl-3-butylamino-4-nitrobenzamide (380 mg, 1.51 mmol) in anhydrous THF (20 mL) was added a solution of borane-THF (3.78 mL of a 2 M solution, 7.56 mmol) and the solution was stirred at room temperature 30 min, and then was warmed to reflux overnight. The solution was allowed to cool to room temperature, 1 N HCl was added to quench the reaction, and the aqueous was washed with ethyl acetate. The aqueous was made basic with 1 N NaOH and extracted with ethyl acetate. The combined organic extracts were dried over MgSO4 and concentrated to give the product N-butyl-5-methylaminomethyl-2-nitroaniline (275 mg, 77%), approximately 90% pure by NMR and LCMS.

A solution of N-butyl-5-methylaminomethyl-2-nitroaniline (275 mg, 1.16 mmol), pyridine (0.117 mL, 1.45 mmol) and cyclohexanecarbonyl chloride (0.171 mL, 1.27 mmol) in methylene chloride was stirred at room temperature overnight. The solution was washed with 1 N HCl, dried over MgSO$_4$ and concentrated to a yellow oil. Purification by column chromatography eluting with 50% hexane/ethyl acetate afforded the title compound as a yellow oil (205 mg, 51%).

Following reduction of the nitroaniline to the diaminobenzene derivative as described in Example 2, the product is then converted to the 2-aminobenzimidazole derivative by treatment with cyanogen bromide as described in Example 1. Reaction of this product with an acyl halide as described in Example 1 provides desired compound of formula (I) with R$_4$ in the 6-position and t=1.

Example 5

Synthesis of N-[(4-(3-methoxypropyl)amino-3-nitrophenyl)methyl]-N-methyl-cyclohexanecarboxamide This example illustrates how one obtains compounds of formula (I) having R$_4$ in the 5-position and t=1.

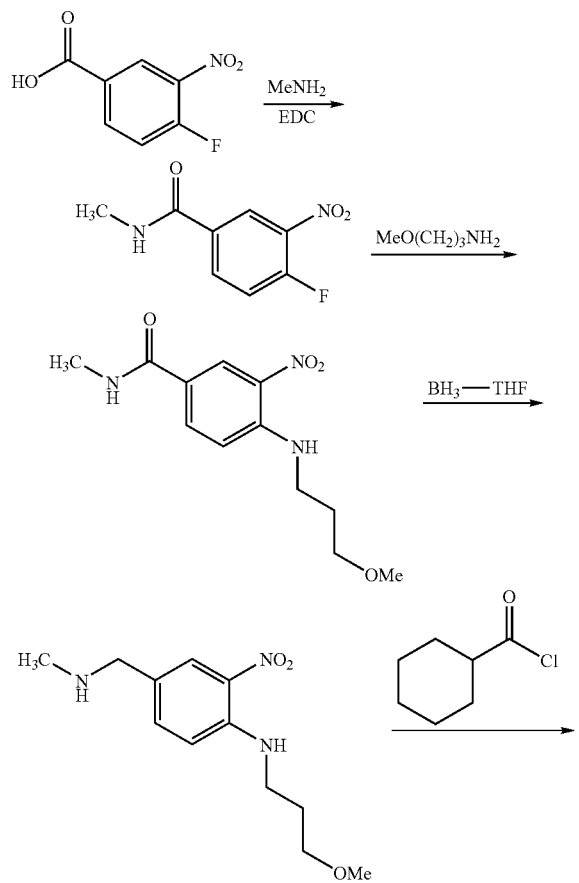

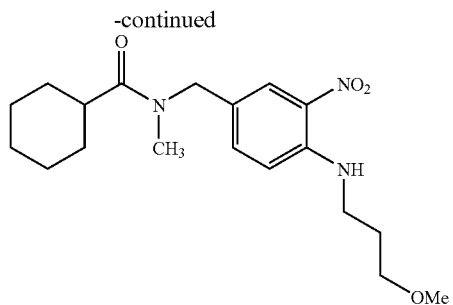

4-Fluoro-3-nitrobenzoic acid (3.00 g, 16.2 mmoles) was dissolved in dichloromethane (100 mL) and cooled in an ice bath to 0–5° C. EDC (3.73 g, 19.5 mmoles) was added followed by dropwise addition of methylamine solution (8.1 mL, 16.2 mmoles, 2.0 M solution in THF). The mixture was allowed to slowly warm to room temperature and stirred for 2 h. The mixture was then diluted with ethyl acetate and washed successively with 1 M HCl, saturated aqueous NaHCO$_3$ and brine. The organic extracts were dried over MgSO$_4$, filtered and concentrated in vacuo to leave 4-fluoro-3-nitro-N-methylbenzamide as a yellow solid (2.94 g, 91%) which was used directly in the next step.

A solution of 4-fluoro-3-nitro-N-methylbenzamide (1.00 g, 5.05 mmoles) in 15 mL dichloromethane was prepared and added dropwise to a stirred solution of 3-methoxypropylamine (0.78 mL, 7.57 mmoles) and N,N-diisopropylethylamine (2.6 mL, 15.1 mmoles) in 10 mL dichloromethane. After stirring at room temperature overnight, TLC (EtOAc) revealed complete conversion to a lower Rf product. The mixture was diluted with ethyl acetate and washed successively with 1 M HCl, saturated aqueous NaHCO$_3$ and brine. The organic extracts were dried over MgSO$_4$, filtered and concentrated in vacuo to leave an orange solid residue. The crude product was dissolved in dichloromethane, adsorbed onto silica gel and then purified by flash column chromatography on silica gel. Elution with ethyl acetate provided pure fractions which were combined and concentrated to yield 4-(3-methoxypropylamino)-3-nitrophenyl-N-methylbenzamide as an orange solid product (1.34 g, 99%). $^1$H NMR (CDCl$_3$) was consistent with the desired product.

BH$_3$ THF solution (17 mL, 17 mmoles, 1.0 M in THF) was added to a solution of 4-(3-methoxypropylamino)-3-nitrophenyl-N-methylbenzamide (0.65 g, 2.4 mmoles) dissolved in 10 mL THF under argon. The mixture was stirred at room temperature for 1 h and then heated to 70° C. for 16 h. The solution was then cooled in an ice bath and quenched by dropwise addition of 1 M HCl. The mixture was diluted with 1 M HCl and washed once with EtOAc. The organic wash was discarded and the aqueous layer was made basic by addition of 50% NaOH/H$_2$O to pH 10–12. The basic solution was then extracted three times with EtOAc. The organic extracts were combined, dried over MgSO$_4$, filtered and concentrated to provide N-(3-methoxypropyl)-4-methylaminomethyl-2-nitroaniline as an orange oil (0.337 g, 55%). The crude product was used directly for the next step.

A solution of N-(3-methoxypropyl)-4-methylaminomethyl-2-nitroaniline (0.337 g, 1.33 mmoles) in 10 mL dichloromethane was treated with N,N-diisopropylethylamine (0.70 mL, 4.0 mmoles) followed by dropwise addition of cyclohexanecarbonyl chloride (0.20 mL, 1.46 mmoles). The mixture was stirred at room temperature for 10 min after which TLC revealed complete conversion to a higher Rf product. The mixture was diluted with EtOAc and washed successively with 1 M HCl, saturated aqueous NaHCO$_3$, and brine. The organic extracts were dried over MgSO$_4$, filtered and concentrated in vacuo to furnish an orange oil. Flash column chromatography on silica gel eluting with 75% EtOAc/hexane provided the title compound as an orange oil (0.240 g, 50%). $^1$H NMR (CDCl$_3$) was consistent with the desired product.

Following reduction of the nitroaniline to the diamino benzene derivative as described in Example 2, the product is then converted to the 2-aminobenzimidazole derivative by treatment with cyanogen bromide as described in Example 1. Reaction of this product with an acyl halide as described in Example 1 provides desired compound of formula (I) with R$_4$ in the 5-position and t=1.

Example 6

Synthesis of 4-cyano-N-[5-[(cyclohexyl-methyl-amino)-methyl]-1-(2-methoxy-ethyl)-1H-benzimidazol-2-yl]-benzamide

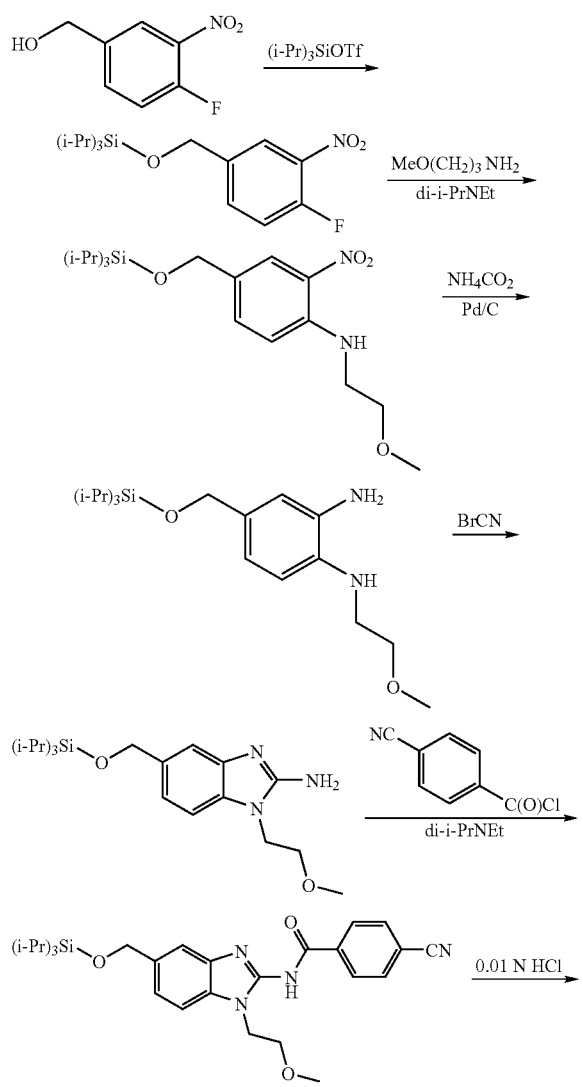

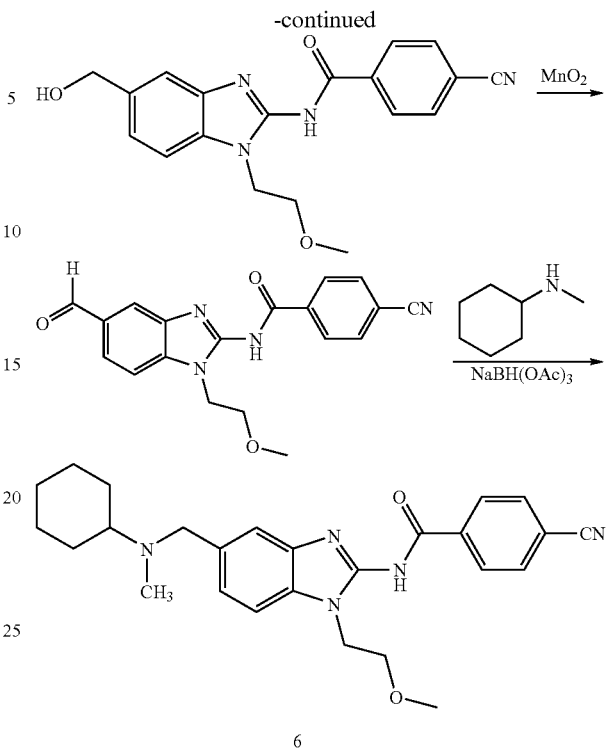

6

To a solution of 4-fluoro-3-nitrobenzyl alcohol (1.023 g, 5.98 mmol) in dichloromethane (50 mL) at room temperature was added 2,6-lutidine (0.836 mL, 7.17 mmol) followed by triisopropylsilyl trifluoromethanesulfonate (1.77 mL, 6.57 mmol). After stirring overnight, the solution was washed with water, the aqueous extracted with dichloromethane, the organics combined, dried over anhydrous magnesium sulfate, and concentrated to afford the tri-isopropylsilyl protected as a brown oil used as is in the next reaction.

To a solution of the above intermediate (~1.0 g, ~2.99 mmol) in acetonitrile (30 mL) at room temperature was added 3-methoxypropylamine (0.457 mL, 4.49 mmol) followed by diisopropylethylamine (1.04 mL, 5.98 mmol). The solution was warmed to 50° C. overnight, cooled to room temperature and concentrated. Dichloromethane was added to the oil, the solution was washed with water, the aqueous extracted with dichloromethane, the organics combined, dried over anhydrous magnesium sulfate, and concentrated to give a brown oil. Purification by silica gel chromatography eluting with 10% ethyl acetate/hexanes afforded the desired substituted nitroaniline as an orange solid (0.72 g, 61% over 2 steps).

To a solution of the above nitroaniline (0.72 g, 1.82 mmol) in ethanol (60 mL) at room temperature was added ammonium formate (1.15 g, 18.2 mmol) followed by 10% palladium on carbon (~0.5 g). After stirring 3 h, the orange solution had turned clear and the reaction appeared complete by TLC. The mixture was filtered through diatomaceous earth washed with methanol and concentrated to give a brown solid. Dichloromethane was added, the solution washed with water, the aqueous extracted with dichloromethane, the organics combined, dried over anhydrous magnesium sulfate, and concentrated to afford N-1-(3-methoxy-propyl)-4-triisopropylsilanyloxymethyl-benzene-1,2-diamine as a brown solid, clean by NMR (604 mg, 91%).

To a solution of the above diamine (582 mg, 1.59 mmol) in ethanol (40 mL) at room temperature was added cyanogen bromide (253 mg, 2.38 mmol). After stirring overnight, the solution was concentrated to a brown solid. Dichloromethane was added, the solution washed with 1 N sodium hydroxide, the aqueous extracted with dichloromethane, the organics combined, dried over anhydrous magnesium sulfate, and concentrated. Purification by silica gel chromatography eluting with 5% methanol/dichloromethane afforded 1-(3-methoxy-propyl)-5-triisopropylsilanyloxymethyl-1H-benzimidazol-2-ylamine as an off-white solid (548 mg, 88%).

To a solution of the above benzimidazolylamine (542 mg, 1.39 mmol) in dichloromethane (30 mL) at room temperature was added diisopropylethylamine (0.484 mL, 2.78 mmol), 4-cyanobenzoyl chloride (253 mg, 1.52 mmol) and dimethylaminopyridine (~10 mg). After stirring overnight at room temperature, the reaction appeared complete by TLC. The solution was washed with water, the aqueous extracted with dichloromethane, the organics combined, dried over anhydrous magnesium sulfate, and concentrated to give a brown oil. Purification by silica gel chromatography eluting with 10% ethyl acetate/hexanes afforded the product 4-cyano-N-[1-(2-methoxy-ethyl)-5-triisopropylsilanyloxymethyl-1H-benzimidazol-2-yl]-benzamide as a white solid (560 mg, 77%).

To a suspension of the above benzamide (169 mg, 0.325 mmol) in dioxane (15 mL) was added 0.01 N HCl (15 mL) and the suspension warmed to 95° C. After 3 hours, the reaction appeared complete by TLC and the solution cooled to room temperature. The solid that crashed out of solution as the reaction cooled was collected by filtration, washed with water, and dried to afford 4-cyano-N-[5-hydroxymethyl-1-(2-methoxy-ethyl)-1H-benzimidazol-2-yl]-benzamide as a yellow solid (109 mg, 92%).

To a solution of 4-cyano-N-[5-hydroxymethyl-1-(2-methoxy-ethyl)-1H-benzimidazol-2-yl]-benzamide (15.4 mg, 0.042 mmol) in acetone (2 mL) was added manganese (IV) oxide (43 mg, 0.42 mmol). After stirring overnight, the black suspension was filtered thru diatomaceous earth and the filtrate concentrated. The filtrate was dissolved in acetone and run through a 2 g SepPak silica gel cartridge to afford 4-cyano-N-[5-formyl-1-(2-methoxy-ethyl)-1H-benzimidazol-2-yl]-benzamide as a white solid (13 mg, 84%).

To a solution of the above aldehyde (13 mg, 0.036 mmol) in dichloromethane (2 mL) and triethylorthoformate (1 mL) was added cyclohexylmethylamine (0.094 mL, 0.72 mmol), acetic acid (1 drop). After 2 h, sodium triacetoxyborohydride was added and the solution stirred overnight. The reaction was quenched with water, the aqueous extracted with dichloromethane, the organics were combined, dried over magnesium sulfate and concentrated to give a yellow solid. Purification by silica gel chromatography eluting with 0.5% ammonium hydroxide/5% methanol/dichloromethane afforded the title compound as a white solid (7 mg, 42%).

What is claimed is:
1. A compound of the formula (I):

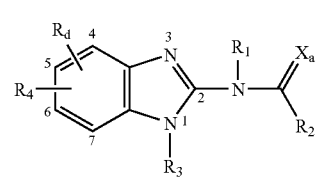

wherein:
$R_1$ is hydrogen or alkyl;
$R_2$ is chosen from aryl and heteroaryl, each $R_2$ is optionally substituted with one or more $R_a$;
$R_3$ is $C_{1-10}$ alkyl chain branched or unbranched optionally substituted with one or more $R_b$,
or $R_3$ is the group:
—$(CH_2)_n$-L-$R_6$, wherein L is chosen from a bond, —NH—C(O)—, —O—C(O)—, —C(O)— and —S(O)$_m$— wherein m is 0, 1 or 2, and wherein said group is optionally substituted by one or more $R_b$;
wherein $R_6$ is independently chosen from hydrogen, hydroxy, alkyl, alkoxy, alkylthio, aryl$C_{0-5}$ alkyl, aryloxy$C_{0-5}$ alkyl, heteroaryl$C_{0-5}$ alkyl, cycloalkyl$C_{0-5}$ alkyl, heterocyclyl$C_{0-5}$ alkyl and amino said amino is optionally mono-or di-substituted by acyl, alkyl, alkoxycarbonyl, cycloalkyl$C_{0-5}$ alkyl, aryl$C_{0-5}$alkyl, heteroaryl$C_{0-5}$ alkyl or heterocyclyl$C_{0-5}$ alkyl;
n is 1–10;
$R_4$ is

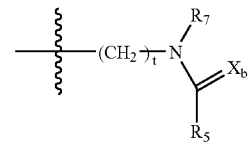

wherein $R_4$ is covalently attached at the indicated 5- or 6-position of the formula (I), t is 0,
$R_5$ is chosen from aryl$C_{0-5}$ alkyl, alkyl, heteroaryl$C_{0-5}$ alkyl, cycloalkyl$C_{0-5}$ alkyl and heterocyclyl$C_{0-5}$ alkyl, each $R_5$ is optionally substituted with one or more $R_c$;
$R_7$ is hydrogen, alkenyl or alkyl;
or $R_5$ and $R_7$ together with the nitrogen atom to which they are attached form:
a 4–7-membered monocyclic ring or
an 8–14-membered bicyclic ring,
wherein each monocyclic or bicyclic ring optionally contains an additional 1 to 3 heteroatoms chosen from N, O and S and each ring is aromatic or nonaromatic, and wherein each monocyclic or bicyclic ring is optionally substituted by one or more $R_c$;
each $R_a$, $R_b$ or $R_c$ are independently chosen from hydrogen, alkyl, alkenyl, alkynyl, cycloalkyl, aryl, arylalkyl, aryloxy, alkoxy, alkylthio, acyl, alkoxycarbonyl, acyloxy, acylamino, sulphonylamino, aminosulfonyl, alkylsulfonyl, carboxy, carboxamide, oxo, hydroxy, halogen, trifluoromethyl, nitrile and amino optionally mono-or -di-substituted by alkyl, acyl or alkoxycarbonyl, wherein any of the above $R_a$, $R_b$ or $R_c$ are optionally halogenated where possible;

$R_d$, covalently attached at the indicated 4-, 5-, 6- or 7-position of the formula (I), is chosen from hydrogen, alkyl, alkoxy and halogen and $X_a$ and $X_b$ are oxygen or sulfur;

or the pharmaceutically acceptable salts, esters, acids, isomers or tautomers thereof.

2. The compound according to claim 1 wherein:

$R_1$ is hydrogen;

$R_2$ is chosen from phenyl, naphthyl, and heteroaryl chosen from thienyl, furanyl, isoxazolyl, oxazolyl, thiazolyl, thiadiazolyl, tetrazolyl, pyrazolyl, pyrrolyl, imidazolyl, pyridinyl, pyrimidinyl, pyrazinyl, pyridazinyl, pyranyl, quinoxalinyl, indolyl, benzimidazolyl, benzoxazolyl, benzothiazolyl, benzothienyl, quinolinyl, quinazolinyl and indazolyl, each $R_2$ is optionally substituted with one or more $R_a$;

$R_3$ is $C_{1-10}$ alkyl chain branched or unbranched optionally substituted with one or more $R_b$, or $R_3$ is:

—$(CH_2)_n$-L-$R_6$, wherein L is chosen from a bond, —O—C(O)—, —C(O)— and —S(O)$_m$— wherein m is 0, 1 or 2, and wherein said group is optionally substituted by one or more $R_b$;

wherein $R_6$ is independently chosen from hydrogen, hydroxy, $C_{1-5}$ alkyl, $C_{1-5}$ alkoxy, $C_{1-5}$ alkylthio, phenyl, naphthyl, benzyl, phenethyl, heteroaryl$C_{0-5}$ alkyl, $C_{3-7}$ cycloalkyl$C_{0-5}$ alkyl, heterocyclyl$C_{0-5}$ alkyl and amino said amino is optionally mono-or di-substituted by $C_{1-5}$ acyl, $C_{1-5}$ alkyl, $C_{1-5}$ alkoxycarbonyl, aryl$C_{0-5}$ alkyl, heteroaryl$C_{0-5}$ alkyl or heterocyclyl$C_{0-5}$ alkyl; and wherein each recited heteroaryl in this paragraph is chosen from thienyl, furanyl, isoxazolyl, oxazolyl, thiazolyl, thiadiazolyl, tetrazolyl, pyrazolyl, pyrrolyl, imidazolyl, pyridinyl, pyrimidinyl, pyrazinyl, pyridazinyl and pyranyl and wherein each recited heterocyclyl in this paragraph is chosen from pyrrolidinyl, morpholinyl, thiomorpholinyl, dioxalanyl, piperidinyl and piperazinyl;

$R_5$ is chosen from phenyl, naphthyl, benzyl, phenethyl, $C_{1-5}$ alkyl and heteroaryl$C_{0-5}$ alkyl wherein the heteroaryl is chosen from thienyl, furanyl, isoxazolyl, oxazolyl, thiazolyl, thiadiazolyl, tetrazolyl, pyrazolyl, pyrrolyl, imidazolyl, pyridinyl, pyrimidinyl, pyrazinyl, pyridazinyl and pyranyl, $C_{3-7}$ cycloalkyl$C_{0-5}$ alkyl and heterocyclyl$C_{0-5}$ alkyl, wherein the heterocyclyl is chosen from aziridinyl, pyrrolidinyl, morpholinyl, thiomorpholinyl, tetrahydrofuranyl, dioxalanyl, piperidinyl and piperazinyl, each $R_5$ is optionally substituted with one or more $R_c$;

each $R_a$, $R_b$ or $R_c$ are independently chosen from hydrogen, $C_{1-5}$ alkyl, $C_{2-5}$ alkenyl, $C_{2-5}$ alkynyl, $C_{3-8}$ cycloalkyl, phenyl, benzyl, phenoxy, $C_{1-5}$ alkoxy, $C_{1-5}$ alkylthio, $C_{1-5}$ acyl, $C_{1-5}$ alkoxycarbonyl, $C_{1-5}$ acyloxy, $C_{1-5}$ acylamino, $C_{1-5}$ sulphonylamino, aminosulfonyl, $C_{1-5}$ alkylsulfonyl, carboxy, carboxamide, oxo, hydroxy, halogen, trifluoromethyl, nitrile and amino optionally mono-or -di-substituted by $C_{1-5}$ alkyl, $C_{1-5}$ acyl or $C_{1-5}$ alkoxycarbonyl, wherein any of the above $R_a$, $R_b$ or $R_c$ are optionally halogenated where possible;

$R_d$ is chosen from hydrogen, $C_{1-3}$ alkyl, $C_{1-3}$ alkoxy and halogen;

$R_7$ is hydrogen, $C_{3-10}$ alkenyl or $C_{1-5}$ alkyl; and $X_a$ is oxygen.

3. The compound according to claim 2 wherein:

$R_2$ is chosen from phenyl, naphthyl and heteroaryl chosen from thienyl, furanyl, isoxazolyl, oxazolyl, imidazolyl, thiadiazolyl, pyrazolyl, pyridinyl, quinoxalinyl and benzothienyl, each $R_2$ is optionally substituted with one or more $R_a$;

$R_6$ is independently chosen from hydroxy, $C_{1-5}$ alkyl, $C_{1-5}$ alkoxy, phenyl, benzyl, phenethyl, heteroaryl$C_{0-5}$ alkyl, heterocyclyl$C_{0-5}$ alkyl, $C_{3-7}$ cycloalkyl and amino said amino is optionally mono-or di-substituted by $C_{1-5}$ acyl, $C_{1-5}$ alkyl, $C_{1-5}$ alkoxycarbonyl, aryl$C_{0-5}$ alkyl or heteroaryl$C_{0-5}$ alkyl;

and wherein each recited heteroaryl in this paragraph is chosen from thienyl, furanyl, isoxazolyl, oxazolyl, thiazolyl, thiadiazolyl, tetrazolyl, pyrazolyl, pyrrolyl and imidazolyl, each optionally substituted by $R_b$;

n is 1–6;

$R_5$ is chosen from phenyl, naphthyl, benzyl, phenethyl, $C_{1-5}$ alkyl and heteroaryl$C_{0-5}$ alkyl wherein the heteroaryl in this paragraph is chosen from thienyl, furanyl, imidazolyl and pyridinyl, $C_{3-7}$ cycloalkyl$C_{0-5}$ alkyl and heterocyclyl$C_{0-5}$ alkyl, wherein the heterocyclyl is chosen from aziridinyl, pyrrolidinyl, tetrahydrofuranyl, tetrahydropyridinyl, morpholinyl, thiomorpholinyl, piperidinyl and piperazinyl, each $R_5$ is optionally substituted with one or more $R_c$;

$R_7$ is hydrogen, propenyl or $C_{1-3}$ alkyl and $R_d$ is chosen from hydrogen and $C_{1-3}$ alkyl.

4. The compound according to claim 3 wherein:

$R_2$ is chosen from phenyl and heteroaryl chosen from thienyl, furanyl, isoxazolyl, thiadiazolyl, pyrazolyl and pyridinyl, each $R_2$ is optionally substituted with one or more $R_a$;

$R_3$ is:

—$(CH_2)_n$—C(O)—$R_6$ or

—$(CH_2)_n$—$R_6$;

wherein $R_6$ is independently chosen from hydroxy, $C_{1-5}$ alkyl, $C_{1-5}$ alkoxy, phenyl, morpholinyl$C_{0-5}$ alkyl, piperazinyl$C_{0-5}$ alkyl, imidazolyl$C_{0-5}$ alkyl, pyrrolidinyl$C_{0-5}$ alkyl, pyrrolidinonyl$C_{0-5}$ alkyl, thienyl$C_{0-5}$ alkyl, $C_{3-7}$ cycloalkyl and amino said amino is optionally mono-or di-substituted by $C_{1-5}$ alkyl or $C_{1-5}$ alkoxycarbonyl;

$R_5$ is chosen from phenyl, furanyl, benzyl, phenethyl, $C_{1-3}$ alkyl and $C_{3-7}$ cycloalkyl$C_{0-5}$ alkyl, each optionally substituted with one or more $R_c$;

each $R_a$, $R_b$ or $R_c$ are independently chosen from $C_{1-5}$ alkyl, $C_{3-8}$ cycloalkyl, phenyl, $C_{1-5}$ alkoxy, amino optionally mono-or -di-substituted by $C_{1-5}$ alkyl, $C_{1-5}$ alkoxycarbonyl, carboxamide, hydroxy, halogen, trifluoromethyl, and nitrile, wherein any of the above $R_a$, $R_b$ or $R_c$ are optionally halogenated where possible;

$R_7$ is $C_{1-3}$ alkyl; and $R_d$ is chosen from hydrogen and methyl.

5. The compound according to claim 4 wherein:

$R_2$ is chosen from phenyl, thienyl, furanyl, isoxazolyl and pyridinyl, each optionally substituted with one or more $R_a$;

$R_5$ is chosen from methyl, $CF_3$, cyclopentyl, phenyl and cyclohexyl, each optionally substituted with one or more $R_c$;

$R_d$ is hydrogen and n is 2–5.

6. The compound according to claim 5 wherein:

$R_2$ is chosen from phenyl, thien-2-yl, isoxazol-5-yl and pyridin-3-yl, each optionally substituted with one or more $R_a$;

$R_6$ is independently chosen from hydroxy, methyl, ethyl, $C_{1-3}$ alkoxy, phenyl, morpholinyl, piperazinyl, imidazolyl, pyrrolidinyl, pyrrolidinonyl, thienyl$C_{0-5}$ alkyl, $C_{3-7}$ cycloalkyl and amino said amino is optionally mono-or di-substituted by $C_{1-5}$ alkyl or $C_{1-5}$ alkoxycarbonyl; and each $R_a$, $R_b$ or $R_c$ are independently chosen from $C_{1-3}$ alkoxy, amino optionally mono-or -di-substituted by $C_{1-3}$ alkyl, carboxamide, hydroxy, fluoro, chloro, bromo, trifluoromethyl, and nitrile.

7. The compound according to one of claims 2–6 wherein: $R_4$ is covalently attached at the indicated 5-position of the formula (I).

8. The compound according to one of claims 2–6 wherein: $R_4$ is covalently attached at the indicated 6-position of the formula (I).

9. A pharmaceutical composition comprising a pharmaceutically effective amount of a compound according to claim 1 and one or more pharmaceutically acceptable carriers and/or adjuvants.

10. A compound chosen from:

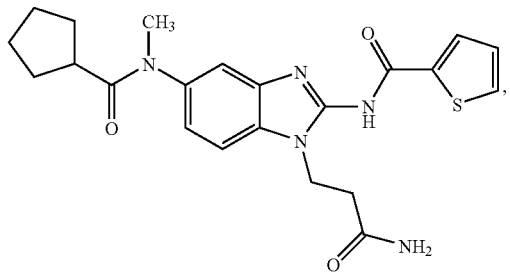

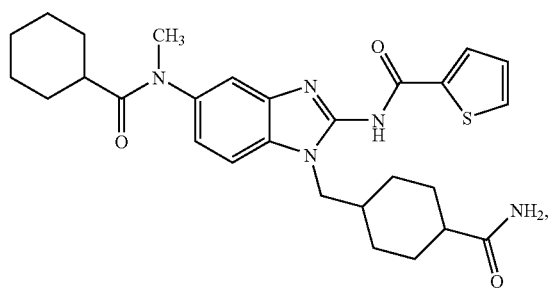

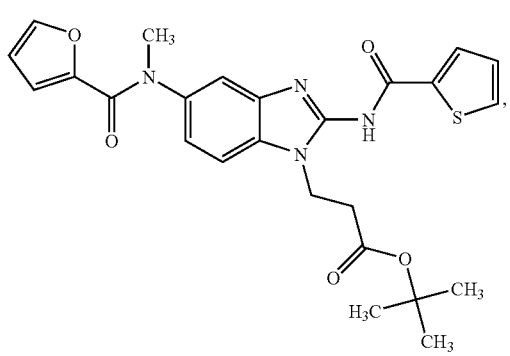

-continued

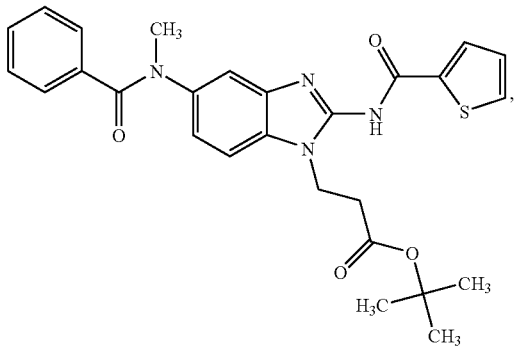

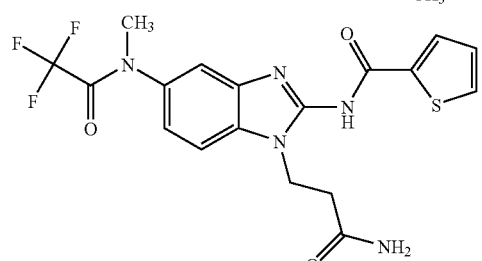

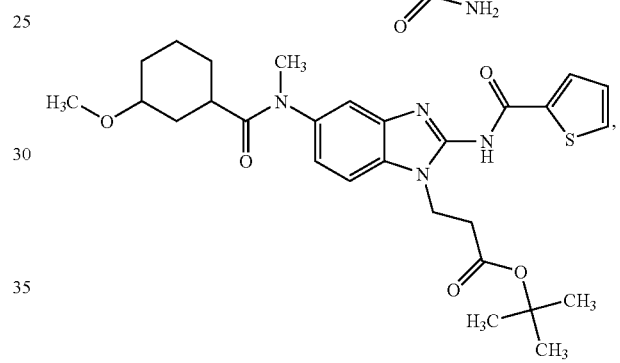

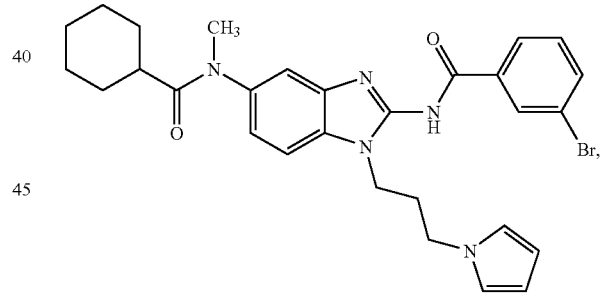

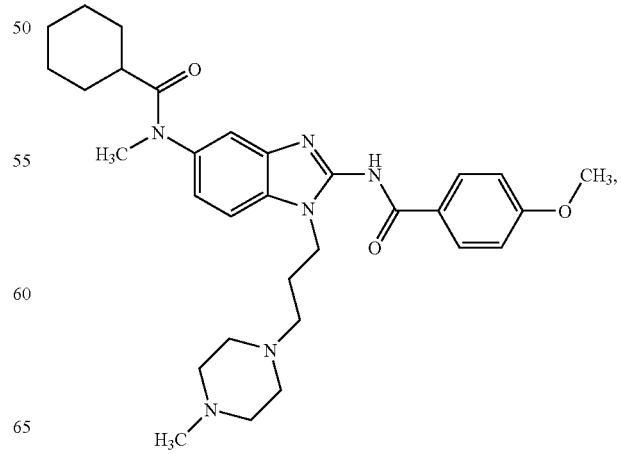

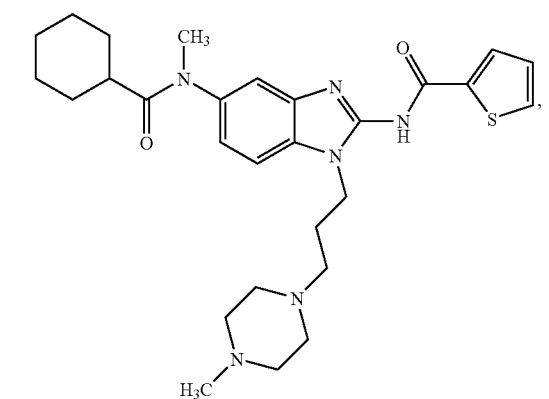
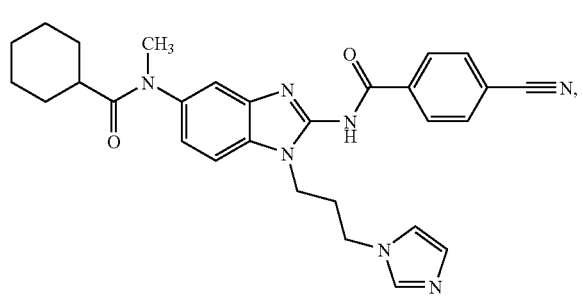
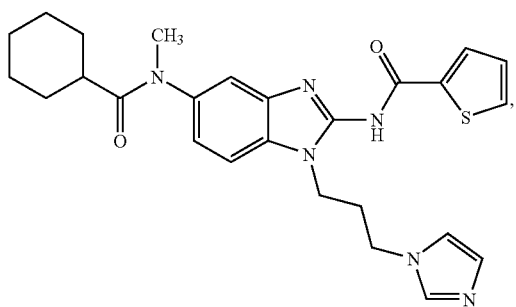
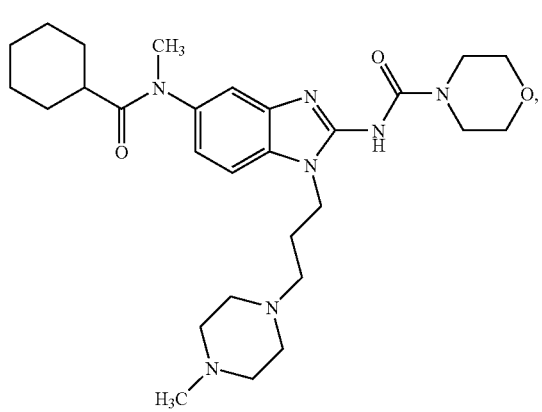
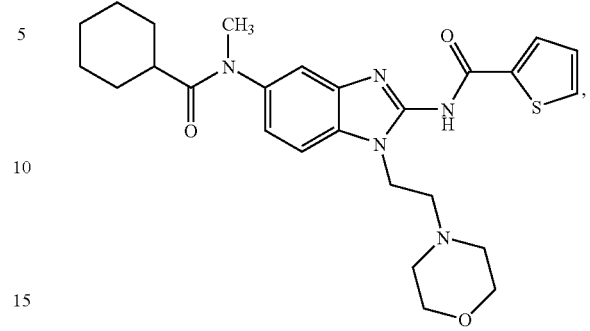
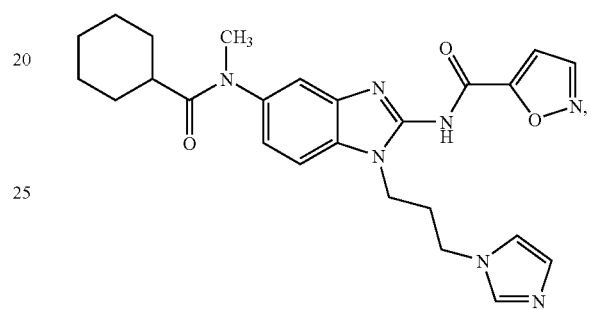
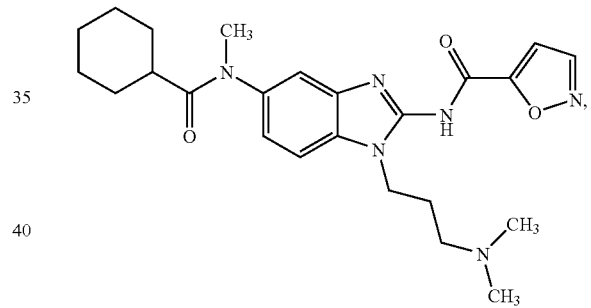
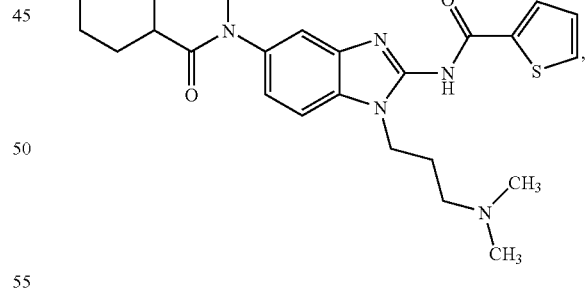
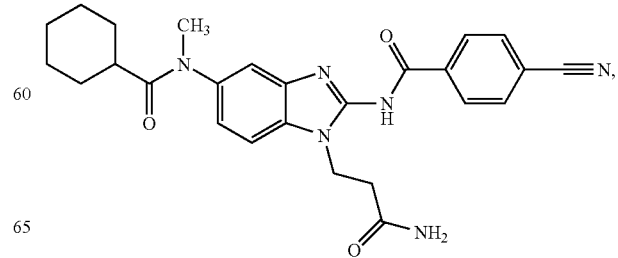

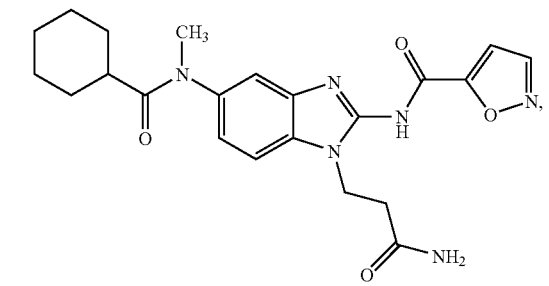
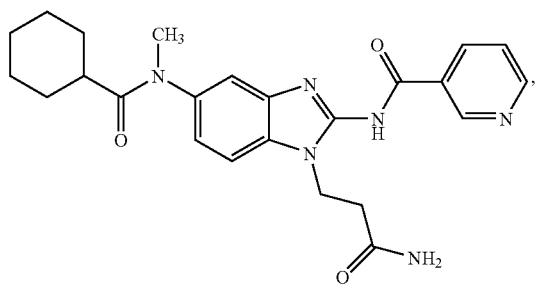
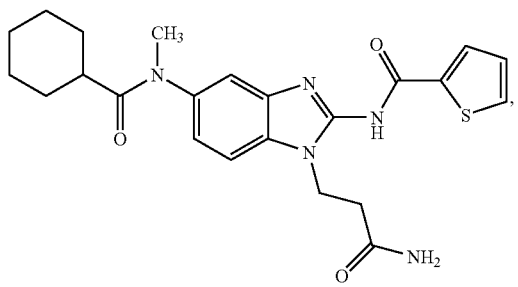
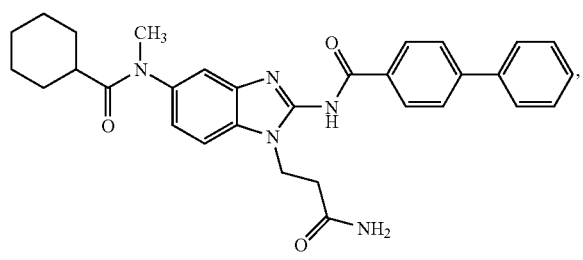
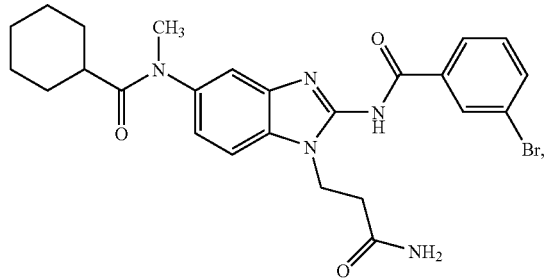
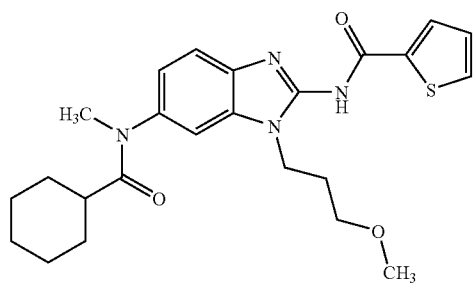
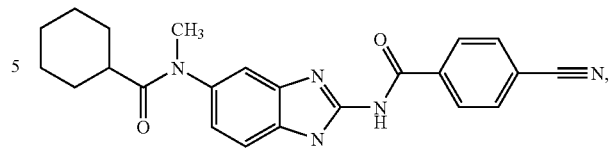
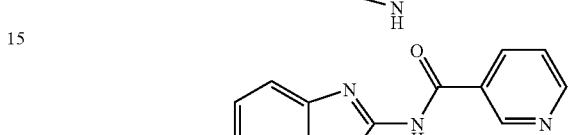
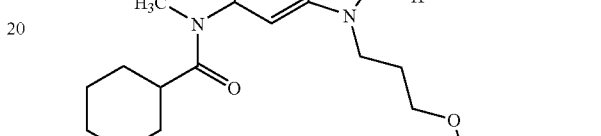
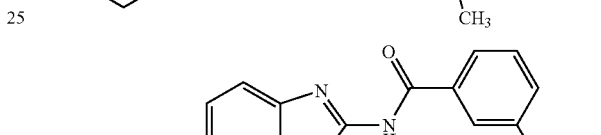
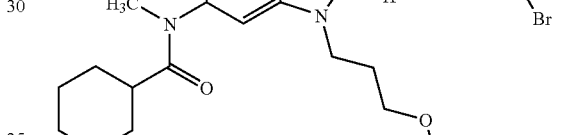
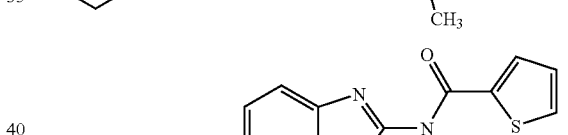
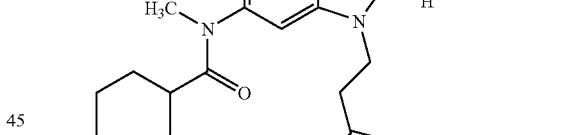
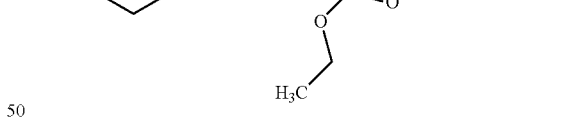
or the pharmaceutically acceptable salts thereof.
11. A compound chosen from:
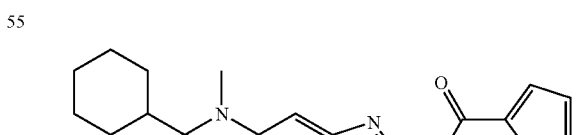
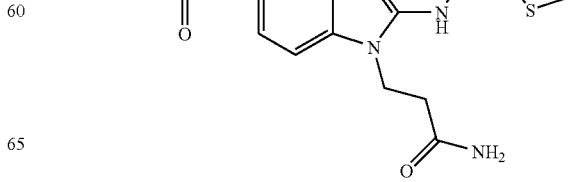

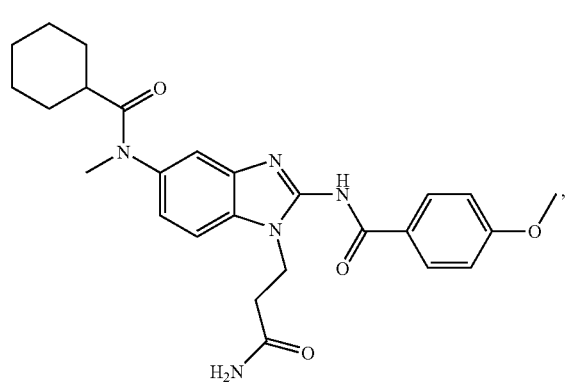
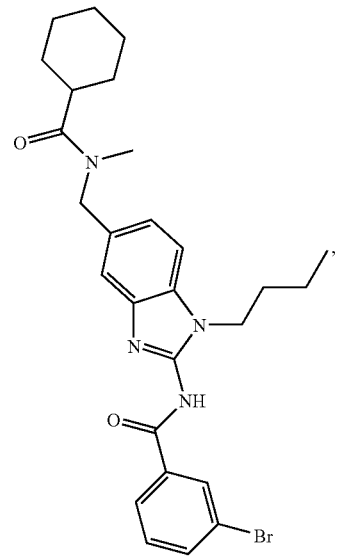
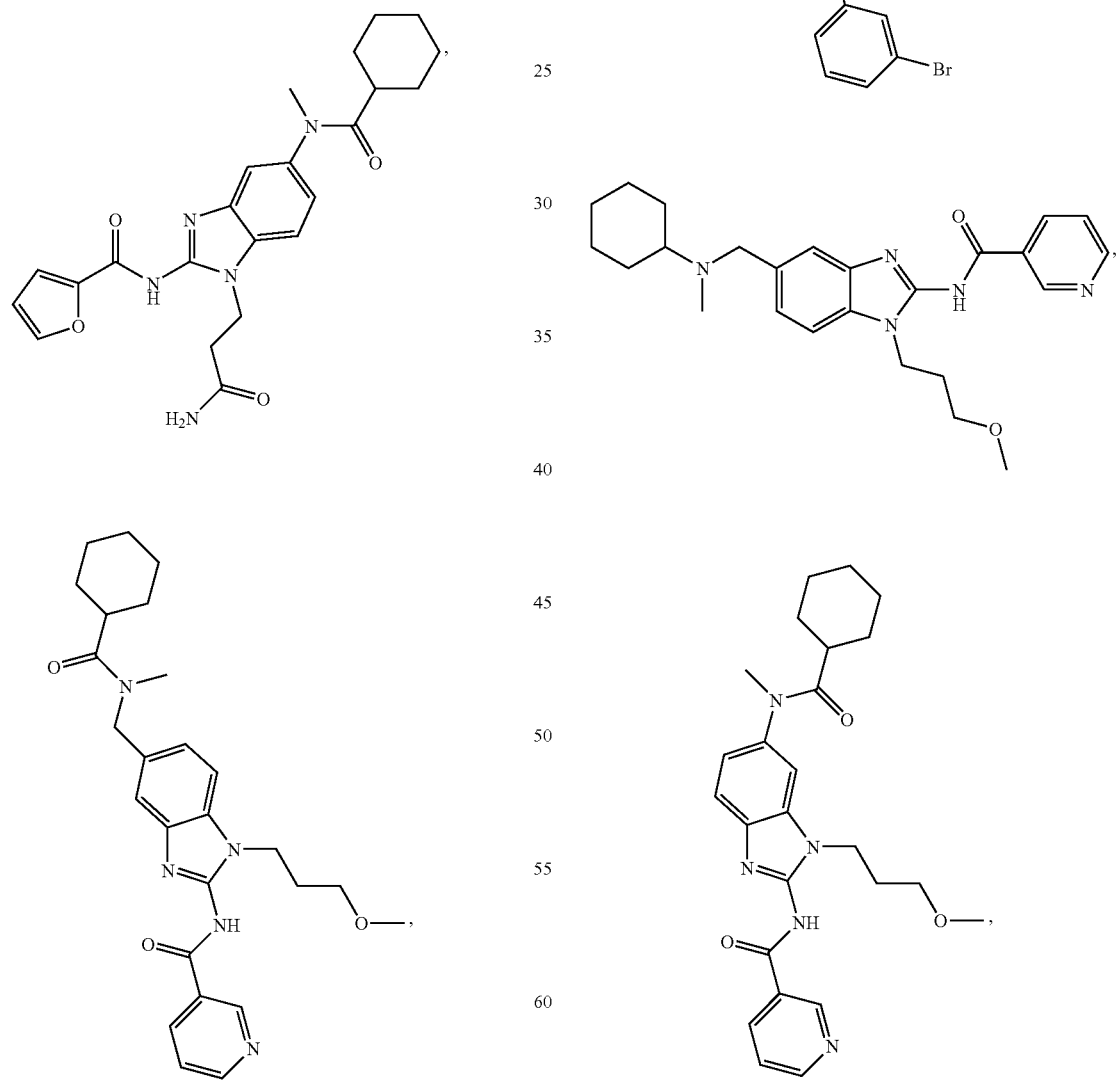

-continued
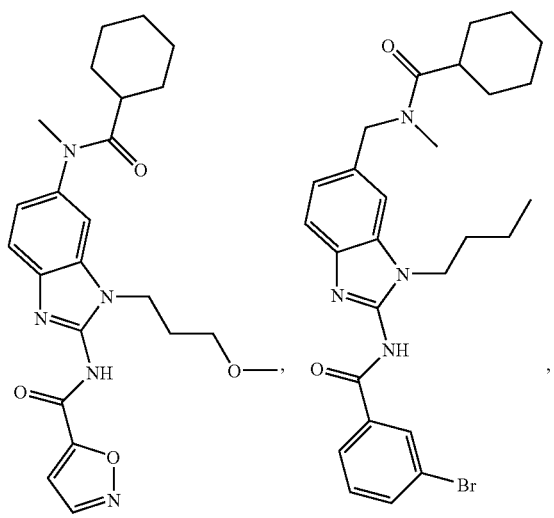
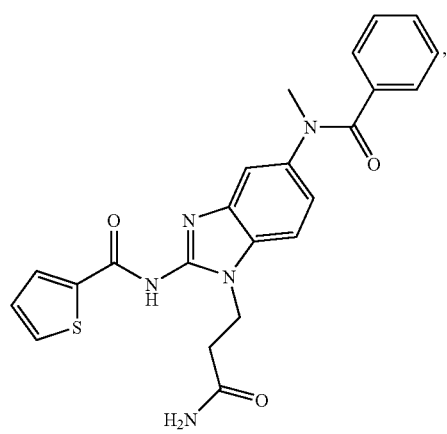
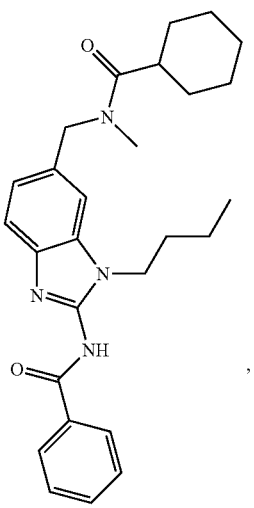
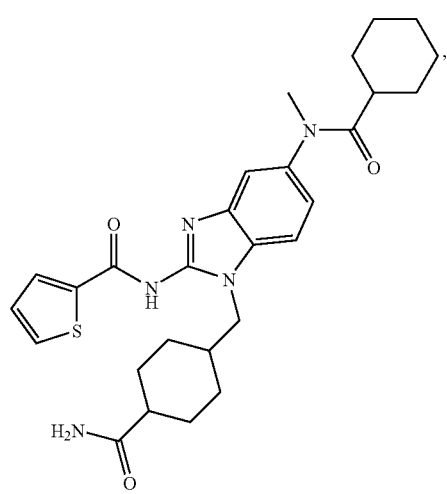
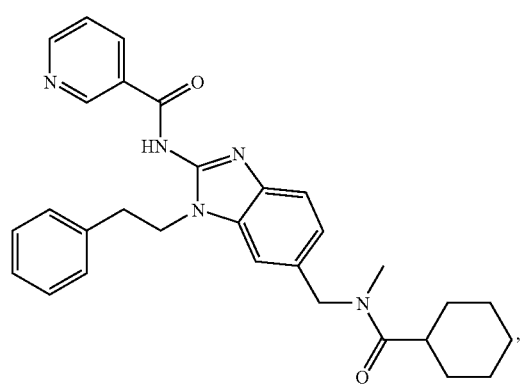
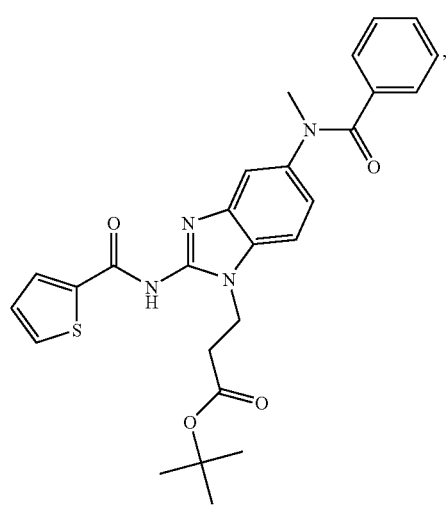

177 178
-continued -continued
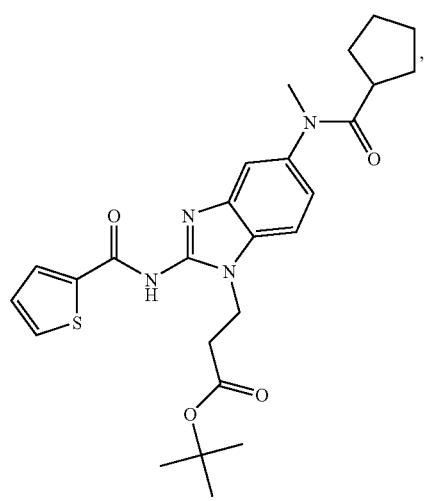
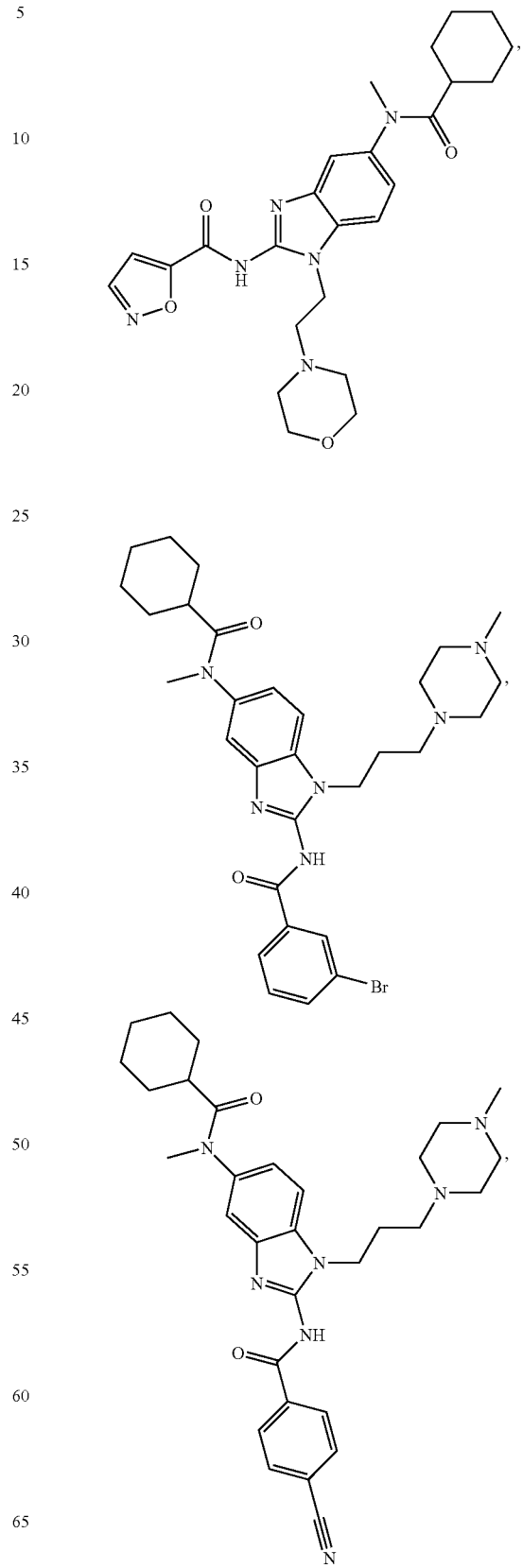

-continued
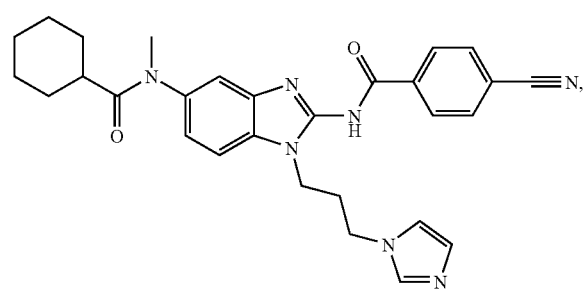
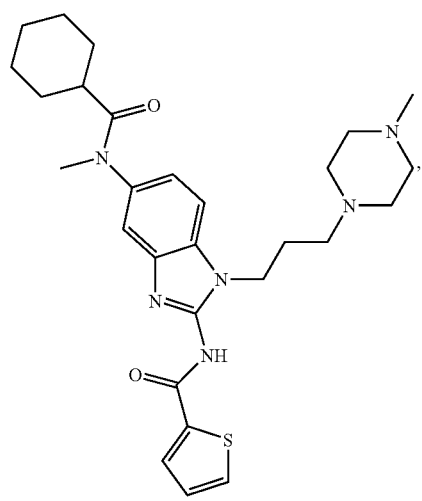
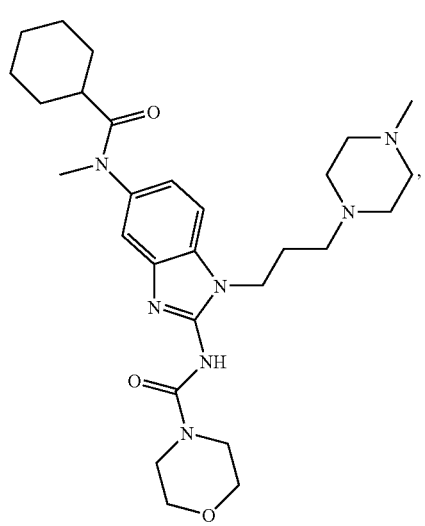
-continued
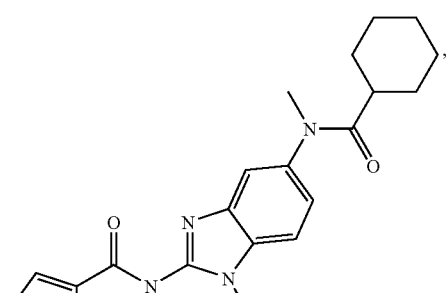
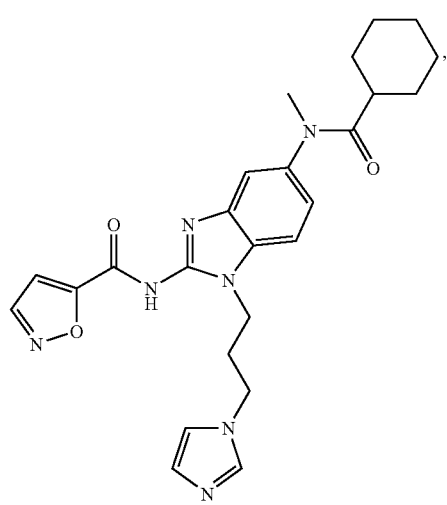
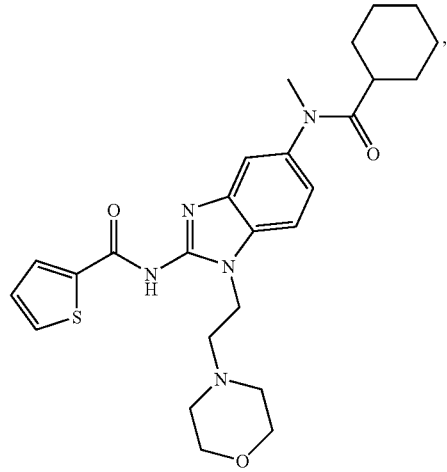

-continued
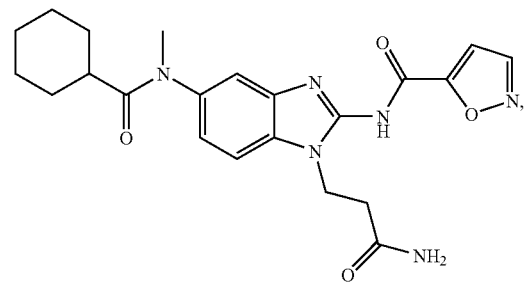
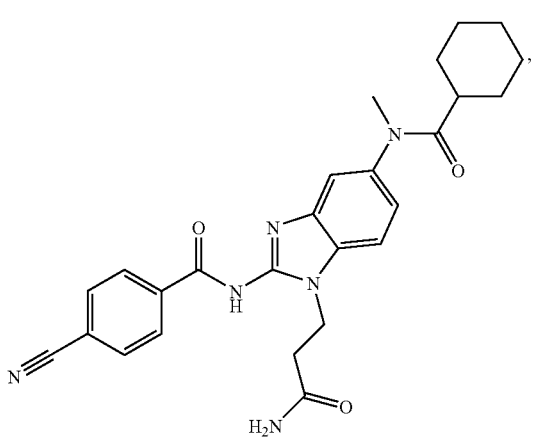
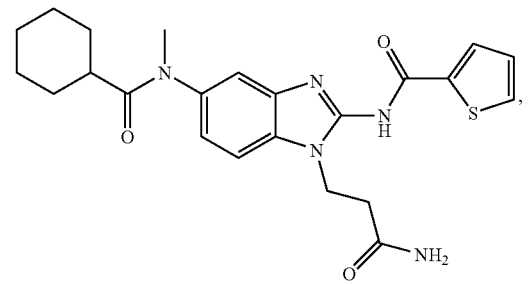
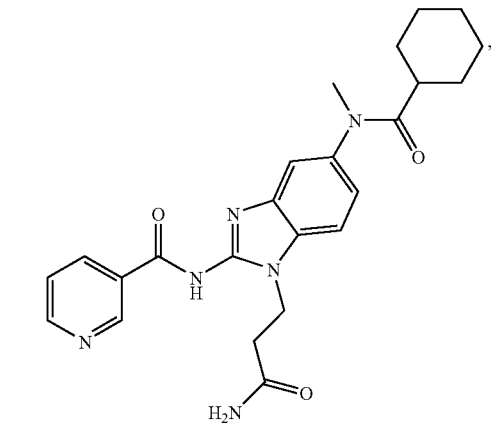
-continued
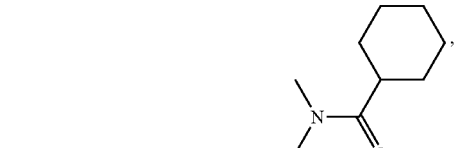
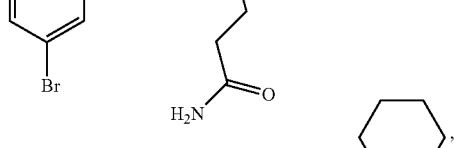
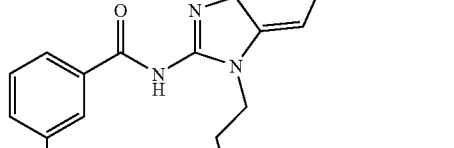
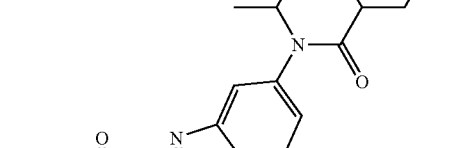
or the pharmaceutically acceptable salts thereof.
* * * * *